United States Patent
Enoki et al.

(10) Patent No.: US 11,795,451 B2
(45) Date of Patent: Oct. 24, 2023

(54) PRIMER FOR NEXT GENERATION SEQUENCER AND A METHOD FOR PRODUCING THE SAME, A DNA LIBRARY OBTAINED THROUGH THE USE OF A PRIMER FOR NEXT GENERATION SEQUENCER AND A METHOD FOR PRODUCING THE SAME, AND A DNA ANALYZING METHOD USING A DNA LIBRARY

(71) Applicant: TOYOTA JIDOSHA KABUSHIKI KAISHA, Toyota (JP)

(72) Inventors: Hiroyuki Enoki, Hamamatsu (JP); Yoshie Takeuchi, Hamamatsu (JP); Minoru Inamori, Kariya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 379 days.

(21) Appl. No.: 16/769,859

(22) PCT Filed: Dec. 21, 2018

(86) PCT No.: PCT/JP2018/047136
§ 371 (c)(1),
(2) Date: Jun. 4, 2020

(87) PCT Pub. No.: WO2019/131470
PCT Pub. Date: Jul. 4, 2019

(65) Prior Publication Data
US 2021/0171941 A1    Jun. 10, 2021

(30) Foreign Application Priority Data

Dec. 25, 2017  (JP) ................. 2017-247826

(51) Int. Cl.
| G16B 30/00 | (2019.01) |
| G16B 40/00 | (2019.01) |
| G16B 25/20 | (2019.01) |
| C12N 15/10 | (2006.01) |
| C12Q 1/6806 | (2018.01) |

(52) U.S. Cl.
CPC ....... *C12N 15/1093* (2013.01); *C12Q 1/6806* (2013.01); *G16B 25/20* (2019.02); *G16B 30/00* (2019.02); *G16B 40/00* (2019.02); *C12Q 2537/165* (2013.01)

(58) Field of Classification Search
None
See application file for complete search history.

(56) References Cited

U.S. PATENT DOCUMENTS

| 9,247,720 B2 | 2/2016 | Chemin et al. |
| 10,023,907 B2 | 7/2018 | Van Eijk et al. |
| 10,093,976 B2 | 10/2018 | Lo et al. |
| 10,095,832 B2 | 10/2018 | Van Eijk et al. |
| 2003/0157515 A1 | 8/2003 | Ohtsubo et al. |
| 2009/0131275 A1 | 5/2009 | Shimamoto et al. |
| 2013/0085083 A1 | 4/2013 | Kamberov et al. |
| 2015/0360193 A1 | 12/2015 | Fan et al. |
| 2016/0326572 A1 | 11/2016 | Schupp et al. |
| 2017/0121765 A1 | 5/2017 | Lee et al. |
| 2017/0335371 A1 | 11/2017 | Osborne et al. |
| 2018/0010120 A1 | 1/2018 | Mellor et al. |
| 2019/0233889 A1 | 8/2019 | Enoki et al. |
| 2020/0071776 A1 | 3/2020 | Enoki et al. |
| 2020/0216879 A1 | 7/2020 | Enoki et al. |

FOREIGN PATENT DOCUMENTS

| CN | 107513576 A | 12/2017 |
| JP | 2003-79375 A | 3/2003 |
| JP | 3972106 B2 | 9/2007 |
| JP | 2008-546404 A | 12/2008 |
| JP | 5389638 B2 | 1/2014 |
| JP | 2017-79735 A | 5/2017 |
| JP | 2018-42548 A | 3/2018 |
| WO | WO 2006/137733 A1 | 12/2006 |
| WO | WO 2010/039991 A2 | 4/2010 |
| WO | WO 2014/140309 A1 | 9/2014 |
| WO | WO 2016/083933 A1 | 6/2016 |
| WO | WO 2016/115550 A1 | 7/2016 |

(Continued)

OTHER PUBLICATIONS

Yoon et al. "PrimerDesign-M: a multiple-alignment based multiple primer design tool for walking across variable genomes" Bioinformatics, 2015, 31(9), pp. 1472-1474 (Year: 2015).*

Mallona et al. "pcrEfficiency: a Web tool for PCR amplification efficiency prediction" BMC Bioinformatics 2011, 12:404, pp. 1-7 (Year: 2011).*

Kampke et al. "Efficient primer design algorithms" Bioinformatics 2001, vol. 17, No. 3, pp. 214-225 (Year: 2001).*

Kozarewa et al. ("96-Plex Molecular Barcoding for the Illumina Genome Analyzer", High-Throughput Next Generation Sequencing: Methods and Applications, Young Min Kwon and Steven C. Rieke (eds.), Methods in Molecular Biology, vol. 733, pp. 279-298 (Year: 2011).*

(Continued)

*Primary Examiner* — Olivia M. Wise
(74) *Attorney, Agent, or Firm* — Oblon, McClelland, Maier & Neustadt, L.L.P.

(57) ABSTRACT

This invention provides a primer used for a next-generation sequencer that can provide a large number of reads. On the basis of the sequence: 5'-CAAGCAGAAGACGGCAT-ACGAGAT-$N_{5 \ to \ 15}$-GTCTCGTGGGCTCG-GAGATGTGTATAAGA-GACAG-3', wherein $N_{5 \ to \ 15}$ indicates an index sequence of 5 to 15 nucleotides), an index sequence is designed as a nucleotide sequence exhibiting the putative number of reads, which is calculated using the estimation formula designating the number of reads as a purpose variable and the type of nucleotides in the index sequence as an explanatory variable, exceeding a given level.

5 Claims, 2 Drawing Sheets

Specification includes a Sequence Listing.

(56) References Cited

FOREIGN PATENT DOCUMENTS

| WO | WO 2017/123758 A1 | 7/2017 |
| WO | WO 2017/222164 A1 | 12/2017 |

OTHER PUBLICATIONS

Best et al. "Computational analysis of stochastic heterogeneity in PCR amplification efficiency revealed by single molecule barcoding" Nature Scientific Reports 2015, 5:14629, pp. 1-13 (Year: 2015).*

O'Donnell et al. "Indexed PCR Primers Induce Template-Specific Bias in Large-Scale DNA Sequencing Studies" PLOS ONE 2016, 11(3), e0148698, pp. 1-11 (Year: 2016).*

Frank et al. ("BARCRAWL and BARTAB: software tools for the design and implementation of barcoded primers for highly multiplexed DNA sequencing" BMC Bioinformatics 2009, 10:362, pp. 1-13 (Year: 2009).*

Illumina, Illumina Adapter Sequences, Document #1000000002694 v00, Oct. 2015, pp. 1-34 Internet: <URL: https://dnatech.genomecenter.ucdavis.edu/wp-content/uploads/2013/06/illumina-adapter-sequences_1000000002694-00.pdf).

International Search Report and Written Opinion dated Apr. 16, 2019 in PCT/JP2018/047136 filed on Dec. 21, 2018.

Craig et al., "Identification of Genetic Variants Using Barcoded Multiplexed Sequencing", Nat Methods, 2008, vol. 5, No. 10, 16 total pages.

Illumina, New uses of NGS, Library Preparation Using Tailed PCR Method, [online], Jun. 13, 2014, Internet: URL:https://jp.illumina.com/content/dam/illumina-marketing/apac/japan/documents/pdf/2014_techsupport_session5.pdf, 56 total pages (with unedited computer-generated English translation).

Lamble et al., "Improved workflows for high throughput library preparation using the transposome-based nextera system", BMC Biotechnology, 2013, vol. 13, No. 104, 12 total pages.

SEQanswers, [online], Jul. 4, 2012, 01:46 AM, Internet: URL:https://seqanswers.com/forums/showthread.php?p=72834, 6 total pages.

Office Action dated Jul. 14, 2020 in co-pending U.S. Appl. No. 16/313,706, 8 pages.

Office Action dated Sep. 17, 2020 in co-pending U.S. Appl. No. 16/313,706, 17 pages.

Office Action dated Sep. 24, 2020 in co-pending U.S. Appl. No. 16/314,274, 9 pages.

Office Action dated Nov. 12, 2020 in co-pending U.S. Appl. No. 16/613,532, 20 pages.

Office Action dated Aug. 27, 2020 in co-pending U.S. Appl. No. 16/613,532, 10 pages.

Saavedra, J.T., et al., "Mapping Transposon Insertions in Bacterial Genomes by Arbitrarily Primed PCR", current Protocols in Molecular Biology, Apr. 2017, pp. 15.15.1-15.15.15.

Pickard, D., et al., "A Genomewide Mutagenesis Screen Identifies Multiple Genes Contributing to Vi Capsular Expression in *Salmonella enterica* Serovar Typhi", Journal of Bacteriology, 2013, vol. 195, No. 6, 2013, pp. 1320-1326.

Langridge, G.C., et al., "Simultaneous assay of every *Salmonella typhi* gene using one million transposon mutants", Genome Research, 2009, vol. 19, No. 12, XP002682200, pp. 2308-2316.

Yigit, E., et al., "Genome and Metagenome Sequencing: Using the Human Methyl-Binding Domain to Partition Genomic DNA Derived from Plant Tissues", Applications in Plant Sciences, vol. 2 No. 11, 2014, XP55492202, pp. 1-6 with cover page.

Lutz, K.A., et al., "Isolation and analysis of high quality nuclear DNA with reduced organellar DNA for plant genome sequencing and resequencing", BMC Biotechnology 2011, vol. 11, XP21103471, pp. 1-9.

Picelli, S., et al., "Tn5 transposase and tagmentation procedures for massively scaled sequencing projects", Genome Research, Jul. 30, 2014, vol. 24 No. 12, pp. 2033-2040.

Office Action dated May 12, 2021, in co-pending U.S. Appl. No. 16/613,532.

Office Action dated Sep. 21, 2021, in co-pending U.S. Appl. No. 16/613,532.

Office Action dated Feb. 28, 2022, in co-pending U.S. Appl. No. 16/613,532.

Shchelkunov et al., "Plant-Based Vaccines Against Human Hepatitis B Virus", Expert Reviews Vaccines, 2010, 9(8), pp. 947-955. (Year: 2010).

Welch et al., "Data Characterizing the Chloroplast Genomes of Extinct and Endangered Hawaiian Endemic Mints (*Lamiaceae*) and Their Close Relatives", Data in Brief, 2016, 7, pp. 900-922. (Year: 2016).

Welch et al., "The Quest to Resolve Recent Radiations: Plastid Phylogenomics of Extinct and Endangered Hawaiian Endemic Mints (*Lamiaceae*)", Molecular Phylogenetics and Evolution, 2016, 99, pp. 16-33. (Year: 2016).

Office Action dated Oct. 5, 2022, in related U.S. Appl. No. 16/613,532, filed Nov. 14, 2019.

Office Action dated Dec. 2, 2021, in co-pending U.S. Appl. No. 16/613,532.

Non-final Office Action dated May 16, 2023, in U.S. Appl. No. 16/613,532—37 pages.

Scitable, Primer, Nature Education, 2014, 1-2. Obtained from: https://www.nature.com/scitable/definition/primer-305/#:-:text=A%20primer%20is%20a%20short,before%20DNA%20repiication%20can%20occur on May 9, 2023. (Year: 2014)—2 pages.

McMaster University, Amplicon Libraries for Illumina Sequencing, 2017, 1-6. Obtained from: https://genomics.healthisci.mcmaster.ca/wp-conten t/uploads/2022/06 /amplicon_libra ries_171031.pdf on May 10, 2023. (Year: 2017) 6 pages.

Advisory Action dated Feb. 27, 2023, in U.S. Appl. No. 16/613,532, 7 pages.

* cited by examiner

[Fig. 1]
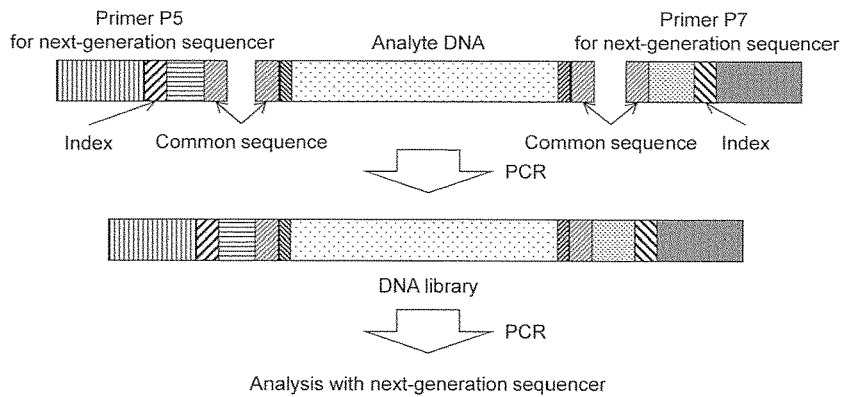
[Fig. 2]
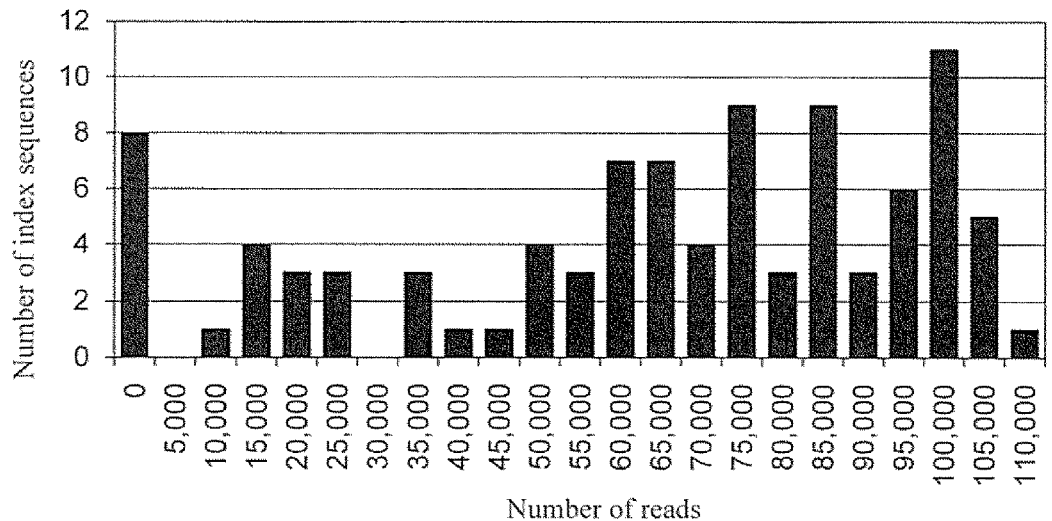
[Fig. 3]
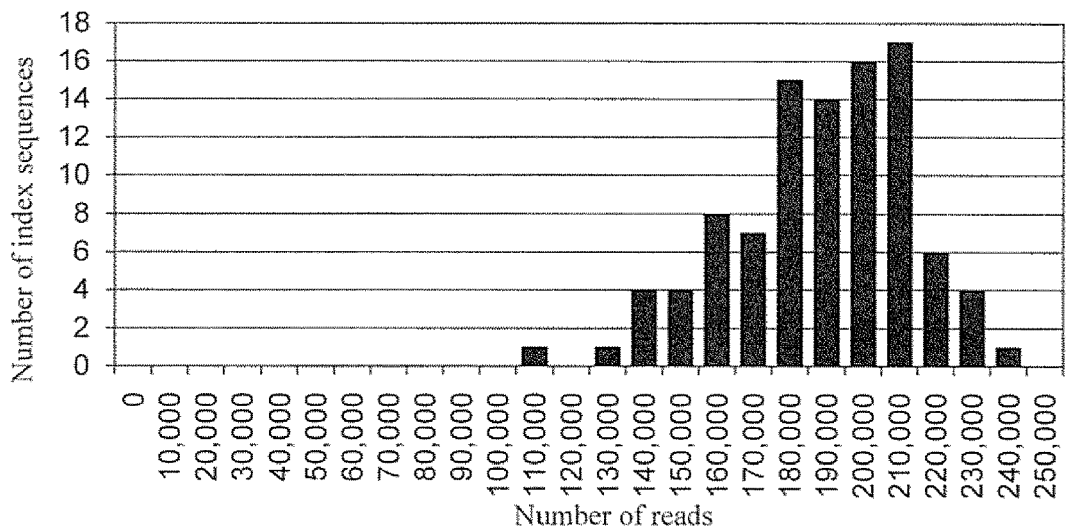

[Fig. 4]
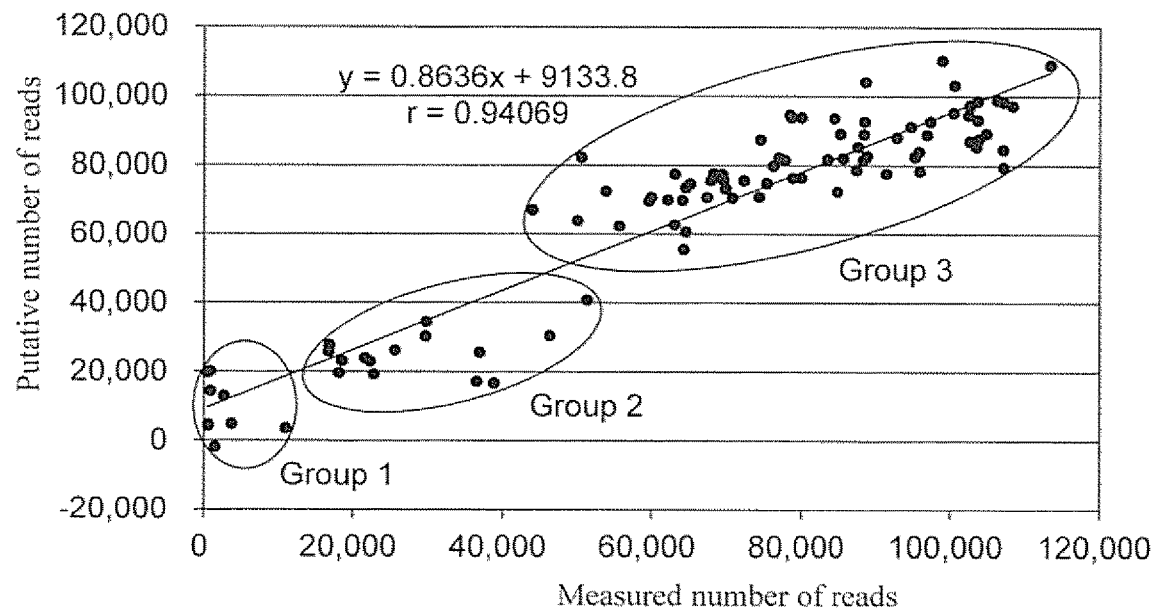
[Fig. 5]
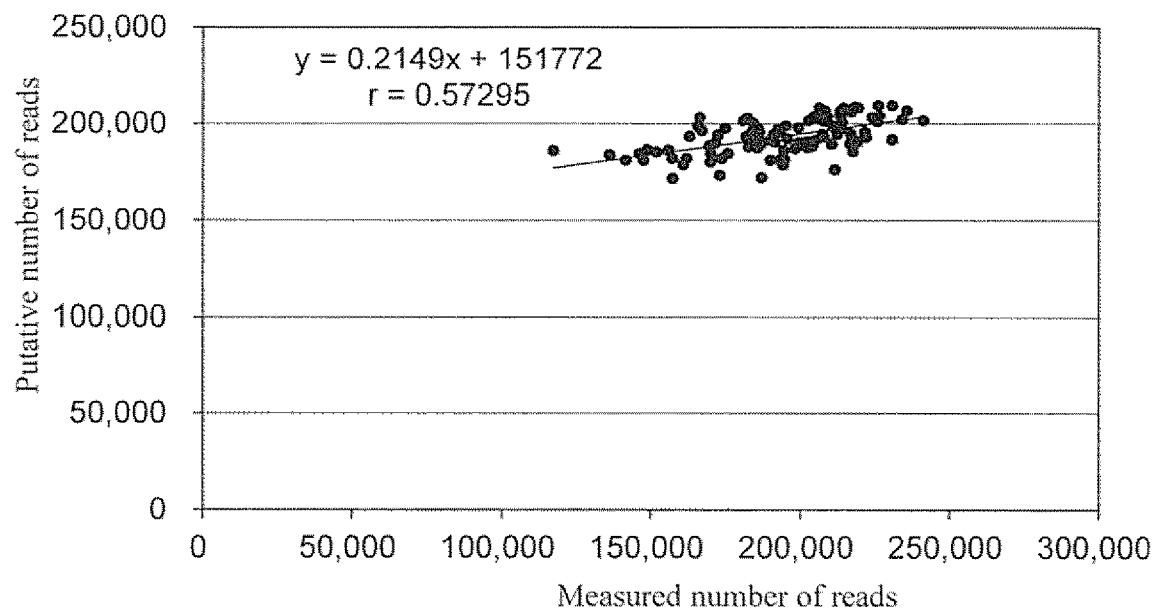

PRIMER FOR NEXT GENERATION SEQUENCER AND A METHOD FOR PRODUCING THE SAME, A DNA LIBRARY OBTAINED THROUGH THE USE OF A PRIMER FOR NEXT GENERATION SEQUENCER AND A METHOD FOR PRODUCING THE SAME, AND A DNA ANALYZING METHOD USING A DNA LIBRARY

TECHNICAL FIELD

The present invention relates to a primer used for a next-generation sequencer having an index that enables simultaneous analysis of a plurality of analytes, a method for producing the same, a DNA library using the primer used for a next-generation sequencer, a method for producing the same, and a method of genomic DNA analysis using the DNA library.

BACKGROUND ART

A next-generation sequencer (NGS) is an apparatus that can read nucleotide sequences of many DNA fragments in parallel. For example, for the use of the next-generation sequencer (Illumina), adaptors are ligated to both ends of each of tens of millions to hundreds of millions of DNA fragments that have been randomly cleaved and 5' terminuses thereof are immobilized on the flow cell via adaptors. Subsequently, the 5' terminal adaptor that has been immobilized on the flow cell in advance is annealed to the 3' terminal adaptor sequence of the DNA fragment to form a bridged DNA fragment. A nucleic acid amplification reaction is carried out with the aid of a DNA polymerase in that state, so that many single-stranded DNA fragments can be topically amplified and immobilized. The next-generation sequencer performs sequencing with the use of the resulting single-stranded DNA as a template. Thus, sequence information as enormous as 40 to 200 Gb can be obtained via single analysis.

Sequencing with the use of a next-generation sequencer is carried out by a method in which fluorescence-labeled dNTP uptake is analyzed under a fluorescence microscope. Specifically, dNTP that is blocked with a protective group and fluorescence-labeled at the 3' terminus is used. dNTP complementary to the single-stranded DNA fragment is incorporated with the aid of DNA polymerase, dNTP is excited with a laser beam, and the fluorescence is read under a fluorescence microscope. The protective group is removed from dNTP, and the subsequent nucleotide is then analyzed in the same manner. Thus, the next-generation sequencer continuously analyzes each nucleotide of the single-stranded DNA immobilized on the flow cell.

In particular, according to the next-generation sequencer, an index (it is also referred to as an "index sequence" or a "barcode sequence") is provided to an adaptor to be ligated to the analyte DNA fragment, so that DNA fragments derived from a plurality of samples can be distinguished from each other. As described above, specifically, enormous sequence information can be obtained via a single analysis, and the origin of the sample from which the sequence information concerning the DNA fragment of interest is derived can be identified with the use of the index sequence included in the sequence information as the indicator.

As described in Non-Patent Literature 1, however, analysis with the use of the next-generation sequencer utilizing the index sequence was disadvantageous in terms of a significant variation in the number of reads depending on the index sequence. In Non-Patent Literature 1, however, a difference concerning properties of the index sequence is not systemically analyzed, and accuracy of analysis with the use of the next-generation sequencer using the index sequence was insufficient, disadvantageously.

In the past, a method in which universal tail sequences each comprising a different nucleotide sequence is added to each of a pair of primers, multiplex PCR is carried out with the use of the pair of primers, and a group of amplicons applied to the next-generation sequencer (i.e., amplicons with the same index sequence) is obtained has been known (Patent Literature 1). For the purpose of improving the efficiency of analysis of large quantities of samples, in addition, a method of using a pair of primers each containing an adaptor, an index, and a target DNA-specific sequence to prepare a DNA library for the next-generation sequencer has been known (Patent Literature 2). The primer disclosed in Patent Literature 2 is an integrated primer composed of a primer that specifically binds to the target DNA such as a hyper variable region of human mitochondrial DNA, an adaptor primer that is necessary for production of an NGS library, an index primer, and a sequencing primer.

CITATION LIST

Non Patent Literature

NPL 1: David W. Craig et al., Nat. Methods, October 2008; 5 (10): 887-893

PATENT LITERATURE

{PTL 1}
US 2016/0326572 A1
{PTL 2}
JP 2017-79735 A

SUMMARY OF INVENTION

Technical Problem

When using a primer used for a next-generation sequencer comprising an index, however, a problem concerning the significantly decreased number of reads depending on the index sequence remains unsolved, and no technique that can dissolve such problem has been known at present. Under the above circumstances, the present invention provides a primer used for a next-generation sequencer that can achieve a large number of reads and a method for producing such primer by elucidating the correlation between the nucleotide sequence of the index and the number of reads. The present invention also provides a DNA library using a primer used for a next-generation sequencer that can achieve a large number of reads, a method for producing such DNA library, and a method of genomic DNA analysis using such DNA library.

Solution to Problem

The present inventors have conducted concentrated studies in order to solve the above problems. As a result, they elucidated the correlation between the index sequence and the number of reads of the primer used for a next-generation sequencer comprising the index sequence and demonstrated that the number of reads could be deduced based on the nucleotide sequence of the index sequence. They discovered that a primer used for a next-generation sequencer that could achieve a large number of reads can be produced by designing an index sequence that can achieve the putative number of reads exceeding a given level. This has led to the completion of the present invention.

The present invention includes the following.

(1) A primer used for a next-generation sequencer comprising a nucleotide sequence of 5'-CAAGCAGAAGACGGCATACGAGAT (SEQ ID NO: 1)-$N_{5\ to\ 15}$-GTCTCGTGGGCTCGGAGATGTGTATAAGAGACAG (SEQ ID NO: 2)-3', wherein $N_{5\ to\ 15}$ indicates an index sequence of 5 to 15 nucleotides and the index sequence designed as a nucleotide sequence exhibiting a putative number of reads exceeding a given level, which is calculated based on an estimation formula that designates the number of reads as a purpose variable and a type of nucleotide in the index sequence as an explanatory variable.

(2) The primer used for a next-generation sequencer according to (1), wherein the index sequence is composed of 8 nucleotides (N: 8; SEQ ID NO: 67).

(3) The primer used for a next-generation sequencer according to (1), wherein the estimation formula includes items comprising a type of a nucleotide and a coefficient in accordance therewith concerning the N number of nucleotides constituting the index sequence.

(4) The primer used for a next-generation sequencer according to (1), wherein the given level is from 15,000 to 25,000.

(5) The primer used for a next-generation sequencer according to (1), which comprises a nucleotide sequence selected from the group consisting of SEQ ID NOs: 262 to 963.

(6) A method for producing a primer used for a next-generation sequencer comprising: a step of calculating, for the primer used for a next-generation sequencer comprising a nucleotide sequence of 5'-CAAGCAGAAGACGGCATACGAGAT (SEQ ID NO: 1)-$N_{5\ to\ 15}$-GTCTCGTGGGCTCGGAGATGTGTATAAGAGACAG (SEQ ID NO: 2)-3', wherein $N_{5\ to\ 15}$ indicates an index sequence of 5 to 15 nucleotides, a putative number of reads based on a nucleotide sequence of the index sequence in accordance with an estimation formula that designates the number of reads as a purpose variable and a type of a nucleotide in the index sequence as an explanatory variable to design a nucleotide sequence as a nucleotide sequence of the index sequence where the calculated putative number of reads exceeds a given level; and a step of synthesizing a nucleotide sequence comprising the index sequence designed in the above step.

(7) The method for producing the primer used for a next-generation sequencer according to (6), wherein the index sequence is composed of 8 nucleotides (N: 8; SEQ ID NO: 67).

(8) The method for producing the primer used for a next-generation sequencer according to (6), wherein the estimation formula includes items comprising a type of nucleotide and a coefficient in accordance therewith concerning the N number of nucleotides constituting the index sequence.

(9) The method for producing the primer used for a next-generation sequencer according to (6), wherein the given level is from 15,000 to 25,000.

(10) The method for producing the primer used for a next-generation sequencer according to (6), wherein a sequence of nucleotides 25 to 32 in a nucleotide sequence selected from the group consisting of SEQ ID NOs: 262 to 963 is designed as a nucleotide sequence of the index sequence.

(11) A DNA library comprising a DNA fragment comprising, at one end of the analyte DNA, a nucleotide sequence of the primer used for a next-generation sequencer according to any of (1) to (5).

(12) The DNA library according to (11), wherein the analyte DNA is a fragment obtained via nucleic acid amplification or a fragment obtained via genomic DNA fragmentation.

(13) The DNA library according to (11), wherein the analyte DNA is a fragment obtained by performing a nucleic acid amplification reaction in a reaction solution containing genomic DNA and a random primer at high concentration, and the random primer comprises, at the 5' terminus, a nucleotide sequence complementary to a nucleotide sequence at the 3' terminus of the primer used for a next-generation sequencer.

(14) A method for producing a DNA library comprising a step of performing a nucleic acid amplification reaction with the use of the primer used for a next-generation sequencer according to any of (1) to (5) above and analyte DNA comprising, at the 5' terminus, a nucleotide sequence complementary to a nucleotide sequence at the 3' terminus of the primer used for a next-generation sequencer.

(15) The method for producing a DNA library according to (14), wherein the analyte DNA is a fragment obtained via nucleic acid amplification or a fragment obtained via genomic DNA fragmentation.

(16) The method for producing a DNA library according to (14), wherein the analyte DNA is a fragment obtained by performing a nucleic acid amplification reaction in a reaction solution containing genomic DNA and a random primer at high concentration, and the random primer comprises, at the 5' terminus, a nucleotide sequence complementary to a nucleotide sequence at the 3' terminus of the primer used for a next-generation sequencer.

(17) A method of DNA analysis comprising analyzing the DNA library according to any of (11) to (13) using a next-generation sequencer and determining a nucleotide sequence of a DNA fragment contained in the DNA library.

Advantageous Effects of Invention

The present invention provides a primer used for a next-generation sequencer that can avoid inconvenience, such as a decreased number of reads caused by the index sequence, and provide a large number of reads, a method for producing the same, a DNA library produced with the use of the primer used for a next-generation sequencer, and a method for producing the same.

With the use of the DNA library produced using the primer used for a next-generation sequencer according to the present invention, the amount of data (i.e., the number of reads) varying among samples can be prevented, and DNA analysis can be performed with high accuracy.

BRIEF DESCRIPTION OF DRAWINGS

FIG. 1 shows a characteristic diagram schematically demonstrating a scheme of an analysis performed with the use of a next-generation sequencer using a primer used for a next-generation sequencer.

FIG. 2 shows a characteristic diagram demonstrating a correlation between a type of the index sequence of the primer P7 used for a next-generation sequencer and the number of reads.

FIG. 3 shows a characteristic diagram demonstrating a correlation between a type of the index sequence of the primer P5 used for a next-generation sequencer and the number of reads.

FIG. 4 shows a characteristic diagram demonstrating a correlation between the putative number of reads determined in accordance with an estimation formula based on types of nucleotides constituting the index sequence of the primer P7 used for a next-generation sequencer and the measured number of reads.

FIG. 5 shows a characteristic diagram demonstrating a correlation between the putative number of reads determined in accordance with an estimation formula based on types of nucleotides constituting the index sequence of the primer P5 used for a next-generation sequencer and the measured number of reads.

DESCRIPTION OF EMBODIMENTS

Hereafter, the present invention is described in greater detail.

The primer used for a next-generation sequencer according to the present invention comprises a nucleotide sequence of 5'-CAAGCAGAAGACGGCATACGAGAT (SEQ ID NO: 1)-$N_{5\ to\ 15}$-GTCTCGTGGGCTCGAGATGTGTATAAGAGACAG (SEQ ID NO: 2)-3', wherein $N_{5\ to\ 15}$ indicates an index sequence of 5 to 15 nucleotides. In the nucleotide sequence indicated above, the index sequence indicated as "$N_{5\ to\ 15}$" is a sequence designed as described in detail below. For example, such sequence can be used as an index for distinguishing samples from each other. Specifically, any index sequence may be used, as long as it is designed in the manner as described below. For example, a different index sequence may be designed for each of a plurality of samples. Thus, sample attribution of the nucleotide sequence analyzed with the use of the next-generation sequencer can be clearly identified on the basis of the index sequence (i.e., multiplex analysis).

FIG. 1 schematically shows a scheme of an analysis performed with the use of a next-generation sequencer using a primer used for a next-generation sequencer. The primer used for a next-generation sequencer according to the present invention is based on a primer that is referred to as P7 of the next-generation sequencer (NGS) provided by Illumina. When preparing a DNA library applied to the next-generation sequencer, PCR is carried out using the primer P7 used for a next-generation sequencer and the primer P5 used for a next-generation sequencer. While the primer P5 used for a next-generation sequencer shown in FIG. 1 comprises an index sequence, the primer may not comprise an index sequence.

As shown in FIG. 1, a DNA fragment comprising the analyte DNA between the primer P7 used for a next-generation sequencer and the primer P5 used for a next-generation sequencer can be obtained by PCR using the primer P7 used for a next-generation sequencer and the primer P5 used for a next-generation sequencer. A group of DNA fragments obtained by PCR is referred to as a DNA library or a DNA library used for the next-generation sequencer.

As shown in FIG. 1, the DNA library obtained in the manner described below is analyzed using the next-generation sequencer (Illumina). The next-generation sequencer outputs data of nucleotide sequences concerning many reads as a result of analysis of the DNA library (i.e., the data of nucleotide sequences including the nucleotide sequence of the analyte DNA).

Analyte DNA is not particularly limited, and it can be, for example, a DNA fragment derived from genomic DNA derived from a target organism, the genome of which is to be analyzed, DNA prepared for epigenome analysis or DNA prepared for transcript analysis, or an amplification product obtained with the use of genomic DNA as a template (i.e., an amplicon).

Index Sequence Design

The index sequence of the primer used for a next-generation sequencer according to the present invention is designed in a manner such that a sufficiently large number of reads can be obtained when analyzing the nucleotide sequences of the DNA library with the use of the next-generation sequencer. When designing an index sequence, specifically, an estimation formula that designates the number of reads as a purpose variable and types of nucleotides in the index sequence as an explanatory variable is prepared. In order to prepare such estimation formula, at the outset, a primer used for a next-generation sequencer having an index sequence comprising a particular nucleotide sequence is synthesized, and the number of reads attained with the use of the primer used for a next-generation sequencer is analyzed. Thus, the estimation formula can be calculated on the basis of the nucleotide sequence of the index sequence and the number of reads.

When calculating an estimation formula, specifically, various types of algorithms that are generally used for correlational analysis can be adopted, although algorithm is not limited thereto. More specifically, a method of sparse modeling, such as the least absolute shrinkage and selection operator (Lasso), can be adopted. According to the method of L1 regularized estimation among the sparse modeling methods, a coefficient of insignificant parameters can be deduced to be 0, and an estimation formula consisting of adequate parameters can be obtained.

For example, an estimation formula includes items including coefficients determined for each nucleotide at a given position in the index sequence and an intercept. By designating particular nucleotides at all the positions in the index sequence, accordingly, the putative number of reads can be determined. With the application of the sparse modeling method, such as LASSO, an estimation formula that designates the coefficient of insignificant parameters; i.e., a nucleotide that is not significantly involved in an increase/decrease in the number of reads, as 0 can be calculated.

When designing an index sequence composed of, for example, an index sequence of 8 nucleotides (N: 8); i.e., an index sequence composed of nucleotides 1 to 8 in the 5' to 3' direction, more specifically, an estimation formula can be designed to lead to a decreased putative number of reads when nucleotide 1 is adenine or guanine and an increased putative number of reads when it is cytosine. An estimation formula can also be designed to lead to an increased putative number of reads when nucleotide 2 is adenine or thymine and a decreased putative number of reads when nucleotide 2 is guanine. Further, an estimation formula can also be designed to lead to an increased putative number of reads when nucleotide 3 is adenine or thymine and a decreased putative number of reads when nucleotide 3 is guanine. Further, an estimation formula can also be designed to lead to an increased putative number of reads when nucleotide 4 is adenine and a decreased putative number of reads when nucleotide 4 is cytosine or guanine. Further, an estimation formula can also be designed to lead to an increased putative number of reads when nucleotide 5 is adenine and a decreased putative number of reads when nucleotide 5 is guanine. Further, an estimation formula can also be designed to lead to an increased putative number of reads when nucleotide 6 is cytosine and a decreased putative number of reads when nucleotide 6 is thymine. Further, an estimation formula can also be designed to lead to a decreased putative number of reads when nucleotide 7 is adenine and an increased putative number of reads when nucleotide 7 is guanine. Further, an estimation formula can also be designed to lead to a decreased putative number of reads when nucleotide 8 is guanine and an increased putative number of reads when nucleotide 8 is thymine.

In particular, an estimation formula can be designed to result in a putative number of reads decreased to a significant extent when nucleotide 1 is adenine or guanine, nucleotide 2 is guanine, and nucleotide 8 is guanine. In addition, an estimation formula can be designed to result in a putative number of reads increased to a significant extent when nucleotide 2 is adenine or thymine, nucleotide 3 is adenine, and nucleotide 5 is adenine.

More specifically, a coefficient for each type of a nucleotide in the index sequence and an intercept can be designated as shown in the table below.

TABLE 1

| Intercept | 81720.7 |
|---|---|
| A1 | −65033.1 |
| C1 | 1326.4 |
| G1 | −16997.0 |
| T1 | 0.0 |
| A2 | 10936.3 |
| C2 | 0.0 |
| G2 | −12399.2 |
| T2 | 11712.9 |
| A3 | 12112.2 |
| C3 | 0.0 |
| G3 | −623.5 |
| T3 | 5964.4 |
| A4 | 6884.5 |
| C4 | −5664.4 |
| G4 | −6049.9 |
| T4 | 0.0 |
| A5 | 9257.0 |
| C5 | 0.0 |
| G5 | −6210.8 |
| T5 | 0.0 |
| A6 | 0.0 |
| C6 | −644.0 |
| G6 | 0.0 |
| T6 | 3.2 |
| A7 | −3575.9 |
| C7 | 0.0 |
| G7 | 1013.1 |
| T7 | 0.0 |
| A8 | 0.0 |
| C8 | 0.0 |
| G8 | −8607.7 |
| T8 | 6490.3 |

In Table 1, "A1" indicates an embodiment in which nucleotide 1 in the 5' to 3' direction of the index sequence is adenine. Each of other notations also indicates a position in the 5' to 3' direction of the index sequence and a type of nucleotide.

With the use of the estimation formula shown in the table above, for example, the putative number of reads obtained when a particular nucleotide sequence is designated for an index sequence can be determined. The estimation formulae prepared in the manner described above are not limited to those exemplified in Table 1, and the results attained with the formulae are highly correlated with the measured value (correlational coefficient: 0.9 or higher). By calculating the putative number of reads for each nucleotide sequence of an index sequence with the use of the estimation formula and selecting a nucleotide sequence exhibiting a putative number of reads exceeding a given level, a large number of reads can be obtained.

When designing an index sequence, the putative number of reads designated as a threshold is not particularly limited, and it can be adequately determined in accordance with a type of data analysis of interest. For example, a threshold of the putative number of reads can be set in a range from 15,000 to 25,000, preferably from 17,000 to 23,000, more preferably from 19,000 to 21,000, and further preferably from 19,500 to 20,500. As described in detail in the examples below, a group of nucleotide sequences with a significantly small number of reads is identified for the nucleotide sequence of the index sequence. The putative number of reads of the group of nucleotide sequences was calculated and found to be about 20,000 and specifically 20,051.8 at a maximum. By adjusting the threshold to about 20,000, for example, 20,052, accordingly, an index sequence that can actually obtain a large number of reads can be designed.

With the use of the estimation formula shown in Table 1, the nucleotide sequence of the primer used for a next-generation sequencer comprising an index sequence with the putative number of reads exceeding 20,052 was identified (described in detail in the examples below). A specific example of the primer used for a next-generation sequencer according to the present invention is a nucleotide sequence selected from the group consisting of SEQ ID NOs: 262 to 963.

Application to Next-Generation Sequencing

A nucleic acid amplification reaction is carried out with the use of the primer used for a next-generation sequencer according to the present invention described above. Thus, a DNA library used for a next-generation sequencer (i.e., a DNA library for a next-generation sequencer) can be prepared. Specifically, PCR is carried out in a reaction solution containing the primer P7 used for a next-generation sequencer according to the present invention, analyte DNA, and the primer P5 used for a next-generation sequencer, as shown in FIG. 1. Analyte DNA comprises, at both terminuses, a sequence that is in common with the primer P7 used for a next-generation sequencer and a sequence that is in common with the primer P5 used for a next-generation sequencer, respectively. In the nucleic acid amplification reaction, accordingly, the primers P7 and P5 used for a next-generation sequencer are annealed to the both terminuses of analyte DNA, and a nucleic acid amplification reaction with the use of analyte DNA as a template proceeds. As a result, a group of nucleic acid fragments (a DNA library) comprising the primer P5 used for a next-generation sequencer, analyte DNA, and the primer P7 used for a next-generation sequencer in that order can be obtained, as shown in FIG. 1.

Since the resulting DNA library comprises, at both terminuses, the primers P5 and P7 used for a next-generation sequencer, it can be applied to the next-generation sequencer (Illumina). In addition, the resulting DNA library comprises the primer P7 used for a next-generation sequencer according to the present invention. Accordingly, a larger number of reads can be analyzed with the use of the next-generation sequencer. Specifically, the number of reads close to the putative number of reads determined in accordance with the estimation formula described above can be analyzed.

The next-generation sequencer performs sequencing by amplifying the target DNA on the flow cell via bridge PCR and the sequencing-by-synthesis method while conducting synthesis.

A nucleic acid amplification reaction can be performed with the use of a reaction solution containing the primer P7 used for a next-generation sequencer according to the present invention, analyte DNA, and the primer P5 used for a next-generation sequencer without particular limitation. General conditions for a nucleic acid amplification reaction can be adopted. For example, the reaction solution contains analyte DNA as a template, the primers P5 and P7 used for a next-generation sequencer, DNA polymerase, deoxyribonucleotide triphosphate (dNTP; i.e., a mixture of dATP, dCTP, dTTP, and dGTP) as a substrate, and a buffer.

In particular, the concentration of the primers P5 and P7 used for a next-generation sequencer can be 0.01 to 5.0 microM, preferably 0.1 to 2.5 microM, and most preferably 0.3 to 0.7 microM.

While the amount of analyte DNA used as a template in the nucleic acid amplification reaction is not particularly limited, it is preferably 0.1 to 1000 ng, more preferably 1 to 500 ng, further preferably 5 to 200 ng, and most preferably 10 to 100 ng, when the amount of the reaction solution is 50 microliters.

A method for preparing an analyte DNA fragment serving as a template is not particularly limited. A reaction solution after the completion of the nucleic acid amplification reaction using the random primer described in detail below may be used without any processing. Alternatively, analyte DNA may be purified from the reaction solution and used.

Also, a type of DNA polymerase, a concentration of deoxyribonucleotide triphosphate as a substrate (dNTP; i.e., a mixture of dATP, dCTP, dTTP, and dGTP), a buffer composition, and thermal cycling conditions adopted for the nucleic acid amplification reaction can be in accordance with the conditions adopted for general nucleic acid amplification reactions. A nucleic acid amplification reaction involving the use of a primer used for a next-generation sequencer may be carried out by the hot start method, or amplified fragments may be obtained via a nucleic acid amplification reaction.

As described above, a DNA library applicable to the next-generation sequencing apparatus can be prepared with the use of a first DNA fragment obtained with the use of a random primer as a template and a second DNA fragment amplified with the use of the next-generation sequencer.

Analyte DNA

An example of analyte DNA is an amplified product (amplicon) obtained from genomic DNA or the like as a template. An amplified product can be obtained by, for example, performing a nucleic acid amplification reaction in a reaction solution containing a primer having an arbitrary nucleotide sequence (hereafter referred to as a "random primer") at high concentration. When a primer concentration is high herein, such concentration is higher than a concentration of the primer used in a conventional nucleic acid amplification reaction. Specifically, the method involves the use of a random primer at concentration higher than that of the primer used in a conventional nucleic acid amplification reaction. A template contained in the reaction solution can be genomic DNA prepared from an analyte organism.

In the method, a target organism species is not limited, and any organism species, such as animals including humans, plants, microorganisms, and viruses, can be targets. According to the method, specifically, many amplified products can be obtained from any organism species as analyte DNAs.

According to the method, nucleic acid fragments (a group of nucleic acid fragments) can be amplified with high reproducibility by defining the random primer concentration as described above. The term "reproducibility" used herein refers to a degree of consistency among nucleic acid fragments amplified as a result of nucleic acid amplification reactions performed a plurality of times with the use of the same template and the same random primer. Specifically, the term "high reproducibility" (or when reproducibility is high) herein refers to a high degree of consistency among nucleic acid fragments amplified as a result of nucleic acid amplification reactions performed a plurality of times with the use of the same template and the same random primer.

A degree of reproducibility can be determined by, for example, performing nucleic acid amplification reactions a plurality of times with the use of the same template and the same random primer, subjecting the amplified fragments to electrophoresis, calculating the Spearman's rank correlation coefficient of the obtained fluorescence unit (FU), and evaluating the degree of reproducibility based on the coefficient. The Spearman's rank correlation coefficient is generally represented by the symbol $\rho$ (rho). For example, an experiment can be evaluated as reproducible when rho is greater than 0.9.

The sequence of a random primer that can be used in the method is not limited. For example, a nucleotide sequence of 9 to 30 nucleotides can be used. In particular, a random primer is composed of an arbitrary sequence of 9 to 30 nucleotides, and a type of nucleotide (a type of sequence) is not particularly limited. A random primer is composed of one or more types of nucleotides, preferably 1 to 10,000 types of nucleotides, more preferably 1 to 1,000 types of nucleotides, further preferably 1 to 100 types of nucleotides, and most preferably 1 to 96 types of nucleotides. With the use of a random primer composed of the number of nucleotides described above (a group of nucleotides), amplified nucleic acid fragments can be obtained with higher reproducibility. When a random primer is composed of a plurality of nucleotide sequences, all the nucleotide sequences are not necessarily composed of the same number of nucleotides (9 to 30 nucleotides), and the sequence may comprise a plurality of nucleotide sequences of different lengths.

In order to obtain a particular amplicon by means of the nucleic acid amplification reaction, in general, a nucleotide sequence of a primer is designed in accordance with the amplicon. For example, a pair of primers is designed to sandwich a position corresponding to an amplicon in the template DNA such as genomic DNA. In this case, primers are designed to hybridize to a particular region in the template. Thus, primers can be referred to as "specific primers."

Unlike a primer that is designed to obtain a particular amplicon, in contrast, a random primer is not designed to hybridize to a particular region in template DNA, but it is designed to obtain a random amplicon. A random primer may comprise an arbitrary nucleotide sequence, and it can be involved in random amplicon amplification by incidentally hybridizing to a complementary region in the template DNA.

Specifically, a random primer can be composed of an arbitrary nucleotide sequence involved in random amplicon amplification, as described above. An arbitrary sequence is not particularly limited. For example, a nucleotide sequence of nucleotides selected randomly from the group consisting of adenine, guanine, cytosine, and thymine may be designed, or a specific nucleotide sequence may be designed. Examples of specific nucleotide sequences include a nucleotide sequence comprising a restriction enzyme recognition sequence or a nucleotide sequence comprising an adaptor sequence used for the next-generation sequencer.

When a plurality of types of nucleotides are designed as random primers, a plurality of nucleotide sequences of given lengths can be designed by randomly selecting nucleotides from the group consisting of adenine, guanine, cytosine, and thymine. When a plurality of types of nucleotides are designed as random primers, a plurality of nucleotide sequences composed of common regions of particular nucleotide sequences and un-common regions of arbitrary nucleotide sequences can be designed. An un-common region may be composed of a nucleotide sequence of nucleotides randomly selected from the group consisting of adenine, guanine, cytosine, and thymine, 4 types of nucleotides in combination (i.e., adenine, guanine, cytosine, and thymine), or some of nucleotides selected from among the 4 types of nucleotides described above in combination. A common region is not particularly limited, and it may be composed of any nucleotide sequence. For example, a common region can be composed of a nucleotide sequence comprising a restriction enzyme recognition sequence, a nucleotide sequence comprising an adaptor sequence applied to the next-generation sequencer, or a nucleotide sequence common among a particular gene family.

When a plurality of nucleotide sequences of given lengths are designed as random primers by randomly selecting nucleotides from among the four types of nucleotides, such nucleotide sequences are preferably designed in such a manner that 30% or more, preferably 50% or more, more preferably 70% or more, and further preferably 90% or more of the full-length sequences exhibit 70% or lower, more preferably 60% or lower, further preferably 50% or lower, and most preferably 40% or lower identity. Thus, amplified fragments can be obtained over the entire genomic DNA of the target organism species. Specifically, homogeneity among amplified fragments can be improved.

When a plurality of nucleotide sequences each composed of a common region of a particular nucleotide sequence and an un-common region of an arbitrary nucleotide sequence are designed as a plurality of random primers, for example, each sequence can be designed to comprise a 3' terminal region of several nucleotides as an un-common region and a remaining 5' terminal region as a common region. By designating a 3'-terminal region of the "n" number of nucleotides as an un-common region, $4^n$ types of random primers can be designed. The "n" number can be 1 to 5, preferably 2 to 4, and more preferably 2 or 3.

As a random primer comprising a common region and an un-common region, for example, a total of 16 types of random primers each comprising a 5' terminal region as an adaptor sequence applied to the next-generation sequencer (i.e., a common region) and a 3'-terminal region of 2 nucleotides (i.e., an un-common region) can be designed. If a 3' terminal region is of 3 nucleotides (an un-common region), a total of 64 types of random primers can be designed. As types of random primers are increased, amplified fragments can be more extensively obtained over the entire genomic DNA of the target organism species. When designing a random primer comprising a common region and an un-common region, accordingly, a 3' terminal region is preferably composed of 3 nucleotides.

After 64 types of nucleotide sequences each composed of a common region and an un-common region of 3 nucleotides are designed, for example, up to 63 types of random primers selected from among the 64 types of nucleotide sequences may be used. In other words, more satisfactory results of analysis may occasionally be obtained via nucleic acid amplification reactions or with the use of the next-generation sequencer with the use of up to 63 types of random primers, in comparison with the use of all the 64 types of random primers. When 64 types of random primers are used, specifically, the number of reads of a particular nucleic acid fragment may occasionally be increased to a significant extent. In such a case, more satisfactory results of analysis can be obtained with the use of up to 63 types of random primers selected from among the 64 types of random primers while excluding one or more random primers involved in amplification of the particular nucleic acid fragment.

When 16 types of random primers each composed of a common region and an un-common region of 2 nucleotides are designed, also, more satisfactory results of analysis can occasionally be obtained via nucleic acid amplification reactions or with the use of the next-generation sequencer when up to 15 types of random primers selected from among the 16 types of random primers are used.

A nucleotide sequence used as a random primer is preferably designed to adjust GC content within a range of 5% to 95%, more preferably within a range of 10% to 90%, further preferably within a range of 15% to 80%, and most preferably within a range of 20% to 70%. With the use of the nucleotide sequence with GC content within the range described above as a random primer, an amplified nucleic acid fragment can be obtained with higher reproducibility. GC content is a proportion of guanine and cytosine relative to the entire nucleotide chain.

A nucleotide sequence used as a random primer is preferably designed to adjust the length of continuous nucleotides to 80% or less, more preferably 70% or less, further preferably 60% or less, and most preferably 50% or less, relative to the full-length sequence. Alternatively, a nucleotide sequence used as a random primer is preferably designed to adjust the number of continuous nucleotides to 8 or less, more preferably 7 or less, further preferably 6 or less, and most preferably 5 or less. With the use of the nucleotide sequence with the number of continuous nucleotides within the range described above as a random primer, an amplified nucleic acid fragment can be obtained with higher reproducibility.

A nucleotide sequence used as a random primer is preferably designed to refrain from comprising a complementary region of 6 nucleotides or more, more preferably 5 nucleotides or more, and further preferably 4 nucleotides or more in a molecule. Thus, formation of a double strand in the molecule can be prevented, and an amplified nucleic acid fragment can be obtained with higher reproducibility.

When designing a plurality of types of nucleotide sequences as random primers, further, each nucleotide sequence is preferably designed to refrain from comprising a complementary region of 6 nucleotides or more, more preferably 5 nucleotides or more, and further preferably 4 nucleotides or more. Thus, formation of a double strand between nucleotides can be prevented, and an amplified nucleic acid fragment can be obtained with higher reproducibility.

When designing a plurality of types of nucleotide sequences as random primers, in addition, it is preferable that each nucleotide sequence is designed in such a manner that 3'-terminal sequences of 6 nucleotides or more, preferably 5 nucleotides or more, and more preferably 4 nucleotides or more refrain from being complementary to each other. Thus, double strand formation between nucleotides can be prevented, and an amplified nucleic acid fragment can be obtained with higher reproducibility.

The term "complementary region" or "complementary sequence" refers to, for example, a region or sequence having identity of 80% to 100% (e.g., regions or sequences of 4 or 5 nucleotides in regions of 5 nucleotides are complementary to each other) or a region or sequence having identity of 90% to 100% (e.g., regions or sequences of 5 nucleotides in regions of 5 nucleotides are complementary to each other).

A nucleotide sequence used as a random primer is preferably designed to have a Tm value suitable for the thermal cycling conditions in the nucleic acid amplification reaction (the annealing temperature, in particular). A Tm value can be calculated by a known method of calculation, such as nearest-neighbor base paring, the Wallace method, or the GC content percentage method, although the method is not particularly limited thereto. Specifically, a nucleotide sequence used as a random primer is preferably designed to have a Tm value of 10 to 85 degrees C., more preferably 12 to 75 degrees C., further preferably 14 to 70 degrees C., and most preferably 16 to 65 degrees C. Thus, an amplified nucleic acid fragment can be obtained with higher reproducibility under given thermal cycling conditions (a given annealing temperature, in particular) in the nucleic acid amplification reaction.

When designing a plurality of types of nucleotide sequences as random primers, nucleotide sequences are preferably designed in such a manner that a variation in Tm values among a plurality of nucleotide sequences is 50 degrees C. or lower, preferably 45 degrees C. or lower, more preferably 40 degrees C. or lower, and most preferably 35 degrees C. or lower. Thus, an amplified nucleic acid fragment can be obtained with higher reproducibility under given thermal cycling conditions (a given annealing temperature, in particular) in the nucleic acid amplification reaction.

According to the method, many amplified fragments are obtained via nucleic acid amplification reactions involving the use of the random primers and genomic DNA as a template. In the nucleic acid amplification reaction, in particular, the random primer concentration in the reaction solution is adjusted to be higher than that used in a conventional nucleic acid amplification reaction. Thus, many amplified fragments can be obtained with the use of genomic DNA as a template while achieving high reproducibility.

In the nucleic acid amplification reaction, an amplified fragment is synthesized in a reaction solution containing genomic DNA as a template, the random primers described above, DNA polymerase, deoxyribonucleotide triphosphate as a substrate (dNTP; a mixture of dATP, dCTP, dTTP, and dGTP), and a buffer under the given thermal cycling conditions. In the nucleic acid amplification reaction, the reaction solution is required to contain $Mg^{2+}$ at a given concentration, and the buffer in the composition described above contains $MgCl_2$. When the buffer does not contain $MgCl_2$, the reaction solution should contain $MgCl_2$ in addition to the components described above.

In the nucleic acid amplification reaction, it is preferable that the random primer concentration be adequately determined in accordance with the nucleotide length of the random primer. When a plurality of types of nucleotide sequences of different nucleotide lengths are used as random primers, the average nucleotide length may be adopted as the nucleotide length of the random primer (it may be a simple average or weighted average including the amount of nucleotides).

Specifically, the nucleic acid amplification reaction is carried out with the use of a random primer of 9 to 30 nucleotides while adjusting the random primer concentration at 4 to 200 microM, and preferably 4 to 100 microM. By conducting the nucleic acid amplification reaction under such conditions, many amplified fragment, and, in particular, many amplified fragments of 100 to 500 nucleotides, can be obtained while achieving high reproducibility.

The amount of genomic DNA serving as a template in the nucleic acid amplification reaction is not particularly limited, and it is preferably 0.1 to 1,000 ng, more preferably 1 to 500 ng, further preferably 5 to 200 ng, and most preferably 10 to 100 ng, when the amount of the reaction solution is 50 microliters. Thus, an amplification reaction with the use of a random primer is not inhibited, and many amplified fragments can be obtained while achieving high reproducibility.

A method for preparing genomic DNA is not particularly limited, and a conventional method can be adopted. With the use of a commercialized kit, genomic DNA can be easily prepared from the target organism species. Genomic DNA extracted from an organism by a conventional technique or with the use of a commercialized kit may be used without further processing. Alternatively, genomic DNA extracted from an organism and purified or genomic DNA subjected to restriction enzyme treatment or ultrasonic treatment may be used.

DNA polymerase used in the nucleic acid amplification reaction is not particularly limited, and an enzyme having DNA polymerase activity under thermal cycling conditions for the nucleic acid amplification reaction can be used. Specifically, thermostable DNA polymerase used for a general nucleic acid amplification reaction can be used. Examples of DNA polymerases include DNA polymerase derived from thermophilic bacteria, such as Taq DNA polymerase, and DNA polymerase derived from ultrathermophilic Archaea, such as KOD DNA polymerase or Pfu DNA polymerase. In the nucleic acid amplification reaction, in particular, use of Pfu DNA polymerase in combination with the random primer is preferable. With the use of such DNA polymerase, many amplified fragments can be obtained with higher certainty while achieving high reproducibility.

In the nucleic acid amplification reaction, the concentration of deoxyribonucleotide triphosphate serving as a substrate (dNTP; i.e., a mixture of dATP, dCTP, dTTP, and dGTP) is not particularly limited, and it can be 5 microM to 0.6 mM, preferably 10 microM to 0.4 mM, and more preferably 20 microM to 0.2 mM. Thus, errors caused by erroneous incorporation by DNA polymerase can be prevented, and many amplified fragments can be obtained while achieving high reproducibility.

A buffer used in the nucleic acid amplification reaction is not particularly limited, and a buffer contains $MgCl_2$ as described above. An example thereof is a solution containing Tris-HCl (pH 8.3) and KCl. While the concentration of $Mg^{2+}$ is not particularly limited, for example, it can be 0.1 to 4.0 mM, preferably 0.2 to 3.0 mM, more preferably 0.3 to 2.0 mM, and further preferably 0.5 to 1.5 mM. Thus, many amplified fragments can be obtained while achieving high reproducibility.

The thermal cycling conditions in the nucleic acid amplification reaction are not particularly limited, and general thermal cycling conditions can be adopted. For example, a thermal cycle is composed of: the initial thermal denaturation by which genomic DNA as a template is dissociated into single strands; repetition of a "thermal denaturation, annealing, and extension" cycle a plurality of times (e.g., 20 to 40 times); and optional extension for a given period of time; followed by storage in the end.

Thermal denaturation can be carried out at, for example, 93 to 99 degrees C., preferably 95 to 98 degrees C., and more preferably 97 to 98 degrees C. Annealing temperature varies depending on a Tm value of the random primer, and it can be, for example, 30 to 70 degrees C., preferably 35 to 68 degrees C., and more preferably 37 to 65 degrees C. Extension can be carried out at, for example, 70 to 76 degrees C., preferably 71 to 75 degrees C., and more preferably 72 to 74 degrees C. Storage can be carried out at, for example, 4 degrees C.

The initial thermal denaturation can be carried out within the temperature range described above for a period of time of, for example, 5 seconds to 10 minutes, preferably 10 seconds to 5 minutes, and more preferably 30 seconds to 2 minutes. Thermal denaturation in the "thermal denaturation, annealing, and extension" cycle can be carried out within the temperature range described above for a period of time of, for example, 2 seconds to 5 minutes, preferably 5 seconds to 2 minutes, and more preferably 10 seconds to 1 minute. Annealing in the "thermal denaturation, annealing, and extension" cycle can be carried out within the temperature range described above for a period of time of, for example, 1 second to 3 minutes, preferably 3 seconds to 2 minutes, and more preferably 5 seconds to 1 minute. Extension in the "thermal denaturation, annealing, and extension" cycle can be carried out within the temperature range described above for a period of time of, for example, 1 second to 3 minutes, preferably 3 seconds to 2 minutes, and more preferably 5 seconds to 1 minute.

In the method, an amplified fragment may be obtained via a nucleic acid amplification reaction involving the hot-start method. The hot-start method avoids a non-specific amplification caused by mispriming or primer-dimer formation before the "thermal denaturation, annealing, and extension" cycle. The hot-start method uses an enzyme with the DNA polymerase activity thereof being suppressed by binding an anti-DNA polymerase antibody to the enzyme or via chemical modification thereof. Thus, DNA polymerase activity is suppressed, and a non-specific reaction before the thermal cycle can be avoided. In the hot-start method, temperature is set at a high level in the first thermal cycle, DNA polymerase activity is thus restored, and the subsequent nucleic acid amplification reaction proceeds.

As described above, the nucleic acid amplification reaction is performed with the use of the random primer of 9 to 30 nucleotides by adjusting the random primer concentration to 4 to 200 microM in the reaction solution. Thus, many amplified fragments can be obtained with the use of genomic DNA as a template and the random primer. The nucleic acid amplification reaction can be performed with very high reproducibility when the random primer of 9 to 30 nucleotides is used and the random primer concentration is adjusted to 4 to 200 microM. By performing the nucleic acid amplification reaction described above, specifically, many amplified fragments can be obtained while achieving very high reproducibility.

Also, the nucleic acid amplification reaction is performed with the use of the random primer of 9 to 30 nucleotides by adjusting the random primer concentration to 4 to 200 microM in the reaction solution. Thus, in particular, many amplified fragments of about 100 to 500 nucleotides can be obtained with the use of genomic DNA as a template. Such many amplified fragments of about 100 to 500 nucleotides are suitable for mass-analysis of nucleotide sequences with the use of, for example, the next-generation sequencer in terms of size, and sequence information can be obtained with high accuracy. According to the present invention, specifically, DNA fragments of about 100 to 500 nucleotides can be prepared.

Further, the nucleic acid amplification reaction is performed with the use of the random primer of 9 to 30 nucleotides by adjusting the random primer concentration to 4 to 200 microM in the reaction solution. Thus, amplified fragments can be obtained uniformly over the entire genomic DNA. In other words, DNA fragments are amplified throughout the genome instead of a given exclusive region of genomic DNA by the nucleic acid amplification reaction using the random primer.

After the completion of the nucleic acid amplification reaction with the use of the random primer, the resulting amplified fragments can be subjected to restriction enzyme treatment, size selection treatment, sequence capture treatment, or other treatment. Thus, particular amplified fragments (i.e., a fragment comprising a particular restriction enzyme site, an amplified fragment of a particular size, or an amplified fragment comprising a particular sequence) can be obtained from among the resulting amplified fragments.

Method of Genomic DNA Analysis

With the use of the amplicon prepared in the manner described above, genomic DNA analysis, such as genotype analysis, can be performed. The amplicon prepared in the manner described above has very high reproducibility, a size thereof is suitable for the next-generation sequencer, and it is uniform throughout the genome. Accordingly, the amplicon prepared in the manner described above can be used as a DNA marker (it is also referred to as a "genetic marker" or "gene marker"). The term "DNA marker" used herein extensively refers to a characteristic nucleotide sequence existing within genomic DNA. A DNA marker can be a nucleotide sequence in the genome that serves as a marker concerning genetic traits. A DNA marker can be used for, for example, genotype identification, linkage mapping, gene mapping, breeding comprising a step of selection using a marker, back cross using a marker, mapping of a quantitative trait locus, bulk segregant analysis, variety identification, or linkage disequilibrium mapping.

With the use of the primer used for a next-generation sequencer according to the present invention, in particular, the nucleotide sequence of the amplicon prepared in the manner described above is determined with the use of the next-generation sequencer or the like, and the presence or absence of the DNA marker can be determined on the basis of the resulting nucleotide sequence.

For example, the presence or absence of the DNA marker can be determined on the basis of the number of reads of the nucleotide sequence. The next-generation sequencer is not particularly limited, and it is a nucleotide sequencing apparatus that is capable of utilizing the primer used for a next-generation sequencer according to the present invention, that is also referred to as the "second-generation sequence," and that is capable of simultaneous and parallel determination of nucleotide sequences of tens of millions of DNA fragments. The sequencing principle of the next-generation sequencer is not particularly limited. For example, target DNA is amplified on the flow cell via bridge PCR and sequencing-by-synthesis, and sequencing is performed with synthesis. Specific examples of the next-generation sequencer include MiniSeq, MiSeq, NextSeq, HiSeq, and HiSeq X Series (Illumina).

Alternatively, the nucleotide sequence of the amplicon prepared in the manner described above is compared with a reference nucleotide sequence. Thus, the presence or absence of the DNA marker can be determined. A reference nucleotide sequence is a known standard sequence, such as a known sequence stored in a database. Specifically, an amplicon of a given organism is prepared as described above, the nucleotide sequence thereof is determined, and the nucleotide sequence is compared with a reference nucleotide sequence. A nucleotide sequence that is different from the reference nucleotide sequence can be determined as a DNA marker associated with the given organism (i.e., a characteristic nucleotide sequence existing within genomic DNA). The identified DNA marker can be further analyzed in accordance with a conventional technique, and the correlation thereof with a genetic trait (a phenotype) can be determined. Specifically, a DNA marker associated with a phenotype (it is occasionally referred to as a "selection marker") can be identified from among the DNA markers identified in the manner described above.

In addition, the nucleotide sequence of the amplicon prepared in the manner described above is compared with the nucleotide sequence of the amplicon prepared with the use of genomic DNA derived from another organism or another tissue. Thus, the presence or absence of the DNA marker can be determined. Specifically, amplicons of two or more organisms or two different tissues are prepared as described above, nucleotide sequences thereof are determined, and the nucleotide sequences thereof are compared. The nucleotide sequence determined to be different can be designated as a DNA marker (a characteristic nucleotide sequence existing within genomic DNA) associated with the tested organism or tissue. The identified DNA marker can be further analyzed in accordance with a conventional technique, and the correlation thereof with a genetic trait (a phenotype) can be determined. Specifically, a DNA marker associated with a phenotype (it is occasionally referred to as a "selection marker") can be identified from among the DNA markers identified in the manner described above.

The nucleotide sequence information analyzed with the use of the primer used for a next-generation sequencer according to the present invention as described above can be used for various types of analyses, such as metagenomics analysis that investigates diversity of microorganisms, genomic mutation analysis of somatic cells such as tumor tissues, genotype analysis utilizing microarrays, ploidy analysis, calculation of the chromosome number, analysis of increase/decrease in the chromosome number, analysis of partial insertion, deletion, replication, or translocation of the chromosome, analysis of foreign genome inclusion, parentage diagnosis, or hybrid seed purity ex-amination.

EXAMPLES

Hereafter, the present invention is described in greater detail with reference to the examples, although the technical scope of the present invention is not limited to the following examples.

Example 1

In this example, the primers P7 and P5 used for the next-generation sequencer (Illumina) were analyzed in terms of the correlation between the index sequence and the amount of the data obtained with the use of the next-generation sequencer, and primers suitable for analysis using the next-generation sequencer were developed.

1. Materials

In this example, genomic DNA extracted from the rice variety Nipponbare using the DNeasy Plant Mini kit (QIAGEN) and purified was used.

2. Method 2.1 Design of Random Primer

As random primers, 63 types of nucleotide sequences each composed of a total of 13 nucleotides: i.e., 10 nucleotides (GTTACACACG) (SEQ ID NO: 1516) at the 3' terminus of the Nextera adapter sequence for the next-generation sequencer (Illumina) and arbitrary 3 nucleotides except for TGC added to the 3' terminus of the 10-nucleotide sequence, were designed (Table 2).

TABLE 2

| Random primer | SEQ ID NO: |
|---|---|
| TAAGAGACAGAAA | 3 |
| TAAGAGACAGAAC | 4 |
| TAAGAGACAGAAG | 5 |
| TAAGAGACAGAAT | 6 |
| TAAGAGACAGACA | 7 |
| TAAGAGACAGACC | 8 |
| TAAGAGACAGACG | 9 |
| TAAGAGACAGACT | 10 |
| TAAGAGACAGAGA | 11 |
| TAAGAGACAGAGC | 12 |
| TAAGAGACAGAGG | 13 |
| TAAGAGACAGAGT | 14 |
| TAAGAGACAGATA | 15 |
| TAAGAGACAGATC | 16 |
| TAAGAGACAGATG | 17 |
| TAAGAGACAGATT | 18 |
| TAAGAGACAGCAA | 19 |
| TAAGAGACAGCAC | 20 |
| TAAGAGACAGCAG | 21 |
| TAAGAGACAGCAT | 22 |
| TAAGAGACAGCCA | 23 |
| TAAGAGACAGCCC | 24 |
| TAAGAGACAGCCG | 25 |
| TAAGAGACAGCCT | 26 |
| TAAGAGACAGCGA | 27 |

TABLE 2-continued

| Random primer | SEQ ID NO: |
|---|---|
| TAAGAGACAGCGC | 28 |
| TAAGAGACAGCGG | 29 |
| TAAGAGACAGCGT | 30 |
| TAAGAGACAGCTA | 31 |
| TAAGAGACAGCTC | 32 |
| TAAGAGACAGCTG | 33 |
| TAAGAGACAGCTT | 34 |
| TAAGAGACAGGAA | 35 |
| TAAGAGACAGGAC | 36 |
| TAAGAGACAGGAG | 37 |
| TAAGAGACAGGAT | 38 |
| TAAGAGACAGGCA | 39 |
| TAAGAGACAGGCC | 40 |
| TAAGAGACAGGCG | 41 |
| TAAGAGACAGGCT | 42 |
| TAAGAGACAGGGA | 43 |
| TAAGAGACAGGGC | 44 |
| TAAGAGACAGGGG | 45 |
| TAAGAGACAGGGT | 46 |
| TAAGAGACAGGTA | 47 |
| TAAGAGACAGGTC | 48 |
| TAAGAGACAGGTG | 49 |
| TAAGAGACAGGTT | 50 |
| TAAGAGACAGTAA | 51 |
| TAAGAGACAGTAC | 52 |
| TAAGAGACAGTAG | 53 |
| TAAGAGACAGTAT | 54 |
| TAAGAGACAGTCA | 55 |
| TAAGAGACAGTCC | 56 |
| TAAGAGACAGTCG | 57 |
| TAAGAGACAGTCT | 58 |
| TAAGAGACAGTGA | 59 |
| TAAGAGACAGTGG | 60 |
| TAAGAGACAGTGT | 61 |
| TAAGAGACAGTTA | 62 |
| TAAGAGACAGTTC | 63 |
| TAAGAGACAGTTG | 64 |
| TAAGAGACAGTTT | 65 |

3.2 Preparation of Analyte DNA

To the rice-derived genomic DNA (30 ng) described in 1. above (Materials), a 0.2 mM dNTP mixture, 1.0 mM MgCl$_2$, 1.25 units of DNA polymerase (PrimeSTAR, TAKARA), and a random primer (final concentration; 40 microM) were added, and a reaction solution was prepared while adjusting the final reaction level to 50 microliters. The resultant was subjected to PCR under thermal cycling conditions comprising 98 degrees C. for 2 minutes and 30 cycles of 98 degrees C. for 10 seconds, 50 degrees C. for 15 seconds, and 72 degrees C. for 20 seconds, followed by storage at 4 degrees C. Thus, many analyte DNAs were prepared with the use of the random primer and the rice-derived genomic DNA as a template.

3.3. Preparation of DNA Library for Next-Generation Sequencer

To the analyte DNA (1 microliter) prepared in 3.2 above, a 0.2 mM dNTP mixture, 1.0 mM MgCl$_2$, 1.25 units of DNA polymerase (PrimeSTAR, TAKARA), and 0.25 microM each of the primers P7 and P5 used for a next-generation sequencer were added, and a reaction solution (50 microliters) was prepared.

The primers P7 and P5 used for a next-generation sequencer were prepared based on the sequence information of the Nextera adaptor (Illumina) shown in Table 3. In Table 3 below, 8 nucleotides indicated by asterisks constitute an index sequence. The index sequence of P5 is a reverse complementary sequence of the index sequence of P7.

TABLE 3

| Primer | Sequence * | SEQ ID NO: |
|---|---|---|
| Primer P5 for next-generation sequencer | AATGATACGGCGACCACCGA GATCTACAC******** TCGTCGGCAGCGTCAGATGT GTATAAGAGACAG | 66 |
| Primer P7 for next-generation sequencer | CAAGCAGAAGACGGCATACG AGAT******** GTCTCGTGGGCTCGGAGATG TGTATAAGAGACAG | 67 |

More specifically, the primers P7 used for a next-generation sequencer comprising 96 types of index sequences were designed (Table 4). When the primer P7 used for a next-generation sequencer shown in Table 4 was used, the primer P5 used for a next-generation sequencer composed of the sequence: AATGATACGGCGACCACCGAGATCTA-CACCGCGCAGA TCGTCGGCAGCGTCA-GATGTGTATAAGAGACAG (SEQ ID NO: 1517), was used. A DNA library prepared with the use of the primer P7 used for a next-generation sequencer shown in Table 4 is referred to as "DNA library 1."

TABLE 4

| Primer P7 for next-generation sequencer | Index | Number of reads | SEQ ID NO |
|---|---|---|---|
| CAAGCAGAAGACGGCATACGAGATGTGATACTGTCTCGTGGGCTCGGAGATGTGTATAAGAGACAG | AGTATCAC | 2698 | 68 |
| CAAGCAGAAGACGGCATACGAGATGAGCGCGTGTCTCGTGGGCTCGGAGATGTGTATAAGAGACAG | ACGCGCTC | 11021 | 69 |
| CAAGCAGAAGACGGCATACGAGATGCATCTCGGTCTCGTGGGCTCGGAGATGTGTATAAGAGACAG | CGAGATGC | 102619 | 70 |
| CAAGCAGAAGACGGCATACGAGATTCGTACGTGTCTCGTGGGCTCGGAGATGTGTATAAGAGACAG | ACGTACGA | 36922 | 71 |
| CAAGCAGAAGACGGCATACGAGATTATCGTCGGTCTCGTGGGCTCGGAGATGTGTATAAGAGACAG | CGACGATA | 74371 | 72 |
| CAAGCAGAAGACGGCATACGAGATTGCACAGAGTCTCGTGGGCTCGGAGATGTGTATAAGAGACAG | TCTGTGCA | 77759 | 73 |
| CAAGCAGAAGACGGCATACGAGATCGTATGACGTCTCGTGGGCTCGGAGATGTGTATAAGAGACAG | GTCATACG | 65129 | 74 |
| CAAGCAGAAGACGGCATACGAGATTCGATCTCGTCTCGTGGGCTCGGAGATGTGTATAAGAGACAG | GAGATCGA | 77012 | 75 |
| CAAGCAGAAGACGGCATACGAGATATATGACAGTCTCGTGGGCTCGGAGATGTGTATAAGAGACAG | TGTCATAT | 83490 | 76 |
| CAAGCAGAAGACGGCATACGAGATGCTATCGTGTCTCGTGGGCTCGGAGATGTGTATAAGAGACAG | ACGATAGC | 21633 | 77 |
| CAAGCAGAAGACGGCATACGAGATCTGTGTGTGTCTCGTGGGCTCGGAGATGTGTATAAGAGACAG | ACACACAG | 18188 | 78 |
| CAAGCAGAAGACGGCATACGAGATTATACTGCGTCTCGTGGGCTCGGAGATGTGTATAAGAGACAG | GCAGTATA | 59936 | 79 |
| CAAGCAGAAGACGGCATACGAGATACTGTCGTGTCTCGTGGGCTCGGAGATGTGTATAAGAGACAG | ACGACAGT | 46354 | 80 |
| CAAGCAGAAGACGGCATACGAGATGAGCTATAGTCTCGTGGGCTCGGAGATGTGTATAAGAGACAG | TATAGCTC | 103670 | 81 |
| CAAGCAGAAGACGGCATACGAGATTGTGTCGTGTCTCGTGGGCTCGGAGATGTGTATAAGAGACAG | ACGACACA | 22327 | 82 |
| CAAGCAGAAGACGGCATACGAGATGTGACTATGTCTCGTGGGCTCGGAGATGTGTATAAGAGACAG | ATAGTCAC | 29747 | 83 |
| CAAGCAGAAGACGGCATACGAGATTATACAGTGTCTCGTGGGCTCGGAGATGTGTATAAGAGACAG | ACTGTATA | 38852 | 84 |
| CAAGCAGAAGACGGCATACGAGATATATGAGCGAGTCTCGTGGGCTCGGAGATGTGTATAAGAGACAG | TCGCTCAT | 68292 | 85 |
| CAAGCAGAAGACGGCATACGAGATAGATCAGAGTCTCGTGGGCTCGGAGATGTGTATAAGAGACAG | TCTGATCT | 102628 | 86 |
| CAAGCAGAAGACGGCATACGAGATAGTCTGCAGTCTCGTGGGCTCGGAGATGTGTATAAGAGACAG | TGCAGACT | 79949 | 87 |
| CAAGCAGAAGACGGCATACGAGATCGCTGTGAGTCTCGTGGGCTCGGAGATGTGTATAAGAGACAG | TCACAGCG | 96884 | 88 |
| CAAGCAGAAGACGGCATACGAGATGTCTATGTGTCTCGTGGGCTCGGAGATGTGTATAAGAGACAG | ACATAGAC | 29836 | 89 |
| CAAGCAGAAGACGGCATACGAGATCTGATGTGGTCTCGTGGGCTCGGAGATGTGTATAAGAGACAG | CACATCAG | 92829 | 90 |
| CAAGCAGAAGACGGCATACGAGATCGCACTATGTCTCGTGGGCTCGGAGATGTGTATAAGAGACAG | ATAGTGCG | 16800 | 91 |
| CAAGCAGAAGACGGCATACGAGATAGTGTGCGGTCTCGTGGGCTCGGAGATGTGTATAAGAGACAG | CGCACACT | 95836 | 92 |
| CAAGCAGAAGACGGCATACGAGATCGTATCGCGTCTCGTGGGCTCGGAGATGTGTATAAGAGACAG | GCGATACG | 55672 | 93 |
| CAAGCAGAAGACGGCATACGAGATGCACTCTAGTCTCGTGGGCTCGGAGATGTGTATAAGAGACAG | TAGAGTGC | 84433 | 94 |
| CAAGCAGAAGACGGCATACGAGATTACGACACGTCTCGTGGGCTCGGAGATGTGTATAAGAGACAG | GTGTCGTA | 69554 | 95 |
| CAAGCAGAAGACGGCATACGAGATTCTGCTCAGTCTCGTGGGCTCGGAGATGTGTATAAGAGACAG | TGAGCAGA | 78854 | 96 |
| CAAGCAGAAGACGGCATACGAGATTCGTGACTGTCTCGTGGGCTCGGAGATGTGTATAAGAGACAG | AGTCACGA | 902 | 97 |
| CAAGCAGAAGACGGCATACGAGATTGTATCTAGTCTCGTGGGCTCGGAGATGTGTATAAGAGACAG | TAGATACA | 106290 | 98 |
| CAAGCAGAAGACGGCATACGAGATGTGCGTACGTCTCGTGGGCTCGGAGATGTGTATAAGAGACAG | GTACGCAC | 84862 | 99 |
| CAAGCAGAAGACGGCATACGAGATCACTACTCGTCTCGTGGGCTCGGAGATGTGTATAAGAGACAG | GAGTAGTG | 72290 | 100 |
| CAAGCAGAAGACGGCATACGAGATTGAGCGTCGTCTCGTGGGCTCGGAGATGTGTATAAGAGACAG | GACGCTCA | 59639 | 101 |
| CAAGCAGAAGACGGCATACGAGATTGACGTCTGTCTCGTGGGCTCGGAGATGTGTATAAGAGACAG | AGACGTCA | 599 | 102 |
| CAAGCAGAAGACGGCATACGAGATACAGTGAGGTCTCGTGGGCTCGGAGATGTGTATAAGAGACAG | CTCACTGT | 113481 | 103 |
| CAAGCAGAAGACGGCATACGAGATGACTCTCAGTCTCGTGGGCTCGGAGATGTGTATAAGAGACAG | TGAGAGTC | 107121 | 104 |
| CAAGCAGAAGACGGCATACGAGATAGCGCGCTGTCTCGTGGGCTCGGAGATGTGTATAAGAGACAG | AGCGCGCT | 3743 | 105 |

TABLE 4-continued

| Primer P7 for next-generation sequencer | Index | Number of reads | SEQ ID NO |
|---|---|---|---|
| CAAGCAGAAGACGGCATACGAGATCTGTAGAGGTCTCGTGGGCTCGGAGATGTGTATAAGAGACAG | CTCTACAG | 94729 | 106 |
| CAAGGAGAAGACGGCATACGAGATATGCGATAGTCTCGTGGGCTCGGAGATGTGTATAAGAGACAG | TATCGCAT | 88451 | 107 |
| CAAGGAGAAGACGGCATACGAGATGAGACATGGTCTCGTGGGCTCGGAGATGTGTATAAGAGACAG | CATGTCTC | 103682 | 108 |
| CAAGGAGAAGACGGCATACGAGATGTCATGTGGTCTCGTGGGCTCGGAGATGTGTATAAGAGACAG | CACATGAC | 108326 | 109 |
| CAAGCAGAAGACGGCATACGAGATTCATGATAGTCTCGTGGGCTCGGAGATGTGTATAAGAGACAG | TATCATGA | 100548 | 110 |
| CAAGGAGAAGACGGCATACGAGATGTCATCTCGTCTCGTGGGCTCGGAGATGTGTATAAGAGACAG | GAGATGAC | 95911 | 111 |
| CAAGCAGAAGACGGCATACGAGATAGTGTCGCGTCTCGTGGGCTCGGAGATGTGTATAAGAGACAG | GCGACACT | 63077 | 112 |
| CAAGCAGAAGACGGCATACGAGATGCTGACGTGTCTCGTGGGCTCGGAGATGTGTATAAGAGACAG | ACGTCAGC | 36541 | 113 |
| CAAGCAGAAGACGGCATACGAGATGATCAGCTGTCTCGTGGGCTCGGAGATGTGTATAAGAGACAG | AGCTGATC | 1524 | 114 |
| CAAGCAGAAGACGGCATACGAGATTATCTCTAGTCTCGTGGGCTCGGAGATGTGTATAAGAGACAG | TAGAGATA | 97320 | 115 |
| CAAGGAGAAGACGGCATACGAGATGCAGAGCTGTCTCGTGGGCTCGGAGATGTGTATAAGAGACAG | AGCTCTGC | 76234 | 116 |
| CAAGCAGAAGACGGCATACGAGATTGCTAGCGGTCTCGTGGGCTCGGAGATGTGTATAAGAGACAG | CGCTAGCA | 69861 | 117 |
| CAAGCAGAAGACGGCATACGAGATCGTATCTCGTCTCGTGGGCTCGGAGATGTGTATAAGAGACAG | GAGATACG | 88530 | 118 |
| CAAGCAGAAGACGGCATACGAGATCTGATATAGTCTCGTGGGCTCGGAGATGTGTATAAGAGACAG | TATATCAG | 43949 | 119 |
| CAAGCAGAAGACGGCATACGAGATTAGTGCGCGTCTCGTGGGCTCGGAGATGTGTATAAGAGACAG | GCGCACTA | 50049 | 120 |
| CAAGCAGAAGACGGCATACGAGATCTAGTGCAGTCTCGTGGGCTCGGAGATGTGTATAAGAGACAG | TGCACTAG | 88820 | 121 |
| CAAGCAGAAGACGGCATACGAGATGATGTCACGTCTCGTGGGCTCGGAGATGTGTATAAGAGACAG | GTGACATC | 64527 | 122 |
| CAAGCAGAAGACGGCATACGAGATATAGAGCGGTCTCGTGGGCTCGGAGATGTGTATAAGAGACAG | CGCTCTAT | 51356 | 123 |
| CAAGGAGAAGACGGCATACGAGATAGACATATGTCTCGTGGGCTCGGAGATGTGTATAAGAGACAG | ATATGTCT | 102442 | 124 |
| CAAGGAGAAGACGGCATACGAGATCGATCATGGTCTCGTGGGCTCGGAGATGTGTATAAGAGACAG | CATGATCG | 74522 | 125 |
| CAAGCAGAAGACGGCATACGAGATACATAGCGGTCTCGTGGGCTCGGAGATGTGTATAAGAGACAG | CGCTATGT | 87460 | 126 |
| CAAGCAGAAGACGGCATACGAGATATCGACACGTCTCGTGGGCTCGGAGATGTGTATAAGAGACAG | GTGTCGAT | 70762 | 127 |
| CAAGCAGAAGACGGCATACGAGATTACACACGGTCTCGTGGGCTCGGAGATGTGTATAAGAGACAG | CGTGTGTA | 78672 | 128 |
| CAAGCAGAAGACGGCATACGAGATTACGCATGGTCTCGTGGGCTCGGAGATGTGTATAAGAGACAG | CATGCGTA | 87658 | 129 |
| CAAGCAGAAGACGGCATACGAGATCGTGAGTGGTCTCGTGGGCTCGGAGATGTGTATAAGAGACAG | CACTCACG | 16880 | 130 |
| CAAGGAGAAGACGGCATACGAGATGTCTGCATGTCTCGTGGGCTCGGAGATGTGTATAAGAGACAG | ATGCAGAC | 88654 | 131 |
| CAAGCAGAAGACGGCATACGAGATGCATGAGTCTCGTGGGCTCGGAGATGTGTATAAGAGACAG | TCATATGC | 466 | 132 |
| CAAGGAGAAGACGGCATACGAGATTGCTCTCTGTCTCGTGGGCTCGGAGATGTGTATAAGAGACAG | AGAGAGCA | 79993 | 133 |
| CAAGGAGAAGACGGCATACGAGATGACACATGGTCTCGTGGGCTCGGAGATGTGTATAAGAGACAG | CATGTGTC | 67887 | 134 |
| CAAGGAGAAGACGGCATACGAGATCTGAGCAGGTCTCGTGGGCTCGGAGATGTGTATAAGAGACAG | CTGCTCAG | 69388 | 135 |
| CAAGGAGAAGACGGCATACGAGATGACATGCGGTCTCGTGGGCTCGGAGATGTGTATAAGAGACAG | CGCATGTC | 85651 | 136 |
| CAAGCAGAAGACGGGATAGGAGATTCTGACGAGTCTCGTGGGCTCGGAGATGTGTATAAGAGACAG | TCGTCAGA | 18576 | 137 |
| CAAGCAGAAGACGGCATACGAGATTACAGTGTGTCTCGTGGGCTCGGAGATGTGTATAAGAGACAG | ACACTGTA | 50570 | 138 |
| CAAGCAGAAGACGGCATACGAGATGATCGCAGGTCTCGTGGGCTCGGAGATGTGTATAAGAGACAG | CTGCGATC | 103807 | 139 |
| CAAGGAGAAGACGGCATACGAGATACATGACGGTCTCGTGGGCTCGGAGATGTGTATAAGAGACAG | CGTCATGT | 88366 | 140 |
| CAAGGAGAAGACGGCATACGAGATCTAGATGAGTCTCGTGGGCTCGGAGATGTGTATAAGAGACAG | TCATCTAG | 98908 | 141 |
| CAAGGAGAAGACGGCATACGAGATGCGTCTAGGTCTCGTGGGCTCGGAGATGTGTATAAGAGACAG | CTAGACGC | 53858 | 142 |
| CAAGCAGAAGACGGCATACGAGATACTCGTGCGTCTCGTGGGCTCGGAGATGTGTATAAGAGACAG | GCACGAGT | 95266 | 143 |

TABLE 4-continued

| Primer P7 for next-generation sequencer | Index | Number of reads | SEQ ID NO |
|---|---|---|---|
| CAAGGAGAAGACGGCATACGAGATICACGCTGGTCTCGTGGGCTCGGAGATGTGTATAAGAGACAG | CAGCGTGA | 577 | 144 |
| CAAGCAGAAGACGGCATACGAGATCTAGATCTGTCTCGTGGGCTCGGAGATGTGTATAAGAGACAG | AGATCTAG | 64106 | 145 |
| CAAGGAGAAGACGGCATACGAGATCGATAGCAGTCTCGTGGGCTCGGAGATGTGTATAAGAGACAG | TGCTATCG | 900 | 146 |
| CAAGCAGAAGACGGCATACGAGATATCGTACTGTCTCGTGGGCTCGGAGATGTGTATAAGAGACAG | AGTACGAT | 103699 | 147 |
| CAAGGAGAAGACGGCATACGAGATTCATGTACGTGTCGTGGGCTCGGAGATGTGTATAAGAGACAG | GTACATGA | 107163 | 148 |
| CAAGCAGAAGACGGCATACGAGATTAGTGACGGTCTCGTGGGCTCGGAGATGTGTATAAGAGACAG | CGTCACTA | 107188 | 149 |
| CAAGCAGAAGACGGCATACGAGATCACGATAGGTCTCGTGGGCTCGGAGATGTGTATAAGAGACAG | CTATCGTG | 78472 | 150 |
| CAAGCAGAAGACGGCATACGAGATACACACTGGTCTCGTGGGCTCGGAGATGTGTATAAGAGACAG | CAGTGTGT | 63028 | 151 |
| CAAGCAGAAGACGGCATACGAGATCGTCTAGCGTCTCGTGGGCTCGGAGATGTGTATAAGAGACAG | GCTAGACG | 67417 | 152 |
| CAAGCAGAAGACGGCATACGAGATTAGCTAGCGTCTCGTGGGCTCGGAGATGTGTATAAGAGACAG | GCTAGCTA | 62143 | 153 |
| CAAGCAGAAGACGGCATACGAGATTCGACGTCGTCTCGTGGGCTCGGAGATTIGTATAAGAGACAG | GACGTCGA | 104854 | 154 |
| CAAGCAGAAGACGGCATACGAGATAGCATCACGTCTCGTGGGCTCGGAGATGTGTATAAGAGACAG | GTGATGCT | 64287 | 155 |
| CAAGCAGAAGACGGCATACGAGATCGAGACGCGTCTCGTGGGCTCGGAGATGTGTATAAGAGACAG | GCGTCTCG | 64524 | 156 |
| CAAGCAGAAGACGGCATACGAGATCGCGAGCAGTCTCGTGGGCTCGGAGATGTGTATAAGAGACAG | TGCTCGCG | 100457 | 157 |
| CAAGCAGAAGACGGCATACGAGATTAGTCGTAGTCTCGTGGGCTCGGAGATGTGTATAAGAGACAG | TACGACTA | 25668 | 158 |
| CAAGCAGAAGACGGCATACGAGATCGTAGTATGTCTCGTGGGCTCGGAGATGTGTATAAGAGACAG | ATACTACG | 91426 | 159 |
| CAAGCAGAAGACGGCATACGAGATTCACGTACGTCTCGTGGGCTCGGAGATGTGTATAAGAGACAG | GTACGTGA | 75359 | 160 |
| CAAGGAGAAGACGGCATACGAGATGCATGGCGGTCTCGTGGGCTCGGAGATGTGTATAAGAGACAG | CGCGATGC | 103505 | 161 |
| CAAGGAGAAGACGGCATACGAGATATCATGTCGTCTCGTGGGCTCGGAGATGTGTATAAGAGACAG | GACATGAT | 22828 | 162 |
| CAAGCAGAAGACGGCATACGAGATCTATGCATGTCTCGTGGGCTCGGAGATGTGTATAAGAGACAG | ATGCATAG | 85282 | 163 |

Separately, the primers P5 used for a next-generation sequencer comprising 98 types of index sequences were designed (Table 5). When the primer P5 used for a next-generation sequencer shown in Table 5 was used, the primer P7 used for a next-generation sequencer composed of the sequence: CAAGCAGAAGACGGCATACGAGAT-TCGTCAGAGTCTCGT GGGCTCG-GAGATGTGTATAAGAGACAG (SEQ ID NO: 1518), was used. A DNA library prepared with the use of the primer P5 used for a next-generation sequencer shown in Table 5 is referred to as "DNA library 2."

TABLE 5

| Primer P5 for next-generation sequencer | Index | Number of reads | SEQ ID NO |
|---|---|---|---|
| AATGATACGGCGACCACCGAGATCTACACCTGCTCGTTCGTCGGCAGCGTCAGATGTGTATAAGAGACAG | CTGCTCGT | 184097 | 164 |
| AATGATACGGCGACCACCGAGATCTACACTGCGACGATCGTCGGCAGCGTCAGATGTGTATAAGAGACAG | TGCGACGA | 148883 | 165 |
| AATGATACGGCGACCACCGAGATCTACACCACATGCTTCGTCGGCAGCGTCAGATGTGTATAAGAGACAG | CACATGCT | 202711 | 166 |
| AATGATACGGCGACCACCGAGATCTACACATACTCATTCGTCGGCAGCGTCAGATGTGTATAAGAGACAG | ATACTCAT | 206240 | 167 |
| AATGATACGGCGACCACCGAGATCTACACGATGCACGTCGTCGGCAGCGTCAGATGTGTATAAGAGACAG | GATGCACG | 184211 | 168 |
| AATGATACGGCGACCACCGAGATCTACACGTAGTGCTTCGTCGGCAGCGTCAGATGTGTATAAGAGACAG | GTAGTGCT | 217994 | 169 |
| AATGATACGGCGACCACCGAGATCTACACATGATAGTTCGTCGGCAGCGTCAGATGTGTATAAGAGACAG | ATGATAGT | 208012 | 170 |
| AATGATACGGCGACCACCGAGATCTACACCTCGCTAGTCGTCGGCAGCGTCAGATGTGTATAAGAGACAG | CTCGCTAG | 161874 | 171 |
| AATGATACGGCGACCACCGAGATCTACACGCTGAGAGTCGTCGGCAGCGTCAGATGTGTATAAGAGACAG | GCTGAGAG | 194463 | 172 |
| AATGATACGGCGACCACCGAGATCTACACAGCACGAGTCGTCGGCAGCGTCAGATGTGTATAAGAGACAG | AGCACGAG | 216430 | 173 |

TABLE 5-continued

| Primer P5 for next-generation sequencer | Index | Number of reads | SEQ ID NO |
|---|---|---|---|
| AATGATACGGCGACCACCGAGATCTACACTGTCAGAGTCGTCGGCAGCGTCAGATGTGTATAAGAGACAG | TGTCAGAG | 117194 | 174 |
| AATGATACGGCGACCACCGAGATCTACACGCGCAGTATCGTCGGCAGCGTCAGATGTGTATAAGAGACAG | GCGCAGTA | 217454 | 175 |
| AATGATACGGCGACCACCGAGATCTACACCATCAGCGTCGTCGGCAGCGTCAGATGTGTATAAGAGACAG | CATCAGCG | 204045 | 176 |
| AATGATACGGCGACCACCGAGATCTACACTACGAGCATCGTCGGCAGCGTCAGATGTGTATAAGAGACAG | TACGAGCA | 207318 | 177 |
| AATGATACGGCGACCACCGAGATCTACACAGCAGACTTCGTCGGCAGCGTCAGATGTGTATAAGAGACAG | AGCAGACT | 199285 | 178 |
| AATGATACGGCGACCACCGAGATCTACACCAGTACATTCGTCGGCAGCGTCAGATGTGTATAAGAGACAG | CAGTACAT | 213283 | 179 |
| AATGATACGGCGACCACCGAGATCTACACGAGTATGATCGTCGGCAGCGTCAGATGTGTATAAGAGACAG | GAGTATGA | 194615 | 180 |
| AATGATACGGCGACCACCGAGATCTACACTATCACATTCGTCGGCAGCGTCAGATGTGTATAAGAGACAG | TATCACAT | 234075 | 181 |
| AATGATACGGCGACCACCGAGATCTACACCACAGTCATCGTCGGCAGCGTCAGATGTGTATAAGAGACAG | CACAGTCA | 146176 | 182 |
| AATGATACGGCGACCACCGAGATCTACACTGCAGCTATCGTCGGCAGCGTCAGATGTGTATAAGAGACAG | TGCAGCTA | 219031 | 183 |
| AATGATACGGCGACCACCGAGATCTACACGCGAGCAGTCGTCGGCAGCGTCAGATGTGTATAAGAGACAG | GCGAGCAG | 199643 | 184 |
| AATGATACGGCGACCACCGAGATCTACACGACAGCGTTCGTCGGCAGCGTCAGATGTGTATAAGAGACAG | GACAGCGT | 166387 | 185 |
| AATGATACGGCGACCACCGAGATCTACACAGCTCGAGTCGTCGGCAGCGTCAGATGTGTATAAGAGACAG | AGCTCGAG | 182808 | 186 |
| AATGATACGGCGACCACCGAGATCTACACTAGATCATTCGTCGGCAGCGTCAGATGTGTATAAGAGACAG | TAGATCAT | 208157 | 187 |
| AATGATACGGCGACCACCGAGATCTACACCGCAGTGATCGTCGGCAGCGTCAGATGTGTATAAGAGACAG | CGCAGTGA | 211346 | 188 |
| AATGATACGGCGACCACCGAGATCTACACCGTACTGATCGTCGGCAGCGTCAGATGTGTATAAGAGACAG | CGTACTGA | 194225 | 189 |
| AATGATACGGCGACCACCGAGATCTACACTCAGATGTTCGTCGGCAGCGTCAGATGTGTATAAGAGACAG | TCAGATGT | 165740 | 190 |
| AATGATACGGCGACCACCGAGATCTACACCTCTCTGATCGTCGGCAGCGTCAGATGTGTATAAGAGACAG | CTCTCTGA | 157184 | 191 |
| AATGATACGGCGACCACCGAGATCTACACTCAGCATATCGTCGGCAGCGTCAGATGTGTATAAGAGACAG | TCAGCATA | 226142 | 192 |
| AATGATACGGCGACCACCGAGATCTACACCATACAGATCGTCGGCAGCGTCAGATGTGTATAAGAGACAG | CATACAGA | 195115 | 193 |
| AATGATACGGCGACCACCGAGATCTACACCGAGACGATCGTCGGCAGCGTCAGATGTGTATAAGAGACAG | CGAGACGA | 186104 | 194 |
| AATGATACGGCGACCACCGAGATCTACACCTCGACAGTCGTCGGCAGCGTCAGATGTGTATAAGAGACAG | CTCGACAG | 175716 | 195 |
| AATGATACGGCGACCACCGAGATCTACACGTAGATGATCGTCGGCAGCGTCAGATGTGTATAAGAGACAG | GTAGATGA | 198272 | 196 |
| AATGATACGGCGACCACCGAGATCTACACCATCTCAGTCGTCGGCAGCGTCAGATGTGTATAAGAGACAG | CATCTCAG | 162985 | 197 |
| AATGATACGGCGACCACCGAGATCTACACTGAGCTCATCGTCGGCAGCGTCAGATGTGTATAAGAGACAG | TGAGCTCA | 190928 | 198 |
| AATGATACGGCGACCACCGAGATCTACACTAGAGCGTTCGTCGGCAGCGTCAGATGTGTATAAGAGACAG | TAGAGCGT | 213271 | 199 |
| AATGATACGGCGACCACCGAGATCTACACAGATAGCATCGTCGGCAGCGTCAGATGTGTATAAGAGACAG | AGATAGCA | 207685 | 200 |
| AATGATACGGCGACCACCGAGATCTACACAGACTGAGTCGTCGGCAGCGTCAGATGTGTATAAGAGACAG | AGACTGAG | 192521 | 201 |
| AATGATACGGCGACCACCGAGATCTACACGCTACATATCGTCGGCAGCGTCAGATGTGTATAAGAGACAG | GCTACATA | 221694 | 202 |
| AATGATACGGCGACCACCGAGATCTACACATAGCTATTCGTCGGCAGCGTCAGATGTGTATAAGAGACAG | ATAGCTAT | 241220 | 203 |
| AATGATACGGCGACCACCGAGATCTACACATCGAGTATCGTCGGCAGCGTCAGATGTGTATAAGAGACAG | ATCGAGTA | 155902 | 204 |
| AATGATACGGCGACCACCGAGATCTACACGATGTGATTCGTCGGCAGCGTCAGATGTGTATAAGAGACAG | GATGTGAT | 224048 | 205 |
| AATGATACGGCGACCACCGAGATCTACACGATCAGTATCGTCGGCAGCGTCAGATGTGTATAAGAGACAG | GATCAGTA | 191406 | 206 |
| AATGATACGGCGACCACCGAGATCTACACTATGTACTTCGTCGGCAGCGTCAGATGTGTATAAGAGACAG | TATGTACT | 230743 | 207 |
| AATGATACGGCGACCACCGAGATCTACACTCACTGCATCGTCGGCAGCGTCAGATGTGTATAAGAGACAG | TCACTGCA | 226410 | 208 |
| AATGATACGGCGACCACCGAGATCTACACACACATATTCGTCGGCAGCGTCAGATGTGTATAAGAGACAG | ACACATAT | 216612 | 209 |
| AATGATACGGCGACCACCGAGATCTACACCTCTCTAGTCGTCGGCAGCGTCAGATGTGTATAAGAGACAG | CTCTCTAG | 173746 | 210 |
| AATGATACGGCGACCACCGAGATCTACACGTGAGTGTTCGTCGGCAGCGTCAGATGTGTATAAGAGACAG | GTGAGTGT | 186292 | 211 |

TABLE 5-continued

| Primer P5 for next-generation sequencer | Index | Number of reads | SEQ ID NO |
|---|---|---|---|
| AATGATACGGCGACCACCGAGATCTACACCATCGATGTCGTCGGCAGCGTCAGATGTGTATAAGAGACAG | CATCGATG | 193175 | 212 |
| AATGATACGGCGACCACCGAGATCTACACGATGCACTTCGTCGGCAGCGTCAGATGTGTATAAGAGACAG | GATGCACT | 219388 | 213 |
| AATGATACGGCGACCACCGAGATCTACACCGTACTCGTCGTCGGCAGCGTCAGATGTGTATAAGAGACAG | CGTACTCG | 160838 | 214 |
| AATGATACGGCGACCACCGAGATCTACACTGAGTGCATCGTCGGCAGCGTCAGATGTGTATAAGAGACAG | TGAGTGCA | 225841 | 215 |
| AATGATACGGCGACCACCGAGATCTACACCGCGATGATCGTCGGCAGCGTCAGATGTGTATAAGAGACAG | CGCGATGA | 186952 | 216 |
| AATGATACGGCGACCACCGAGATCTACACTGATCGCATCGTCGGCAGCGTCAGATGTGTATAAGAGACAG | TGATCGCA | 204285 | 217 |
| AATGATACGGCGACCACCGAGATCTACACCGCGACTATCGTCGGCAGCGTCAGATGTGTATAAGAGACAG | CGCGACTA | 193193 | 218 |
| AATGATACGGCGACCACCGAGATCTACACATACGCATTCGTCGGCAGCGTCAGATGTGTATAAGAGACAG | ATACGCAT | 214235 | 219 |
| AATGATACGGCGACCACCGAGATCTACACCGAGCGCTTCGTCGGCAGCGTCAGATGTGTATAAGAGACAG | CGAGCGCT | 216910 | 220 |
| AATGATACGGCGACCACCGAGATCTACACACTACGATTCGTCGGCAGCGTCAGATGTGTATAAGAGACAG | ACTACGAT | 213769 | 221 |
| AATGATACGGCGACCACCGAGATCTACACTGCAGCAGTCGTCGGCAGCGTCAGATGTGTATAAGAGACAG | TGCAGCAG | 202449 | 222 |
| AATGATACGGCGACCACCGAGATCTACACAGTACTCGTCGTCGGCAGCGTCAGATGTGTATAAGAGACAG | AGTACTCG | 169853 | 223 |
| AATGATACGGCGACCACCGAGATCTACACCTGAGTGTTCGTCGGCAGCGTCAGATGTGTATAAGAGACAG | CTGAGTGT | 185566 | 224 |
| AATGATACGGCGACCACCGAGATCTACACGTGAGTGATCGTCGGCAGCGTCAGATGTGTATAAGAGACAG | GTGAGTGA | 189950 | 225 |
| AATGATACGGCGACCACCGAGATCTACACTGTCGTCATCGTCGGCAGCGTCAGATGTGTATAAGAGACAG | TGTCGTCA | 147602 | 226 |
| AATGATACGGCGACCACCGAGATCTACACCACGAGCTTCGTCGGCAGCGTCAGATGTGTATAAGAGACAG | CACGAGCT | 185881 | 227 |
| AATGATACGGCGACCACCGAGATCTACACGAGACTCTTCGTCGGCAGCGTCAGATGTGTATAAGAGACAG | GAGACTCT | 166991 | 228 |
| AATGATACGGCGACCACCGAGATCTACACCATGTCACTCGTCGGCAGCGTCAGATGTGTATAAGAGACAG | CATGTCAC | 169567 | 229 |
| AATGATACGGCGACCACCGAGATCTACACCGTGTACGTCGTCGGCAGCGTCAGATGTGTATAAGAGACAG | CGTGTACG | 203769 | 230 |
| AATGATACGGCGACCACCGAGATCTACACTCGTAGATTCGTCGGCAGCGTCAGATGTGTATAAGAGACAG | TCGTAGAT | 174792 | 231 |
| AATGATACGGCGACCACCGAGATCTACACAGCTGACATCGTCGGCAGCGTCAGATGTGTATAAGAGACAG | AGCTGACA | 171467 | 232 |
| AATGATACGGCGACCACCGAGATCTACACCGTCATCATCGTCGGCAGCGTCAGATGTGTATAAGAGACAG | CGTCATCA | 157255 | 233 |
| AATGATACGGCGACCACCGAGATCTACACTACTCACGTCGTCGGCAGCGTCAGATGTGTATAAGAGACAG | TACTCACG | 207149 | 234 |
| AATGATACGGCGACCACCGAGATCTACACCAGTAGCGTCGTCGGCAGCGTCAGATGTGTATAAGAGACAG | CAGTAGCG | 210288 | 235 |
| AATGATACGGCGACCACCGAGATCTACACCATGTAGTTCGTCGGCAGCGTCAGATGTGTATAAGAGACAG | CATGTAGT | 213173 | 236 |
| AATGATACGGCGACCACCGAGATCTACACTAGAGACGTCGTCGGCAGCGTCAGATGTGTATAAGAGACAG | TAGAGACG | 180905 | 237 |
| AATGATACGGCGACCACCGAGATCTACACCGTCTCAGTCGTCGGCAGCGTCAGATGTGTATAAGAGACAG | CGTCTCAG | 151938 | 238 |
| AATGATACGGCGACCACCGAGATCTACACTACATGCATCGTCGGCAGCGTCAGATGTGTATAAGAGACAG | TACATGCA | 210596 | 239 |
| AATGATACGGCGACCACCGAGATCTACACTACTAGCATCGTCGGCAGCGTCAGATGTGTATAAGAGACAG | TACTAGCA | 212182 | 240 |
| AATGATACGGCGACCACCGAGATCTACACATGACAGATCGTCGGCAGCGTCAGATGTGTATAAGAGACAG | ATGACAGA | 186220 | 241 |
| AATGATACGGCGACCACCGAGATCTACACACAGCGTATCGTCGGCAGCGTCAGATGTGTATAAGAGACAG | ACAGCGTA | 182287 | 242 |
| AATGATACGGCGACCACCGAGATCTACACCATGCACTTCGTCGGCAGCGTCAGATGTGTATAAGAGACAG | CATGCACT | 235606 | 243 |
| AATGATACGGCGACCACCGAGATCTACACTCGAGCGTTCGTCGGCAGCGTCAGATGTGTATAAGAGACAG | TCGAGCGT | 206819 | 244 |
| AATGATACGGCGACCACCGAGATCTACACCGCACGAGTCGTCGGCAGCGTCAGATGTGTATAAGAGACAG | CGCACGAG | 182693 | 245 |
| AATGATACGGCGACCACCGAGATCTACACCACAGTATTCGTCGGCAGCGTCAGATGTGTATAAGAGACAG | CACAGTAT | 195608 | 246 |
| AATGATACGGCGACCACCGAGATCTACACAGTCATCATCGTCGGCAGCGTCAGATGTGTATAAGAGACAG | AGTCATCA | 173057 | 247 |
| AATGATACGGCGACCACCGAGATCTACACTGACTATATCGTCGGCAGCGTCAGATGTGTATAAGAGACAG | TGACTATA | 208986 | 248 |
| AATGATACGGCGACCACCGAGATCTACACTCGCATATTCGTCGGGAGCGTCAGATGTGTATAAGAGACAG | TCGCATAT | 202226 | 249 |

TABLE 5-continued

| Primer P5 for next-generation sequencer | Index | Number of reads | SEQ ID NO |
|---|---|---|---|
| AATGATACGGCGACCACCGAGATCTACACATCGATGTTCGTCGGCAGCGTCAGATGTGTATAAGAGACAG | ATCGATGT | 170032 | 250 |
| AATGATACGGCGACCACCGAGATCTACACCGACAGCGTCGTCGGCAGCGTCAGATGTGTATAAGAGACAG | CGACAGCG | 204799 | 251 |
| AATGATACGGCGACCACCGAGATCTACACATCGTGTATCGTCGGCAGCGTCAGATGTGTATAAGAGACAG | ATCGTGTA | 187161 | 252 |
| AATGATACGGCGACCACCGAGATCTACACGCATGTAGTCGTCGGCAGCGTCAGATGTGTATAAGAGACAG | GCATGTAG | 190133 | 253 |
| AATGATACGGCGACCACCGAGATCTACACAGAGATCATCGTCGGCAGCGTCAGATGTGTATAAGAGACAG | AGAGATCA | 136140 | 254 |
| AATGATACGGCGACCACCGAGATCTACACCGTCAGTATCGTCGGCAGCGTCAGATGTGTATAAGAGACAG | CGTCAGTA | 141604 | 255 |
| AATGATACGGCGACCACCGAGATCTACACGCGTAGATTCGTCGGCAGCGTCAGATGTGTATAAGAGACAG | GCGTAGAT | 172444 | 256 |
| AATGATACGGCGACCACCGAGATCTACACGTACTACATCGTCGGCAGCGTCAGATGTGTATAAGAGACAG | GTACTACA | 204499 | 257 |
| AATGATACGGCGACCACCGAGATCTACACGCGAGACATCGTCGGCAGCGTCAGATGTGTATAAGAGACAG | GCGAGACA | 181860 | 258 |
| AATGATACGGCGACCACCGAGATCTACACGATAGACGTCGTCGGCAGCGTCAGATGTGTATAAGAGACAG | GATAGACG | 211211 | 259 |
| AATGATACGGCGACCACCGAGATCTACACTATACTAGTCGTCGGCAGCGTCAGATGTGTATAAGAGACAG | TATACTAG | 230695 | 260 |
| AATGATACGGCGACCACCGAGATCTACACTGCTCGCATCGTCGGCAGCGTCAGATGTGTATAAGAGACAG | TGCTCGCA | 222050 | 261 |

The nucleic acid amplification reactions to prepare DNA library 1 and DNA library 2 were carried out under thermal cycling conditions comprising 95 degrees C. for 2 minutes, 25 cycles of 98 degrees C. for 15 seconds, 55 degrees C. for 15 seconds, and 72 degrees C. for 20 seconds, and 72 degrees C. for 1 minute, followed by storage at 4 degrees C. The DNA libraries prepared via the nucleic acid amplification reactions were purified with the use of the MinElute PCR Purification Kit (QIAGEN).

3.4 Analysis Using Next-Generation Sequencer

With the use of the MiSeq Reagent Kit V2 500 Cycle (Illumina), the DNA libraries 1 and 2 prepared in 3.3 above were analyzed via 100 base paired-end sequencing. The number of reads concerning the DNA libraries 1 and 2 obtained as a result of analysis are shown in Table 4 and Table 5.

3.5 Analysis of Index Sequence and Amount of Data

On the basis of the number of reads for each primer used for a next-generation sequencer obtained as a result of analysis conducted in 3.4 above, the correlation between 8 nucleotides of the index sequence contained in the primer used for a next-generation sequencer and the amount of data was analyzed by the GLMNET LASSO method, and an estimation formula for calculating the number of reads based on the analyzed correlation and the types of nucleotides included in the index sequence was prepared. The correlational efficient between the putative number of reads calculated with the estimation formula and the measured number of reads was determined.

4. Results 4.1 Distribution of the Number of Reads of Each Primer Used for a Next-Generation Sequencer In order to evaluate the influence of the primer used for a next-generation sequencer on the amount of data caused by different index sequences, the distribution of the number of reads of each of the primers P7 and P5 used for a next-generation sequencer comprising different index sequences was inspected. In the case of DNA library 1 in which the primer P7 used for a next-generation sequencer has a different index sequence, there were 9 types of index sequences (94%) exhibiting the number of reads of 15,000 or less, relative to the average number of the reads of the whole (i.e., 66,961.7), and the average was 2,492.2, which was 3.7% of the average of the whole (FIG. 2). Also, there were 22 types of index sequences (220%) exhibiting the number of reads of 40,000 or less, and the average was 16,237.6, which was 24.3% of the average of the whole. In the case of DNA library 2 in which the primer P5 used for a next-generation sequencer has a different index sequence, the average number of the reads of the whole was 191,523.1. That is, all the index sequences exhibited the number of reads of 100,000 or less (FIG. 3).

4.2. Correlation Between Index Sequence and Number of Reads

DNA library 1 and DNA library 2 were separately analyzed with the use of the next-generation sequencer, the correlation between the index sequence and the number of reads was analyzed based on the results of analysis by the GLMNET LASSO method, and the estimation formula that calculates the correlation between the nucleotide type and the number of reads of the index sequence was prepared. Specifically, an estimation formula designating the number of reads as a purpose variable and a nucleotide type of the index sequence as an explanatory variable was prepared. FIG. 4 shows the correlation between the putative number of reads calculated with the use of the estimation formula prepared for DNA library 1 and the measured number of reads. As shown in FIG. 4, the correlational coefficient (r) between the putative number of reads determined with the estimation formula and the measured number of reads based on types of nucleotides constituting the index sequence was 0.94069 (r: 0.94069). As shown in FIG. 4, plots of the putative number of reads and the measured number of reads were classified into: Group 1 with a very small number of reads; Group 3 with a large number of reads; and Group 2 with a number of reads therebetween. The maximal putative number of reads determined based on the index sequence of the primer P7 used for a next-generation sequencer of Group 1 was 20,051.8. The putative number of reads determined based on the index sequence of the primer P7 used for a next-generation sequencer of Group 3 was 50,000 or greater.

Separately, an estimation formula concerning DNA library 2 was also calculated, the correlational coefficient (r) between the putative number of reads determined based on the types of nucleotides constituting index sequence and the measured number of reads was determined, and the correlational coefficient (r) was 0.57295 (FIG. 5). Specifically, no correlation was observed between the types of nucleotides constituting the index sequence and the number of reads concerning the primer P5 used for a next-generation sequencer.

4.3 Design of the Index Sequence of the Primer P7 Used for a Next-Generation Sequencer In the case of DNA library 1 in which the primer P7 used for a next-generation sequencer has a different index sequence, the correlational coefficient between the number of reads and the putative number of reads calculated by the GLMNET LASSO method was 0.9 or higher. On the basis thereof, the estimation formula prepared for DNA library 1 by the GLMNET LASSO method was evaluated to be capable of calculating the putative number of reads with high accuracy based on types of nucleotides constituting the index sequence. Specifically, the estimation formula prepared by the GLMNET LASSO method contains items and segments including a coefficient calculated for each nucleotide at a given position in an index sequence as shown below.

Putative number: $-65033.1 \times (A1) + 1326.4 \times (C1) - 16997 \times (G1) + 10936.3 \times (A2) - 12399.2 \times (G2) + 11712.9 \times (T2) + 12112.2 \times (A3) - 623.5 \times (G3) + 5964.4 \times (T3) + 6884.5 \times (A4) - 5664.4 \times (C4) - 6049.9 \times (G4) + 9257 \times (A5) - 6210.8 \times (G5) - 644 \times (C6) + 3.2 \times (T6) - 3575.9 \times (A7) + 1013.1 \times (G7) - 8607.7 \times (G8) + 6490.3 \times (T8) + 81720.7$ In the estimation formula, (A1) is a parameter to which "1" is assigned when the first nucleotide in the 5' to 3' direction in the index sequence is adenine and "0" is assigned under other conditions. Other notations also refer to positions in the 5' to 3' direction in the index sequence and nucleotide types, which are parameters to which "1" or "0" is assigned.

With the use of the estimation formula prepared in the manner described above, the primer P7 used for a next-generation sequencer exhibiting a putative number of 20,052 or higher (which is deduced to be Group 2 or 3) and the primer P7 used for a next-generation sequencer exhibiting a putative number of 50,000 or higher (which is deduced to be Group 3) were selected (Tables 6 and 7). In the nucleotide sequences shown in Tables 6 and 7, "N" represents an arbitrary nucleotide selected from among adenine, cytosine, guanine, and thymine.

TABLE 6

Table 6: Primer P7 for next-generation sequencer and index thereof

| Primer P7 for next-generation sequencer | Index | SEQ ID NO |
|---|---|---|
| CAAGCAGAAGACGGCATACGAGATCNNCTTTTGTCTCGTGGGCTCGGAGATGTGTATAAGAGACAG | AAAAGNNG | 262 |
| CAAGCAGAAGACGGCATACGAGATCCTCGTTTGTCTCGTGGGCTCGGAGATGTGTATAAGAGACAG | AAACGAGG | 263 |
| CAAGCAGAAGACGGCATACGAGATCCCCGTTTGTCTCGTGGGCTCGGAGATGTGTATAAGAGACAG | AAACGGGG | 264 |
| CAAGCAGAAGACGGCATACGAGATCCACGTTTGTCTCGTGGGCTCGGAGATGTGTATAAGAGACAG | AAACGTGG | 265 |
| CAAGCAGAAGACGGCATACGAGATNNNTNTTTGTCTCGTGGGCTCGGAGATGTGTATAAGAGACAG | AAANANNN | 266 |
| CAAGCAGAAGACGGCATACGAGATNNNGNTTTGTCTCGTGGGCTCGGAGATGTGTATAAGAGACAG | AAANCNNN | 267 |
| CAAGCAGAAGACGGCATACGAGATTNNCNTTTGTCTCGTGGGCTCGGAGATGTGTATAAGAGACAG | AAANGNNA | 268 |
| CAAGCAGAAGACGGCATACGAGATGNNCNTTTGTCTCGTGGGCTCGGAGATGTGTATAAGAGACAG | AAANGNNC | 269 |
| CAAGCAGAAGACGGCATACGAGATANNCNTTTGTCTCGTGGGCTCGGAGATGTGTATAAGAGACAG | AAANGNNT | 270 |
| CAAGCAGAAGACGGCATACGAGATNNNANTTTGTCTCGTGGGCTCGGAGATGTGTATAAGAGACAG | AAANTNNN | 271 |
| CAAGCAGAAGACGGCATACGAGATCNNCATTTGTCTCGTGGGCTCGGAGATGTGTATAAGAGACAG | AAATGNNG | 272 |
| CAAGCAGAAGACGGCATACGAGATCNNTTGTTGTCTCGTGGGCTCGGAGATGTGTATAAGAGACAG | AACAANNG | 273 |
| CAAGCAGAAGACGGCATACGAGATTNNGTGTTGTCTCGTGGGCTCGGAGATGTGTATAAGAGACAG | AACACNNA | 274 |
| CAAGCAGAAGACGGCATACGAGATGNNGTGTTGTCTCGTGGGCTCGGAGATGTGTATAAGAGACAG | AACACNNC | 275 |
| CAAGCAGAAGACGGCATACGAGATCNNGTGTTGTCTCGTGGGCTCGGAGATGTGTATAAGAGACAG | AACACNNG | 276 |
| CAAGCAGAAGACGGCATACGAGATCCNCTGTTGTCTCGTGGGCTCGGAGATGTGTATAAGAGACAG | AACAGNGG | 277 |
| CAAGCAGAAGACGGCATACGAGATTNNCTGTTGTCTCGTGGGCTCGGAGATGTGTATAAGAGACAG | AACAGNNA | 278 |
| CAAGCAGAAGACGGCATACGAGATGNNCTGTTGTCTCGTGGGCTCGGAGATGTGTATAAGAGACAG | AACAGNNC | 279 |
| CAAGCAGAAGACGGCATACGAGATANNCTGTTGTCTCGTGGGCTCGGAGATGTGTATAAGAGACAG | AACAGNNT | 280 |
| CAAGCAGAAGACGGCATACGAGATTNNATGTTGTCTCGTGGGCTCGGAGATGTGTATAAGAGACAG | AACATNNA | 281 |
| CAAGCAGAAGACGGCATACGAGATGNNATGTTGTCTCGTGGGCTCGGAGATGTGTATAAGAGACAG | AACATNNC | 282 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATCNNATGTTGTCTCGTGGGCTCGGAGATGTGTATAAGAGACAG | AACATNNG | 283 |
| CAAGCAGAAGACGGCATACGAGATCGNTGGTTGTCTCGTGGGCTCGGAGATGTGTATAAGAGACAG | AACCANCG | 284 |
| CAAGCAGAAGACGGCATACGAGATCCNTGGTTGTCTCGTGGGCTCGGAGATGTGTATAAGAGACAG | AACCANGG | 285 |
| CAAGCAGAAGACGGCATACGAGATCANTGGTTGTCTCGTGGGCTCGGAGATGTGTATAAGAGACAG | AACCANTG | 286 |
| CAAGCAGAAGACGGCATACGAGATTGNGGGTTGTCTCGTGGGCTCGGAGATGTGTATAAGAGACAG | AACCCNCA | 287 |
| CAAGCAGAAGACGGCATACGAGATGGNGGGTTGTCTCGTGGGCTCGGAGATGTGTATAAGAGACAG | AACCCNCC | 288 |
| CAAGCAGAAGACGGCATACGAGATTCNGGTTGTCTCGTGGGCTCGGAGATGTGTATAAGAGACAG | AACCCNGA | 289 |
| CAAGCAGAAGACGGCATACGAGATGCNGGGTTGTCTCGTGGGCTCGGAGATGTGTATAAGAGACAG | AACCCNGC | 290 |
| CAAGCAGAAGACGGCATACGAGATTANGGTTGTCTCGTGGGCTCGGAGATGTGTATAAGAGACAG | AACCCNTA | 291 |
| CAAGCAGAAGACGGCATACGAGATGANGGGTTGTCTCGTGGGCTCGGAGATGTGTATAAGAGACAG | AACCCNTC | 292 |
| CAAGCAGAAGACGGCATACGAGATAGNCGGTTGTCTCGTGGGCTCGGAGATGTGTATAAGAGACAG | AACCGNCT | 293 |
| CAAGCAGAAGACGGCATACGAGATACNCGGTTGTCTCGTGGGCTCGGAGATGTGTATAAGAGACAG | AACCGNGT | 294 |
| CAAGCAGAAGACGGCATACGAGATAANCGGTTGTCTCGTGGGCTCGGAGATGTGTATAAGAGACAG | AACCGNTT | 295 |
| CAAGCAGAAGACGGCATACGAGATTGNAGGTTGTCTCGTGGGCTCGGAGATGTGTATAAGAGACAG | AACCTNCA | 296 |
| CAAGCAGAAGACGGCATACGAGATGGNAGGTTGTCTCGTGGGCTCGGAGATGTGTATAAGAGACAG | AACCTNCC | 297 |
| CAAGCAGAAGACGGCATACGAGATTCNAGGTTGTCTCGTGGGCTCGGAGATGTGTATAAGAGACAG | AACCTNGA | 298 |
| CAAGCAGAAGACGGCATACGAGATGCNAGGTTGTCTCGTGGGCTCGGAGATGTGTATAAGAGACAG | AACCTNGC | 299 |
| CAAGCAGAAGACGGCATACGAGATTANAGGTTGTCTCGTGGGCTCGGAGATGTGTATAAGAGACAG | AACCTNTA | 300 |
| CAAGCAGAAGACGGCATACGAGATGANAGGTTGTCTCGTGGGCTCGGAGATGTGTATAAGAGACAG | AACCTNTC | 301 |
| CAAGCAGAAGACGGCATACGAGATCGNTCGTTGTCTCGTGGGCTCGGAGATGTGTATAAGAGACAG | AACGANCG | 302 |
| CAAGCAGAAGACGGCATACGAGATCCNTCGTTGTCTCGTGGGCTCGGAGATGTGTATAAGAGACAG | AACGANGG | 303 |
| CAAGCAGAAGACGGCATACGAGATCANTCGTTGTCTCGTGGGCTCGGAGATGTGTATAAGAGACAG | AACGANTG | 304 |
| CAAGCAGAAGACGGCATACGAGATTGNGCGTTGTCTCGTGGGCTCGGAGATGTGTATAAGAGACAG | AACGCNCA | 305 |
| CAAGCAGAAGACGGCATACGAGATGGNGCGTTGTCTCGTGGGCTCGGAGATGTGTATAAGAGACAG | AACGCNCC | 306 |
| CAAGCAGAAGACGGCATACGAGATTCNGCGTTGTCTCGTGGGCTCGGAGATGTGTATAAGAGACAG | AACGCNGA | 307 |
| CAAGCAGAAGACGGCATACGAGATGCNGCGTTGTCTCGTGGGCTCGGAGATGTGTATAAGAGACAG | AACGCNGC | 308 |
| CAAGCAGAAGACGGCATACGAGATTANGCGTTGTCTCGTGGGCTCGGAGATGTGTATAAGAGACAG | AACGCNTA | 309 |
| CAAGCAGAAGACGGCATACGAGATGANGCGTTGTCTCGTGGGCTCGGAGATGTGTATAAGAGACAG | AACGCNTC | 310 |
| CAAGCAGAAGACGGCATACGAGATAGNCCGTTGTCTCGTGGGCTCGGAGATGTGTATAAGAGACAG | AACGGNCT | 311 |
| CAAGCAGAAGACGGCATACGAGATACNCCGTTGTCTCGTGGGCTCGGAGATGTGTATAAGAGACAG | AACGGNGT | 312 |
| CAAGCAGAAGACGGCATACGAGATAANCCGTTGTCTCGTGGGCTCGGAGATGTGTATAAGAGACAG | AACGGNTT | 313 |
| CAAGCAGAAGACGGCATACGAGATTGNACGTTGTCTCGTGGGCTCGGAGATGTGTATAAGAGACAG | AACGTNCA | 314 |
| CAAGCAGAAGACGGCATACGAGATGGNACGTTGTCTCGTGGGCTCGGAGATGTGTATAAGAGACAG | AACGTNCC | 315 |
| CAAGCAGAAGACGGCATACGAGATTCNACGTTGTCTCGTGGGCTCGGAGATGTGTATAAGAGACAG | AACGTNGA | 316 |
| CAAGCAGAAGACGGCATACGAGATGCNACGTTGTCTCGTGGGCTCGGAGATGTGTATAAGAGACAG | AACGTNGC | 317 |
| CAAGCAGAAGACGGCATACGAGATTANACGTTGTCTCGTGGGCTCGGAGATGTGTATAAGAGACAG | AACGTNTA | 318 |
| CAAGCAGAAGACGGCATACGAGATGANACGTTGTCTCGTGGGCTCGGAGATGTGTATAAGAGACAG | AACGTNTC | 319 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATTNNTNGTTGTCTCGTGGGCTCGGAGATGTGTATAAGAGACAG | AACNANNA | 320 |
| CAAGCAGAAGACGGCATACGAGATGNNTNGTTGTCTCGTGGGCTCGGAGATGTGTATAAGAGACAG | AACNANNC | 321 |
| CAAGCAGAAGACGGCATACGAGATANNTNGTTGTCTCGTGGGCTCGGAGATGTGTATAAGAGACAG | AACNANNT | 322 |
| CAAGCAGAAGACGGCATACGAGATANNGNGTTGTCTCGTGGGCTCGGAGATGTGTATAAGAGACAG | AACNCNNT | 323 |
| CAAGCAGAAGACGGCATACGAGATANNANGTTGTCTCGTGGGCTCGGAGATGTGTATAAGAGACAG | AACNTNNT | 324 |
| CAAGCAGAAGACGGCATACGAGATCNNTAGTTGTCTCGTGGGCTCGGAGATGTGTATAAGAGACAG | AACTANNG | 325 |
| CAAGCAGAAGACGGCATACGAGATTNNGAGTTGTCTCGTGGGCTCGGAGATGTGTATAAGAGACAG | AACTCNNA | 326 |
| CAAGCAGAAGACGGCATACGAGATGNNGAGTTGTCTCGTGGGCTCGGAGATGTGTATAAGAGACAG | AACTCNNC | 327 |
| CAAGCAGAAGACGGCATACGAGATTGNCAGTTGTCTCGTGGGCTCGGAGATGTGTATAAGAGACAG | AACTGNCA | 328 |
| CAAGCAGAAGACGGCATACGAGATGGNCAGTTGTCTCGTGGGCTCGGAGATGTGTATAAGAGACAG | AACTGNCC | 329 |
| CAAGCAGAAGACGGCATACGAGATTCNCAGTTGTCTCGTGGGCTCGGAGATGTGTATAAGAGACAG | AACTGNGA | 330 |
| CAAGCAGAAGACGGCATACGAGATGCNCAGTTGTCTCGTGGGCTCGGAGATGTGTATAAGAGACAG | AACTGNGC | 331 |
| CAAGCAGAAGACGGCATACGAGATANNCAGTTGTCTCGTGGGCTCGGAGATGTGTATAAGAGACAG | AACTGNNT | 332 |
| CAAGCAGAAGACGGCATACGAGATTANCAGTTGTCTCGTGGGCTCGGAGATGTGTATAAGAGACAG | AACTGNTA | 333 |
| CAAGCAGAAGACGGCATACGAGATGANCAGTTGTCTCGTGGGCTCGGAGATGTGTATAAGAGACAG | AACTGNTC | 334 |
| CAAGCAGAAGACGGCATACGAGATTNNAAGTTGTCTCGTGGGCTCGGAGATGTGTATAAGAGACAG | AACTTNNA | 335 |
| CAAGCAGAAGACGGCATACGAGATGNNAAGTTGTCTCGTGGGCTCGGAGATGTGTATAAGAGACAG | AACTTNNC | 336 |
| CAAGCAGAAGACGGCATACGAGATCNNTTCTTGTCTCGTGGGCTCGGAGATGTGTATAAGAGACAG | AAGAANNG | 337 |
| CAAGCAGAAGACGGCATACGAGATTNNGTCTTGTCTCGTGGGCTCGGAGATGTGTATAAGAGACAG | AAGACNNA | 338 |
| CAAGCAGAAGACGGCATACGAGATGNNGTCTTGTCTCGTGGGCTCGGAGATGTGTATAAGAGACAG | AAGACNNC | 339 |
| CAAGCAGAAGACGGCATACGAGATCNNGTCTTGTCTCGTGGGCTCGGAGATGTGTATAAGAGACAG | AAGACNNG | 340 |
| CAAGCAGAAGACGGCATACGAGATCCTCTCTTGTCTCGTGGGCTCGGAGATGTGTATAAGAGACAG | AAGAGAGG | 341 |
| CAAGCAGAAGACGGCATACGAGATCCCCTCTTGTCTCGTGGGCTCGGAGATGTGTATAAGAGACAG | AAGAGGGG | 342 |
| CAAGCAGAAGACGGCATACGAGATTNNCTCTTGTCTCGTGGGCTCGGAGATGTGTATAAGAGACAG | AAGAGNNA | 343 |
| CAAGCAGAAGACGGCATACGAGATGNNCTCTTGTCTCGTGGGCTCGGAGATGTGTATAAGAGACAG | AAGAGNNC | 344 |
| CAAGCAGAAGACGGCATACGAGATANNCTCTTGTCTCGTGGGCTCGGAGATGTGTATAAGAGACAG | AAGAGNNT | 345 |
| CAAGCAGAAGACGGCATACGAGATCCACTCTTGTCTCGTGGGCTCGGAGATGTGTATAAGAGACAG | AAGAGTGG | 346 |
| CAAGCAGAAGACGGCATACGAGATTNNATCTTGTCTCGTGGGCTCGGAGATGTGTATAAGAGACAG | AAGATNNA | 347 |
| CAAGCAGAAGACGGCATACGAGATGNNATCTTGTCTCGTGGGCTCGGAGATGTGTATAAGAGACAG | AAGATNNC | 348 |
| CAAGCAGAAGACGGCATACGAGATCNNATCTTGTCTCGTGGGCTCGGAGATGTGTATAAGAGACAG | AAGATNNG | 349 |
| CAAGCAGAAGACGGCATACGAGATCGNTGCTTGTCTCGTGGGCTCGGAGATGTGTATAAGAGACAG | AAGCANCG | 350 |
| CAAGCAGAAGACGGCATACGAGATCCNTGCTTGTCTCGTGGGCTCGGAGATGTGTATAAGAGACAG | AAGCANGG | 351 |
| CAAGCAGAAGACGGCATACGAGATCANTGCTTGTCTCGTGGGCTCGGAGATGTGTATAAGAGACAG | AAGCANTG | 352 |
| CAAGCAGAAGACGGCATACGAGATTGNGGCTTGTCTCGTGGGCTCGGAGATGTGTATAAGAGACAG | AAGCCNCA | 353 |
| CAAGCAGAAGACGGCATACGAGATGGNGGCTTGTCTCGTGGGCTCGGAGATGTGTATAAGAGACAG | AAGCCNCC | 354 |
| CAAGCAGAAGACGGCATACGAGATTCNGGCTTGTCTCGTGGGCTCGGAGATGTGTATAAGAGACAG | AAGCCNGA | 355 |
| CAAGCAGAAGACGGCATACGAGATGCNGGCTTGTCTCGTGGGCTCGGAGATGTGTATAAGAGACAG | AAGCCNGC | 356 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATTANGGCTTGTCTCGTGGGCTCGGAGATGTGTATAAGAGACAG | AAGCCNTA | 357 |
| CAAGCAGAAGACGGCATACGAGATGANGGCTTGTCTCGTGGGCTCGGAGATGTGTATAAGAGACAG | AAGCCNTC | 358 |
| CAAGCAGAAGACGGCATACGAGATAGNCGCTTGTCTCGTGGGCTCGGAGATGTGTATAAGAGACAG | AAGCGNCT | 359 |
| CAAGCAGAAGACGGCATACGAGATACNCGCTTGTCTCGTGGGCTCGGAGATGTGTATAAGAGACAG | AAGCGNGT | 360 |
| CAAGCAGAAGACGGCATACGAGATAANCGCTTGTCTCGTGGGCTCGGAGATGTGTATAAGAGACAG | AAGCGNTT | 361 |
| CAAGCAGAAGACGGCATACGAGATTGNAGCTTGTCTCGTGGGCTCGGAGATGTGTATAAGAGACAG | AAGCTNCA | 362 |
| CAAGCAGAAGACGGCATACGAGATGGNAGCTTGTCTCGTGGGCTCGGAGATGTGTATAAGAGACAG | AAGCTNCC | 363 |
| CAAGCAGAAGACGGCATACGAGATTCNAGCTTGTCTCGTGGGCTCGGAGATGTGTATAAGAGACAG | AAGCTNGA | 364 |
| CAAGCAGAAGACGGCATACGAGATGCNAGCTTGTCTCGTGGGCTCGGAGATGTGTATAAGAGACAG | AAGCTNGC | 365 |
| CAAGCAGAAGACGGCATACGAGATTANAGCTTGTCTCGTGGGCTCGGAGATGTGTATAAGAGACAG | AAGCTNTA | 366 |
| CAAGCAGAAGACGGCATACGAGATGANAGCTTGTCTCGTGGGCTCGGAGATGTGTATAAGAGACAG | AAGCTNTC | 367 |
| CAAGCAGAAGACGGCATACGAGATCGNTCCTTGTCTCGTGGGCTCGGAGATGTGTATAAGAGACAG | AAGGANCG | 368 |
| CAAGCAGAAGACGGCATACGAGATCCNTCCTTGTCTCGTGGGCTCGGAGATGTGTATAAGAGACAG | AAGGANGG | 369 |
| CAAGCAGAAGACGGCATACGAGATCANTCCTTGTCTCGTGGGCTCGGAGATGTGTATAAGAGACAG | AAGGANTG | 370 |
| CAAGCAGAAGACGGCATACGAGATTGNCCTTGTCTCGTGGGCTCGGAGATGTGTATAAGAGACAG | AAGGCNCA | 371 |
| CAAGCAGAAGACGGCATACGAGATGGNCCTTGTCTCGTGGGCTCGGAGATGTGTATAAGAGACAG | AAGGCNCC | 372 |
| CAAGCAGAAGACGGCATACGAGATTCNGCCTTGTCTCGTGGGCTCGGAGATGTGTATAAGAGACAG | AAGGCNGA | 373 |
| CAAGCAGAAGACGGCATACGAGATGCNGCCTTGTCTCGTGGGCTCGGAGATGTGTATAAGAGACAG | AAGGCNGC | 374 |
| CAAGCAGAAGACGGCATACGAGATTANGCCTTGTCTCGTGGGCTCGGAGATGTGTATAAGAGACAG | AAGGCNTA | 375 |
| CAAGCAGAAGACGGCATACGAGATGANGCCTTGTCTCGTGGGCTCGGAGATGTGTATAAGAGACAG | AAGGCNTC | 376 |
| CAAGCAGAAGACGGCATACGAGATAGNCCCTTGTCTCGTGGGCTCGGAGATGTGTATAAGAGACAG | AAGGGNCT | 377 |
| CAAGCAGAAGACGGCATACGAGATACNCCCTTGTCTCGTGGGCTCGGAGATGTGTATAAGAGACAG | AAGGGNGT | 378 |
| CAAGCAGAAGACGGCATACGAGATAANCCCTTGTCTCGTGGGCTCGGAGATGTGTATAAGAGACAG | AAGGGNTT | 379 |
| CAAGCAGAAGACGGCATACGAGATTGNACCTTGTCTCGTGGGCTCGGAGATGTGTATAAGAGACAG | AAGGTNCA | 380 |
| CAAGCAGAAGACGGCATACGAGATGGNACCTTGTCTCGTGGGCTCGGAGATGTGTATAAGAGACAG | AAGGTNCC | 381 |
| CAAGCAGAAGACGGCATACGAGATTCNACCTTGTCTCGTGGGCTCGGAGATGTGTATAAGAGACAG | AAGGTNGA | 382 |
| CAAGCAGAAGACGGCATACGAGATGCNACCTTGTCTCGTGGGCTCGGAGATGTGTATAAGAGACAG | AAGGTNGC | 383 |
| CAAGCAGAAGACGGCATACGAGATTANACCTTGTCTCGTGGGCTCGGAGATGTGTATAAGAGACAG | AAGGTNTA | 384 |
| CAAGCAGAAGACGGCATACGAGATGANACCTTGTCTCGTGGGCTCGGAGATGTGTATAAGAGACAG | AAGGTNTC | 385 |
| CAAGCAGAAGACGGCATACGAGATTNNTNCTTGTCTCGTGGGCTCGGAGATGTGTATAAGAGACAG | AAGNANNA | 386 |
| CAAGCAGAAGACGGCATACGAGATGNNTNCTTGTCTCGTGGGCTCGGAGATGTGTATAAGAGACAG | AAGNANNC | 387 |
| CAAGCAGAAGACGGCATACGAGATANNTNCTTGTCTCGTGGGCTCGGAGATGTGTATAAGAGACAG | AAGNANNT | 388 |
| CAAGCAGAAGACGGCATACGAGATANNGNCTTGTCTCGTGGGCTCGGAGATGTGTATAAGAGACAG | AAGNCNNT | 389 |
| CAAGCAGAAGACGGCATACGAGATANNANCTTGTCTCGTGGGCTCGGAGATGTGTATAAGAGACAG | AAGNTNNT | 390 |
| CAAGCAGAAGACGGCATACGAGATCNNTACTTGTCTCGTGGGCTCGGAGATGTGTATAAGAGACAG | AAGTANNG | 391 |
| CAAGCAGAAGACGGCATACGAGATTNNGACTTGTCTCGTGGGCTCGGAGATGTGTATAAGAGACAG | AAGTCNNA | 392 |
| CAAGCAGAAGACGGCATACGAGATGNNGACTTGTCTCGTGGGCTCGGAGATGTGTATAAGAGACAG | AAGTCNNC | 393 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATTGNCACTTGTCTCGTGGGCTCGGAGATGTGTATAAGAGACAG | AAGTGNCA | 394 |
| CAAGCAGAAGACGGCATACGAGATGGNCACTTGTCTCGTGGGCTCGGAGATGTGTATAAGAGACAG | AAGTGNCC | 395 |
| CAAGCAGAAGACGGCATACGAGATTCNCACTTGTCTCGTGGGCTCGGAGATGTGTATAAGAGACAG | AAGTGNGA | 396 |
| CAAGCAGAAGACGGCATACGAGATGCNCACTTGTCTCGTGGGCTCGGAGATGTGTATAAGAGACAG | AAGTGNGC | 397 |
| CAAGCAGAAGACGGCATACGAGATANNCACTTGTCTCGTGGGCTCGGAGATGTGTATAAGAGACAG | AAGTGNNT | 398 |
| CAAGCAGAAGACGGCATACGAGATTANCACTTGTCTCGTGGGCTCGGAGATGTGTATAAGAGACAG | AAGTGNTA | 399 |
| CAAGCAGAAGACGGCATACGAGATGANCACTTGTCTCGTGGGCTCGGAGATGTGTATAAGAGACAG | AAGTGNTC | 400 |
| CAAGCAGAAGACGGCATACGAGATTNNAACTTGTCTCGTGGGCTCGGAGATGTGTATAAGAGACAG | AAGTTNNA | 401 |
| CAAGCAGAAGACGGCATACGAGATGNNAACTTGTCTCGTGGGCTCGGAGATGTGTATAAGAGACAG | AAGTTNNC | 402 |
| CAAGCAGAAGACGGCATACGAGATCNNGTATTGTCTCGTGGGCTCGGAGATGTGTATAAGAGACAG | AATACNNG | 403 |
| CAAGCAGAAGACGGCATACGAGATTNNCTATTGTCTCGTGGGCTCGGAGATGTGTATAAGAGACAG | AATAGNNA | 404 |
| CAAGCAGAAGACGGCATACGAGATGNNCTATTGTCTCGTGGGCTCGGAGATGTGTATAAGAGACAG | AATAGNNC | 405 |
| CAAGCAGAAGACGGCATACGAGATCNNCTATTGTCTCGTGGGCTCGGAGATGTGTATAAGAGACAG | AATAGNNG | 406 |
| CAAGCAGAAGACGGCATACGAGATCNNATATTGTCTCGTGGGCTCGGAGATGTGTATAAGAGACAG | AATATNNG | 407 |
| CAAGCAGAAGACGGCATACGAGATCCTGGATTGTCTCGTGGGCTCGGAGATGTGTATAAGAGACAG | AATCCAGG | 408 |
| CAAGCAGAAGACGGCATACGAGATCCCGGATTGTCTCGTGGGCTCGGAGATGTGTATAAGAGACAG | AATCCGGG | 409 |
| CAAGCAGAAGACGGCATACGAGATCCAGGATTGTCTCGTGGGCTCGGAGATGTGTATAAGAGACAG | AATCCTGG | 410 |
| CAAGCAGAAGACGGCATACGAGATTGNCGATTGTCTCGTGGGCTCGGAGATGTGTATAAGAGACAG | AATCGNCA | 411 |
| CAAGCAGAAGACGGCATACGAGATGGNCGATTGTCTCGTGGGCTCGGAGATGTGTATAAGAGACAG | AATCGNCC | 412 |
| CAAGCAGAAGACGGCATACGAGATTCNCGATTGTCTCGTGGGCTCGGAGATGTGTATAAGAGACAG | AATCGNGA | 413 |
| CAAGCAGAAGACGGCATACGAGATGCNCGATTGTCTCGTGGGCTCGGAGATGTGTATAAGAGACAG | AATCGNGC | 414 |
| CAAGCAGAAGACGGCATACGAGATTANCGATTGTCTCGTGGGCTCGGAGATGTGTATAAGAGACAG | AATCGNTA | 415 |
| CAAGCAGAAGACGGCATACGAGATGANCGATTGTCTCGTGGGCTCGGAGATGTGTATAAGAGACAG | AATCGNTC | 416 |
| CAAGCAGAAGACGGCATACGAGATCCTAGATTGTCTCGTGGGCTCGGAGATGTGTATAAGAGACAG | AATCTAGG | 417 |
| CAAGCAGAAGACGGCATACGAGATCCCAGATTGTCTCGTGGGCTCGGAGATGTGTATAAGAGACAG | AATCTGGG | 418 |
| CAAGCAGAAGACGGCATACGAGATCCAAGATTGTCTCGTGGGCTCGGAGATGTGTATAAGAGACAG | AATCTTGG | 419 |
| CAAGCAGAAGACGGCATACGAGATTGNCCATTGTCTCGTGGGCTCGGAGATGTGTATAAGAGACAG | AATGGNCA | 420 |
| CAAGCAGAAGACGGCATACGAGATGGNCCATTGTCTCGTGGGCTCGGAGATGTGTATAAGAGACAG | AATGGNCC | 421 |
| CAAGCAGAAGACGGCATACGAGATTCNCCATTGTCTCGTGGGCTCGGAGATGTGTATAAGAGACAG | AATGGNGA | 422 |
| CAAGCAGAAGACGGCATACGAGATGCNCCATTGTCTCGTGGGCTCGGAGATGTGTATAAGAGACAG | AATGGNGC | 423 |
| CAAGCAGAAGACGGCATACGAGATTANCCATTGTCTCGTGGGCTCGGAGATGTGTATAAGAGACAG | AATGGNTA | 424 |
| CAAGCAGAAGACGGCATACGAGATGANCCATTGTCTCGTGGGCTCGGAGATGTGTATAAGAGACAG | AATGGNTC | 425 |
| CAAGCAGAAGACGGCATACGAGATNNNTNATTGTCTCGTGGGCTCGGAGATGTGTATAAGAGACAG | AATNANNN | 426 |
| CAAGCAGAAGACGGCATACGAGATTNNGNATTGTCTCGTGGGCTCGGAGATGTGTATAAGAGACAG | AATNCNNA | 427 |
| CAAGCAGAAGACGGCATACGAGATGNNGNATTGTCTCGTGGGCTCGGAGATGTGTATAAGAGACAG | AATNCNNC | 428 |
| CAAGCAGAAGACGGCATACGAGATANNGNATTGTCTCGTGGGCTCGGAGATGTGTATAAGAGACAG | AATNCNNT | 429 |
| CAAGCAGAAGACGGCATACGAGATANNCNATTGTCTCGTGGGCTCGGAGATGTGTATAAGAGACAG | AATNGNNT | 430 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATTNNANATTGTCTCGTGGGTCGGAGATGTGTATAAGAGACAG | AATNTNNA | 431 |
| CAAGCAGAAGACGGCATACGAGATGNNANATTGTCTCGTGGGCTCGGAGATGTGTATAAGAGACAG | AATNTNNC | 432 |
| CAAGCAGAAGACGGCATACGAGATANNANATTGTCTCGTGGGCTCGGAGATGTGTATAAGAGACAG | AATNTNNT | 433 |
| CAAGCAGAAGACGGCATACGAGATCNNGAATTGTCTCGTGGGCTCGGAGATGTGTATAAGAGACAG | AATTCNNG | 434 |
| CAAGCAGAAGACGGCATACGAGATTNNCAATTGTCTCGTGGGCTCGGAGATGTGTATAAGAGACAG | AATTGNNA | 435 |
| CAAGCAGAAGACGGCATACGAGATGNNCAATTGTCTCGTGGGCTCGGAGATGTGTATAAGAGACAG | AATTGNNC | 436 |
| CAAGCAGAAGACGGCATACGAGATCNNAAATTGTCTCGTGGGCTCGGAGATGTGTATAAGAGACAG | AATTTNNG | 437 |
| CAAGCAGAAGACGGCATACGAGATCNNTTTGTCTCGTGGGCTCGGAGATGTGTATAAGAGACAG | ACAAANNG | 438 |
| CAAGCAGAAGACGGCATACGAGATTNNGTTGTCTCGTGGGCTCGGAGATGTGTATAAGAGACAG | ACAACNNA | 439 |
| CAAGCAGAAGACGGCATACGAGATGNNGTTGTCTCGTGGGCTCGGAGATGTGTATAAGAGACAG | ACAACNNC | 440 |
| CAAGCAGAAGACGGCATACGAGATCNNGTTGTCTCGTGGGCTCGGAGATGTGTATAAGAGACAG | ACAACNNG | 441 |
| CAAGCAGAAGACGGCATACGAGATCGNCTTGTCTCGTGGGCTCGGAGATGTGTATAAGAGACAG | ACAAGNCG | 442 |
| CAAGCAGAAGACGGCATACGAGATCCNCTTGTCTCGTGGGCTCGGAGATGTGTATAAGAGACAG | ACAAGNGG | 443 |
| CAAGCAGAAGACGGCATACGAGATTNNCTTGTCTCGTGGGCTCGGAGATGTGTATAAGAGACAG | ACAAGNNA | 444 |
| CAAGCAGAAGACGGCATACGAGATGNNCTTGTCTCGTGGGCTCGGAGATGTGTATAAGAGACAG | ACAAGNNC | 445 |
| CAAGCAGAAGACGGCATACGAGATANNCTTGTCTCGTGGGCTCGGAGATGTGTATAAGAGACAG | ACAAGNNT | 446 |
| CAAGCAGAAGACGGCATACGAGATCANCTTGTCTCGTGGGCTCGGAGATGTGTATAAGAGACAG | ACAAGNTG | 447 |
| CAAGCAGAAGACGGCATACGAGATTNNATTGTCTCGTGGGCTCGGAGATGTGTATAAGAGACAG | ACAATNNA | 448 |
| CAAGCAGAAGACGGCATACGAGATGNNATTGTCTCGTGGGCTCGGAGATGTGTATAAGAGACAG | ACAATNNC | 449 |
| CAAGCAGAAGACGGCATACGAGATCNNATTGTCTCGTGGGCTCGGAGATGTGTATAAGAGACAG | ACAATNNG | 450 |
| CAAGCAGAAGACGGCATACGAGATCTTTGTGTCTCGTGGGCTCGGAGATGTGTATAAGAGACAG | ACACAAAG | 451 |
| CAAGCAGAAGACGGCATACGAGATCTCTGTGTCTCGTGGGCTCGGAGATGTGTATAAGAGACAG | ACACAGAG | 452 |
| CAAGCAGAAGACGGCATACGAGATCGNTGTGTCTCGTGGGCTCGGAGATGTGTATAAGAGACAG | ACACANCG | 453 |
| CAAGCAGAAGACGGCATACGAGATCCNTGTGTCTCGTGGGCTCGGAGATGTGTATAAGAGACAG | ACACANGG | 454 |
| CAAGCAGAAGACGGCATACGAGATCANTGTGTCTCGTGGGCTCGGAGATGTGTATAAGAGACAG | ACACANTG | 455 |
| CAAGCAGAAGACGGCATACGAGATCTATGTGTCTCGTGGGCTCGGAGATGTGTATAAGAGACAG | ACACATAG | 456 |
| CAAGCAGAAGACGGCATACGAGATTGNGGTGTCTCGTGGGCTCGGAGATGTGTATAAGAGACAG | ACACCNCA | 457 |
| CAAGCAGAAGACGGCATACGAGATGGNGGTGTCTCGTGGGCTCGGAGATGTGTATAAGAGACAG | ACACCNCC | 458 |
| CAAGCAGAAGACGGCATACGAGATTCNGGTGTCTCGTGGGCTCGGAGATGTGTATAAGAGACAG | ACACCNGA | 459 |
| CAAGCAGAAGACGGCATACGAGATGCNGGTGTCTCGTGGGCTCGGAGATGTGTATAAGAGACAG | ACACCNGC | 460 |
| CAAGCAGAAGACGGCATACGAGATTANGGTGTCTCGTGGGCTCGGAGATGTGTATAAGAGACAG | ACACCNTA | 461 |
| CAAGCAGAAGACGGCATACGAGATGANGGTGTCTCGTGGGCTCGGAGATGTGTATAAGAGACAG | ACACCNTC | 462 |
| CAAGCAGAAGACGGCATACGAGATAGNCGTGTCTCGTGGGCTCGGAGATGTGTATAAGAGACAG | ACACGNCT | 463 |
| CAAGCAGAAGACGGCATACGAGATACNCGTGTCTCGTGGGCTCGGAGATGTGTATAAGAGACAG | ACACGNGT | 464 |
| CAAGCAGAAGACGGCATACGAGATAANCGTGTCTCGTGGGCTCGGAGATGTGTATAAGAGACAG | ACACGNTT | 465 |
| CAAGCAGAAGACGGCATACGAGATTGNAGTGTCTCGTGGGCTCGGAGATGTGTATAAGAGACAG | ACACTNCA | 466 |
| CAAGCAGAAGACGGCATACGAGATGGNAGTGTCTCGTGGGCTCGGAGATGTGTATAAGAGACAG | ACACTNCC | 467 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATTCNAGTGTGTCTCGTGGGCTCGGAGATGTGTATAAGAGACAG | ACACTNGA | 468 |
| CAAGCAGAAGACGGCATACGAGATGCNAGTGTGTCTCGTGGGCTCGGAGATGTGTATAAGAGACAG | ACACTNGC | 469 |
| CAAGCAGAAGACGGCATACGAGATTANAGTGTGTCTCGTGGGCTCGGAGATGTGTATAAGAGACAG | ACACTNTA | 470 |
| CAAGCAGAAGACGGCATACGAGATGANAGTGTGTCTCGTGGGCTCGGAGATGTGTATAAGAGACAG | ACACTNTC | 471 |
| CAAGCAGAAGACGGCATACGAGATCGNTCTGTGTCTCGTGGGCTCGGAGATGTGTATAAGAGACAG | ACAGANCG | 472 |
| CAAGCAGAAGACGGCATACGAGATCCNTCTGTGTCTCGTGGGCTCGGAGATGTGTATAAGAGACAG | ACAGANGG | 473 |
| CAAGCAGAAGACGGCATACGAGATCANTCTGTGTCTCGTGGGCTCGGAGATGTGTATAAGAGACAG | ACAGANTG | 474 |
| CAAGCAGAAGACGGCATACGAGATTGNCTGTGTCTCGTGGGCTCGGAGATGTGTATAAGAGACAG | ACAGCNCA | 475 |
| CAAGCAGAAGACGGCATACGAGATGGNCTGTGTCTCGTGGGCTCGGAGATGTGTATAAGAGACAG | ACAGCNCC | 476 |
| CAAGCAGAAGACGGCATACGAGATTCNGCTGTGTCTCGTGGGCTCGGAGATGTGTATAAGAGACAG | ACAGCNGA | 477 |
| CAAGCAGAAGACGGCATACGAGATGCNGCTGTGTCTCGTGGGCTCGGAGATGTGTATAAGAGACAG | ACAGCNGC | 478 |
| CAAGCAGAAGACGGCATACGAGATTANGCTGTGTCTCGTGGGCTCGGAGATGTGTATAAGAGACAG | ACAGCNTA | 479 |
| CAAGCAGAAGACGGCATACGAGATGANGCTGTGTCTCGTGGGCTCGGAGATGTGTATAAGAGACAG | ACAGCNTC | 480 |
| CAAGCAGAAGACGGCATACGAGATAGNCCTGTGTCTCGTGGGCTCGGAGATGTGTATAAGAGACAG | ACAGGNCT | 481 |
| CAAGCAGAAGACGGCATACGAGATACNCCTGTGTCTCGTGGGCTCGGAGATGTGTATAAGAGACAG | ACAGGNGT | 482 |
| CAAGCAGAAGACGGCATACGAGATAANCCTGTGTCTCGTGGGCTCGGAGATGTGTATAAGAGACAG | ACAGGNTT | 483 |
| CAAGCAGAAGACGGCATACGAGATTGNACTGTGTCTCGTGGGCTCGGAGATGTGTATAAGAGACAG | ACAGTNCA | 484 |
| CAAGCAGAAGACGGCATACGAGATGGNACTGTGTCTCGTGGGCTCGGAGATGTGTATAAGAGACAG | ACAGTNCC | 485 |
| CAAGCAGAAGACGGCATACGAGATTCNACTGTGTCTCGTGGGCTCGGAGATGTGTATAAGAGACAG | ACAGTNGA | 486 |
| CAAGCAGAAGACGGCATACGAGATGCNACTGTGTCTCGTGGGCTCGGAGATGTGTATAAGAGACAG | ACAGTNGC | 487 |
| CAAGCAGAAGACGGCATACGAGATTANACTGTGTCTCGTGGGCTCGGAGATGTGTATAAGAGACAG | ACAGTNTA | 488 |
| CAAGCAGAAGACGGCATACGAGATGANACTGTGTCTCGTGGGCTCGGAGATGTGTATAAGAGACAG | ACAGTNTC | 489 |
| CAAGCAGAAGACGGCATACGAGATTNNTNTGTGTCTCGTGGGCTCGGAGATGTGTATAAGAGACAG | ACANANNA | 490 |
| CAAGCAGAAGACGGCATACGAGATGNNTNTGTGTCTCGTGGGCTCGGAGATGTGTATAAGAGACAG | ACANANNC | 491 |
| CAAGCAGAAGACGGCATACGAGATANNGNTGTGTCTCGTGGGCTCGGAGATGTGTATAAGAGACAG | ACANCNNT | 492 |
| CAAGCAGAAGACGGCATACGAGATANNANTGTGTCTCGTGGGCTCGGAGATGTGTATAAGAGACAG | ACANTNNT | 493 |
| CAAGCAGAAGACGGCATACGAGATCNNTATGTGTCTCGTGGGCTCGGAGATGTGTATAAGAGACAG | ACATANNG | 494 |
| CAAGCAGAAGACGGCATACGAGATCGTGATGTGTCTCGTGGGCTCGGAGATGTGTATAAGAGACAG | ACATCACG | 495 |
| CAAGCAGAAGACGGCATACGAGATCATGATGTGTCTCGTGGGCTCGGAGATGTGTATAAGAGACAG | ACATCATG | 496 |
| CAAGCAGAAGACGGCATACGAGATCGCGATGTGTCTCGTGGGCTCGGAGATGTGTATAAGAGACAG | ACATCGCG | 497 |
| CAAGCAGAAGACGGCATACGAGATCACGATGTGTCTCGTGGGCTCGGAGATGTGTATAAGAGACAG | ACATCGTG | 498 |
| CAAGCAGAAGACGGCATACGAGATCCNGATGTGTCTCGTGGGCTCGGAGATGTGTATAAGAGACAG | ACATCNGG | 499 |
| CAAGCAGAAGACGGCATACGAGATTNNGATGTGTCTCGTGGGCTCGGAGATGTGTATAAGAGACAG | ACATCNNA | 500 |
| CAAGCAGAAGACGGCATACGAGATGNNGATGTGTCTCGTGGGCTCGGAGATGTGTATAAGAGACAG | ACATCNNC | 501 |
| CAAGCAGAAGACGGCATACGAGATCGAGATGTGTCTCGTGGGCTCGGAGATGTGTATAAGAGACAG | ACATCTCG | 502 |
| CAAGCAGAAGACGGCATACGAGATCAAGATGTGTCTCGTGGGCTCGGAGATGTGTATAAGAGACAG | ACATCTTG | 503 |
| CAAGCAGAAGACGGCATACGAGATTGNCATGTGTCTCGTGGGCTCGGAGATGTGTATAAGAGACAG | ACATGNCA | 504 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATGGNCATGTGTCTCGTGGGCTCGGAGATGTGTATAAGAGACAG | ACATGNCC | 505 |
| CAAGCAGAAGACGGCATACGAGATTCNCATGTGTCTCGTGGGCTCGGAGATGTGTATAAGAGACAG | ACATGNGA | 506 |
| CAAGCAGAAGACGGCATACGAGATGCNCATGTGTCTCGTGGGCTCGGAGATGTGTATAAGAGACAG | ACATGNGC | 507 |
| CAAGCAGAAGACGGCATACGAGATANNCATGTGTCTCGTGGGCTCGGAGATGTGTATAAGAGACAG | ACATGNNT | 508 |
| CAAGCAGAAGACGGCATACGAGATTANCATGTGTCTCGTGGGCTCGGAGATGTGTATAAGAGACAG | ACATGNTA | 509 |
| CAAGCAGAAGACGGCATACGAGATGANCATGTGTCTCGTGGGCTCGGAGATGTGTATAAGAGACAG | ACATGNTC | 510 |
| CAAGCAGAAGACGGCATACGAGATCGTAATGTGTCTCGTGGGCTCGGAGATGTGTATAAGAGACAG | ACATTACG | 511 |
| CAAGCAGAAGACGGCATACGAGATCATAATGTGTCTCGTGGGCTCGGAGATGTGTATAAGAGACAG | ACATTATG | 512 |
| CAAGCAGAAGACGGCATACGAGATCGCAATGTGTCTCGTGGGCTCGGAGATGTGTATAAGAGACAG | ACATTGCG | 513 |
| CAAGCAGAAGACGGCATACGAGATCACAATGTGTCTCGTGGGCTCGGAGATGTGTATAAGAGACAG | ACATTGTG | 514 |
| CAAGCAGAAGACGGCATACGAGATCCNAATGTGTCTCGTGGGCTCGGAGATGTGTATAAGAGACAG | ACATTNGG | 515 |
| CAAGCAGAAGACGGCATACGAGATTNNAATGTGTCTCGTGGGCTCGGAGATGTGTATAAGAGACAG | ACATTNNA | 516 |
| CAAGCAGAAGACGGCATACGAGATGNNAATGTGTCTCGTGGGCTCGGAGATGTGTATAAGAGACAG | ACATTNNC | 517 |
| CAAGCAGAAGACGGCATACGAGATCGAAATGTGTCTCGTGGGCTCGGAGATGTGTATAAGAGACAG | ACATTTCG | 518 |
| CAAGCAGAAGACGGCATACGAGATCAAAATGTGTCTCGTGGGCTCGGAGATGTGTATAAGAGACAG | ACATTTTG | 519 |
| CAAGCAGAAGACGGCATACGAGATCTTTTGGTGTCTCGTGGGCTCGGAGATGTGTATAAGAGACAG | ACCAAAAG | 520 |
| CAAGCAGAAGACGGCATACGAGATCTCTTGGTGTCTCGTGGGCTCGGAGATGTGTATAAGAGACAG | ACCAAGAG | 521 |
| CAAGCAGAAGACGGCATACGAGATCGNTTGGTGTCTCGTGGGCTCGGAGATGTGTATAAGAGACAG | ACCAANCG | 522 |
| CAAGCAGAAGACGGCATACGAGATCCNTTGGTGTCTCGTGGGCTCGGAGATGTGTATAAGAGACAG | ACCAANGG | 523 |
| CAAGCAGAAGACGGCATACGAGATTNNTTGGTGTCTCGTGGGCTCGGAGATGTGTATAAGAGACAG | ACCAANNA | 524 |
| CAAGCAGAAGACGGCATACGAGATGNNTTGGTGTCTCGTGGGCTCGGAGATGTGTATAAGAGACAG | ACCAANNC | 525 |
| CAAGCAGAAGACGGCATACGAGATCANTTGGTGTCTCGTGGGCTCGGAGATGTGTATAAGAGACAG | ACCAANTG | 526 |
| CAAGCAGAAGACGGCATACGAGATCTATTGGTGTCTCGTGGGCTCGGAGATGTGTATAAGAGACAG | ACCAATAG | 527 |
| CAAGCAGAAGACGGCATACGAGATTGNGTGGTGTCTCGTGGGCTCGGAGATGTGTATAAGAGACAG | ACCACNCA | 528 |
| CAAGCAGAAGACGGCATACGAGATGGNGTGGTGTCTCGTGGGCTCGGAGATGTGTATAAGAGACAG | ACCACNCC | 529 |
| CAAGCAGAAGACGGCATACGAGATTCNGTGGTGTCTCGTGGGCTCGGAGATGTGTATAAGAGACAG | ACCACNGA | 530 |
| CAAGCAGAAGACGGCATACGAGATGCNGTGGTGTCTCGTGGGCTCGGAGATGTGTATAAGAGACAG | ACCACNGC | 531 |
| CAAGCAGAAGACGGCATACGAGATANNGTGGTGTCTCGTGGGCTCGGAGATGTGTATAAGAGACAG | ACCACNNT | 532 |
| CAAGCAGAAGACGGCATACGAGATTANGTGGTGTCTCGTGGGCTCGGAGATGTGTATAAGAGACAG | ACCACNTA | 533 |
| CAAGCAGAAGACGGCATACGAGATGANGTGGTGTCTCGTGGGCTCGGAGATGTGTATAAGAGACAG | ACCACNTC | 534 |
| CAAGCAGAAGACGGCATACGAGATATTCTGGTGTCTCGTGGGCTCGGAGATGTGTATAAGAGACAG | ACCAGAAT | 535 |
| CAAGCAGAAGACGGCATACGAGATATCCTGGTGTCTCGTGGGCTCGGAGATGTGTATAAGAGACAG | ACCAGGAT | 536 |
| CAAGCAGAAGACGGCATACGAGATAGNCTGGTGTCTCGTGGGCTCGGAGATGTGTATAAGAGACAG | ACCAGNCT | 537 |
| CAAGCAGAAGACGGCATACGAGATACNCTGGTGTCTCGTGGGCTCGGAGATGTGTATAAGAGACAG | ACCAGNGT | 538 |
| CAAGCAGAAGACGGCATACGAGATAANCTGGTGTCTCGTGGGCTCGGAGATGTGTATAAGAGACAG | ACCAGNTT | 539 |
| CAAGCAGAAGACGGCATACGAGATATACTGGTGTCTCGTGGGCTCGGAGATGTGTATAAGAGACAG | ACCAGTAT | 540 |
| CAAGCAGAAGACGGCATACGAGATTGNATGGTGTCTCGTGGGCTCGGAGATGTGTATAAGAGACAG | ACCATNCA | 541 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATGGNATGGTGTCTCGTGGGCTCGGAGATGTGTATAAGAGACAG | ACCATNCC | 542 |
| CAAGCAGAAGACGGCATACGAGATTCNATGGTGTCTCGTGGGCTCGGAGATGTGTATAAGAGACAG | ACCATNGA | 543 |
| CAAGCAGAAGACGGCATACGAGATGCNATGGTGTCTCGTGGGCTCGGAGATGTGTATAAGAGACAG | ACCATNGC | 544 |
| CAAGCAGAAGACGGCATACGAGATANNATGGTGTCTCGTGGGCTCGGAGATGTGTATAAGAGACAG | ACCATNNT | 545 |
| CAAGCAGAAGACGGCATACGAGATTANATGGTGTCTCGTGGGCTCGGAGATGTGTATAAGAGACAG | ACCATNTA | 546 |
| CAAGCAGAAGACGGCATACGAGATGANATGGTGTCTCGTGGGCTCGGAGATGTGTATAAGAGACAG | ACCATNTC | 547 |
| CAAGCAGAAGACGGCATACGAGATTGTTGGGTGTCTCGTGGGCTCGGAGATGTGTATAAGAGACAG | ACCCAACA | 548 |
| CAAGCAGAAGACGGCATACGAGATGGTTGGGTGTCTCGTGGGCTCGGAGATGTGTATAAGAGACAG | ACCCAACC | 549 |
| CAAGCAGAAGACGGCATACGAGATTATTGGGTGTCTCGTGGGCTCGGAGATGTGTATAAGAGACAG | ACCCAATA | 550 |
| CAAGCAGAAGACGGCATACGAGATGATTGGGTGTCTCGTGGGCTCGGAGATGTGTATAAGAGACAG | ACCCAATC | 551 |
| CAAGCAGAAGACGGCATACGAGATTGCTGGGTGTCTCGTGGGCTCGGAGATGTGTATAAGAGACAG | ACCCAGCA | 552 |
| CAAGCAGAAGACGGCATACGAGATGGCTGGGTGTCTCGTGGGCTCGGAGATGTGTATAAGAGACAG | ACCCAGCC | 553 |
| CAAGCAGAAGACGGCATACGAGATTACTGGGTGTCTCGTGGGCTCGGAGATGTGTATAAGAGACAG | ACCCAGTA | 554 |
| CAAGCAGAAGACGGCATACGAGATGACTGGGTGTCTCGTGGGCTCGGAGATGTGTATAAGAGACAG | ACCCAGTC | 555 |
| CAAGCAGAAGACGGCATACGAGATTCNTGGGTGTCTCGTGGGCTCGGAGATGTGTATAAGAGACAG | ACCCANGA | 556 |
| CAAGCAGAAGACGGCATACGAGATGCNTGGGTGTCTCGTGGGCTCGGAGATGTGTATAAGAGACAG | ACCCANGC | 557 |
| CAAGCAGAAGACGGCATACGAGATTGATGGGTGTCTCGTGGGCTCGGAGATGTGTATAAGAGACAG | ACCCATCA | 558 |
| CAAGCAGAAGACGGCATACGAGATGGATGGGTGTCTCGTGGGCTCGGAGATGTGTATAAGAGACAG | ACCCATCC | 559 |
| CAAGCAGAAGACGGCATACGAGATTAATGGGTGTCTCGTGGGCTCGGAGATGTGTATAAGAGACAG | ACCCATTA | 560 |
| CAAGCAGAAGACGGCATACGAGATGAATGGGTGTCTCGTGGGCTCGGAGATGTGTATAAGAGACAG | ACCCATTC | 561 |
| CAAGCAGAAGACGGCATACGAGATTCNTCGGTGTCTCGTGGGCTCGGAGATGTGTATAAGAGACAG | ACCGANGA | 562 |
| CAAGCAGAAGACGGCATACGAGATGCNTCGGTGTCTCGTGGGCTCGGAGATGTGTATAAGAGACAG | ACCGANGC | 563 |
| CAAGCAGAAGACGGCATACGAGATTNNTAGGTGTCTCGTGGGCTCGGAGATGTGTATAAGAGACAG | ACCTANNA | 564 |
| CAAGCAGAAGACGGCATACGAGATGNNTAGGTGTCTCGTGGGCTCGGAGATGTGTATAAGAGACAG | ACCTANNC | 565 |
| CAAGCAGAAGACGGCATACGAGATAGNGAGGTGTCTCGTGGGCTCGGAGATGTGTATAAGAGACAG | ACCTCNCT | 566 |
| CAAGCAGAAGACGGCATACGAGATACNGAGGTGTCTCGTGGGCTCGGAGATGTGTATAAGAGACAG | ACCTCNGT | 567 |
| CAAGCAGAAGACGGCATACGAGATAANGAGGTGTCTCGTGGGCTCGGAGATGTGTATAAGAGACAG | ACCTCNTT | 568 |
| CAAGCAGAAGACGGCATACGAGATAGNAAGGTGTCTCGTGGGCTCGGAGATGTGTATAAGAGACAG | ACCTTNCT | 569 |
| CAAGCAGAAGACGGCATACGAGATACNAAGGTGTCTCGTGGGCTCGGAGATGTGTATAAGAGACAG | ACCTTNGT | 570 |
| CAAGCAGAAGACGGCATACGAGATAANAAGGTGTCTCGTGGGCTCGGAGATGTGTATAAGAGACAG | ACCTTNTT | 571 |
| CAAGCAGAAGACGGCATACGAGATCGNTTCGTGTCTCGTGGGCTCGGAGATGTGTATAAGAGACAG | ACGAANCG | 572 |
| CAAGCAGAAGACGGCATACGAGATCCNTTCGTGTCTCGTGGGCTCGGAGATGTGTATAAGAGACAG | ACGAANGG | 573 |
| CAAGCAGAAGACGGCATACGAGATTNNTTCGTGTCTCGTGGGCTCGGAGATGTGTATAAGAGACAG | ACGAANNA | 574 |
| CAAGCAGAAGACGGCATACGAGATGNNTTCGTGTCTCGTGGGCTCGGAGATGTGTATAAGAGACAG | ACGAANNC | 575 |
| CAAGCAGAAGACGGCATACGAGATCANTTCGTGTCTCGTGGGCTCGGAGATGTGTATAAGAGACAG | ACGAANTG | 576 |
| CAAGCAGAAGACGGCATACGAGATTGNTCGTGTCTCGTGGGCTCGGAGATGTGTATAAGAGACAG | ACGACNCA | 577 |
| CAAGCAGAAGACGGCATACGAGATGGNTCGTGTCTCGTGGGCTCGGAGATGTGTATAAGAGACAG | ACGACNCC | 578 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATTCNGTCGTGTCTCGTGGGCTCGGAGATGTGTATAAGAGACAG | ACGACNGA | 579 |
| CAAGCAGAAGACGGCATACGAGATGCNGTCGTGTCTCGTGGGCTCGGAGATGTGTATAAGAGACAG | ACGACNGC | 580 |
| CAAGCAGAAGACGGCATACGAGATANNGTCGTGTCTCGTGGGCTCGGAGATGTGTATAAGAGACAG | ACGACNNT | 581 |
| CAAGCAGAAGACGGCATACGAGATTANGTCGTGTCTCGTGGGCTCGGAGATGTGTATAAGAGACAG | ACGACNTA | 582 |
| CAAGCAGAAGACGGCATACGAGATGANGTCGTGTCTCGTGGGCTCGGAGATGTGTATAAGAGACAG | ACGACNTC | 583 |
| CAAGCAGAAGACGGCATACGAGATAGNCTCGTGTCTCGTGGGCTCGGAGATGTGTATAAGAGACAG | ACGAGNCT | 584 |
| CAAGCAGAAGACGGCATACGAGATACNCTCGTGTCTCGTGGGCTCGGAGATGTGTATAAGAGACAG | ACGAGNGT | 585 |
| CAAGCAGAAGACGGCATACGAGATAANCTCGTGTCTCGTGGGCTCGGAGATGTGTATAAGAGACAG | ACGAGNTT | 586 |
| CAAGCAGAAGACGGCATACGAGATTGNATCGTGTCTCGTGGGCTCGGAGATGTGTATAAGAGACAG | ACGATNCA | 587 |
| CAAGCAGAAGACGGCATACGAGATGGNATCGTGTCTCGTGGGCTCGGAGATGTGTATAAGAGACAG | ACGATNCC | 588 |
| CAAGCAGAAGACGGCATACGAGATTCNATCGTGTCTCGTGGGCTCGGAGATGTGTATAAGAGACAG | ACGATNGA | 589 |
| CAAGCAGAAGACGGCATACGAGATGCNATCGTGTCTCGTGGGCTCGGAGATGTGTATAAGAGACAG | ACGATNGC | 590 |
| CAAGCAGAAGACGGCATACGAGATANNATCGTGTCTCGTGGGCTCGGAGATGTGTATAAGAGACAG | ACGATNNT | 591 |
| CAAGCAGAAGACGGCATACGAGATTANATCGTGTCTCGTGGGCTCGGAGATGTGTATAAGAGACAG | ACGATNTA | 592 |
| CAAGCAGAAGACGGCATACGAGATGANATCGTGTCTCGTGGGCTCGGAGATGTGTATAAGAGACAG | ACGATNTC | 593 |
| CAAGCAGAAGACGGCATACGAGATTCTTGCGTGTCTCGTGGGCTCGGAGATGTGTATAAGAGACAG | ACGCAAGA | 594 |
| CAAGCAGAAGACGGCATACGAGATGCTTGCGTGTCTCGTGGGCTCGGAGATGTGTATAAGAGACAG | ACGCAAGC | 595 |
| CAAGCAGAAGACGGCATACGAGATTCCTGCGTGTCTCGTGGGCTCGGAGATGTGTATAAGAGACAG | ACGCAGGA | 596 |
| CAAGCAGAAGACGGCATACGAGATGCCTGCGTGTCTCGTGGGCTCGGAGATGTGTATAAGAGACAG | ACGCAGGC | 597 |
| CAAGCAGAAGACGGCATACGAGATTCATGCGTGTCTCGTGGGCTCGGAGATGTGTATAAGAGACAG | ACGCATGA | 598 |
| CAAGCAGAAGACGGCATACGAGATGCATGCGTGTCTCGTGGGCTCGGAGATGTGTATAAGAGACAG | ACGCATGC | 599 |
| CAAGCAGAAGACGGCATACGAGATTCTTCCGTGTCTCGTGGGCTCGGAGATGTGTATAAGAGACAG | ACGGAAGA | 600 |
| CAAGCAGAAGACGGCATACGAGATGCTTCCGTGTCTCGTGGGCTCGGAGATGTGTATAAGAGACAG | ACGGAAGC | 601 |
| CAAGCAGAAGACGGCATACGAGATTCCTCCGTGTCTCGTGGGCTCGGAGATGTGTATAAGAGACAG | ACGGAGGA | 602 |
| CAAGCAGAAGACGGCATACGAGATGCCTCCGTGTCTCGTGGGCTCGGAGATGTGTATAAGAGACAG | ACGGAGGC | 603 |
| CAAGCAGAAGACGGCATACGAGATTCATCCGTGTCTCGTGGGCTCGGAGATGTGTATAAGAGACAG | ACGGATGA | 604 |
| CAAGCAGAAGACGGCATACGAGATGCATCCGTGTCTCGTGGGCTCGGAGATGTGTATAAGAGACAG | ACGGATGC | 605 |
| CAAGCAGAAGACGGCATACGAGATTNNTACGTGTCTCGTGGGCTCGGAGATGTGTATAAGAGACAG | ACGTANNA | 606 |
| CAAGCAGAAGACGGCATACGAGATGNNTACGTGTCTCGTGGGCTCGGAGATGTGTATAAGAGACAG | ACGTANNC | 607 |
| CAAGCAGAAGACGGCATACGAGATAGNGACGTGTCTCGTGGGCTCGGAGATGTGTATAAGAGACAG | ACGTCNCT | 608 |
| CAAGCAGAAGACGGCATACGAGATACNGACGTGTCTCGTGGGCTCGGAGATGTGTATAAGAGACAG | ACGTCNGT | 609 |
| CAAGCAGAAGACGGCATACGAGATAANGACGTGTCTCGTGGGCTCGGAGATGTGTATAAGAGACAG | ACGTCNTT | 610 |
| CAAGCAGAAGACGGCATACGAGATAGNAACGTGTCTCGTGGGCTCGGAGATGTGTATAAGAGACAG | ACGTTNCT | 611 |
| CAAGCAGAAGACGGCATACGAGATACNAACGTGTCTCGTGGGCTCGGAGATGTGTATAAGAGACAG | ACGTTNGT | 612 |
| CAAGCAGAAGACGGCATACGAGATAANAACGTGTCTCGTGGGCTCGGAGATGTGTATAAGAGACAG | ACGTTNTT | 613 |
| CAAGCAGAAGACGGCATACGAGATANNTNNGTGTCTCGTGGGCTCGGAGATGTGTATAAGAGACAG | ACNNANNT | 614 |
| CAAGCAGAAGACGGCATACGAGATCNNTTAGTGTCTCGTGGGCTCGGAGATGTGTATAAGAGACAG | ACTAANNG | 615 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATCGNGTAGTGTCTCGTGGGCTCGGAGATGTGTATAAGAGACAG | ACTACNCG | 616 |
| CAAGCAGAAGACGGCATACGAGATCCNGTAGTGTCTCGTGGGCTCGGAGATGTGTATAAGAGACAG | ACTACNGG | 617 |
| CAAGCAGAAGACGGCATACGAGATTNNGTAGTGTCTCGTGGGCTCGGAGATGTGTATAAGAGACAG | ACTACNNA | 618 |
| CAAGCAGAAGACGGCATACGAGATGNNGTAGTGTCTCGTGGGCTCGGAGATGTGTATAAGAGACAG | ACTACNNC | 619 |
| CAAGCAGAAGACGGCATACGAGATANNGTAGTGTCTCGTGGGCTCGGAGATGTGTATAAGAGACAG | ACTACNNT | 620 |
| CAAGCAGAAGACGGCATACGAGATCANGTAGTGTCTCGTGGGCTCGGAGATGTGTATAAGAGACAG | ACTACNTG | 621 |
| CAAGCAGAAGACGGCATACGAGATTGNCTAGTGTCTCGTGGGCTCGGAGATGTGTATAAGAGACAG | ACTAGNCA | 622 |
| CAAGCAGAAGACGGCATACGAGATGGNCTAGTGTCTCGTGGGCTCGGAGATGTGTATAAGAGACAG | ACTAGNCC | 623 |
| CAAGCAGAAGACGGCATACGAGATTCNCTAGTGTCTCGTGGGCTCGGAGATGTGTATAAGAGACAG | ACTAGNGA | 624 |
| CAAGCAGAAGACGGCATACGAGATGCNCTAGTGTCTCGTGGGCTCGGAGATGTGTATAAGAGACAG | ACTAGNGC | 625 |
| CAAGCAGAAGACGGCATACGAGATANNCTAGTGTCTCGTGGGCTCGGAGATGTGTATAAGAGACAG | ACTAGNNT | 626 |
| CAAGCAGAAGACGGCATACGAGATTANCTAGTGTCTCGTGGGCTCGGAGATGTGTATAAGAGACAG | ACTAGNTA | 627 |
| CAAGCAGAAGACGGCATACGAGATGANCTAGTGTCTCGTGGGCTCGGAGATGTGTATAAGAGACAG | ACTAGNTC | 628 |
| CAAGCAGAAGACGGCATACGAGATCGNATAGTGTCTCGTGGGCTCGGAGATGTGTATAAGAGACAG | ACTATNCG | 629 |
| CAAGCAGAAGACGGCATACGAGATCCNATAGTGTCTCGTGGGCTCGGAGATGTGTATAAGAGACAG | ACTATNGG | 630 |
| CAAGCAGAAGACGGCATACGAGATTNNATAGTGTCTCGTGGGCTCGGAGATGTGTATAAGAGACAG | ACTATNNA | 631 |
| CAAGCAGAAGACGGCATACGAGATGNNATAGTGTCTCGTGGGCTCGGAGATGTGTATAAGAGACAG | ACTATNNC | 632 |
| CAAGCAGAAGACGGCATACGAGATANNATAGTGTCTCGTGGGCTCGGAGATGTGTATAAGAGACAG | ACTATNNT | 633 |
| CAAGCAGAAGACGGCATACGAGATCANATAGTGTCTCGTGGGCTCGGAGATGTGTATAAGAGACAG | ACTATNTG | 634 |
| CAAGCAGAAGACGGCATACGAGATAGNGGAGTGTCTCGTGGGCTCGGAGATGTGTATAAGAGACAG | ACTCCNCT | 635 |
| CAAGCAGAAGACGGCATACGAGATACNGGAGTGTCTCGTGGGCTCGGAGATGTGTATAAGAGACAG | ACTCCNGT | 636 |
| CAAGCAGAAGACGGCATACGAGATAANGGAGTGTCTCGTGGGCTCGGAGATGTGTATAAGAGACAG | ACTCCNTT | 637 |
| CAAGCAGAAGACGGCATACGAGATAGNAGAGTGTCTCGTGGGCTCGGAGATGTGTATAAGAGACAG | ACTCTNCT | 638 |
| CAAGCAGAAGACGGCATACGAGATACNAGAGTGTCTCGTGGGCTCGGAGATGTGTATAAGAGACAG | ACTCTNGT | 639 |
| CAAGCAGAAGACGGCATACGAGATAANAGAGTGTCTCGTGGGCTCGGAGATGTGTATAAGAGACAG | ACTCTNTT | 640 |
| CAAGCAGAAGACGGCATACGAGATAGNCAGTGTCTCGTGGGCTCGGAGATGTGTATAAGAGACAG | ACTGCNCT | 641 |
| CAAGCAGAAGACGGCATACGAGATACNCAGTGTCTCGTGGGCTCGGAGATGTGTATAAGAGACAG | ACTGCNGT | 642 |
| CAAGCAGAAGACGGCATACGAGATAANCAGTGTCTCGTGGGCTCGGAGATGTGTATAAGAGACAG | ACTGCNTT | 643 |
| CAAGCAGAAGACGGCATACGAGATAGNACAGTGTCTCGTGGGCTCGGAGATGTGTATAAGAGACAG | ACTGTNCT | 644 |
| CAAGCAGAAGACGGCATACGAGATACNACAGTGTCTCGTGGGCTCGGAGATGTGTATAAGAGACAG | ACTGTNGT | 645 |
| CAAGCAGAAGACGGCATACGAGATAANACAGTGTCTCGTGGGCTCGGAGATGTGTATAAGAGACAG | ACTGTNTT | 646 |
| CAAGCAGAAGACGGCATACGAGATTNNTNAGTGTCTCGTGGGCTCGGAGATGTGTATAAGAGACAG | ACTNANNA | 647 |
| CAAGCAGAAGACGGCATACGAGATGNNTNAGTGTCTCGTGGGCTCGGAGATGTGTATAAGAGACAG | ACTNANNC | 648 |
| CAAGCAGAAGACGGCATACGAGATCGNTAAGTGTCTCGTGGGCTCGGAGATGTGTATAAGAGACAG | ACTTANCG | 649 |
| CAAGCAGAAGACGGCATACGAGATCCNTAAGTGTCTCGTGGGCTCGGAGATGTGTATAAGAGACAG | ACTTANGG | 650 |
| CAAGCAGAAGACGGCATACGAGATCANTAAGTGTCTCGTGGGCTCGGAGATGTGTATAAGAGACAG | ACTTANTG | 651 |
| CAAGCAGAAGACGGCATACGAGATTGNGAAGTGTCTCGTGGGCTCGGAGATGTGTATAAGAGACAG | ACTTCNCA | 652 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATGGNGAAGTGTCTCGTGGGCTCGGAGATGTGTATAAGAGACAG | ACTTCNCC | 653 |
| CAAGCAGAAGACGGCATACGAGATTCNGAAGTGTCTCGTGGGCTCGGAGATGTGTATAAGAGACAG | ACTTCNGA | 654 |
| CAAGCAGAAGACGGCATACGAGATGCNGAAGTGTCTCGTGGGCTCGGAGATGTGTATAAGAGACAG | ACTTCNGC | 655 |
| CAAGCAGAAGACGGCATACGAGATANNGAAGTGTCTCGTGGGCTCGGAGATGTGTATAAGAGACAG | ACTTCNNT | 656 |
| CAAGCAGAAGACGGCATACGAGATTANGAAGTGTCTCGTGGGCTCGGAGATGTGTATAAGAGACAG | ACTTCNTA | 657 |
| CAAGCAGAAGACGGCATACGAGATGANGAAGTGTCTCGTGGGCTCGGAGATGTGTATAAGAGACAG | ACTTCNTC | 658 |
| CAAGCAGAAGACGGCATACGAGATAGNCAAGTGTCTCGTGGGCTCGGAGATGTGTATAAGAGACAG | ACTTGNCT | 659 |
| CAAGCAGAAGACGGCATACGAGATACNCAAGTGTCTCGTGGGCTCGGAGATGTGTATAAGAGACAG | ACTTGNGT | 660 |
| CAAGCAGAAGACGGCATACGAGATAANCAAGTGTCTCGTGGGCTCGGAGATGTGTATAAGAGACAG | ACTTGNTT | 661 |
| CAAGCAGAAGACGGCATACGAGATTGNAAAGTGTCTCGTGGGCTCGGAGATGTGTATAAGAGACAG | ACTTTNCA | 662 |
| CAAGCAGAAGACGGCATACGAGATGGNAAAGTGTCTCGTGGGCTCGGAGATGTGTATAAGAGACAG | ACTTTNCC | 663 |
| CAAGCAGAAGACGGCATACGAGATTCNAAAGTGTCTCGTGGGCTCGGAGATGTGTATAAGAGACAG | ACTTTNGA | 664 |
| CAAGCAGAAGACGGCATACGAGATGCNAAAGTGTCTCGTGGGCTCGGAGATGTGTATAAGAGACAG | ACTTTNGC | 665 |
| CAAGCAGAAGACGGCATACGAGATANNAAAGTGTCTCGTGGGCTCGGAGATGTGTATAAGAGACAG | ACTTTNNT | 666 |
| CAAGCAGAAGACGGCATACGAGATTANAAAGTGTCTCGTGGGCTCGGAGATGTGTATAAGAGACAG | ACTTTNTA | 667 |
| CAAGCAGAAGACGGCATACGAGATGANAAAGTGTCTCGTGGGCTCGGAGATGTGTATAAGAGACAG | ACTTTNTC | 668 |
| CAAGCAGAAGACGGCATACGAGATCTTTTCTGTCTCGTGGGCTCGGAGATGTGTATAAGAGACAG | AGAAAAAG | 669 |
| CAAGCAGAAGACGGCATACGAGATCTCTTTCTGTCTCGTGGGCTCGGAGATGTGTATAAGAGACAG | AGAAAGAG | 670 |
| CAAGCAGAAGACGGCATACGAGATCGNTTTCTGTCTCGTGGGCTCGGAGATGTGTATAAGAGACAG | AGAAANCG | 671 |
| CAAGCAGAAGACGGCATACGAGATCCNTTTCTGTCTCGTGGGCTCGGAGATGTGTATAAGAGACAG | AGAAANGG | 672 |
| CAAGCAGAAGACGGCATACGAGATTNNTTTCTGTCTCGTGGGCTCGGAGATGTGTATAAGAGACAG | AGAAANNA | 673 |
| CAAGCAGAAGACGGCATACGAGATGNNTTTCTGTCTCGTGGGCTCGGAGATGTGTATAAGAGACAG | AGAAANNC | 674 |
| CAAGCAGAAGACGGCATACGAGATCANTTTCTGTCTCGTGGGCTCGGAGATGTGTATAAGAGACAG | AGAAANTG | 675 |
| CAAGCAGAAGACGGCATACGAGATCTATTTCTGTCTCGTGGGCTCGGAGATGTGTATAAGAGACAG | AGAAATAG | 676 |
| CAAGCAGAAGACGGCATACGAGATTGNTTCTGTCTCGTGGGCTCGGAGATGTGTATAAGAGACAG | AGAACNCA | 677 |
| CAAGCAGAAGACGGCATACGAGATGGNTTCTGTCTCGTGGGCTCGGAGATGTGTATAAGAGACAG | AGAACNCC | 678 |
| CAAGCAGAAGACGGCATACGAGATTCNGTTCTGTCTCGTGGGCTCGGAGATGTGTATAAGAGACAG | AGAACNGA | 679 |
| CAAGCAGAAGACGGCATACGAGATGCNGTTCTGTCTCGTGGGCTCGGAGATGTGTATAAGAGACAG | AGAACNGC | 680 |
| CAAGCAGAAGACGGCATACGAGATANNGTTCTGTCTCGTGGGCTCGGAGATGTGTATAAGAGACAG | AGAACNNT | 681 |
| CAAGCAGAAGACGGCATACGAGATTANGTTCTGTCTCGTGGGCTCGGAGATGTGTATAAGAGACAG | AGAACNTA | 682 |
| CAAGCAGAAGACGGCATACGAGATGANGTTCTGTCTCGTGGGCTCGGAGATGTGTATAAGAGACAG | AGAACNTC | 683 |
| CAAGCAGAAGACGGCATACGAGATAGNCTTCTGTCTCGTGGGCTCGGAGATGTGTATAAGAGACAG | AGAAGNCT | 684 |
| CAAGCAGAAGACGGCATACGAGATACNCTTCTGTCTCGTGGGCTCGGAGATGTGTATAAGAGACAG | AGAAGNGT | 685 |
| CAAGCAGAAGACGGCATAGGAGATAANCTTCTGTCTCGTGGGCTCGGAGATGTGTATAAGAGACAG | AGAAGNTT | 686 |
| CAAGCAGAAGACGGCATACGAGATTGNATTCTGTCTCGTGGGCTCGGAGATGTGTATAAGAGACAG | AGAATNCA | 687 |
| CAAGCAGAAGACGGCATACGAGATGGNATTCTGTCTCGTGGGCTCGGAGATGTGTATAAGAGACAG | AGAATNCC | 688 |
| CAAGCAGAAGACGGCATACGAGATTCNATTCTGTCTCGTGGGCTCGGAGATGTGTATAAGAGACAG | AGAATNGA | 689 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATGCNATTCTGTCTCGTGGGCTCGGAGATGTGTATAAGAGACAG | AGAATNGC | 690 |
| CAAGCAGAAGACGGCATACGAGATANNATTCTGTCTCGTGGGCTCGGAGATGTGTATAAGAGACAG | AGAATNNT | 691 |
| CAAGCAGAAGACGGCATACGAGATTANATTCTGTCTCGTGGGCTCGGAGATGTGTATAAGAGACAG | AGAATNTA | 692 |
| CAAGCAGAAGACGGCATACGAGATGANATTCTGTCTCGTGGGCTCGGAGATGTGTATAAGAGACAG | AGAATNTC | 693 |
| CAAGCAGAAGACGGCATACGAGATTCNTGTCTCGTGGGCTCGGAGATGTGTATAAGAGACAG | AGACANGA | 694 |
| CAAGCAGAAGACGGCATACGAGATGCNTGTCTCGTGGGCTCGGAGATGTGTATAAGAGACAG | AGACANGC | 695 |
| CAAGCAGAAGACGGCATACGAGATTCTTCTGTCTCGTGGGCTCGGAGATGTGTATAAGAGACAG | AGAGAAGA | 696 |
| CAAGCAGAAGACGGCATACGAGATGCTTCTGTCTCGTGGGCTCGGAGATGTGTATAAGAGACAG | AGAGAAGC | 697 |
| CAAGCAGAAGACGGCATACGAGATTCCTCTGTCTCGTGGGCTCGGAGATGTGTATAAGAGACAG | AGAGAGGA | 698 |
| CAAGCAGAAGACGGCATACGAGATGCCTCTGTCTCGTGGGCTCGGAGATGTGTATAAGAGACAG | AGAGAGGC | 699 |
| CAAGCAGAAGACGGCATACGAGATTCATCTGTCTCGTGGGCTCGGAGATGTGTATAAGAGACAG | AGAGATGA | 700 |
| CAAGCAGAAGACGGCATACGAGATGCATCTGTCTCGTGGGCTCGGAGATGTGTATAAGAGACAG | AGAGATGC | 701 |
| CAAGCAGAAGACGGCATACGAGATANNTNTCTGTCTCGTGGGCTCGGAGATGTGTATAAGAGACAG | AGANANNT | 702 |
| CAAGCAGAAGACGGCATACGAGATTNNTATCTGTCTCGTGGGCTCGGAGATGTGTATAAGAGACAG | AGATANNA | 703 |
| CAAGCAGAAGACGGCATACGAGATGNNTATCTGTCTCGTGGGCTCGGAGATGTGTATAAGAGACAG | AGATANNC | 704 |
| CAAGCAGAAGACGGCATACGAGATAGNGATCTGTCTCGTGGGCTCGGAGATGTGTATAAGAGACAG | AGATCNCT | 705 |
| CAAGCAGAAGACGGCATACGAGATACNGATCTGTCTCGTGGGCTCGGAGATGTGTATAAGAGACAG | AGATCNGT | 706 |
| CAAGCAGAAGACGGCATACGAGATAANGATCTGTCTCGTGGGCTCGGAGATGTGTATAAGAGACAG | AGATCNTT | 707 |
| CAAGCAGAAGACGGCATACGAGATAGNAATCTGTCTCGTGGGCTCGGAGATGTGTATAAGAGACAG | AGATTNCT | 708 |
| CAAGCAGAAGACGGCATACGAGATACNAATCTGTCTCGTGGGCTCGGAGATGTGTATAAGAGACAG | AGATTNGT | 709 |
| CAAGCAGAAGACGGCATACGAGATAANAATCTGTCTCGTGGGCTCGGAGATGTGTATAAGAGACAG | AGATTNTT | 710 |
| CAAGCAGAAGACGGCATACGAGATTGTTTGCTGTCTCGTGGGCTCGGAGATGTGTATAAGAGACAG | AGCAAACA | 711 |
| CAAGCAGAAGACGGCATACGAGATGGTTTGCTGTCTCGTGGGCTCGGAGATGTGTATAAGAGACAG | AGCAAACC | 712 |
| CAAGCAGAAGACGGCATACGAGATTATTTGCTGTCTCGTGGGCTCGGAGATGTGTATAAGAGACAG | AGCAAATA | 713 |
| CAAGCAGAAGACGGCATACGAGATGATTTGCTGTCTCGTGGGCTCGGAGATGTGTATAAGAGACAG | AGCAAATC | 714 |
| CAAGCAGAAGACGGCATACGAGATTGCTTGCTGTCTCGTGGGCTCGGAGATGTGTATAAGAGACAG | AGCAAGCA | 715 |
| CAAGCAGAAGACGGCATACGAGATGGCTTGCTGTCTCGTGGGCTCGGAGATGTGTATAAGAGACAG | AGCAAGCC | 716 |
| CAAGCAGAAGACGGCATACGAGATTACTTGCTGTCTCGTGGGCTCGGAGATGTGTATAAGAGACAG | AGCAAGTA | 717 |
| CAAGCAGAAGACGGCATACGAGATGACTTGCTGTCTCGTGGGCTCGGAGATGTGTATAAGAGACAG | AGCAAGTC | 718 |
| CAAGCAGAAGACGGCATACGAGATTCNTTGCTGTCTCGTGGGCTCGGAGATGTGTATAAGAGACAG | AGCAANGA | 719 |
| CAAGCAGAAGACGGCATACGAGATGCNTTGCTGTCTCGTGGGCTCGGAGATGTGTATAAGAGACAG | AGCAANGC | 720 |
| CAAGCAGAAGACGGCATACGAGATANNTTGCTGTCTCGTGGGCTCGGAGATGTGTATAAGAGACAG | AGCAANNT | 721 |
| CAAGCAGAAGACGGCATACGAGATTGATTGCTGTCTCGTGGGCTCGGAGATGTGTATAAGAGACAG | AGCAATCA | 722 |
| CAAGCAGAAGACGGCATACGAGATGGATTGCTGTCTCGTGGGCTCGGAGATGTGTATAAGAGACAG | AGCAATCC | 723 |
| CAAGCAGAAGACGGCATACGAGATTAATTGCTGTCTCGTGGGCTCGGAGATGTGTATAAGAGACAG | AGCAATTA | 724 |
| CAAGCAGAAGACGGCATACGAGATGAATTGCTGTCTCGTGGGCTCGGAGATGTGTATAAGAGACAG | AGCAATTC | 725 |
| CAAGCAGAAGACGGCATACGAGATACNTAGCTGTCTCGTGGGCTCGGAGATGTGTATAAGAGACAG | AGCTANGT | 726 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATTCNTTCCTGTCTCGTGGGCTCGGAGATGTGTATAAGAGACAG | AGGAANGA | 727 |
| CAAGCAGAAGACGGCATACGAGATGCNTTCCTGTCTCGTGGGCTCGGAGATGTGTATAAGAGACAG | AGGAANGC | 728 |
| CAAGCAGAAGACGGCATACGAGATANNTTCCTGTCTCGTGGGCTCGGAGATGTGTATAAGAGACAG | AGGAANNT | 729 |
| CAAGCAGAAGACGGCATACGAGATACTTACCTGTCTCGTGGGCTCGGAGATGTGTATAAGAGACAG | AGGTAAGT | 730 |
| CAAGCAGAAGACGGCATACGAGATACCTACCTGTCTCGTGGGCTCGGAGATGTGTATAAGAGACAG | AGGTAGGT | 731 |
| CAAGCAGAAGACGGCATACGAGATACATACCTGTCTCGTGGGCTCGGAGATGTGTATAAGAGACAG | AGGTATGT | 732 |
| CAAGCAGAAGACGGCATACGAGATTNNTTACTGTCTCGTGGGCTCGGAGATGTGTATAAGAGACAG | AGTAANNA | 733 |
| CAAGCAGAAGACGGCATACGAGATGNNTTACTGTCTCGTGGGCTCGGAGATGTGTATAAGAGACAG | AGTAANNC | 734 |
| CAAGCAGAAGACGGCATACGAGATANNTTACTGTCTCGTGGGCTCGGAGATGTGTATAAGAGACAG | AGTAANNT | 735 |
| CAAGCAGAAGACGGCATACGAGATAGNTACTGTCTCGTGGGCTCGGAGATGTGTATAAGAGACAG | AGTACNCT | 736 |
| CAAGCAGAAGACGGCATACGAGATACNTACTGTCTCGTGGGCTCGGAGATGTGTATAAGAGACAG | AGTACNGT | 737 |
| CAAGCAGAAGACGGCATACGAGATAANGTACTGTCTCGTGGGCTCGGAGATGTGTATAAGAGACAG | AGTACNTT | 738 |
| CAAGCAGAAGACGGCATACGAGATATAGTACTGTCTCGTGGGCTCGGAGATGTGTATAAGAGACAG | AGTACTAT | 739 |
| CAAGCAGAAGACGGCATACGAGATAGNATACTGTCTCGTGGGCTCGGAGATGTGTATAAGAGACAG | AGTATNCT | 740 |
| CAAGCAGAAGACGGCATACGAGATACNATACTGTCTCGTGGGCTCGGAGATGTGTATAAGAGACAG | AGTATNGT | 741 |
| CAAGCAGAAGACGGCATACGAGATAANATACTGTCTCGTGGGCTCGGAGATGTGTATAAGAGACAG | AGTATNTT | 742 |
| CAAGCAGAAGACGGCATACGAGATATAATACTGTCTCGTGGGCTCGGAGATGTGTATAAGAGACAG | AGTATTAT | 743 |
| CAAGCAGAAGACGGCATACGAGATAGTTGACTGTCTCGTGGGCTCGGAGATGTGTATAAGAGACAG | AGTCAACT | 744 |
| CAAGCAGAAGACGGCATACGAGATAATTGACTGTCTCGTGGGCTCGGAGATGTGTATAAGAGACAG | AGTCAATT | 745 |
| CAAGCAGAAGACGGCATACGAGATAGCTGACTGTCTCGTGGGCTCGGAGATGTGTATAAGAGACAG | AGTCAGCT | 746 |
| CAAGCAGAAGACGGCATACGAGATAACTGACTGTCTCGTGGGCTCGGAGATGTGTATAAGAGACAG | AGTCAGTT | 747 |
| CAAGCAGAAGACGGCATACGAGATACNTGACTGTCTCGTGGGCTCGGAGATGTGTATAAGAGACAG | AGTCANGT | 748 |
| CAAGCAGAAGACGGCATACGAGATAGATGACTGTCTCGTGGGCTCGGAGATGTGTATAAGAGACAG | AGTCATCT | 749 |
| CAAGCAGAAGACGGCATACGAGATAAATGACTGTCTCGTGGGCTCGGAGATGTGTATAAGAGACAG | AGTCATTT | 750 |
| CAAGCAGAAGACGGCATACGAGATACNTCACTGTCTCGTGGGCTCGGAGATGTGTATAAGAGACAG | AGTGANGT | 751 |
| CAAGCAGAAGACGGCATACGAGATTCTTAACTGTCTCGTGGGCTCGGAGATGTGTATAAGAGACAG | AGTTAAGA | 752 |
| CAAGCAGAAGACGGCATACGAGATGCTTAACTGTCTCGTGGGCTCGGAGATGTGTATAAGAGACAG | AGTTAAGC | 753 |
| CAAGCAGAAGACGGCATACGAGATTCCTAACTGTCTCGTGGGCTCGGAGATGTGTATAAGAGACAG | AGTTAGGA | 754 |
| CAAGCAGAAGACGGCATACGAGATGCCTAACTGTCTCGTGGGCTCGGAGATGTGTATAAGAGACAG | AGTTAGGC | 755 |
| CAAGCAGAAGACGGCATACGAGATANNTAACTGTCTCGTGGGCTCGGAGATGTGTATAAGAGACAG | AGTTANNT | 756 |
| CAAGCAGAAGACGGCATACGAGATTCATAACTGTCTCGTGGGCTCGGAGATGTGTATAAGAGACAG | AGTTATGA | 757 |
| CAAGCAGAAGACGGCATACGAGATGCATAACTGTCTCGTGGGCTCGGAGATGTGTATAAGAGACAG | AGTTATGC | 758 |
| CAAGCAGAAGACGGCATACGAGATCNNCTTATGTCTCGTGGGCTCGGAGATGTGTATAAGAGACAG | ATAAGNNG | 759 |
| CAAGCAGAAGACGGCATACGAGATCCNCGTATGTCTCGTGGGCTCGGAGATGTGTATAAGAGACAG | ATACGNGG | 760 |
| CAAGCAGAAGACGGCATACGAGATCCTCCTATGTCTCGTGGGCTCGGAGATGTGTATAAGAGACAG | ATAGGAGG | 761 |
| CAAGCAGAAGACGGCATACGAGATCCCCCTATGTCTCGTGGGCTCGGAGATGTGTATAAGAGACAG | ATAGGGGG | 762 |
| CAAGCAGAAGACGGCATACGAGATCCACCTATGTCTCGTGGGCTCGGAGATGTGTATAAGAGACAG | ATAGGTGG | 763 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATNNNTNTATGTCTCGTGGGCTCGGAGATGTGTATAAGAGACAG | ATANANNN | 764 |
| CAAGCAGAAGACGGCATACGAGATNNNGNTATGTCTCGTGGGCTCGGAGATGTGTATAAGAGACAG | ATANCNNN | 765 |
| CAAGCAGAAGACGGCATACGAGATTNNCNTATGTCTCGTGGGCTCGGAGATGTGTATAAGAGACAG | ATANGNNA | 766 |
| CAAGCAGAAGACGGCATACGAGATGNNCNTATGTCTCGTGGGCTCGGAGATGTGTATAAGAGACAG | ATANGNNC | 767 |
| CAAGCAGAAGACGGCATACGAGATANNCNTATGTCTCGTGGGCTCGGAGATGTGTATAAGAGACAG | ATANGNNT | 768 |
| CAAGCAGAAGACGGCATACGAGATNNNANTATGTCTCGTGGGCTCGGAGATGTGTATAAGAGACAG | ATANTNNN | 769 |
| CAAGCAGAAGACGGCATACGAGATCNNCATATGTCTCGTGGGCTCGGAGATGTGTATAAGAGACAG | ATATGNNG | 770 |
| CAAGCAGAAGACGGCATACGAGATCNNTTGATGTCTCGTGGGCTCGGAGATGTGTATAAGAGACAG | ATCAANNG | 771 |
| CAAGCAGAAGACGGCATACGAGATTNNGTGATGTCTCGTGGGCTCGGAGATGTGTATAAGAGACAG | ATCACNNA | 772 |
| CAAGCAGAAGACGGCATACGAGATGNNGTGATGTCTCGTGGGCTCGGAGATGTGTATAAGAGACAG | ATCACNNC | 773 |
| CAAGCAGAAGACGGCATACGAGATCNNGTGATGTCTCGTGGGCTCGGAGATGTGTATAAGAGACAG | ATCACNNG | 774 |
| CAAGCAGAAGACGGCATACGAGATCGTCTGATGTCTCGTGGGCTCGGAGATGTGTATAAGAGACAG | ATCAGACG | 775 |
| CAAGCAGAAGACGGCATACGAGATCATCTGATGTCTCGTGGGCTCGGAGATGTGTATAAGAGACAG | ATCAGATG | 776 |
| CAAGCAGAAGACGGCATACGAGATCGCCTGATGTCTCGTGGGCTCGGAGATGTGTATAAGAGACAG | ATCAGGCG | 777 |
| CAAGCAGAAGACGGCATACGAGATCACCTGATGTCTCGTGGGCTCGGAGATGTGTATAAGAGACAG | ATCAGGTG | 778 |
| CAAGCAGAAGACGGCATACGAGATCCNCTGATGTCTCGTGGGCTCGGAGATGTGTATAAGAGACAG | ATCAGNGG | 779 |
| CAAGCAGAAGACGGCATACGAGATTNNCTGATGTCTCGTGGGCTCGGAGATGTGTATAAGAGACAG | ATCAGNNA | 780 |
| CAAGCAGAAGACGGCATACGAGATGNNCTGATGTCTCGTGGGCTCGGAGATGTGTATAAGAGACAG | ATCAGNNC | 781 |
| CAAGCAGAAGACGGCATACGAGATANNCTGATGTCTCGTGGGCTCGGAGATGTGTATAAGAGACAG | ATCAGNNT | 782 |
| CAAGCAGAAGACGGCATACGAGATCGACTGATGTCTCGTGGGCTCGGAGATGTGTATAAGAGACAG | ATCAGTCG | 783 |
| CAAGCAGAAGACGGCATACGAGATCAACTGATGTCTCGTGGGCTCGGAGATGTGTATAAGAGACAG | ATCAGTTG | 784 |
| CAAGCAGAAGACGGCATACGAGATTNNATGATGTCTCGTGGGCTCGGAGATGTGTATAAGAGACAG | ATCATNNA | 785 |
| CAAGCAGAAGACGGCATACGAGATGNNATGATGTCTCGTGGGCTCGGAGATGTGTATAAGAGACAG | ATCATNNC | 786 |
| CAAGCAGAAGACGGCATACGAGATCNNATGATGTCTCGTGGGCTCGGAGATGTGTATAAGAGACAG | ATCATNNG | 787 |
| CAAGCAGAAGACGGCATACGAGATCGNTGATGTCTCGTGGGCTCGGAGATGTGTATAAGAGACAG | ATCCANCG | 788 |
| CAAGCAGAAGACGGCATACGAGATCCNTGGATGTCTCGTGGGCTCGGAGATGTGTATAAGAGACAG | ATCCANGG | 789 |
| CAAGCAGAAGACGGCATACGAGATCANTGGATGTCTCGTGGGCTCGGAGATGTGTATAAGAGACAG | ATCCANTG | 790 |
| CAAGCAGAAGACGGCATACGAGATTGNGGATGTCTCGTGGGCTCGGAGATGTGTATAAGAGACAG | ATCCCNCA | 791 |
| CAAGCAGAAGACGGCATACGAGATGGNGGATGTCTCGTGGGCTCGGAGATGTGTATAAGAGACAG | ATCCCNCC | 792 |
| CAAGCAGAAGACGGCATACGAGATTCNGGATGTCTCGTGGGCTCGGAGATGTGTATAAGAGACAG | ATCCCNGA | 793 |
| CAAGCAGAAGACGGCATACGAGATGCNGGATGTCTCGTGGGCTCGGAGATGTGTATAAGAGACAG | ATCCCNGC | 794 |
| CAAGCAGAAGACGGCATACGAGATTANGGATGTCTCGTGGGCTCGGAGATGTGTATAAGAGACAG | ATCCCNTA | 795 |
| CAAGCAGAAGACGGCATACGAGATGANGGATGTCTCGTGGGCTCGGAGATGTGTATAAGAGACAG | ATCCCNTC | 796 |
| CAAGCAGAAGACGGCATACGAGATAGNCGGATGTCTCGTGGGCTCGGAGATGTGTATAAGAGACAG | ATCCGNCT | 797 |
| CAAGCAGAAGACGGCATACGAGATACNCGGATGTCTCGTGGGCTCGGAGATGTGTATAAGAGACAG | ATCCGNGT | 798 |
| CAAGCAGAAGACGGCATACGAGATAANCGGATGTCTCGTGGGCTCGGAGATGTGTATAAGAGACAG | ATCCGNTT | 799 |
| CAAGCAGAAGACGGCATACGAGATTGNAGGATGTCTCGTGGGCTCGGAGATGTGTATAAGAGACAG | ATCCTNCA | 800 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATGGNAGGATGTCTCGTGGGCTCGGAGATGTGTATAAGAGACAG | ATCCTNCC | 801 |
| CAAGCAGAAGACGGCATACGAGATTCNAGGATGTCTCGTGGGCTCGGAGATGTGTATAAGAGACAG | ATCCTNGA | 802 |
| CAAGCAGAAGACGGCATACGAGATGCNAGGATGTCTCGTGGGCTCGGAGATGTGTATAAGAGACAG | ATCCTNGC | 803 |
| CAAGCAGAAGACGGCATACGAGATTANAGGATGTCTCGTGGGCTCGGAGATGTGTATAAGAGACAG | ATCCTNTA | 804 |
| CAAGCAGAAGACGGCATACGAGATGANAGGATGTCTCGTGGGCTCGGAGATGTGTATAAGAGACAG | ATCCTNTC | 805 |
| CAAGCAGAAGACGGCATACGAGATCGNTCGATGTCTCGTGGGCTCGGAGATGTGTATAAGAGACAG | ATCGANCG | 806 |
| CAAGCAGAAGACGGCATACGAGATCCNTCGATGTCTCGTGGGCTCGGAGATGTGTATAAGAGACAG | ATCGANGG | 807 |
| CAAGCAGAAGACGGCATACGAGATCANTCGATGTCTCGTGGGCTCGGAGATGTGTATAAGAGACAG | ATCGANTG | 808 |
| CAAGCAGAAGACGGCATACGAGATTGNGCGATGTCTCGTGGGCTCGGAGATGTGTATAAGAGACAG | ATCGCNCA | 809 |
| CAAGCAGAAGACGGCATACGAGATGGNGCGATGTCTCGTGGGCTCGGAGATGTGTATAAGAGACAG | ATCGCNCC | 810 |
| CAAGCAGAAGACGGCATACGAGATTCNGCGATGTCTCGTGGGCTCGGAGATGTGTATAAGAGACAG | ATCGCNGA | 811 |
| CAAGCAGAAGACGGCATACGAGATGCNGCGATGTCTCGTGGGCTCGGAGATGTGTATAAGAGACAG | ATCGCNGC | 812 |
| CAAGCAGAAGACGGCATACGAGATTANGCGATGTCTCGTGGGCTCGGAGATGTGTATAAGAGACAG | ATCGCNTA | 813 |
| CAAGCAGAAGACGGCATACGAGATGANGCGATGTCTCGTGGGCTCGGAGATGTGTATAAGAGACAG | ATCGCNTC | 814 |
| CAAGCAGAAGACGGCATACGAGATAGNCCGATGTCTCGTGGGCTCGGAGATGTGTATAAGAGACAG | ATCGGNCT | 815 |
| CAAGCAGAAGACGGCATACGAGATACNCCGATGTCTCGTGGGCTCGGAGATGTGTATAAGAGACAG | ATCGGNGT | 816 |
| CAAGCAGAAGACGGCATACGAGATAANCCGATGTCTCGTGGGCTCGGAGATGTGTATAAGAGACAG | ATCGGNTT | 817 |
| CAAGCAGAAGACGGCATACGAGATTGNACGATGTCTCGTGGGCTCGGAGATGTGTATAAGAGACAG | ATCGTNCA | 818 |
| CAAGCAGAAGACGGCATACGAGATGGNACGATGTCTCGTGGGCTCGGAGATGTGTATAAGAGACAG | ATCGTNCC | 819 |
| CAAGCAGAAGACGGCATACGAGATTCNACGATGTCTCGTGGGCTCGGAGATGTGTATAAGAGACAG | ATCGTNGA | 820 |
| CAAGCAGAAGACGGCATACGAGATGCNACGATGTCTCGTGGGCTCGGAGATGTGTATAAGAGACAG | ATCGTNGC | 821 |
| CAAGCAGAAGACGGCATACGAGATTANACGATGTCTCGTGGGCTCGGAGATGTGTATAAGAGACAG | ATCGTNTA | 822 |
| CAAGCAGAAGACGGCATACGAGATGANACGATGTCTCGTGGGCTCGGAGATGTGTATAAGAGACAG | ATCGTNTC | 823 |
| CAAGCAGAAGACGGCATACGAGATTNNTNGATGTCTCGTGGGCTCGGAGATGTGTATAAGAGACAG | ATCNANNA | 824 |
| CAAGCAGAAGACGGCATACGAGATGNNTNGATGTCTCGTGGGCTCGGAGATGTGTATAAGAGACAG | ATCNANNC | 825 |
| CAAGCAGAAGACGGCATACGAGATANNTNGATGTCTCGTGGGCTCGGAGATGTGTATAAGAGACAG | ATCNANNT | 826 |
| CAAGCAGAAGACGGCATACGAGATANNGNGATGTCTCGTGGGCTCGGAGATGTGTATAAGAGACAG | ATCNCNNT | 827 |
| CAAGCAGAAGACGGCATACGAGATANNANGATGTCTCGTGGGCTCGGAGATGTGTATAAGAGACAG | ATCNTNNT | 828 |
| CAAGCAGAAGACGGCATACGAGATCNNTAGATGTCTCGTGGGCTCGGAGATGTGTATAAGAGACAG | ATCTANNG | 829 |
| CAAGCAGAAGACGGCATACGAGATCCNGAGATGTCTCGTGGGCTCGGAGATGTGTATAAGAGACAG | ATCTCNGG | 830 |
| CAAGCAGAAGACGGCATACGAGATTNNGAGATGTCTCGTGGGCTCGGAGATGTGTATAAGAGACAG | ATCTCNNA | 831 |
| CAAGCAGAAGACGGCATACGAGATGNNGAGATGTCTCGTGGGCTCGGAGATGTGTATAAGAGACAG | ATCTCNNC | 832 |
| CAAGCAGAAGACGGCATACGAGATTGNCAGATGTCTCGTGGGCTCGGAGATGTGTATAAGAGACAG | ATCTGNCA | 833 |
| CAAGCAGAAGACGGCATACGAGATGGNCAGATGTCTCGTGGGCTCGGAGATGTGTATAAGAGACAG | ATCTGNCC | 834 |
| CAAGCAGAAGACGGCATACGAGATTCNCAGATGTCTCGTGGGCTCGGAGATGTGTATAAGAGACAG | ATCTGNGA | 835 |
| CAAGCAGAAGACGGCATACGAGATGCNCAGATGTCTCGTGGGCTCGGAGATGTGTATAAGAGACAG | ATCTGNGC | 836 |
| CAAGCAGAAGACGGCATACGAGATANNCAGATGTCTCGTGGGCTCGGAGATGTGTATAAGAGACAG | ATCTGNNT | 837 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATTANCAGATGTCTCGTGGGCTCGGAGATGTGTATAAGAGACAG | ATCTGNTA | 838 |
| CAAGCAGAAGACGGCATACGAGATGANCAGATGTCTCGTGGGCTCGGAGATGTGTATAAGAGACAG | ATCTGNTC | 839 |
| CAAGCAGAAGACGGCATACGAGATCCNAAGATGTCTCGTGGGCTCGGAGATGTGTATAAGAGACAG | ATCTTNGG | 840 |
| CAAGCAGAAGACGGCATACGAGATTNNAAGATGTCTCGTGGGCTCGGAGATGTGTATAAGAGACAG | ATCTTNNA | 841 |
| CAAGCAGAAGACGGCATACGAGATGNNAAGATGTCTCGTGGGCTCGGAGATGTGTATAAGAGACAG | ATCTTNNC | 842 |
| CAAGCAGAAGACGGCATACGAGATCNNTTCATGTCTCGTGGGCTCGGAGATGTGTATAAGAGACAG | ATGAANNG | 843 |
| CAAGCAGAAGACGGCATACGAGATTNNGTCATGTCTCGTGGGCTCGGAGATGTGTATAAGAGACAG | ATGACNNA | 844 |
| CAAGCAGAAGACGGCATACGAGATGNNGTCATGTCTCGTGGGCTCGGAGATGTGTATAAGAGACAG | ATGACNNC | 845 |
| CAAGCAGAAGACGGCATACGAGATCNNGTCATGTCTCGTGGGCTCGGAGATGTGTATAAGAGACAG | ATGACNNG | 846 |
| CAAGCAGAAGACGGCATACGAGATCCNCTCATGTCTCGTGGGCTCGGAGATGTGTATAAGAGACAG | ATGAGNGG | 847 |
| CAAGCAGAAGACGGCATACGAGATTNNCTCATGTCTCGTGGGCTCGGAGATGTGTATAAGAGACAG | ATGAGNNA | 848 |
| CAAGCAGAAGACGGCATACGAGATGNNCTCATGTCTCGTGGGCTCGGAGATGTGTATAAGAGACAG | ATGAGNNC | 849 |
| CAAGCAGAAGACGGCATACGAGATANNCTCATGTCTCGTGGGCTCGGAGATGTGTATAAGAGACAG | ATGAGNNT | 850 |
| CAAGCAGAAGACGGCATACGAGATTNNATCATGTCTCGTGGGCTCGGAGATGTGTATAAGAGACAG | ATGATNNA | 851 |
| CAAGCAGAAGACGGCATACGAGATGNNATCATGTCTCGTGGGCTCGGAGATGTGTATAAGAGACAG | ATGATNNC | 852 |
| CAAGCAGAAGACGGCATACGAGATCNNATCATGTCTCGTGGGCTCGGAGATGTGTATAAGAGACAG | ATGATNNG | 853 |
| CAAGCAGAAGACGGCATACGAGATCGNTGCATGTCTCGTGGGCTCGGAGATGTGTATAAGAGACAG | ATGCANCG | 854 |
| CAAGCAGAAGACGGCATACGAGATCCNTGCATGTCTCGTGGGCTCGGAGATGTGTATAAGAGACAG | ATGCANGG | 855 |
| CAAGCAGAAGACGGCATACGAGATCANTGCATGTCTCGTGGGCTCGGAGATGTGTATAAGAGACAG | ATGCANTG | 856 |
| CAAGCAGAAGACGGCATACGAGATTGNGGCATGTCTCGTGGGCTCGGAGATGTGTATAAGAGACAG | ATGCCNCA | 857 |
| CAAGCAGAAGACGGCATACGAGATGGNGGCATGTCTCGTGGGCTCGGAGATGTGTATAAGAGACAG | ATGCCNCC | 858 |
| CAAGCAGAAGACGGCATACGAGATTCNGGCATGTCTCGTGGGCTCGGAGATGTGTATAAGAGACAG | ATGCCNGA | 859 |
| CAAGCAGAAGACGGCATACGAGATGCNGGCATGTCTCGTGGGCTCGGAGATGTGTATAAGAGACAG | ATGCCNGC | 860 |
| CAAGCAGAAGACGGCATACGAGATTANGGCATGTCTCGTGGGCTCGGAGATGTGTATAAGAGACAG | ATGCCNTA | 861 |
| CAAGCAGAAGACGGCATACGAGATGANGGCATGTCTCGTGGGCTCGGAGATGTGTATAAGAGACAG | ATGCCNTC | 862 |
| CAAGCAGAAGACGGCATACGAGATAGNCGCATGTCTCGTGGGCTCGGAGATGTGTATAAGAGACAG | ATGCGNCT | 863 |
| CAAGCAGAAGACGGCATACGAGATACNCGCATGTCTCGTGGGCTCGGAGATGTGTATAAGAGACAG | ATGCGNGT | 864 |
| CAAGCAGAAGACGGCATACGAGATAANCGCATGTCTCGTGGGCTCGGAGATGTGTATAAGAGACAG | ATGCGNTT | 865 |
| CAAGCAGAAGACGGCATACGAGATTGNAGCATGTCTCGTGGGCTCGGAGATGTGTATAAGAGACAG | ATGCTNCA | 866 |
| CAAGCAGAAGACGGCATACGAGATGGNAGCATGTCTCGTGGGCTCGGAGATGTGTATAAGAGACAG | ATGCTNCC | 867 |
| CAAGCAGAAGACGGCATACGAGATTCNAGCATGTCTCGTGGGCTCGGAGATGTGTATAAGAGACAG | ATGCTNGA | 868 |
| CAAGCAGAAGACGGCATACGAGATGCNAGCATGTCTCGTGGGCTCGGAGATGTGTATAAGAGACAG | ATGCTNGC | 869 |
| CAAGCAGAAGACGGCATACGAGATTANAGCATGTCTCGTGGGCTCGGAGATGTGTATAAGAGACAG | ATGCTNTA | 870 |
| CAAGCAGAAGACGGCATACGAGATGANAGCATGTCTCGTGGGCTCGGAGATGTGTATAAGAGACAG | ATGCTNTC | 871 |
| CAAGCAGAAGACGGCATACGAGATCGNTCCATGTCTCGTGGGCTCGGAGATGTGTATAAGAGACAG | ATGGANCG | 872 |
| CAAGCAGAAGACGGCATACGAGATCCNTCCATGTCTCGTGGGCTCGGAGATGTGTATAAGAGACAG | ATGGANGG | 873 |
| CAAGCAGAAGACGGCATACGAGATCANTCCATGTCTCGTGGGCTCGGAGATGTGTATAAGAGACAG | ATGGANTG | 874 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATTGNGCCATGTCTCGTGGGCTCGGAGATGTGTATAAGAGACAG | ATGGCNCA | 875 |
| CAAGCAGAAGACGGCATACGAGATGGNGCCATGTCTCGTGGGCTCGGAGATGTGTATAAGAGACAG | ATGGCNCC | 876 |
| CAAGCAGAAGACGGCATACGAGATTCNGCCATGTCTCGTGGGCTCGGAGATGTGTATAAGAGACAG | ATGGCNGA | 877 |
| CAAGCAGAAGACGGCATACGAGATGCNGCCATGTCTCGTGGGCTCGGAGATGTGTATAAGAGACAG | ATGGCNGC | 878 |
| CAAGCAGAAGACGGCATACGAGATTANGCCATGTCTCGTGGGCTCGGAGATGTGTATAAGAGACAG | ATGGCNTA | 879 |
| CAAGCAGAAGACGGCATACGAGATGANGCCATGTCTCGTGGGCTCGGAGATGTGTATAAGAGACAG | ATGGCNTC | 880 |
| CAAGCAGAAGACGGCATACGAGATAGNCCCATGTCTCGTGGGCTCGGAGATGTGTATAAGAGACAG | ATGGGNCT | 881 |
| CAAGCAGAAGACGGCATACGAGATACNCCCATGTCTCGTGGGCTCGGAGATGTGTATAAGAGACAG | ATGGGNGT | 882 |
| CAAGCAGAAGACGGCATACGAGATAANCCCATGTCTCGTGGGCTCGGAGATGTGTATAAGAGACAG | ATGGGNTT | 883 |
| CAAGCAGAAGACGGCATACGAGATTGNACCATGTCTCGTGGGCTCGGAGATGTGTATAAGAGACAG | ATGGTNCA | 884 |
| CAAGCAGAAGACGGCATACGAGATGGNACCATGTCTCGTGGGCTCGGAGATGTGTATAAGAGACAG | ATGGTNCC | 885 |
| CAAGCAGAAGACGGCATACGAGATTCNACCATGTCTCGTGGGCTCGGAGATGTGTATAAGAGACAG | ATGGTNGA | 886 |
| CAAGCAGAAGACGGCATACGAGATGCNACCATGTCTCGTGGGCTCGGAGATGTGTATAAGAGACAG | ATGGTNGC | 887 |
| CAAGCAGAAGACGGCATACGAGATTANACCATGTCTCGTGGGCTCGGAGATGTGTATAAGAGACAG | ATGGTNTA | 888 |
| CAAGCAGAAGACGGCATACGAGATGANACCATGTCTCGTGGGCTCGGAGATGTGTATAAGAGACAG | ATGGTNTC | 889 |
| CAAGCAGAAGACGGCATACGAGATTNNTNCATGTCTCGTGGGCTCGGAGATGTGTATAAGAGACAG | ATGNANNA | 890 |
| CAAGCAGAAGACGGCATACGAGATGNNTNCATGTCTCGTGGGCTCGGAGATGTGTATAAGAGACAG | ATGNANNC | 891 |
| CAAGCAGAAGACGGCATACGAGATANNTNCATGTCTCGTGGGCTCGGAGATGTGTATAAGAGACAG | ATGNANNT | 892 |
| CAAGCAGAAGACGGCATACGAGATANNGNCATGTCTCGTGGGCTCGGAGATGTGTATAAGAGACAG | ATGNCNNT | 893 |
| CAAGCAGAAGACGGCATACGAGATANNANCATGTCTCGTGGGCTCGGAGATGTGTATAAGAGACAG | ATGNTNNT | 894 |
| CAAGCAGAAGACGGCATACGAGATCNNTACATGTCTCGTGGGCTCGGAGATGTGTATAAGAGACAG | ATGTANNG | 895 |
| CAAGCAGAAGACGGCATACGAGATCCTGACATGTCTCGTGGGCTCGGAGATGTGTATAAGAGACAG | ATGTCAGG | 896 |
| CAAGCAGAAGACGGCATACGAGATCCCGACATGTCTCGTGGGCTCGGAGATGTGTATAAGAGACAG | ATGTCGGG | 897 |
| CAAGCAGAAGACGGCATACGAGATTNNGACATGTCTCGTGGGCTCGGAGATGTGTATAAGAGACAG | ATGTCNNA | 898 |
| CAAGCAGAAGACGGCATACGAGATGNNGACATGTCTCGTGGGCTCGGAGATGTGTATAAGAGACAG | ATGTCNNC | 899 |
| CAAGCAGAAGACGGCATACGAGATCCAGACATGTCTCGTGGGCTCGGAGATGTGTATAAGAGACAG | ATGTCTGG | 900 |
| CAAGCAGAAGACGGCATACGAGATTGNCACATGTCTCGTGGGCTCGGAGATGTGTATAAGAGACAG | ATGTGNCA | 901 |
| CAAGCAGAAGACGGCATACGAGATGGNCACATGTCTCGTGGGCTCGGAGATGTGTATAAGAGACAG | ATGTGNCC | 902 |
| CAAGCAGAAGACGGCATACGAGATTCNCACATGTCTCGTGGGCTCGGAGATGTGTATAAGAGACAG | ATGTGNGA | 903 |
| CAAGCAGAAGACGGCATACGAGATGCNCACATGTCTCGTGGGCTCGGAGATGTGTATAAGAGACAG | ATGTGNGC | 904 |
| CAAGCAGAAGACGGCATACGAGATANNCACATGTCTCGTGGGCTCGGAGATGTGTATAAGAGACAG | ATGTGNNT | 905 |
| CAAGCAGAAGACGGCATACGAGATTANCACATGTCTCGTGGGCTCGGAGATGTGTATAAGAGACAG | ATGTGNTA | 906 |
| CAAGCAGAAGACGGCATACGAGATGANCACATGTCTCGTGGGCTCGGAGATGTGTATAAGAGACAG | ATGTGNTC | 907 |
| CAAGCAGAAGACGGCATACGAGATCCTAACATGTCTCGTGGGCTCGGAGATGTGTATAAGAGACAG | ATGTTAGG | 908 |
| CAAGCAGAAGACGGCATACGAGATCCCAACATGTCTCGTGGGCTCGGAGATGTGTATAAGAGACAG | ATGTTGGG | 909 |
| CAAGCAGAAGACGGCATACGAGATTNNAACATGTCTCGTGGGCTCGGAGATGTGTATAAGAGACAG | ATGTTNNA | 910 |
| CAAGCAGAAGACGGCATACGAGATGNNAACATGTCTCGTGGGCTCGGAGATGTGTATAAGAGACAG | ATGTTNNC | 911 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATCCAAACATGTCTCGTGGGCTCGGAGATGTGTATAAGAGACAG | ATGTTTGG | 912 |
| CAAGCAGAAGACGGCATACGAGATCNNGTAATGTCTCGTGGGCTCGGAGATGTGTATAAGAGACAG | ATTACNNG | 913 |
| CAAGCAGAAGACGGCATACGAGATTNNCTAATGTCTCGTGGGCTCGGAGATGTGTATAAGAGACAG | ATTAGNNA | 914 |
| CAAGCAGAAGACGGCATACGAGATGNNCTAATGTCTCGTGGGCTCGGAGATGTGTATAAGAGACAG | ATTAGNNC | 915 |
| CAAGCAGAAGACGGCATACGAGATCNNCTAATGTCTCGTGGGCTCGGAGATGTGTATAAGAGACAG | ATTAGNNG | 916 |
| CAAGCAGAAGACGGCATACGAGATCNNATAATGTCTCGTGGGCTCGGAGATGTGTATAAGAGACAG | ATTATNNG | 917 |
| CAAGCAGAAGACGGCATACGAGATCGTGGAATGTCTCGTGGGCTCGGAGATGTGTATAAGAGACAG | ATTCCACG | 918 |
| CAAGCAGAAGACGGCATACGAGATCATGGAATGTCTCGTGGGCTCGGAGATGTGTATAAGAGACAG | ATTCCATG | 919 |
| CAAGCAGAAGACGGCATACGAGATCGCGGAATGTCTCGTGGGCTCGGAGATGTGTATAAGAGACAG | ATTCCGCG | 920 |
| CAAGCAGAAGACGGCATACGAGATCACGGAATGTCTCGTGGGCTCGGAGATGTGTATAAGAGACAG | ATTCCGTG | 921 |
| CAAGCAGAAGACGGCATACGAGATCCNGGAATGTCTCGTGGGCTCGGAGATGTGTATAAGAGACAG | ATTCCNGG | 922 |
| CAAGCAGAAGACGGCATACGAGATCGAGGAATGTCTCGTGGGCTCGGAGATGTGTATAAGAGACAG | ATTCCTCG | 923 |
| CAAGCAGAAGACGGCATACGAGATCAAGGAATUTCTCGTGGGCTCGGAGATUTGTATAAGAGACAG | ATTCCTTG | 924 |
| CAAGCAGAAGACGGCATACGAGATTGNCAATGTCTCGTGGGCTCGGAGATGTGTATAAGAGACAG | ATTCGNCA | 925 |
| CAAGCAGAAGACGGCATACGAGATGGNCAATGTCTCGTGGGCTCGGAGATGTGTATAAGAGACAG | ATTCGNCC | 926 |
| CAAGCAGAAGACGGCATACGAGATTCNCAATGTCTCGTGGGCTCGGAGATGTGTATAAGAGACAG | ATTCGNGA | 927 |
| CAAGCAGAAGACGGCATACGAGATGCNCAATGTCTCGTGGGCTCGGAGATGTGTATAAGAGACAG | ATTCGNGC | 928 |
| CAAGCAGAAGACGGCATACGAGATTANCAATGTCTCGTGGGCTCGGAGATGTGTATAAGAGACAG | ATTCGNTA | 929 |
| CAAGCAGAAGACGGCATACGAGATGANCAATGTCTCGTGGGCTCGGAGATGTGTATAAGAGACAG | ATTCGNTC | 930 |
| CAAGCAGAAGACGGCATACGAGATCGTAGAATGTCTCGTGGGCTCGGAGATGTGTATAAGAGACAG | ATTCTACG | 931 |
| CAAGCAGAAGACGGCATACGAGATCATAGAATGTCTCGTGGGCTCGGAGATGTGTATAAGAGACAG | ATTCTATG | 932 |
| CAAGCAGAAGACGGCATACGAGATCGCAGAATGTCTCGTGGGCTCGGAGATGTGTATAAGAGACAG | ATTCTGCG | 933 |
| CAAGCAGAAGACGGCATACGAGATCACAGAATGTCTCGTGGGCTCGGAGATGTGTATAAGAGACAG | ATTCTGTG | 934 |
| CAAGCAGAAGACGGCATACGAGATCCNAGAATGTCTCGTGGGCTCGGAGATGTGTATAAGAGACAG | ATTCTNGG | 935 |
| CAAGCAGAAGACGGCATACGAGATCGAAGAATGTCTCGTGGGCTCGGAGATGTGTATAAGAGACAG | ATTCTTCG | 936 |
| CAAGCAGAAGACGGCATACGAGATCAAAGAATGTCTCGTGGGCTCGGAGATGTGTATAAGAGACAG | ATTCTTTG | 937 |
| CAAGCAGAAGACGGCATACGAGATCCNGCAATGTCTCGTGGGCTCGGAGATGTGTATAAGAGACAG | ATTGCNGG | 938 |
| CAAGCAGAAGACGGCATACGAGATTGNCCAATGTTTCGTGGGCTCGGAGATGTGTATAAGAGACAG | ATTGGNCA | 939 |
| CAAGCAGAAGACGGCATACGAGATGGNCCAATGTCTCGTGGGCTCGGAGATGTGTATAAGAGACAG | ATTGGNCC | 940 |
| CAAGCAGAAGACGGCATACGAGATTCNCCAATGTCTCGTGGGCTCGGAGATGTGTATAAGAGACAG | ATTGGNGA | 941 |
| CAAGCAGAAGACGGCATACGAGATGCNCCAATGTCTCGTGGGCTCGGAGATGTGTATAAGAGACAG | ATTGGNGC | 942 |
| CAAGCAGAAGACGGCATACGAGATTANCCAATGTCTCGTGGGCTCGGAGATGTGTATAAGAGACAG | ATTGGNTA | 943 |
| CAAGCAGAAGACGGCATACGAGATGANCCAATGTCTCGTGGGCTCGGAGATGTGTATAAGAGACAG | ATTGGNTC | 944 |
| CAAGCAGAAGACGGCATACGAGATCCNACAATGTCTCGTGGGCTCGGAGATGTGTATAAGAGACAG | ATTGTNGG | 945 |
| CAAGCAGAAGACGGCATACGAGATNNNTNAATGTCTCGTGGGCTCGGAGATGTGTATAAGAGACAG | ATTNANNN | 946 |
| CAAGCAGAAGACGGCATACGAGATTNNGNAATGTCTCGTGGGCTCGGAGATGTGTATAAGAGACAG | ATTNCNNA | 947 |
| CAAGCAGAAGACGGCATACGAGATGNNGNAATGTCTCGTGGGCTCGGAGATGTGTATAAGAGACAG | ATTNCNNC | 948 |

TABLE 6-continued

Table 6: Primer P7 for next-generation sequencer and index thereof

| Primer P7 for next-generation sequencer | Index | SEQ ID NO |
|---|---|---|
| CAAGCAGAAGACGGCATACGAGATANNGNAATGTCTCGTGGGCTCGGAGATGTGTATAAGAGACAG | ATTNCNNT | 949 |
| CAAGCAGAAGACGGCATACGAGATANNCNAATGTCTCGTGGGCTCGGAGATGTGTATAAGAGACAG | ATTNGNNT | 950 |
| CAAGCAGAAGACGGCATACGAGATTNNANAATGTCTCGTGGGCTCGGAGATGTGTATAAGAGACAG | ATTNTNNA | 951 |
| CAAGCAGAAGACGGCATACGAGATGNNANAATGTCTCGTGGGCTCGGAGATGTGTATAAGAGACAG | ATTNTNNC | 952 |
| CAAGCAGAAGACGGCATACGAGATANNANAATGTCTCGTGGGCTCGGAGATGTGTATAAGAGACAG | ATTNTNNT | 953 |
| CAAGCAGAAGACGGCATACGAGATCNNGAAATGTCTCGTGGGCTCGGAGATGTGTATAAGAGACAG | ATTTCNNG | 954 |
| CAAGCAGAAGACGGCATACGAGATCCTCAAATGTCTCGTGGGCTCGGAGATGTGTATAAGAGACAG | ATTTGAGG | 955 |
| CAAGCAGAAGACGGCATACGAGATCCCCAAATGTCTCGTGGGCTCGGAGATGTGTATAAGAGACAG | ATTTGGGG | 956 |
| CAAGCAGAAGACGGCATACGAGATTNNCAAATGTCTCGTGGGCTCGGAGATGTGTATAAGAGACAG | ATTTGNNA | 957 |
| CAAGCAGAAGACGGCATACGAGATGNNCAAATGTCTCGTGGGCTCGGAGATGTGTATAAGAGACAG | ATTTGNNC | 958 |
| CAAGCAGAAGACGGCATACGAGATCCACAAATGTCTCGTGGGCTCGGAGATGTGTATAAGAGACAG | ATTTGTGG | 959 |
| CAAGCAGAAGACGGCATACGAGATCNNAAAATGTCTCGTGGGCTCGGAGATGTGTATAAGAGACAG | ATTTTNNG | 960 |
| CAAGCAGAAGACGGCATACGAGATNNNNNNNGGTCTCGTGGGCTCGGAGATGTGTATAAGAGACAG | CNNNNNNN | 961 |
| CAAGCAGAAGACGGCATACGAGATNNNNNNNCGTCTCGTGGGCTCGGAGATGTGTATAAGAGACAG | GNNNNNNN | 962 |
| CAAGCAGAAGACGGCATACGAGATNNNNNNNAGTCTCGTGGGCTCGGAGATGTGTATAAGAGACAG | TNNNNNNN | 963 |

TABLE 7

Table 7: Primer P7 for next-generation sequencer and index thereof

| Primer P7 for next-generation sequencer | Index | SEQ ID NO |
|---|---|---|
| CAAGCAGAAGACGGCATACGAGATTNNTTTTTGTCTCGTGGGCTCGGAGATGTGTATAAGAGACAG | AAAAANNA | 964 |
| CAAGCAGAAGACGGCATACGAGATGNNTTTTTGTCTCGTGGGCTCGGAGATGTGTATAAGAGACAG | AAAAANNC | 965 |
| CAAGCAGAAGACGGCATACGAGATANNTTTTTGTCTCGTGGGCTCGGAGATGTGTATAAGAGACAG | AAAAANNT | 966 |
| CAAGCAGAAGACGGCATACGAGATAGNTTTTGTCTCGTGGGCTCGGAGATGTGTATAAGAGACAG | AAAACNCT | 967 |
| CAAGCAGAAGACGGCATACGAGATACNTTTTGTCTCGTGGGCTCGGAGATGTGTATAAGAGACAG | AAAACNGT | 968 |
| CAAGCAGAAGACGGCATACGAGATAANGTTTTGTCTCGTGGGCTCGGAGATGTGTATAAGAGACAG | AAAACNTT | 969 |
| CAAGCAGAAGACGGCATACGAGATAGNATTTTGTCTCGTGGGCTCGGAGATGTGTATAAGAGACAG | AAAATNCT | 970 |
| CAAGCAGAAGACGGCATACGAGATACNATTTTGTCTCGTGGGCTCGGAGATGTGTATAAGAGACAG | AAAATNGT | 971 |
| CAAGCAGAAGACGGCATACGAGATAANATTTTGTCTCGTGGGCTCGGAGATGTGTATAAGAGACAG | AAAATNTT | 972 |
| CAAGCAGAAGACGGCATACGAGATACNTGTTTGTCTCGTGGGCTCGGAGATGTGTATAAGAGACAG | AAACANGT | 973 |
| CAAGCAGAAGACGGCATACGAGATACTTCTTTGTCTCGTGGGCTCGGAGATGTGTATAAGAGACAG | AAAGAAGT | 974 |
| CAAGCAGAAGACGGCATACGAGATACCTCTTTGTCTCGTGGGCTCGGAGATGTGTATAAGAGACAG | AAAGAGGT | 975 |
| CAAGCAGAAGACGGCATACGAGATACATCTTTGTCTCGTGGGCTCGGAGATGTGTATAAGAGACAG | AAAGATGT | 976 |
| CAAGCAGAAGACGGCATACGAGATTCTTATTTGTCTCGTGGGCTCGGAGATGTGTATAAGAGACAG | AAATAAGA | 977 |
| CAAGCAGAAGACGGCATACGAGATGCTTATTTGTCTCGTGGGCTCGGAGATGTGTATAAGAGACAG | AAATAAGC | 978 |
| CAAGCAGAAGACGGCATACGAGATTCCTATTTGTCTCGTGGGCTCGGAGATGTGTATAAGAGACAG | AAATAGGA | 979 |
| CAAGCAGAAGACGGCATACGAGATGCCTATTTGTCTCGTGGGCTCGGAGATGTGTATAAGAGACAG | AAATAGGC | 980 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATANNTATTTGTCTCGTGGGCTCGGAGATGTGTATAAGAGACAG | AAATANNT | 981 |
| CAAGCAGAAGACGGCATACGAGATTCATATTTGTCTCGTGGGCTCGGAGATGTGTATAAGAGACAG | AAATATGA | 982 |
| CAAGCAGAAGACGGCATACGAGATGCATATTTGTCTCGTGGGCTCGGAGATGTGTATAAGAGACAG | AAATATGC | 983 |
| CAAGCAGAAGACGGCATACGAGATAGTTTGTTGTCTCGTGGGCTCGGAGATGTGTATAAGAGACAG | AACAAACT | 984 |
| CAAGCAGAAGACGGCATACGAGATAATTTGTTGTCTCGTGGGCTCGGAGATGTGTATAAGAGACAG | AACAAATT | 985 |
| CAAGCAGAAGACGGCATACGAGATAGCTTGTTGTCTCGTGGGCTCGGAGATGTGTATAAGAGACAG | AACAAGCT | 986 |
| CAAGCAGAAGACGGCATACGAGATAACTTGTTGTCTCGTGGGCTCGGAGATGTGTATAAGAGACAG | AACAAGTT | 987 |
| CAAGCAGAAGACGGCATACGAGATACNTTGTTGTCTCGTGGGCTCGGAGATGTGTATAAGAGACAG | AACAANGT | 988 |
| CAAGCAGAAGACGGCATACGAGATAGATTGTTGTCTCGTGGGCTCGGAGATGTGTATAAGAGACAG | AACAATCT | 989 |
| CAAGCAGAAGACGGCATACGAGATAAATTGTTGTCTCGTGGGCTCGGAGATGTGTATAAGAGACAG | AACAATTT | 990 |
| CAAGCAGAAGACGGCATACGAGATACNTTCTTGTCTCGTGGGCTCGGAGATGTGTATAAGAGACAG | AAGAANGT | 991 |
| CAAGCAGAAGACGGCATACGAGATTCNTTATTGTCTCGTGGGCTCGGAGATGTGTATAAGAGACAG | AATAANGA | 992 |
| CAAGCAGAAGACGGCATACGAGATGCNTTATTGTCTCGTGGGCTCGGAGATGTGTATAAGAGACAG | AATAANGC | 993 |
| CAAGCAGAAGACGGCATACGAGATANNTTATTGTCTCGTGGGCTCGGAGATGTGTATAAGAGACAG | AATAANNT | 994 |
| CAAGCAGAAGACGGCATACGAGATACTTAATTGTCTCGTGGGCTCGGAGATGTGTATAAGAGACAG | AATTAAGT | 995 |
| CAAGCAGAAGACGGCATACGAGATACCTAATTGTCTCGTGGGCTCGGAGATGTGTATAAGAGACAG | AATTAGGT | 996 |
| CAAGCAGAAGACGGCATACGAGATACATAATTGTCTCGTGGGCTCGGAGATGTGTATAAGAGACAG | AATTATGT | 997 |
| CAAGCAGAAGACGGCATACGAGATAGNTTTGTGTCTCGTGGGCTCGGAGATGTGTATAAGAGACAG | ACAAANCT | 998 |
| CAAGCAGAAGACGGCATACGAGATACNTTTGTGTCTCGTGGGCTCGGAGATGTGTATAAGAGACAG | ACAAANGT | 999 |
| CAAGCAGAAGACGGCATACGAGATAANTTTGTGTCTCGTGGGCTCGGAGATGTGTATAAGAGACAG | ACAAANTT | 1000 |
| CAAGCAGAAGACGGCATACGAGATTNNTTTATGTCTCGTGGGCTCGGAGATGTGTATAAGAGACAG | ATAAANNA | 1001 |
| CAAGCAGAAGACGGCATACGAGATGNNTTTATGTCTCGTGGGCTCGGAGATGTGTATAAGAGACAG | ATAAANNC | 1002 |
| CAAGCAGAAGACGGCATACGAGATANNTTTATGTCTCGTGGGCTCGGAGATGTGTATAAGAGACAG | ATAAANNT | 1003 |
| CAAGCAGAAGACGGCATACGAGATATTGTTATGTCTCGTGGGCTCGGAGATGTGTATAAGAGACAG | ATAACAAT | 1004 |
| CAAGCAGAAGACGGCATACGAGATATCGTTATGTCTCGTGGGCTCGGAGATGTGTATAAGAGACAG | ATAACGAT | 1005 |
| CAAGCAGAAGACGGCATACGAGATAGNGTTATGTCTCGTGGGCTCGGAGATGTGTATAAGAGACAG | ATAACNCT | 1006 |
| CAAGCAGAAGACGGCATACGAGATACNGTTATGTCTCGTGGGCTCGGAGATGTGTATAAGAGACAG | ATAACNGT | 1007 |
| CAAGCAGAAGACGGCATACGAGATAANGTTATGTCTCGTGGGCTCGGAGATGTGTATAAGAGACAG | ATAACNTT | 1008 |
| CAAGCAGAAGACGGCATACGAGATATAGTTATGTCTCGTGGGCTCGGAGATGTGTATAAGAGACAG | ATAACTAT | 1009 |
| CAAGCAGAAGACGGCATACGAGATATTATTATGTCTCGTGGGCTCGGAGATGTGTATAAGAGACAG | ATAATAAT | 1010 |
| CAAGCAGAAGACGGCATACGAGATATCATTATGTCTCGTGGGCTCGGAGATGTGTATAAGAGACAG | ATAATGAT | 1011 |
| CAAGCAGAAGACGGCATACGAGATAGNATTATGTCTCGTGGGCTCGGAGATGTGTATAAGAGACAG | ATAATNCT | 1012 |
| CAAGCAGAAGACGGCATACGAGATACNATTATGTCTCGTGGGCTCGGAGATGTGTATAAGAGACAG | ATAATNGT | 1013 |
| CAAGCAGAAGACGGCATACGAGATAANATTATGTCTCGTGGGCTCGGAGATGTGTATAAGAGACAG | ATAATNTT | 1014 |
| CAAGCAGAAGACGGCATACGAGATATAATTATGTCTCGTGGGCTCGGAGATGTGTATAAGAGACAG | ATAATTAT | 1015 |
| CAAGCAGAAGACGGCATACGAGATAGTTGTATGTCTCGTGGGCTCGGAGATGTGTATAAGAGACAG | ATACAACT | 1016 |
| CAAGCAGAAGACGGCATACGAGATAATTGTATGTCTCGTGGGCTCGGAGATGTGTATAAGAGACAG | ATACAATT | 1017 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATAGCTGTATGTCTCGTGGGCTCGGAGATGTGTATAAGAGACAG | ATACAGCT | 1018 |
| CAAGCAGAAGACGGCATACGAGATAACTGTATGTCTCGTGGGCTCGGAGATGTGTATAAGAGACAG | ATACAGTT | 1019 |
| CAAGCAGAAGACGGCATACGAGATACNTGTATGTCTCGTGGGCTCGGAGATGTGTATAAGAGACAG | ATACANGT | 1020 |
| CAAGCAGAAGACGGCATACGAGATAGATGTATGTCTCGTGGGCTCGGAGATGTGTATAAGAGACAG | ATACATCT | 1021 |
| CAAGCAGAAGACGGCATACGAGATAAATGTATGTCTCGTGGGCTCGGAGATGTGTATAAGAGACAG | ATACATTT | 1022 |
| CAAGCAGAAGACGGCATACGAGATAGTTCTATGTCTCGTGGGCTCGGAGATGTGTATAAGAGACAG | ATAGAACT | 1023 |
| CAAGCAGAAGACGGCATACGAGATAATTCTATGTCTCGTGGGCTCGGAGATGTGTATAAGAGACAG | ATAGAATT | 1024 |
| CAAGCAGAAGACGGCATACGAGATAGCTCTATGTCTCGTGGGCTCGGAGATGTGTATAAGAGACAG | ATAGAGCT | 1025 |
| CAAGCAGAAGACGGCATACGAGATAACTCTATGTCTCGTGGGCTCGGAGATGTGTATAAGAGACAG | ATAGAGTT | 1026 |
| CAAGCAGAAGACGGCATACGAGATACNTCTATGTCTCGTGGGCTCGGAGATGTGTATAAGAGACAG | ATAGANGT | 1027 |
| CAAGCAGAAGACGGCATACGAGATAGATCTATGTCTCGTGGGCTCGGAGATGTGTATAAGAGACAG | ATAGATCT | 1028 |
| CAAGCAGAAGACGGCATACGAGATAAATCTATGTCTCGTGGGCTCGGAGATGTGTATAAGAGACAG | ATAGATTT | 1029 |
| CAAGCAGAAGACGGCATACGAGATTCNTATATGTCTCGTGGGCTCGGAGATGTGTATAAGAGACAG | ATATANGA | 1030 |
| CAAGCAGAAGACGGCATACGAGATGCNTATATGTCTCGTGGGCTCGGAGATGTGTATAAGAGACAG | ATATANGC | 1031 |
| CAAGCAGAAGACGGCATACGAGATANNTATATGTCTCGTGGGCTCGGAGATGTGTATAAGAGACAG | ATATANNT | 1032 |
| CAAGCAGAAGACGGCATACGAGATAGNTTGATGTCTCGTGGGCTCGGAGATGTGTATAAGAGACAG | ATCAANCT | 1033 |
| CAAGCAGAAGACGGCATACGAGATACNTTGATGTCTCGTGGGCTCGGAGATGTGTATAAGAGACAG | ATCAANGT | 1034 |
| CAAGCAGAAGACGGCATACGAGATAANTTGATGTCTCGTGGGCTCGGAGATGTGTATAAGAGACAG | ATCAANTT | 1035 |
| CAAGCAGAAGACGGCATACGAGATAGTTTCATGTCTCGTGGGCTCGGAGATGTGTATAAGAGACAG | ATGAAACT | 1036 |
| CAAGCAGAAGACGGCATACGAGATAATTTCATGTCTCGTGGGCTCGGAGATGTGTATAAGAGACAG | ATGAAATT | 1037 |
| CAAGCAGAAGACGGCATACGAGATAGCTTCATGTCTCGTGGGCTCGGAGATGTGTATAAGAGACAG | ATGAAGCT | 1038 |
| CAAGCAGAAGACGGCATACGAGATAACTTCATGTCTCGTGGGCTCGGAGATGTGTATAAGAGACAG | ATGAAGTT | 1039 |
| CAAGCAGAAGACGGCATACGAGATACNTTCATGTCTCGTGGGCTCGGAGATGTGTATAAGAGACAG | ATGAANGT | 1040 |
| CAAGCAGAAGACGGCATACGAGATAGATTCATGTCTCGTGGGCTCGGAGATGTGTATAAGAGACAG | ATGAATCT | 1041 |
| CAAGCAGAAGACGGCATACGAGATAAATTCATGTCTCGTGGGCTCGGAGATGTGTATAAGAGACAG | ATGAATTT | 1042 |
| CAAGCAGAAGACGGCATACGAGATTGTTTAATGTCTCGTGGGCTCGGAGATGTGTATAAGAGACAG | ATTAAACA | 1043 |
| CAAGCAGAAGACGGCATACGAGATGGTTTAATGTCTCGTGGGCTCGGAGATGTGTATAAGAGACAG | ATTAAACC | 1044 |
| CAAGCAGAAGACGGCATACGAGATTATTTAATGTCTCGTGGGCTCGGAGATGTGTATAAGAGACAG | ATTAAATA | 1045 |
| CAAGCAGAAGACGGCATACGAGATGATTTAATGTCTCGTGGGCTCGGAGATGTGTATAAGAGACAG | ATTAAATC | 1046 |
| CAAGCAGAAGACGGCATACGAGATTGCTTAATGTCTCGTGGGCTCGGAGATGTGTATAAGAGACAG | ATTAAGCA | 1047 |
| CAAGCAGAAGACGGCATACGAGATGGCTTAATGTCTCGTGGGCTCGGAGATGTGTATAAGAGACAG | ATTAAGCC | 1048 |
| CAAGCAGAAGACGGCATACGAGATTACTTAATGTCTCGTGGGCTCGGAGATGTGTATAAGAGACAG | ATTAAGTA | 1049 |
| CAAGCAGAAGACGGCATACGAGATGACTTAATGTCTCGTGGGCTCGGAGATGTGTATAAGAGACAG | ATTAAGTC | 1050 |
| CAAGCAGAAGACGGCATACGAGATTCNTTAATGTCTCGTGGGCTCGGAGATGTGTATAAGAGACAG | ATTAANGA | 1051 |
| CAAGCAGAAGACGGCATACGAGATGCNTTAATGTCTCGTGGGCTCGGAGATGTGTATAAGAGACAG | ATTAANGC | 1052 |
| CAAGCAGAAGACGGCATACGAGATANNTTAATGTCTCGTGGGCTCGGAGATGTGTATAAGAGACAG | ATTAANNT | 1053 |
| CAAGCAGAAGACGGCATACGAGATTGATTAATGTCTCGTGGGCTCGGAGATGTGTATAAGAGACAG | ATTAATCA | 1054 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATGGATTAATGTCTCGTGGGCTCGGAGATGTGTATAAGAGACAG | ATTAATCC | 1055 |
| CAAGCAGAAGACGGCATACGAGATTAATTAATGTCTCGTGGGCTCGGAGATGTGTATAAGAGACAG | ATTAATTA | 1056 |
| CAAGCAGAAGACGGCATACGAGATGAATTAATGTCTCGTGGGCTCGGAGATGTGTATAAGAGACAG | ATTAATTC | 1057 |
| CAAGCAGAAGACGGCATACGAGATAGTTAAATGTCTCGTGGGCTCGGAGATGTGTATAAGAGACAG | ATTTAACT | 1058 |
| CAAGCAGAAGACGGCATACGAGATAATTAAATGTCTCGTGGGCTCGGAGATGTGTATAAGAGACAG | ATTTAATT | 1059 |
| CAAGCAGAAGACGGCATACGAGATAGCTAAATGTCTCGTGGGCTCGGAGATGTGTATAAGAGACAG | ATTTAGCT | 1060 |
| CAAGCAGAAGACGGCATACGAGATAACTAAATGTCTCGTGGGCTCGGAGATGTGTATAAGAGACAG | ATTTAGTT | 1061 |
| CAAGCAGAAGACGGCATACGAGATACNTAAATGTCTCGTGGGCTCGGAGATGTGTATAAGAGACAG | ATTTANGT | 1062 |
| CAAGCAGAAGACGGCATACGAGATAGATAAATGTCTCGTGGGCTCGGAGATGTGTATAAGAGACAG | ATTTATCT | 1063 |
| CAAGCAGAAGACGGCATACGAGATAAATAAATGTCTCGTGGGCTCGGAGATGTGTATAAGAGACAG | ATTTATTT | 1064 |
| CAAGCAGAAGACGGCATACGAGATNNNNNNTGGTCTCGTGGGCTCGGAGATGTGTATAAGAGACAG | CANNNNNN | 1065 |
| CAAGCAGAAGACGGCATACGAGATNNNNNNGGGTCTCGTGGGCTCGGAGATGTGTATAAGAGACAG | CCNNNNNN | 1066 |
| CAAGCAGAAGACGGCATACGAGATNNNNNTCGGTCTCGTGGGCTCGGAGATGTGTATAAGAGACAG | CGANNNNN | 1067 |
| CAAGCAGAAGACGGCATACGAGATCNNCTGCGGTCTCGTGGGCTCGGAGATGTGTATAAGAGACAG | CGCAGNNG | 1068 |
| CAAGCAGAAGACGGCATACGAGATCGTCGGCGGTCTCGTGGGCTCGGAGATGTGTATAAGAGACAG | CGCCGACG | 1069 |
| CAAGCAGAAGACGGCATACGAGATCATCGGCGGTCTCGTGGGCTCGGAGATGTGTATAAGAGACAG | CGCCGATG | 1070 |
| CAAGCAGAAGACGGCATACGAGATCGCCGGCGGTCTCGTGGGCTCGGAGATGTGTATAAGAGACAG | CGCCGGCG | 1071 |
| CAAGCAGAAGACGGCATACGAGATCACCGGCGGTCTCGTGGGCTCGGAGATGTGTATAAGAGACAG | CGCCGGTG | 1072 |
| CAAGCAGAAGACGGCATACGAGATCCNCGGCGGTCTCGTGGGCTCGGAGATGTGTATAAGAGACAG | CGCCGNGG | 1073 |
| CAAGCAGAAGACGGCATACGAGATCGACGGCGGTCTCGTGGGCTCGGAGATGTGTATAAGAGACAG | CGCCGTCG | 1074 |
| CAAGCAGAAGACGGCATACGAGATCAACGGCGGTCTCGTGGGCTCGGAGATGTGTATAAGAGACAG | CGCCGTTG | 1075 |
| CAAGCAGAAGACGGCATACGAGATCCNCCGCGGTCTCGTGGGCTCGGAGATGTGTATAAGAGACAG | CGCGGNGG | 1076 |
| CAAGCAGAAGACGGCATACGAGATNNNTNGCGGTCTCGTGGGCTCGGAGATGTGTATAAGAGACAG | CGCNANNN | 1077 |
| CAAGCAGAAGACGGCATACGAGATNNNGNGCGGTCTCGTGGGCTCGGAGATGTGTATAAGAGACAG | CGCNCNNN | 1078 |
| CAAGCAGAAGACGGCATACGAGATTNNCNGCGGTCTCGTGGGCTCGGAGATGTGTATAAGAGACAG | CGCNGNNA | 1079 |
| CAAGCAGAAGACGGCATACGAGATGNNCNGCGGTCTCGTGGGCTCGGAGATGTGTATAAGAGACAG | CGCNGNNC | 1080 |
| CAAGCAGAAGACGGCATACGAGATANNCNGCGGTCTCGTGGGCTCGGAGATGTGTATAAGAGACAG | CGCNGNNT | 1081 |
| CAAGCAGAAGACGGCATACGAGATNNNANGCGGTCTCGTGGGCTCGGAGATGTGTATAAGAGACAG | CGCNTNNN | 1082 |
| CAAGCAGAAGACGGCATACGAGATCNNCAGCGGTCTCGTGGGCTCGGAGATGTGTATAAGAGACAG | CGCTGNNG | 1083 |
| CAAGCAGAAGACGGCATACGAGATCNNCTCCGGTCTCGTGGGCTCGGAGATGTGTATAAGAGACAG | CGGAGNNG | 1084 |
| CAAGCAGAAGACGGCATACGAGATCCTCGCCGGTCTCGTGGGCTCGGAGATGTGTATAAGAGACAG | CGGCGAGG | 1085 |
| CAAGCAGAAGACGGCATACGAGATCCCCGCCGGTCTCGTGGGCTCGGAGATGTGTATAAGAGACAG | CGGCGGGG | 1086 |
| CAAGCAGAAGACGGCATACGAGATCCACGCCGGTCTCGTGGGCTCGGAGATGTGTATAAGAGACAG | CGGCGTGG | 1087 |
| CAAGCAGAAGACGGCATACGAGATCCTCCCCGGTCTCGTGGGCTCGGAGATGTGTATAAGAGACAG | CGGGGAGG | 1088 |
| CAAGCAGAAGACGGCATACGAGATCCCCCCCGGTCTCGTGGGCTCGGAGATGTGTATAAGAGACAG | CGGGGGGG | 1089 |
| CAAGCAGAAGACGGCATACGAGATCCACCCCGGTCTCGTGGGCTCGGAGATGTGTATAAGAGACAG | CGGGGTGG | 1090 |
| CAAGCAGAAGACGGCATACGAGATNNNTNCCGGTCTCGTGGGCTCGGAGATGTGTATAAGAGACAG | CGGNANNN | 1091 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATNNNGNCCGGTCTCGTGGGCTCGGAGATGTGTATAAGAGACAG | CGGNCNNN | 1092 |
| CAAGCAGAAGACGGCATACGAGATTNNCNCCGGTCTCGTGGGCTCGGAGATGTGTATAAGAGACAG | CGGNGNNA | 1093 |
| CAAGCAGAAGACGGCATACGAGATGNNCNCCGGTCTCGTGGGCTCGGAGATGTGTATAAGAGACAG | CGGNGNNC | 1094 |
| CAAGCAGAAGACGGCATACGAGATANNCNCCGGTCTCGTGGGCTCGGAGATGTGTATAAGAGACAG | CGGNGNNT | 1095 |
| CAAGCAGAAGACGGCATACGAGATNNNANCCGGTCTCGTGGGCTCGGAGATGTGTATAAGAGACAG | CGGNTNNN | 1096 |
| CAAGCAGAAGACGGCATACGAGATCNNCACCGGTCTCGTGGGCTCGGAGATGTGTATAAGAGACAG | CGGTGNNG | 1097 |
| CAAGCAGAAGACGGCATACGAGATNNNNNACGGTCTCGTGGGCTCGGAGATGTGTATAAGAGACAG | CGTNNNNN | 1098 |
| CAAGCAGAAGACGGCATACGAGATNNNNNNAGGTCTCGTGGGCTCGGAGATGTGTATAAGAGACAG | CTNNNNNN | 1099 |
| CAAGCAGAAGACGGCATACGAGATNNNNNTTCGTCTCGTGGGCTCGGAGATGTGTATAAGAGACAG | GAANNNNN | 1100 |
| CAAGCAGAAGACGGCATACGAGATNNNNNGTCGTCTCGTGGGCTCGGAGATGTGTATAAGAGACAG | GACNNNNN | 1101 |
| CAAGCAGAAGACGGCATACGAGATCNNCTCTCGTCTCGTGGGCTCGGAGATGTGTATAAGAGACAG | GAGAGNNG | 1102 |
| CAAGCAGAAGACGGCATACGAGATCNNCGCTCGTCTCGTGGGCTCGGAGATGTGTATAAGAGACAG | GAGCGNNG | 1103 |
| CAAGCAGAAGACGGCATACGAGATCTTCCCTCGTCTCGTGGGCTCGGAGATGTGTATAAGAGACAG | GAGGGAAG | 1104 |
| CAAGCAGAAGACGGCATACGAGATCTCCCCTCGTCTCGTGGGCTCGGAGATGTGTATAAGAGACAG | GAGGGGAG | 1105 |
| CAAGCAGAAGACGGCATACGAGATCGNCCCTCGTCTCGTGGGCTCGGAGATGTGTATAAGAGACAG | GAGGGNCG | 1106 |
| CAAGCAGAAGACGGCATACGAGATCCNCCCTCGTCTCGTGGGCTCGGAGATGTGTATAAGAGACAG | GAGGGNGG | 1107 |
| CAAGCAGAAGACGGCATACGAGATCANCCCTCGTCTCGTGGGCTCGGAGATGTGTATAAGAGACAG | GAGGGNTG | 1108 |
| CAAGCAGAAGACGGCATACGAGATCTACCCTCGTCTCGTGGGCTCGGAGATGTGTATAAGAGACAG | GAGGGTAG | 1109 |
| CAAGCAGAAGACGGCATACGAGATNNNTNCTCGTCTCGTGGGCTCGGAGATGTGTATAAGAGACAG | GAGNANNN | 1110 |
| CAAGCAGAAGACGGCATACGAGATNNNGNCTCGTCTCGTGGGCTCGGAGATGTGTATAAGAGACAG | GAGNCNNN | 1111 |
| CAAGCAGAAGACGGCATACGAGATTNNCNCTCGTCTCGTGGGCTCGGAGATGTGTATAAGAGACAG | GAGNGNNA | 1112 |
| CAAGCAGAAGACGGCATACGAGATGNNCNCTCGTCTCGTGGGCTCGGAGATGTGTATAAGAGACAG | GAGNGNNC | 1113 |
| CAAGCAGAAGACGGCATACGAGATANNCNCTCGTCTCGTGGGCTCGGAGATGTGTATAAGAGACAG | GAGNGNNT | 1114 |
| CAAGCAGAAGACGGCATACGAGATNNNANCTCGTCTCGTGGGCTCGGAGATGTGTATAAGAGACAG | GAGNTNNN | 1115 |
| CAAGCAGAAGACGGCATACGAGATCNNCACTCGTCTCGTGGGCTCGGAGATGTGTATAAGAGACAG | GAGTGNNG | 1116 |
| CAAGCAGAAGACGGCATACGAGATNNNNNATCGTCTCGTGGGCTCGGAGATGTGTATAAGAGACAG | GATNNNNN | 1117 |
| CAAGCAGAAGACGGCATACGAGATNNNNNTGCGTCTCGTGGGCTCGGAGATGTGTATAAGAGACAG | GCANNNNN | 1118 |
| CAAGCAGAAGACGGCATACGAGATCNNGTGGCGTCTCGTGGGCTCGGAGATGTGTATAAGAGACAG | GCCACNNG | 1119 |
| CAAGCAGAAGACGGCATACGAGATTNNCTGGCGTCTCGTGGGCTCGGAGATGTGTATAAGAGACAG | GCCAGNNA | 1120 |
| CAAGCAGAAGACGGCATACGAGATGNNCTGGCGTCTCGTGGGCTCGGAGATGTGTATAAGAGACAG | GCCAGNNC | 1121 |
| CAAGCAGAAGACGGCATACGAGATCNNCTGGCGTCTCGTGGGCTCGGAGATGTGTATAAGAGACAG | GCCAGNNG | 1122 |
| CAAGCAGAAGACGGCATACGAGATCNNATGGCGTCTCGTGGGCTCGGAGATGTGTATAAGAGACAG | GCCATNNG | 1123 |
| CAAGCAGAAGACGGCATACGAGATCGTGGGGCGTCTCGTGGGCTCGGAGATGTGTATAAGAGACAG | GCCCCACG | 1124 |
| CAAGCAGAAGACGGCATACGAGATCATGGGGCGTCTCGTGGGCTCGGAGATGTGTATAAGAGACAG | GCCCCATG | 1125 |
| CAAGCAGAAGACGGCATACGAGATCGCGGGGCGTCTCGTGGGCTCGGAGATGTGTATAAGAGACAG | GCCCCGCG | 1126 |
| CAAGCAGAAGACGGCATACGAGATCACGGGGCGTCTCGTGGGCTCGGAGATGTGTATAAGAGACAG | GCCCCGTG | 1127 |
| CAAGCAGAAGACGGCATACGAGATCCNGGGGCGTCTCGTGGGCTCGGAGATGTGTATAAGAGACAG | GCCCCNGG | 1128 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATCGAGGGGCGTCTCGTGGGCTCGGAGATGTGTATAAGAGACAG | GCCCCTCG | 1129 |
| CAAGCAGAAGACGGCATACGAGATCAAGGGGCGTCTCGTGGGCTCGGAGATGTGTATAAGAGACAG | GCCCCTTG | 1130 |
| CAAGCAGAAGACGGCATACGAGATTGNCGGGCGTCTCGTGGGCTCGGAGATGTGTATAAGAGACAG | GCCCGNCA | 1131 |
| CAAGCAGAAGACGGCATACGAGATGGNCGGGCGTCTCGTGGGCTCGGAGATGTGTATAAGAGACAG | GCCCGNCC | 1132 |
| CAAGCAGAAGACGGCATACGAGATTCNCGGGCGTCTCGTGGGCTCGGAGATGTGTATAAGAGACAG | GCCCGNGA | 1133 |
| CAAGCAGAAGACGGCATACGAGATGCNCGGGCGTCTCGTGGGCTCGGAGATGTGTATAAGAGACAG | GCCCGNGC | 1134 |
| CAAGCAGAAGACGGCATACGAGATTANCGGGCGTCTCGTGGGCTCGGAGATGTGTATAAGAGACAG | GCCCGNTA | 1135 |
| CAAGCAGAAGACGGCATACGAGATGANCGGGCGTCTCGTGGGCTCGGAGATGTGTATAAGAGACAG | GCCCGNTC | 1136 |
| CAAGCAGAAGACGGCATACGAGATCGTAGGGCGTCTCGTGGGCTCGGAGATGTGTATAAGAGACAG | GCCCTACG | 1137 |
| CAAGCAGAAGACGGCATACGAGATCATAGGGCGTCTCGTGGGCTCGGAGATGTGTATAAGAGACAG | GCCCTATG | 1138 |
| CAAGCAGAAGACGGCATACGAGATCGCAGGGCGTCTCGTGGGCTCGGAGATGTGTATAAGAGACAG | GCCCTGCG | 1139 |
| CAAGCAGAAGACGGCATACGAGATCACAGGGCGTCTCGTGGGCTCGGAGATGTGTATAAGAGACAG | GCCCTGTG | 1140 |
| CAAGCAGAAGACGGCATACGAGATCCNAGGGCGTCTCGTGGGCTCGGAGATGTGTATAAGAGACAG | GCCCTNGG | 1141 |
| CAAGCAGAAGACGGCATACGAGATCGAAGGGCGTCTCGTGGGCTCGGAGATGTGTATAAGAGACAG | GCCCTTCG | 1142 |
| CAAGCAGAAGACGGCATACGAGATCAAAGGGCGTCTCGTGGGCTCGGAGATGTGTATAAGAGACAG | GCCCTTTG | 1143 |
| CAAGCAGAAGACGGCATACGAGATCGTGCGGCGTCTCGTGGGCTCGGAGATGTGTATAAGAGACAG | GCCGCACG | 1144 |
| CAAGCAGAAGACGGCATACGAGATCATGCGGCGTCTCGTGGGCTCGGAGATGTGTATAAGAGACAG | GCCGCATG | 1145 |
| CAAGCAGAAGACGGCATACGAGATCGCGCGGCGTCTCGTGGGCTCGGAGATGTGTATAAGAGACAG | GCCGCGCG | 1146 |
| CAAGCAGAAGACGGCATACGAGATCACGCGGCGTCTCGTGGGCTCGGAGATGTGTATAAGAGACAG | GCCGCGTG | 1147 |
| CAAGCAGAAGACGGCATACGAGATCCNGCGGCGTCTCGTGGGCTCGGAGATGTGTATAAGAGACAG | GCCGCNGG | 1148 |
| CAAGCAGAAGACGGCATACGAGATCGAGCGGCGTCTCGTGGGCTCGGAGATGTGTATAAGAGACAG | GCCGCTCG | 1149 |
| CAAGCAGAAGACGGCATACGAGATCAAGCGGCGTCTCGTGGGCTCGGAGATGTGTATAAGAGACAG | GCCGCTTG | 1150 |
| CAAGCAGAAGACGGCATACGAGATTGNCCGGCGTCTCGTGGGCTCGGAGATGTGTATAAGAGACAG | GCCGGNCA | 1151 |
| CAAGCAGAAGACGGCATACGAGATGGNCCGGCGTCTCGTGGGCTCGGAGATGTGTATAAGAGACAG | GCCGGNCC | 1152 |
| CAAGCAGAAGACGGCATACGAGATTCNCCGGCGTCTCGTGGGCTCGGAGATGTGTATAAGAGACAG | GCCGGNGA | 1153 |
| CAAGCAGAAGACGGCATACGAGATGCNCCGGCGTCTCGTGGGCTCGGAGATGTGTATAAGAGACAG | GCCGGNGC | 1154 |
| CAAGCAGAAGACGGCATACGAGATTANCCGGCGTCTCGTGGGCTCGGAGATGTGTATAAGAGACAG | GCCGGNTA | 1155 |
| CAAGCAGAAGACGGCATACGAGATGANCCGGCGTCTCGTGGGCTCGGAGATGTGTATAAGAGACAG | GCCGGNTC | 1156 |
| CAAGCAGAAGACGGCATACGAGATCGTACGGCGTCTCGTGGGCTCGGAGATGTGTATAAGAGACAG | GCCGTACG | 1157 |
| CAAGCAGAAGACGGCATACGAGATCATACGGCGTCTCGTGGGCTCGGAGATGTGTATAAGAGACAG | GCCGTATG | 1158 |
| CAAGCAGAAGACGGCATACGAGATCGCACGGCGTCTCGTGGGCTCGGAGATGTGTATAAGAGACAG | GCCGTGCG | 1159 |
| CAAGCAGAAGACGGCATACGAGATCACACGGCGTCTCGTGGGCTCGGAGATGTGTATAAGAGACAG | GCCGTGTG | 1160 |
| CAAGCAGAAGACGGCATACGAGATCCNACGGCGTCTCGTGGGCTCGGAGATGTGTATAAGAGACAG | GCCGTNGG | 1161 |
| CAAGCAGAAGACGGCATACGAGATCGAACGGCGTCTCGTGGGCTCGGAGATGTGTATAAGAGACAG | GCCGTTCG | 1162 |
| CAAGCAGAAGACGGCATACGAGATCAAACGGCGTCTCGTGGGCTCGGAGATGTGTATAAGAGACAG | GCCGTTTG | 1163 |
| CAAGCAGAAGACGGCATACGAGATNNNTNGGCGTCTCGTGGGCTCGGAGATGTGTATAAGAGACAG | GCCNANNN | 1164 |
| CAAGCAGAAGACGGCATACGAGATTNNGNGGCGTCTCGTGGGCTCGGAGATGTGTATAAGAGACAG | GCCNCNNA | 1165 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATGNNGNGGCGTCTCGTGGGCTCGGAGATGTGTATAAGAGACAG | GCCNCNNC | 1166 |
| CAAGCAGAAGACGGCATACGAGATANNGNGGCGTCTCGTGGGCTCGGAGATGTGTATAAGAGACAG | GCCNCNNT | 1167 |
| CAAGCAGAAGACGGCATACGAGATANNCGGCGTCTCGTGGGCTCGGAGATGTGTATAAGAGACAG | GCCNGNNT | 1168 |
| CAAGCAGAAGACGGCATACGAGATTNNANGGCGTCTCGTGGGCTCGGAGATGTGTATAAGAGACAG | GCCNTNNA | 1169 |
| CAAGCAGAAGACGGCATACGAGATGNNANGGCGTCTCGTGGGCTCGGAGATGTGTATAAGAGACAG | GCCNTNNC | 1170 |
| CAAGCAGAAGACGGCATACGAGATANNANGGCGTCTCGTGGGCTCGGAGATGTGTATAAGAGACAG | GCCNTNNT | 1171 |
| CAAGCAGAAGACGGCATACGAGATCNNGAGGCGTCTCGTGGGCTCGGAGATGTGTATAAGAGACAG | GCCTCNNG | 1172 |
| CAAGCAGAAGACGGCATACGAGATCCNCAGGCGTCTCGTGGGCTCGGAGATGTGTATAAGAGACAG | GCCTGNGG | 1173 |
| CAAGCAGAAGACGGCATACGAGATTNNCAGGCGTCTCGTGGGCTCGGAGATGTGTATAAGAGACAG | GCCTGNNA | 1174 |
| CAAGCAGAAGACGGCATACGAGATGNNCAGGCGTCTCGTGGGCTCGGAGATGTGTATAAGAGACAG | GCCTGNNC | 1175 |
| CAAGCAGAAGACGGCATACGAGATCNNAAGGCGTCTCGTGGGCTCGGAGATGTGTATAAGAGACAG | GCCTTNNG | 1176 |
| CAAGCAGAAGACGGCATACGAGATCNNGTCGCGTCTCGTGGGCTCGGAGATGTGTATAAGAGACAG | GCGACNNG | 1177 |
| CAAGCAGAAGACGGCATACGAGATTNNCTCGCGTCTCGTGGGCTCGGAGATGTGTATAAGAGACAG | GCGAGNNA | 1178 |
| CAAGCAGAAGACGGCATACGAGATGNNCTCGCGTCTCGTGGGCTCGGAGATGTGTATAAGAGACAG | GCGAGNNC | 1179 |
| CAAGCAGAAGACGGCATACGAGATCNNCTCGCGTCTCGTGGGCTCGGAGATGTGTATAAGAGACAG | GCGAGNNG | 1180 |
| CAAGCAGAAGACGGCATACGAGATCNNATCGCGTCTCGTGGGCTCGGAGATGTGTATAAGAGACAG | GCGATNNG | 1181 |
| CAAGCAGAAGACGGCATACGAGATCCNGGCGCGTCTCGTGGGCTCGGAGATGTGTATAAGAGACAG | GCGCCNGG | 1182 |
| CAAGCAGAAGACGGCATACGAGATTGNCGCGCGTCTCGTGGGCTCGGAGATGTGTATAAGAGACAG | GCGCGNCA | 1183 |
| CAAGCAGAAGACGGCATACGAGATGGNCGCGCGTCTCGTGGGCTCGGAGATGTGTATAAGAGACAG | GCGCGNCC | 1184 |
| CAAGCAGAAGACGGCATACGAGATTCNCGCGCGTCTCGTGGGCTCGGAGATGTGTATAAGAGACAG | GCGCGNGA | 1185 |
| CAAGCAGAAGACGGCATACGAGATGCNCGCGCGTCTCGTGGGCTCGGAGATGTGTATAAGAGACAG | GCGCGNGC | 1186 |
| CAAGCAGAAGACGGCATACGAGATTANCGCGCGTCTCGTGGGCTCGGAGATGTGTATAAGAGACAG | GCGCGNTA | 1187 |
| CAAGCAGAAGACGGCATACGAGATGANCGCGCGTCTCGTGGGCTCGGAGATGTGTATAAGAGACAG | GCGCGNTC | 1188 |
| CAAGCAGAAGACGGCATACGAGATCCNAGCGCGTCTCGTGGGCTCGGAGATGTGTATAAGAGACAG | GCGCTNGG | 1189 |
| CAAGCAGAAGACGGCATACGAGATCCTGCCGCGTCTCGTGGGCTCGGAGATGTGTATAAGAGACAG | GCGGCAGG | 1190 |
| CAAGCAGAAGACGGCATACGAGATCCCGCCGCGTCTCGTGGGCTCGGAGATGTGTATAAGAGACAG | GCGGCGGG | 1191 |
| CAAGCAGAAGACGGCATACGAGATCCAGCCGCGTCTCGTGGGCTCGGAGATGTGTATAAGAGACAG | GCGGCTGG | 1192 |
| CAAGCAGAAGACGGCATACGAGATTGNCCCGCGTCTCGTGGGCTCGGAGATGTGTATAAGAGACAG | GCGGGNCA | 1193 |
| CAAGCAGAAGACGGCATACGAGATGGNCCCGCGTCTCGTGGGCTCGGAGATGTGTATAAGAGACAG | GCGGGNCC | 1194 |
| CAAGCAGAAGACGGCATACGAGATTCNCCCGCGTCTCGTGGGCTCGGAGATGTGTATAAGAGACAG | GCGGGNGA | 1195 |
| CAAGCAGAAGACGGCATACGAGATGCNCCCGCGTCTCGTGGGCTCGGAGATGTGTATAAGAGACAG | GCGGGNGC | 1196 |
| CAAGCAGAAGACGGCATACGAGATTANCCCGCGTCTCGTGGGCTCGGAGATGTGTATAAGAGACAG | GCGGGNTA | 1197 |
| CAAGCAGAAGACGGCATACGAGATGANCCCGCGTCTCGTGGGCTCGGAGATGTGTATAAGAGACAG | GCGGGNTC | 1198 |
| CAAGCAGAAGACGGCATACGAGATCCTACCGCGTCTCGTGGGCTCGGAGATGTGTATAAGAGACAG | GCGGTAGG | 1199 |
| CAAGCAGAAGACGGCATACGAGATCCCACCGCGTCTCGTGGGCTCGGAGATGTGTATAAGAGACAG | GCGGTGGG | 1200 |
| CAAGCAGAAGACGGCATACGAGATCCAACCGCGTCTCGTGGGCTCGGAGATGTGTATAAGAGACAG | GCGGTTGG | 1201 |
| CAAGCAGAAGACGGCATACGAGATNNNTNCGCGTCTCGTGGGCTCGGAGATGTGTATAAGAGACAG | GCGNANNN | 1202 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATTNNGNCGCGTCTCGTGGGCTCGGAGATGTGTATAAGAGACAG | GCGNCNNA | 1203 |
| CAAGCAGAAGACGGCATACGAGATGNNGNCGCGTCTCGTGGGCTCGGAGATGTGTATAAGAGACAG | GCGNCNNC | 1204 |
| CAAGCAGAAGACGGCATACGAGATANNGNCGCGTCTCGTGGGCTCGGAGATGTGTATAAGAGACAG | GCGNCNNT | 1205 |
| CAAGCAGAAGACGGCATACGAGATANNCNCGCGTCTCGTGGGCTCGGAGATGTGTATAAGAGACAG | GCGNGNNT | 1206 |
| CAAGCAGAAGACGGCATACGAGATTNNANCGCGTCTCGTGGGCTCGGAGATGTGTATAAGAGACAG | GCGNTNNA | 1207 |
| CAAGCAGAAGACGGCATACGAGATGNNANCGCGTCTCGTGGGCTCGGAGATGTGTATAAGAGACAG | GCGNTNNC | 1208 |
| CAAGCAGAAGACGGCATACGAGATANNANCGCGTCTCGTGGGCTCGGAGATGTGTATAAGAGACAG | GCGNTNNT | 1209 |
| CAAGCAGAAGACGGCATACGAGATCNNGACGCGTCTCGTGGGCTCGGAGATGTGTATAAGAGACAG | GCGTCNNG | 1210 |
| CAAGCAGAAGACGGCATACGAGATCCTCACGCGTCTCGTGGGCTCGGAGATGTGTATAAGAGACAG | GCGTGAGG | 1211 |
| CAAGCAGAAGACGGCATACGAGATCCCCACGCGTCTCGTGGGCTCGGAGATGTGTATAAGAGACAG | GCGTGGGG | 1212 |
| CAAGCAGAAGACGGCATACGAGATTNNCACGCGTCTCGTGGGCTCGGAGATGTGTATAAGAGACAG | GCGTGNNA | 1213 |
| CAAGCAGAAGACGGCATACGAGATGNNCACGCGTCTCGTGGGCTCGGAGATGTGTATAAGAGACAG | GCGTGNNC | 1214 |
| CAAGCAGAAGACGGCATACGAGATCCACACGCGTCTCGTGGGCTCGGAGATGTGTATAAGAGACAG | GCGTGTGG | 1215 |
| CAAGCAGAAGACGGCATACGAGATCNNAACGCGTCTCGTGGGCTCGGAGATGTGTATAAGAGACAG | GCGTTNNG | 1216 |
| CAAGCAGAAGACGGCATACGAGATCNNCTAGCGTCTCGTGGGCTCGGAGATGTGTATAAGAGACAG | GCTAGNNG | 1217 |
| CAAGCAGAAGACGGCATACGAGATCGTCGAGCGTCTCGTGGGCTCGGAGATGTGTATAAGAGACAG | GCTCGACG | 1218 |
| CAAGCAGAAGACGGCATACGAGATCATCGAGCGTCTCGTGGGCTCGGAGATGTGTATAAGAGACAG | GCTCGATG | 1219 |
| CAAGCAGAAGACGGCATACGAGATCGCCGAGCGTCTCGTGGGCTCGGAGATGTGTATAAGAGACAG | GCTCGGCG | 1220 |
| CAAGCAGAAGACGGCATACGAGATCACCGAGCGTCTCGTGGGCTCGGAGATGTGTATAAGAGACAG | GCTCGGTG | 1221 |
| CAAGCAGAAGACGGCATACGAGATCCNCGAGCGTCTCGTGGGCTCGGAGATGTGTATAAGAGACAG | GCTCGNGG | 1222 |
| CAAGCAGAAGACGGCATACGAGATCGACGAGCGTCTCGTGGGCTCGGAGATGTGTATAAGAGACAG | GCTCGTCG | 1223 |
| CAAGCAGAAGACGGCATACGAGATCAACGAGCGTCTCGTGGGCTCGGAGATGTGTATAAGAGACAG | GCTCGTTG | 1224 |
| CAAGCAGAAGACGGCATACGAGATCCNCCAGCGTCTCGTGGGCTCGGAGATGTGTATAAGAGACAG | GCTGGNGG | 1225 |
| CAAGCAGAAGACGGCATACGAGATNNNTNAGCGTCTCGTGGGCTCGGAGATGTGTATAAGAGACAG | GCTNANNN | 1226 |
| CAAGCAGAAGACGGCATACGAGATNNNGNAGCGTCTCGTGGGCTCGGAGATGTGTATAAGAGACAG | GCTNCNNN | 1227 |
| CAAGCAGAAGACGGCATACGAGATTNNCNAGCGTCTCGTGGGCTCGGAGATGTGTATAAGAGACAG | GCTNGNNA | 1228 |
| CAAGCAGAAGACGGCATACGAGATGNNCNAGCGTCTCGTGGGCTCGGAGATGTGTATAAGAGACAG | GCTNGNNC | 1229 |
| CAAGCAGAAGACGGCATACGAGATANNCNAGCGTCTCGTGGGCTCGGAGATGTGTATAAGAGACAG | GCTNGNNT | 1230 |
| CAAGCAGAAGACGGCATACGAGATNNNANAGCGTCTCGTGGGCTCGGAGATGTGTATAAGAGACAG | GCTNTNNN | 1231 |
| CAAGCAGAAGACGGCATACGAGATCNNCAAGCGTCTCGTGGGCTCGGAGATGTGTATAAGAGACAG | GCTTGNNG | 1232 |
| CAAGCAGAAGACGGCATACGAGATCNNGTTCCGTCTCGTGGGCTCGGAGATGTGTATAAGAGACAG | GGAACNNG | 1233 |
| CAAGCAGAAGACGGCATACGAGATTNNCTTCCGTCTCGTGGGCTCGGAGATGTGTATAAGAGACAG | GGAAGNNA | 1234 |
| CAAGCAGAAGACGGCATACGAGATGNNCTTCCGTCTCGTGGGCTCGGAGATGTGTATAAGAGACAG | GGAAGNNC | 1235 |
| CAAGCAGAAGACGGCATACGAGATCNNCTTCCGTCTCGTGGGCTCGGAGATGTGTATAAGAGACAG | GGAAGNNG | 1236 |
| CAAGCAGAAGACGGCATACGAGATCNNATTCCGTCTCGTGGGCTCGGAGATGTGTATAAGAGACAG | GGAATNNG | 1237 |
| CAAGCAGAAGACGGCATACGAGATCGTGGTCCGTCTCGTGGGCTCGGAGATGTGTATAAGAGACAG | GGACCACG | 1238 |
| CAAGCAGAAGACGGCATACGAGATCATGGTCCGTCTCGTGGGCTCGGAGATGTGTATAAGAGACAG | GGACCATG | 1239 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATCGCGGTCCGTCTCGTGGGCTCGGAGATGTGTATAAGAGACAG | GGACCGCG | 1240 |
| CAAGCAGAAGACGGCATACGAGATCACGGTCCGTCTCGTGGGCTCGGAGATGTGTATAAGAGACAG | GGACCGTG | 1241 |
| CAAGCAGAAGACGGCATACGAGATCCNGGTCCGTCTCGTGGGCTCGGAGATGTGTATAAGAGACAG | GGACCNGG | 1242 |
| CAAGCAGAAGACGGCATACGAGATCGAGGTCCGTCTCGTGGGCTCGGAGATGTGTATAAGAGACAG | GGACCTCG | 1243 |
| CAAGCAGAAGACGGCATACGAGATCAAGGTCCGTCTCGTGGGCTCGGAGATGTGTATAAGAGACAG | GGACCTTG | 1244 |
| CAAGCAGAAGACGGCATACGAGATTGNCGTCCGTCTCGTGGGCTCGGAGATGTGTATAAGAGACAG | GGACGNCA | 1245 |
| CAAGCAGAAGACGGCATACGAGATGGNCGTCCGTCTCGTGGGCTCGGAGATGTGTATAAGAGACAG | GGACGNCC | 1246 |
| CAAGCAGAAGACGGCATACGAGATTCNCGTCCGTCTCGTGGGCTCGGAGATGTGTATAAGAGACAG | GGACGNGA | 1247 |
| CAAGCAGAAGACGGCATACGAGATGCNCGTCCGTCTCGTGGGCTCGGAGATGTGTATAAGAGACAG | GGACGNGC | 1248 |
| CAAGCAGAAGACGGCATACGAGATTANCGTCCGTCTCGTGGGCTCGGAGATGTGTATAAGAGACAG | GGACGNTA | 1249 |
| CAAGCAGAAGACGGCATACGAGATGANCGTCCGTCTCGTGGGCTCGGAGATGTGTATAAGAGACAG | GGACGNTC | 1250 |
| CAAGCAGAAGACGGCATACGAGATCGTAGTCCGTCTCGTGGGCTCGGAGATGTGTATAAGAGACAG | GGACTACG | 1251 |
| CAAGCAGAAGACGGCATACGAGATCATAGTCCGTCTCGTGGGCTCGGAGATGTGTATAAGAGACAG | GGACTATG | 1252 |
| CAAGCAGAAGACGGCATACGAGATCGCAGTCCGTCTCGTGGGCTCGGAGATGTGTATAAGAGACAG | GGACTGCG | 1253 |
| CAAGCAGAAGACGGCATACGAGATCACAGTCCGTCTCGTGGGCTCGGAGATGTGTATAAGAGACAG | GGACTGTG | 1254 |
| CAAGCAGAAGACGGCATACGAGATCCNAGTCCGTCTCGTGGGCTCGGAGATGTGTATAAGAGACAG | GGACTNGG | 1255 |
| CAAGCAGAAGACGGCATACGAGATCGAAGTCCGTCTCGTGGGCTCGGAGATGTGTATAAGAGACAG | GGACTTCG | 1256 |
| CAAGCAGAAGACGGCATACGAGATCAAAGTCCGTCTCGTGGGCTCGGAGATGTGTATAAGAGACAG | GGACTTTG | 1257 |
| CAAGCAGAAGACGGCATACGAGATCCNGCTCCGTCTCGTGGGCTCGGAGATGTGTATAAGAGACAG | GGAGCNGG | 1258 |
| CAAGCAGAAGACGGCATACGAGATTGNCCTCCGTCTCGTGGGCTCGGAGATGTGTATAAGAGACAG | GGAGGNCA | 1259 |
| CAAGCAGAAGACGGCATACGAGATGGNCCTCCGTCTCGTGGGCTCGGAGATGTGTATAAGAGACAG | GGAGGNCC | 1260 |
| CAAGCAGAAGACGGCATACGAGATTCNCCTCCGTCTCGTGGGCTCGGAGATGTGTATAAGAGACAG | GGAGGNGA | 1261 |
| CAAGCAGAAGACGGCATACGAGATGCNCCTCCGTCTCGTGGGCTCGGAGATGTGTATAAGAGACAG | GGAGGNGC | 1262 |
| CAAGCAGAAGACGGCATACGAGATTANCCTCCGTCTCGTGGGCTCGGAGATGTGTATAAGAGACAG | GGAGGNTA | 1263 |
| CAAGCAGAAGACGGCATACGAGATGANCCTCCGTCTCGTGGGCTCGGAGATGTGTATAAGAGACAG | GGAGGNTC | 1264 |
| CAAGCAGAAGACGGCATACGAGATCCNACTCCGTCTCGTGGGCTCGGAGATGTGTATAAGAGACAG | GGAGTNGG | 1265 |
| CAAGCAGAAGACGGCATACGAGATNNNTNTCCGTCTCGTGGGCTCGGAGATGTGTATAAGAGACAG | GGANANNN | 1266 |
| CAAGCAGAAGACGGCATACGAGATTNNGNTCCGTCTCGTGGGCTCGGAGATGTGTATAAGAGACAG | GGANCNNA | 1267 |
| CAAGCAGAAGACGGCATACGAGATGNNGNTCCGTCTCGTGGGCTCGGAGATTTGTATAAGAGACAG | GGANCNNC | 1268 |
| CAAGCAGAAGACGGCATACGAGATANNGNTCCGTCTCGTGGGCTCGGAGATGTGTATAAGAGACAG | GGANCNNT | 1269 |
| CAAGCAGAAGACGGCATACGAGATANNCNTCCGTCTCGTGGGCTCGGAGATGTGTATAAGAGACAG | GGANGNNT | 1270 |
| CAAGCAGAAGACGGCATACGAGATTNNANTCCGTCTCGTGGGCTCGGAGATGTGTATAAGAGACAG | GGANTNNA | 1271 |
| CAAGCAGAAGACGGCATACGAGATGNNANTCCGTCTCGTGGGCTCGGAGATGTGTATAAGAGACAG | GGANTNNC | 1272 |
| CAAGCAGAAGACGGCATACGAGATANNANTCCGTCTCGTGGGCTCGGAGATGTGTATAAGAGACAG | GGANTNNT | 1273 |
| CAAGCAGAAGACGGCATACGAGATCNNGATCCGTCTCGTGGGCTCGGAGATGTGTATAAGAGACAG | GGATCNNG | 1274 |
| CAAGCAGAAGACGGCATACGAGATCCTCATCCGTCTCGTGGGCTCGGAGATGTGTATAAGAGACAG | GGATGAGG | 1275 |
| CAAGCAGAAGACGGCATACGAGATCCCCATCCGTCTCGTGGGCTCGGAGATGTGTATAAGAGACAG | GGATGGGG | 1276 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATTNNCATCCGTCTCGTGGGCTCGGAGATGTGTATAAGAGACAG | GGATGNNA | 1277 |
| CAAGCAGAAGACGGCATACGAGATGNNCATCCGTCTCGTGGGCTCGGAGATGTGTATAAGAGACAG | GGATGNNC | 1278 |
| CAAGCAGAAGACGGCATACGAGATCCACATCCGTCTCGTGGGCTCGGAGATGTGTATAAGAGACAG | GGATGTGG | 1279 |
| CAAGCAGAAGACGGCATACGAGATCNNATCCGTCTCGTGGGCTCGGAGATGTGTATAAGAGACAG | GGATTNNG | 1280 |
| CAAGCAGAAGACGGCATACGAGATCNNTTGCCGTCTCGTGGGCTCGGAGATGTGTATAAGAGACAG | GGCAANNG | 1281 |
| CAAGCAGAAGACGGCATACGAGATCGTGTGCCGTCTCGTGGGCTCGGAGATGTGTATAAGAGACAG | GGCACACG | 1282 |
| CAAGCAGAAGACGGCATACGAGATCATGTGCCGTCTCGTGGGCTCGGAGATGTGTATAAGAGACAG | GGCACATG | 1283 |
| CAAGCAGAAGACGGCATACGAGATCGCGTGCCGTCTCGTGGGCTCGGAGATGTGTATAAGAGACAG | GGCACGCG | 1284 |
| CAAGCAGAAGACGGCATACGAGATCACGTGCCGTCTCGTGGGCTCGGAGATGTGTATAAGAGACAG | GGCACGTG | 1285 |
| CAAGCAGAAGACGGCATACGAGATCCNGTGCCGTCTCGTGGGCTCGGAGATGTGTATAAGAGACAG | GGCACNGG | 1286 |
| CAAGCAGAAGACGGCATACGAGATTNNGTGCCGTCTCGTGGGCTCGGAGATGTGTATAAGAGACAG | GGCACNNA | 1287 |
| CAAGCAGAAGACGGCATACGAGATGNNGTGCCGTCTCGTGGGCTCGGAGATGTGTATAAGAGACAG | GGCACNNC | 1288 |
| CAAGCAGAAGACGGCATACGAGATANNGTGCCGTCTCGTGGGCTCGGAGATGTGTATAAGAGACAG | GGCACNNT | 1289 |
| CAAGCAGAAGACGGCATACGAGATCGAGTGCCGTCTCGTGGGCTCGGAGATGTGTATAAGAGACAG | GGCACTCG | 1290 |
| CAAGCAGAAGACGGCATACGAGATCAAGTGCCGTCTCGTGGGCTCGGAGATGTGTATAAGAGACAG | GGCACTTG | 1291 |
| CAAGCAGAAGACGGCATACGAGATTGNCTGCCGTCTCGTGGGCTCGGAGATGTGTATAAGAGAGAG | GGCAGNCA | 1292 |
| CAAGCAGAAGACGGCATACGAGATGGNCTGCCGTCTCGTGGGCTCGGAGATGTGTATAAGAGACAG | GGCAGNCC | 1293 |
| CAAGCAGAAGACGGCATACGAGATTCNCTGCCGTCTCGTGGGCTCGGAGATGTGTATAAGAGACAG | GGCAGNGA | 1294 |
| CAAGCAGAAGACGGCATACGAGATGCNCTGCCGTCTCGTGGGCTCGGAGATGTGTATAAGAGACAG | GGCAGNGC | 1295 |
| CAAGCAGAAGACGGCATACGAGATANNCTGCCGTCTCGTGGGCTCGGAGATGTGTATAAGAGACAG | GGCAGNNT | 1296 |
| CAAGCAGAAGACGGCATACGAGATTANCTGCCGTCTCGTGGGCTCGGAGATGTGTATAAGAGACAG | GGCAGNTA | 1297 |
| CAAGCAGAAGACGGCATACGAGATGANCTGCCGTCTCGTGGGCTCGGAGATGTGTATAAGAGACAG | GGCAGNTC | 1298 |
| CAAGCAGAAGACGGCATACGAGATCGTATGCCGTCTCGTGGGCTCGGAGATGTGTATAAGAGACAG | GGCATACG | 1299 |
| CAAGCAGAAGACGGCATACGAGATCATATGCCGTCTCGTGGGCTCGGAGATGTGTATAAGAGACAG | GGCATATG | 1300 |
| CAAGCAGAAGACGGCATACGAGATCGCATGCCGTCTCGTGGGCTCGGAGATGTGTATAAGAGACAG | GGCATGCG | 1301 |
| CAAGCAGAAGACGGCATACGAGATCACATGCCGTCTCGTGGGCTCGGAGATGTGTATAAGAGACAG | GGCATGTG | 1302 |
| CAAGCAGAAGACGGCATACGAGATCCNATGCCGTCTCGTGGGCTCGGAGATGTGTATAAGAGACAG | GGCATNGG | 1303 |
| CAAGCAGAAGACGGCATACGAGATTNNATGCCGTCTCGTGGGCTCGGAGATGTGTATAAGAGACAG | GGCATNNA | 1304 |
| CAAGCAGAAGACGGCATACGAGATGNNATGCCGTCTCGTGGGCTCGGAGATGTGTATAAGAGACAG | GGCATNNC | 1305 |
| CAAGCAGAAGACGGCATACGAGATANNATGCCGTCTCGTGGGCTCGGAGATGTGTATAAGAGACAG | GGCATNNT | 1306 |
| CAAGCAGAAGACGGCATACGAGATCGAATGCCGTCTCGTGGGCTCGGAGATGTGTATAAGAGACAG | GGCATTCG | 1307 |
| CAAGCAGAAGACGGCATACGAGATCAAATGCCGTCTCGTGGGCTCGGAGATGTGTATAAGAGACAG | GGCATTTG | 1308 |
| CAAGCAGAAGACGGCATACGAGATAGNGGGCCGTCTCGTGGGCTCGGAGATGTGTATAAGAGACAG | GGCCCNCT | 1309 |
| CAAGCAGAAGACGGCATACGAGATACNGGGCCGTCTCGTGGGCTCGGAGATGTGTATAAGAGACAG | GGCCCNGT | 1310 |
| CAAGCAGAAGACGGCATACGAGATAANGGGCCGTCTCGTGGGCTCGGAGATGTGTATAAGAGACAG | GGCCCNTT | 1311 |
| CAAGCAGAAGACGGCATACGAGATAGNAGGCCGTCTCGTGGGCTCGGAGATGTGTATAAGAGACAG | GGCCTNCT | 1312 |
| CAAGCAGAAGACGGCATACGAGATACNAGGCCGTCTCGTGGGCTCGGAGATGTGTATAAGAGACAG | GGCCTNGT | 1313 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATAANAGGCCGTCTCGTGGGCTCGGAGATGTGTATAAGAGACAG | GGCCTNTT | 1314 |
| CAAGCAGAAGACGGCATACGAGATAGNGCGCCGTCTCGTGGGCTCGGAGATGTGTATAAGAGACAG | GGCGCNCT | 1315 |
| CAAGCAGAAGACGGCATACGAGATACNGCGCCGTCTCGTGGGCTCGGAGATGTGTATAAGAGACAG | GGCGCNGT | 1316 |
| CAAGCAGAAGACGGCATACGAGATAANGCGCCGTCTCGTGGGCTCGGAGATGTGTATAAGAGACAG | GGCGCNTT | 1317 |
| CAAGCAGAAGACGGCATACGAGATAGNACGCCGTCTCGTGGGCTCGGAGATGTGTATAAGAGACAG | GGCGTNCT | 1318 |
| CAAGCAGAAGACGGCATACGAGATACNACGCCGTCTCGTGGGCTCGGAGATGTGTATAAGAGACAG | GGCGTNGT | 1319 |
| CAAGCAGAAGACGGCATACGAGATAANACGCCGTCTCGTGGGCTCGGAGATGTGTATAAGAGACAG | GGCGTNTT | 1320 |
| CAAGCAGAAGACGGCATACGAGATTNNTNGCCGTCTCGTGGGCTCGGAGATGTGTATAAGAGACAG | GGCNANNA | 1321 |
| CAAGCAGAAGACGGCATACGAGATGNNTNGCCGTCTCGTGGGCTCGGAGATGTGTATAAGAGACAG | GGCNANNC | 1322 |
| CAAGCAGAAGACGGCATACGAGATANNTNGCCGTCTCGTGGGCTCGGAGATGTGTATAAGAGACAG | GGCNANNT | 1323 |
| CAAGCAGAAGACGGCATACGAGATCGNTAGCCGTCTCGTGGGCTCGGAGATGTGTATAAGAGACAG | GGCTANCG | 1324 |
| CAAGCAGAAGACGGCATACGAGATCCNTAGCCGTCTCGTGGGCTCGGAGATGTGTATAAGAGACAG | GGCTANGG | 1325 |
| CAAGCAGAAGACGGCATACGAGATCANTAGCCGTCTCGTGGGCTCGGAGATGTGTATAAGAGACAG | GGCTANTG | 1326 |
| CAAGCAGAAGACGGCATACGAGATTGNGAGCCGTCTCGTGGGCTCGGAGATGTGTATAAGAGACAG | GGCTCNCA | 1327 |
| CAAGCAGAAGACGGCATACGAGATGGNGAGCCGTCTCGTGGGCTCGGAGATGTGTATAAGAGACAG | GGCTCNCC | 1328 |
| CAAGCAGAAGACGGCATACGAGATTCNGAGCCGTCTCGTGGGCTCGGAGATGTGTATAAGAGACAG | GGCTCNGA | 1329 |
| CAAGCAGAAGACGGCATACGAGATGCNGAGCCGTCTCGTGGGCTCGGAGATGTGTATAAGAGACAG | GGCTCNGC | 1330 |
| CAAGCAGAAGACGGCATACGAGATANNGAGCCGTCTCGTGGGCTCGGAGATGTGTATAAGAGACAG | GGCTCNNT | 1331 |
| CAAGCAGAAGACGGCATACGAGATTANGAGCCGTCTCGTGGGCTCGGAGATGTGTATAAGAGACAG | GGCTCNTA | 1332 |
| CAAGCAGAAGACGGCATACGAGATGANGAGCCGTCTCGTGGGCTCGGAGATGTGTATAAGAGACAG | GGCTCNTC | 1333 |
| CAAGCAGAAGACGGCATACGAGATAGNCAGCCGTCTCGTGGGCTCGGAGATGTGTATAAGAGACAG | GGCTGNCT | 1334 |
| CAAGCAGAAGACGGCATACGAGATACNCAGCCGTCTCGTGGGCTCGGAGATGTGTATAAGAGACAG | GGCTGNGT | 1335 |
| CAAGCAGAAGACGGCATACGAGATAANCAGCCGTCTCGTGGGCTCGGAGATGTGTATAAGAGACAG | GGCTGNTT | 1336 |
| CAAGCAGAAGACGGCATACGAGATTGNAAGCCGTCTCGTGGGCTCGGAGATGTGTATAAGAGACAG | GGCTTNCA | 1337 |
| CAAGCAGAAGACGGCATACGAGATGGNAAGCCGTCTCGTGGGCTCGGAGATGTGTATAAGAGACAG | GGCTTNCC | 1338 |
| CAAGCAGAAGACGGCATACGAGATTCNAAGCCGTCTCGTGGGCTCGGAGATGTGTATAAGAGACAG | GGCTTNGA | 1339 |
| CAAGCAGAAGACGGCATACGAGATGCNAAGCCGTCTCGTGGGCTCGGAGATGTGTATAAGAGACAG | GGCTTNGC | 1340 |
| CAAGCAGAAGACGGCATACGAGATANNAAGCCGTCTCGTGGGCTCGGAGATGTGTATAAGAGACAG | GGCTTNNT | 1341 |
| CAAGCAGAAGACGGCATACGAGATTANAAGCCGTCTCGTGGGCTCGGAGATGTGTATAAGAGACAG | GGCTTNTA | 1342 |
| CAAGCAGAAGACGGCATACGAGATGANAAGCCGTCTCGTGGGCTCGGAGATGTGTATAAGAGACAG | GGCTTNTC | 1343 |
| CAAGCAGAAGACGGCATACGAGATCNNTTCCCGTCTCGTGGGCTCGGAGATGTGTATAAGAGACAG | GGGAANNG | 1344 |
| CAAGCAGAAGACGGCATACGAGATCCNGTCCCGTCTCGTGGGCTCGGAGATGTGTATAAGAGACAG | GGGACNGG | 1345 |
| CAAGCAGAAGACGGCATACGAGATTNNGTCCCGTCTCGTGGGCTCGGAGATGTGTATAAGAGACAG | GGGACNNA | 1346 |
| CAAGCAGAAGACGGCATACGAGATGNNGTCCCGTCTCGTGGGCTCGGAGATGTGTATAAGAGACAG | GGGACNNC | 1347 |
| CAAGCAGAAGACGGCATACGAGATANNGTCCCGTCTCGTGGGCTCGGAGATGTGTATAAGAGACAG | GGGACNNT | 1348 |
| CAAGCAGAAGACGGCATACGAGATTGNCTCCCGTCTCGTGGGCTCGGAGATGTGTATAAGAGACAG | GGGAGNCA | 1349 |
| CAAGCAGAAGACGGCATACGAGATGGNCTCCCGTCTCGTGGGCTCGGAGATGTGTATAAGAGACAG | GGGAGNCC | 1350 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATTCNCTCCCGTCTCGTGGGCTCGGAGATGTGTATAAGAGACAG | GGGAGNGA | 1351 |
| CAAGCAGAAGACGGCATACGAGATGCNCTCCCGTCTCGTGGGCTCGGAGATGTGTATAAGAGACAG | GGGAGNGC | 1352 |
| CAAGCAGAAGACGGCATACGAGATANNCTCCCGTCTCGTGGGCTCGGAGATGTGTATAAGAGACAG | GGGAGNNT | 1353 |
| CAAGCAGAAGACGGCATACGAGATTANCTCCCGTCTCGTGGGCTCGGAGATGTGTATAAGAGACAG | GGGAGNTA | 1354 |
| CAAGCAGAAGACGGCATACGAGATGANCTCCCGTCTCGTGGGCTCGGAGATGTGTATAAGAGACAG | GGGAGNTC | 1355 |
| CAAGCAGAAGACGGCATACGAGATCCNATCCCGTCTCGTGGGCTCGGAGATGTGTATAAGAGACAG | GGGATNGG | 1356 |
| CAAGCAGAAGACGGCATACGAGATTNNATCCCGTCTCGTGGGCTCGGAGATGTGTATAAGAGACAG | GGGATNNA | 1357 |
| CAAGCAGAAGACGGCATACGAGATGNNATCCCGTCTCGTGGGCTCGGAGATGTGTATAAGAGACAG | GGGATNNC | 1358 |
| CAAGCAGAAGACGGCATACGAGATANNATCCCGTCTCGTGGGCTCGGAGATGTGTATAAGAGACAG | GGGATNNT | 1359 |
| CAAGCAGAAGACGGCATACGAGATAGNGGCCCGTCTCGTGGGCTCGGAGATGTGTATAAGAGACAG | GGGCCNCT | 1360 |
| CAAGCAGAAGACGGCATACGAGATACNGGCCCGTCTCGTGGGCTCGGAGATGTGTATAAGAGACAG | GGGCCNGT | 1361 |
| CAAGCAGAAGACGGCATACGAGATAANGGCCCGTCTCGTGGGCTCGGAGATGTGTATAAGAGACAG | GGGCCNTT | 1362 |
| CAAGCAGAAGACGGCATACGAGATAGNAGCCCGTCTCGTGGGCTCGGAGATGTGTATAAGAGACAG | GGGCTNCT | 1363 |
| CAAGCAGAAGACGGCATACGAGATACNAGCCCGTCTCGTGGGCTCGGAGATGTGTATAAGAGACAG | GGGCTNGT | 1364 |
| CAAGCAGAAGACGGCATACGAGATAANAGCCCGTCTCGTGGGCTCGGAGATGTGTATAAGAGACAG | GGGCTNTT | 1365 |
| CAAGCAGAAGACGGCATACGAGATAGNGCCCCGTCTCGTGGGCTCGGAGATGTGTATAAGAGACAG | GGGGCNCT | 1366 |
| CAAGCAGAAGACGGCATACGAGATACNGCCCCGTCTCGTGGGCTCGGAGATGTGTATAAGAGACAG | GGGGCNGT | 1367 |
| CAAGCAGAAGACGGCATACGAGATAANGCCCCGTCTCGTGGGCTCGGAGATGTGTATAAGAGACAG | GGGGCNTT | 1368 |
| CAAGCAGAAGACGGCATACGAGATAGNACCCCGTCTCGTGGGCTCGGAGATGTGTATAAGAGACAG | GGGGTNCT | 1369 |
| CAAGCAGAAGACGGCATACGAGATACNACCCCGTCTCGTGGGCTCGGAGATGTGTATAAGAGACAG | GGGGTNGT | 1370 |
| CAAGCAGAAGACGGCATACGAGATAANACCCCGTCTCGTGGGCTCGGAGATGTGTATAAGAGACAG | GGGGTNTT | 1371 |
| CAAGCAGAAGACGGCATACGAGATTNNTNCCCGTCTCGTGGGCTCGGAGATGTGTATAAGAGACAG | GGGNANNA | 1372 |
| CAAGCAGAAGACGGCATACGAGATGNNTNCCCGTCTCGTGGGCTCGGAGATGTGTATAAGAGACAG | GGGNANNC | 1373 |
| CAAGCAGAAGACGGCATACGAGATANNTNCCCGTCTCGTGGGCTCGGAGATGTGTATAAGAGACAG | GGGNANNT | 1374 |
| CAAGCAGAAGACGGCATACGAGATCGNTACCCGTCTCGTGGGCTCGGAGATGTGTATAAGAGACAG | GGGTANCG | 1375 |
| CAAGCAGAAGACGGCATACGAGATCCNTACCCGTCTCGTGGGCTCGGAGATGTGTATAAGAGACAG | GGGTANGG | 1376 |
| CAAGCAGAAGACGGCATACGAGATCANTACCCGTCTCGTGGGCTCGGAGATGTGTATAAGAGACAG | GGGTANTG | 1377 |
| CAAGCAGAAGACGGCATACGAGATTGNACCCGTCTCGTGGGCTCGGAGATGTGTATAAGAGACAG | GGGTCNCA | 1378 |
| CAAGCAGAAGACGGCATACGAGATGGNACCCGTCTCGTGGGCTCGGAGATGTGTATAAGAGACAG | GGGTCNCC | 1379 |
| CAAGCAGAAGACGGCATACGAGATTCNACCCGTCTCGTGGGCTCGGAGATGTGTATAAGAGACAG | GGGTCNGA | 1380 |
| CAAGCAGAAGACGGCATACGAGATGCNACCCGTCTCGTGGGCTCGGAGATGTGTATAAGAGACAG | GGGTCNGC | 1381 |
| CAAGCAGAAGACGGCATACGAGATANNGACCCGTCTCGTGGGCTCGGAGATGTGTATAAGAGACAG | GGGTCNNT | 1382 |
| CAAGCAGAAGACGGCATACGAGATTANGACCCGTCTCGTGGGCTCGGAGATGTGTATAAGAGACAG | GGGTCNTA | 1383 |
| CAAGCAGAAGACGGCATACGAGATGANGACCCGTCTCGTGGGCTCGGAGATGTGTATAAGAGACAG | GGGTCNTC | 1384 |
| CAAGCAGAAGACGGCATACGAGATAGNCACCCGTCTCGTGGGCTCGGAGATGTGTATAAGAGACAG | GGGTGNCT | 1385 |
| CAAGCAGAAGACGGCATACGAGATACNCACCCGTCTCGTGGGCTCGGAGATGTGTATAAGAGACAG | GGGTGNGT | 1386 |
| CAAGCAGAAGACGGCATACGAGATAANCACCCGTCTCGTGGGCTCGGAGATGTGTATAAGAGACAG | GGGTGNTT | 1387 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATTGNAACCCGTCTCGTGGGCTCGGAGATGTGTATAAGAGACAG | GGGTTNCA | 1388 |
| CAAGCAGAAGACGGCATACGAGATGGNAACCCGTCTCGTGGGCTCGGAGATGTGTATAAGAGACAG | GGGTTNCC | 1389 |
| CAAGCAGAAGACGGCATACGAGATTCNAACCCGTCTCGTGGGCTCGGAGATGTGTATAAGAGACAG | GGGTTNGA | 1390 |
| CAAGCAGAAGACGGCATACGAGATGCNAACCCGTCTCGTGGGCTCGGAGATGTGTATAAGAGACAG | GGGTTNGC | 1391 |
| CAAGCAGAAGACGGCATACGAGATANNAACCCGTCTCGTGGGCTCGGAGATGTGTATAAGAGACAG | GGGTTNNT | 1392 |
| CAAGCAGAAGACGGCATACGAGATTANAACCCGTCTCGTGGGCTCGGAGATGTGTATAAGAGACAG | GGGTTNTA | 1393 |
| CAAGCAGAAGACGGCATACGAGATGANAACCCGTCTCGTGGGCTCGGAGATGTGTATAAGAGACAG | GGGTTNTC | 1394 |
| CAAGCAGAAGACGGCATACGAGATCNNTTACCGTCTCGTGGGCTCGGAGATGTGTATAAGAGACAG | GGTAANNG | 1395 |
| CAAGCAGAAGACGGCATACGAGATTNNGTACCGTCTCGTGGGCTCGGAGATGTGTATAAGAGACAG | GGTACNNA | 1396 |
| CAAGCAGAAGACGGCATACGAGATGNNGTACCGTCTCGTGGGCTCGGAGATGTGTATAAGAGACAG | GGTACNNC | 1397 |
| CAAGCAGAAGACGGCATACGAGATCNNGTACCGTCTCGTGGGCTCGGAGATGTGTATAAGAGACAG | GGTACNNG | 1398 |
| CAAGCAGAAGACGGCATACGAGATCGTCTACCGTCTCGTGGGCTCGGAGATGTGTATAAGAGACAG | GGTAGACG | 1399 |
| CAAGCAGAAGACGGCATACGAGATCATCTACCGTCTCGTGGGCTCGGAGATGTGTATAAGAGACAG | GGTAGATG | 1400 |
| CAAGCAGAAGACGGCATACGAGATCGCCTACCGTCTCGTGGGCTCGGAGATGTGTATAAGAGACAG | GGTAGGCG | 1401 |
| CAAGCAGAAGACGGCATACGAGATCACCTACCGTCTCGTGGGCTCGGAGATGTGTATAAGAGACAG | GGTAGGTG | 1402 |
| CAAGCAGAAGACGGCATACGAGATCCNCTACCGTCTCGTGGGCTCGGAGATGTGTATAAGAGACAG | GGTAGNGG | 1403 |
| CAAGCAGAAGACGGCATACGAGATTNNCTACCGTCTCGTGGGCTCGGAGATGTGTATAAGAGACAG | GGTAGNNA | 1404 |
| CAAGCAGAAGACGGCATACGAGATGNNCTACCGTCTCGTGGGCTCGGAGATGTGTATAAGAGACAG | GGTAGNNC | 1405 |
| CAAGCAGAAGACGGCATACGAGATANNCTACCGTCTCGTGGGCTCGGAGATGTGTATAAGAGACAG | GGTAGNNT | 1406 |
| CAAGCAGAAGACGGCATACGAGATCGACTACCGTCTCGTGGGCTCGGAGATGTGTATAAGAGACAG | GGTAGTCG | 1407 |
| CAAGCAGAAGACGGCATACGAGATCAACTACCGTCTCGTGGGCTCGGAGATGTGTATAAGAGACAG | GGTAGTTG | 1408 |
| CAAGCAGAAGACGGCATACGAGATTNNATACCGTCTCGTGGGCTCGGAGATGTGTATAAGAGACAG | GGTATNNA | 1409 |
| CAAGCAGAAGACGGCATACGAGATGNNATACCGTCTCGTGGGCTCGGAGATGTGTATAAGAGACAG | GGTATNNC | 1410 |
| CAAGCAGAAGACGGCATACGAGATCNNATACCGTCTCGTGGGCTCGGAGATGTGTATAAGAGACAG | GGTATNNG | 1411 |
| CAAGCAGAAGACGGCATACGAGATCGNTGACCGTCTCGTGGGCTCGGAGATGTGTATAAGAGACAG | GGTCANCG | 1412 |
| CAAGCAGAAGACGGCATACGAGATCCNTGACCGTCTCGTGGGCTCGGAGATGTGTATAAGAGACAG | GGTCANGG | 1413 |
| CAAGCAGAAGACGGCATACGAGATCANTGACCGTCTCGTGGGCTCGGAGATGTGTATAAGAGACAG | GGTCANTG | 1414 |
| CAAGCAGAAGACGGCATACGAGATTGNGACCGTCTCGTGGGCTCGGAGATGTGTATAAGAGACAG | GGTCCNCA | 1415 |
| CAAGCAGAAGACGGCATACGAGATGGNGACCGTCTCGTGGGCTCGGAGATGTGTATAAGAGACAG | GGTCCNCC | 1416 |
| CAAGCAGAAGACGGCATACGAGATTCNGACCGTCTCGTGGGCTCGGAGATGTGTATAAGAGACAG | GGTCCNGA | 1417 |
| CAAGCAGAAGACGGCATACGAGATGCNGACCGTCTCGTGGGCTCGGAGATGTGTATAAGAGACAG | GGTCCNGC | 1418 |
| CAAGCAGAAGACGGCATACGAGATTANGGACCGTCTCGTGGGCTCGGAGATGTGTATAAGAGACAG | GGTCCNTA | 1419 |
| CAAGCAGAAGACGGCATACGAGATGANGGACCGTCTCGTGGGCTCGGAGATGTGTATAAGAGACAG | GGTCCNTC | 1420 |
| CAAGCAGAAGACGGCATACGAGATAGNCGACCGTCTCGTGGGCTCGGAGATGTGTATAAGAGACAG | GGTCGNCT | 1421 |
| CAAGCAGAAGACGGCATACGAGATACNCGACCGTCTCGTGGGCTCGGAGATGTGTATAAGAGACAG | GGTCGNGT | 1422 |
| CAAGCAGAAGACGGCATACGAGATAANCGACCGTCTCGTGGGCTCGGAGATGTGTATAAGAGACAG | GGTCGNTT | 1423 |
| CAAGCAGAAGACGGCATACGAGATTGNAGACCGTCTCGTGGGCTCGGAGATGTGTATAAGAGACAG | GGTCTNCA | 1424 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATGGNAGACCGTCTCGTGGGCTCGGAGATGTGTATAAGAGACAG | GGTCTNCC | 1425 |
| CAAGCAGAAGACGGCATACGAGATTCNAGACCGTCTCGTGGGCTCGGAGATGTGTATAAGAGACAG | GGTCTNGA | 1426 |
| CAAGCAGAAGACGGCATACGAGATGCNAGACCGTCTCGTGGGCTCGGAGATGTGTATAAGAGACAG | GGTCTNGC | 1427 |
| CAAGCAGAAGACGGCATACGAGATTANAGACCGTCTCGTGGGCTCGGAGATGTGTATAAGAGACAG | GGTCTNTA | 1428 |
| CAAGCAGAAGACGGCATACGAGATGANAGACCGTCTCGTGGGCTCGGAGATGTGTATAAGAGACAG | GGTCTNTC | 1429 |
| CAAGCAGAAGACGGCATACGAGATCGNTCACCGTCTCGTGGGCTCGGAGATGTGTATAAGAGACAG | GGTGANCG | 1430 |
| CAAGCAGAAGACGGCATACGAGATCCNTCACCGTCTCGTGGGCTCGGAGATGTGTATAAGAGACAG | GGTGANGG | 1431 |
| CAAGCAGAAGACGGCATACGAGATCANTCACCGTCTCGTGGGCTCGGAGATGTGTATAAGAGACAG | GGTGANTG | 1432 |
| CAAGCAGAAGACGGCATACGAGATTGNCACCGTCTCGTGGGCTCGGAGATGTGTATAAGAGACAG | GGTGCNCA | 1433 |
| CAAGCAGAAGACGGCATACGAGATGGNCACCGTCTCGTGGGCTCGGAGATGTGTATAAGAGACAG | GGTGCNCC | 1434 |
| CAAGCAGAAGACGGCATACGAGATTCNCACCGTCTCGTGGGCTCGGAGATGTGTATAAGAGACAG | GGTGCNGA | 1435 |
| CAAGCAGAAGACGGCATACGAGATGCNCACCGTCTCGTGGGCTCGGAGATGTGTATAAGAGACAG | GGTGCNGC | 1436 |
| CAAGCAGAAGACGGCATACGAGATTANGCACCGTCTCGTGGGCTCGGAGATGTGTATAAGAGACAG | GGTGCNTA | 1437 |
| CAAGCAGAAGACGGCATACGAGATGANGCACCGTCTCGTGGGCTCGGAGATGTGTATAAGAGACAG | GGTGCNTC | 1438 |
| CAAGCAGAAGACGGCATACGAGATAGNCCACCGTCTCGTGGGCTCGGAGATGTGTATAAGAGACAG | GGTGGNCT | 1439 |
| CAAGCAGAAGACGGCATACGAGATACNCCACCGTCTCGTGGGCTCGGAGATGTGTATAAGAGACAG | GGTGGNGT | 1440 |
| CAAGCAGAAGACGGCATACGAGATAANCCACCGTCTCGTGGGCTCGGAGATGTGTATAAGAGACAG | GGTGGNTT | 1441 |
| CAAGCAGAAGACGGCATACGAGATTGNACACCGTCTCGTGGGCTCGGAGATGTGTATAAGAGACAG | GGTGTNCA | 1442 |
| CAAGCAGAAGACGGCATACGAGATGGNACACCGTCTCGTGGGCTCGGAGATGTGTATAAGAGACAG | GGTGTNCC | 1443 |
| CAAGCAGAAGACGGCATACGAGATTCNACACCGTCTCGTGGGCTCGGAGATGTGTATAAGAGACAG | GGTGTNGA | 1444 |
| CAAGCAGAAGACGGCATACGAGATGCNACACCGTCTCGTGGGCTCGGAGATGTGTATAAGAGACAG | GGTGTNGC | 1445 |
| CAAGCAGAAGACGGCATACGAGATTANACACCGTCTCGTGGGCTCGGAGATGTGTATAAGAGACAG | GGTGTNTA | 1446 |
| CAAGCAGAAGACGGCATACGAGATGANACACCGTCTCGTGGGCTCGGAGATGTGTATAAGAGACAG | GGTGTNTC | 1447 |
| CAAGCAGAAGACGGCATACGAGATTNNTNACCGTCTCGTGGGCTCGGAGATGTGTATAAGAGACAG | GGTNANNA | 1448 |
| CAAGCAGAAGACGGCATACGAGATGNNTNACCGTCTCGTGGGCTCGGAGATGTGTATAAGAGACAG | GGTNANNC | 1449 |
| CAAGCAGAAGACGGCATACGAGATANNTNACCGTCTCGTGGGCTCGGAGATGTGTATAAGAGACAG | GGTNANNT | 1450 |
| CAAGCAGAAGACGGCATACGAGATANNGNACCGTCTCGTGGGCTCGGAGATGTGTATAAGAGACAG | GGTNCNNT | 1451 |
| CAAGCAGAAGACGGCATACGAGATANNANACCGTCTCGTGGGCTCGGAGATGTGTATAAGAGACAG | GGTNTNNT | 1452 |
| CAAGCAGAAGACGGCATACGAGATCNNTAACCGTCTCGTGGGCTCGGAGATGTGTATAAGAGACAG | GGTTANNG | 1453 |
| CAAGCAGAAGACGGCATACGAGATCCNGAACCGTCTCGTGGGCTCGGAGATGTGTATAAGAGACAG | GGTTCNGG | 1454 |
| CAAGCAGAAGACGGCATACGAGATTNNGAACCGTCTCGTGGGCTCGGAGATGTGTATAAGAGACAG | GGTTCNNA | 1455 |
| CAAGCAGAAGACGGCATACGAGATGNNGAACCGTCTCGTGGGCTCGGAGATGTGTATAAGAGACAG | GGTTCNNC | 1456 |
| CAAGCAGAAGACGGCATACGAGATTGNCAACCGTCTCGTGGGCTCGGAGATGTGTATAAGAGACAG | GGTTGNCA | 1457 |
| CAAGCAGAAGACGGCATACGAGATGGNCAACCGTCTCGTGGGCTCGGAGATGTGTATAAGAGACAG | GGTTGNCC | 1458 |
| CAAGCAGAAGACGGCATACGAGATTCNCAACCGTCTCGTGGGCTCGGAGATGTGTATAAGAGACAG | GGTTGNGA | 1459 |
| CAAGCAGAAGACGGCATACGAGATGCNCAACCGTCTCGTGGGCTCGGAGATGTGTATAAGAGACAG | GGTTGNGC | 1460 |
| CAAGCAGAAGACGGCATACGAGATANNCAACCGTCTCGTGGGCTCGGAGATGTGTATAAGAGACAG | GGTTGNNT | 1461 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATTANCAACCGTCTCGTGGGCTCGGAGATGTGTATAAGAGACAG | GGTTGNTA | 1462 |
| CAAGCAGAAGACGGCATACGAGATGANCAACCGTCTCGTGGGCTCGGAGATGTGTATAAGAGACAG | GGTTGNTC | 1463 |
| CAAGCAGAAGACGGCATACGAGATCCNAAACCGTCTCGTGGGCTCGGAGATGTGTATAAGAGACAG | GGTTTNGG | 1464 |
| CAAGCAGAAGACGGCATACGAGATTNNAAACCGTCTCGTGGGCTCGGAGATGTGTATAAGAGACAG | GGTTTNNA | 1465 |
| CAAGCAGAAGACGGCATACGAGATGNNAAACCGTCTCGTGGGCTCGGAGATGTGTATAAGAGACAG | GGTTTNNC | 1466 |
| CAAGCAGAAGACGGCATACGAGATNNNNNNACGTCTCGTGGGCTCGGAGATGTGTATAAGAGACAG | GTNNNNNN | 1467 |
| CAAGCAGAAGACGGCATACGAGATNNNNNTAGTCTCGTGGGCTCGGAGATGTGTATAAGAGACAG | TANNNNNN | 1468 |
| CAAGCAGAAGACGGCATACGAGATNNNNNGAGTCTCGTGGGCTCGGAGATGTGTATAAGAGACAG | TCNNNNNN | 1469 |
| CAAGCAGAAGACGGCATACGAGATNNNNTCAGTCTCGTGGGCTCGGAGATGTGTATAAGAGACAG | TGANNNNN | 1470 |
| CAAGCAGAAGACGGCATACGAGATCNNCTGCAGTCTCGTGGGCTCGGAGATGTGTATAAGAGACAG | TGCAGNNG | 1471 |
| CAAGCAGAAGACGGCATACGAGATNNNTNGCAGTCTCGTGGGCTCGGAGATGTGTATAAGAGACAG | TGCNANNN | 1472 |
| CAAGCAGAAGACGGCATACGAGATNNNGNGCAGTCTCGTGGGCTCGGAGATGTGTATAAGAGACAG | TGCNCNNN | 1473 |
| CAAGCAGAAGACGGCATACGAGATTNNCNGCAGTCTCGTGGGCTCGGAGATGTGTATAAGAGACAG | TGCNGNNA | 1474 |
| CAAGCAGAAGACGGCATACGAGATGNNCNGCAGTCTCGTGGGCTCGGAGATGTGTATAAGAGACAG | TGCNGNNC | 1475 |
| CAAGCAGAAGACGGCATACGAGATANNCNGCAGTCTCGTGGGCTCGGAGATGTGTATAAGAGACAG | TGCNGNNT | 1476 |
| CAAGCAGAAGACGGCATACGAGATNNNANGCAGTCTCGTGGGCTCGGAGATGTGTATAAGAGACAG | TGCNTNNN | 1477 |
| CAAGCAGAAGACGGCATACGAGATCNNCAGCAGTCTCGTGGGCTCGGAGATGTGTATAAGAGACAG | TGCTGNNG | 1478 |
| CAAGCAGAAGACGGCATACGAGATCNNGTCCAGTCTCGTGGGCTCGGAGATGTGTATAAGAGACAG | TGGACNNG | 1479 |
| CAAGCAGAAGACGGCATACGAGATCNNCTCCAGTCTCGTGGGCTCGGAGATGTGTATAAGAGACAG | TGGAGNNG | 1480 |
| CAAGCAGAAGACGGCATACGAGATCNNATCCAGTCTCGTGGGCTCGGAGATGTGTATAAGAGACAG | TGGATNNG | 1481 |
| CAAGCAGAAGACGGCATACGAGATCNNGGCCAGTCTCGTGGGCTCGGAGATGTGTATAAGAGACAG | TGGCCNNG | 1482 |
| CAAGCAGAAGACGGCATACGAGATCNNAGCCAGTCTCGTGGGCTCGGAGATGTGTATAAGAGACAG | TGGCTNNG | 1483 |
| CAAGCAGAAGACGGCATACGAGATCTTGCCCAGTCTCGTGGGCTCGGAGATGTGTATAAGAGACAG | TGGGCAAG | 1484 |
| CAAGCAGAAGACGGCATACGAGATCTCGCCCAGTCTCGTGGGCTCGGAGATGTGTATAAGAGACAG | TGGGCGAG | 1485 |
| CAAGCAGAAGACGGCATACGAGATCGNGCCCAGTCTCGTGGGCTCGGAGATGTGTATAAGAGACAG | TGGGCNCG | 1486 |
| CAAGCAGAAGACGGCATACGAGATCCNGCCCAGTCTCGTGGGCTCGGAGATGTGTATAAGAGACAG | TGGGCNGG | 1487 |
| CAAGCAGAAGACGGCATACGAGATCANGCCCAGTCTCGTGGGCTCGGAGATGTGTATAAGAGACAG | TGGGCNTG | 1488 |
| CAAGCAGAAGACGGCATACGAGATCTAGCCCAGTCTCGTGGGCTCGGAGATGTGTATAAGAGACAG | TGGGCTAG | 1489 |
| CAAGCAGAAGACGGCATACGAGATCTTACCCAGTCTCGTGGGCTCGGAGATGTGTATAAGAGACAG | TGGGTAAG | 1490 |
| CAAGCAGAAGACGGCATACGAGATCTCACCCAGTCTCGTGGGCTCGGAGATGTGTATAAGAGACAG | TGGGTGAG | 1491 |
| CAAGCAGAAGACGGCATACGAGATCGNACCCAGTCTCGTGGGCTCGGAGATGTGTATAAGAGACAG | TGGGTNCG | 1492 |
| CAAGCAGAAGACGGCATACGAGATCCNACCCAGTCTCGTGGGCTCGGAGATGTGTATAAGAGACAG | TGGGTNGG | 1493 |
| CAAGCAGAAGACGGCATACGAGATCANACCCAGTCTCGTGGGCTCGGAGATGTGTATAAGAGACAG | TGGGTNTG | 1494 |
| CAAGCAGAAGACGGCATACGAGATCTAACCCAGTCTCGTGGGCTCGGAGATGTGTATAAGAGACAG | TGGGTTAG | 1495 |
| CAAGCAGAAGACGGCATACGAGATNNNTNCCAGTCTCGTGGGCTCGGAGATGTGTATAAGAGACAG | TGGNANNN | 1496 |
| CAAGCAGAAGACGGCATACGAGATTNNGNCCAGTCTCGTGGGCTCGGAGATGTGTATAAGAGACAG | TGGNCNNA | 1497 |
| CAAGCAGAAGACGGCATACGAGATGNNGNCCAGTCTCGTGGGCTCGGAGATGTGTATAAGAGACAG | TGGNCNNC | 1498 |

TABLE 7-continued

Table 7: Primer P7 for next-generation sequencer and index thereof

| Primer P7 for next-generation sequencer | Index | SEQ ID NO |
|---|---|---|
| CAAGCAGAAGACGGCATACGAGATANNGNCCAGTCTCGTGGGCTCGGAGATGTGTATAAGAGACAG | TGGNCNNT | 1499 |
| CAAGCAGAAGACGGCATACGAGATTNNCNCCAGTCTCGTGGGCTCGGAGATGTGTATAAGAGACAG | TGGNGNNA | 1500 |
| CAAGCAGAAGACGGCATACGAGATGNNCNCCAGTCTCGTGGGCTCGGAGATGTGTATAAGAGACAG | TGGNGNNC | 1501 |
| CAAGCAGAAGACGGCATACGAGATANNCNCCAGTCTCGTGGGCTCGGAGATGTGTATAAGAGACAG | TGGNGNNT | 1502 |
| CAAGCAGAAGACGGCATACGAGATTNNANCCAGTCTCGTGGGCTCGGAGATGTGTATAAGAGACAG | TGGNTNNA | 1503 |
| CAAGCAGAAGACGGCATACGAGATGNNANCCAGTCTCGTGGGCTCGGAGATGTGTATAAGAGACAG | TGGNTNNC | 1504 |
| CAAGCAGAAGACGGCATACGAGATANNANCCAGTCTCGTGGGCTCGGAGATGTGTATAAGAGACAG | TGGNTNNT | 1505 |
| CAAGCAGAAGACGGCATACGAGATCNNGACCAGTCTCGTGGGCTCGGAGATGTGTATAAGAGACAG | TGGTCNNG | 1506 |
| CAAGCAGAAGACGGCATACGAGATCTTCACCAGTCTCGTGGGCTCGGAGATGTGTATAAGAGACAG | TGGTGAAG | 1507 |
| CAAGCAGAAGACGGCATACGAGATCTCCACCAGTCTCGTGGGCTCGGAGATGTGTATAAGAGACAG | TGGTGGAG | 1508 |
| CAAGCAGAAGACGGCATACGAGATCGNCACCAGTCTCGTGGGCTCGGAGATGTGTATAAGAGACAG | TGGTGNCG | 1509 |
| CAAGCAGAAGACGGCATACGAGATCCNCACCAGTCTCGTGGGCTCGGAGATGTGTATAAGAGACAG | TGGTGNGG | 1510 |
| CAAGCAGAAGACGGCATACGAGATCANCACCAGTCTCGTGGGCTCGGAGATGTGTATAAGAGACAG | TGGTGNTG | 1511 |
| CAAGCAGAAGACGGCATACGAGATCTACACCAGTCTCGTGGGCTCGGAGATGTGTATAAGAGACAG | TGGTGTAG | 1512 |
| CAAGCAGAAGACGGCATACGAGATCNNAACCAGTCTCGTGGGCTCGGAGATGTGTATAAGAGACAG | TGGTTNNG | 1513 |
| CAAGCAGAAGACGGCATACGAGATNNNNNACAGTCTCGTGGGCTCGGAGATGTGTATAAGAGACAG | TGTNNNNN | 1514 |
| CAAGCAGAAGACGGCATACGAGATNNNNNNAAGTCTCGTGGGCTCGGAGATGTGTATAAGAGACAG | TTNNNNNN | 1515 |

5. Discussion

In the examples, the index sequence and the number of reads of the primer used for a next-generation sequencer (Illumina) were analyzed. As a result, no apparent correlation was observed in the primer P5 used for a next-generation sequencer, but an apparent correlation was observed in the primer P7 used for a next-generation sequencer (the correlational coefficient: 0.9 or higher). By calculating the putative number of reads based on the types of nucleotides constituting the index sequence using the estimation formula prepared by the GLMNET LASSO method, in particular, the primers P7 used for a next-generation sequencer with different index sequences were found to be classified into three groups based on the putative number of reads and the measured number of reads. Specifically, Group 1, which provides the number of reads as small as 15,000 or lower and is considered difficult to be subjected to analysis using the next-generation sequencer, was identified. The maximal putative number of reads of the primers P7 used for a next-generation sequencer of Group 1 was 20,051.8. In the examples, accordingly, all the index sequences providing the putative number of reads, which was calculated with the use of the estimation formula using the types of nucleotides constituting the index sequence as parameters, of 20,052 or higher were selected (Table 6). The primers P7 used for a next-generation sequencer comprising the selected index sequences (Table 6) are considered to be capable of providing a large number of reads when applied to the next-generation sequencer.

Since the putative number of reads provided by the primers P7 used for a next-generation sequencer of Group 3 was 50,000 or higher, all the index sequences providing the putative number of reads, which was calculated with the use of the estimation formula using the types of nucleotides constituting the index sequence as parameters, of 50,000 or higher were selected (Table 7). The primers P7 used for a next-generation sequencer comprising the selected index sequences (Table 7) are considered to be capable of providing a larger number of reads when applied to the next-generation sequencer.

INDUSTRIAL APPLICABILITY

With the use of the primer P7 used for a next-generation sequencer designed in the examples, data can be obtained with the use of the next-generation sequencer with higher stability.

The invention claimed is:

1. A method for producing a primer comprising a nucleotide sequence of 5'-CAAGCAGAAGAC GGCATACGAGAT (SEQ ID NO: 1)-$N_{5\ to\ 15}$-GTCTCGTGGGCTCGGAGATGTGTATAAGAGACAG (SEQ ID NO: 2)-3', wherein $N_{5\ to\ 15}$ represents an index sequence of 5 to 15 nucleotides, the method comprising:

(i) calculating for the primer a putative number of reads for multiple index sequences based on a nucleotide sequence of the index sequence in accordance with an estimation formula that designates the putative number of reads as a purpose variable and a type of a nucleotide for each of the nucleotides in the index sequence as an explanatory variable, to select a nucleotide sequence as a nucleotide sequence of the index sequence from index sequences that have a putative number of reads that exceed a given level; and (ii) synthesizing a nucleotide sequence comprising the nucleotide sequence selected in (i), wherein the synthesizing nucleotide sequence is the primer comprising the nucleotide sequence of SEQ ID NO: 1 and SEQ ID NO: 2 and the selected index sequence.

2. The method of claim 1, wherein the index sequence is composed of 8 nucleotides (N: 8; SEQ ID NO: 67).

3. The method of claim 1, wherein the estimation formula includes items comprising a type of nucleotide for each of the nucleotides and a coefficient in accordance therewith concerning the N number of nucleotides constituting the index sequence.

4. The method of claim 1, wherein the given level is selected from 15,000 to 25,000.

5. The method of claim 1, wherein a sequence of nucleotides 25 to 32 in a nucleotide sequence selected from the group consisting of SEQ ID NOs: 262 to 963 is designed as a nucleotide sequence of the index sequence.

* * * * *

SEQUENCE LISTING

<160> NUMBER OF SEQ ID NOS: 1518

<210> SEQ ID NO 1

```
<211> LENGTH: 24
<212> TYPE: DNA
<213> ORGANISM: Artificial
<220> FEATURE:
<223> OTHER INFORMATION: synthetic

<400> SEQUENCE: 1
caagcagaag acggcatacg agat                                          24

<210> SEQ ID NO 2
<211> LENGTH: 34
<212> TYPE: DNA
<213> ORGANISM: Artificial
<220> FEATURE:
<223> OTHER INFORMATION: synthetic

<400> SEQUENCE: 2
gtctcgtggg ctcggagatg tgtataagag acag                               34

<210> SEQ ID NO 3
<211> LENGTH: 13
<212> TYPE: DNA
<213> ORGANISM: Artificial
<220> FEATURE:
<223> OTHER INFORMATION: synthetic

<400> SEQUENCE: 3
taagagacag aaa                                                      13

<210> SEQ ID NO 4
<211> LENGTH: 13
<212> TYPE: DNA
<213> ORGANISM: Artificial
<220> FEATURE:
<223> OTHER INFORMATION: synthetic

<400> SEQUENCE: 4
taagagacag aac                                                      13

<210> SEQ ID NO 5
<211> LENGTH: 13
<212> TYPE: DNA
<213> ORGANISM: Artificial
<220> FEATURE:
<223> OTHER INFORMATION: synthetic

<400> SEQUENCE: 5
taagagacag aag                                                      13

<210> SEQ ID NO 6
<211> LENGTH: 13
<212> TYPE: DNA
<213> ORGANISM: Artificial
<220> FEATURE:
<223> OTHER INFORMATION: synthetic

<400> SEQUENCE: 6
taagagacag aat                                                      13

<210> SEQ ID NO 7
<211> LENGTH: 13
<212> TYPE: DNA
<213> ORGANISM: Artificial
<220> FEATURE:
<223> OTHER INFORMATION: synthetic

<400> SEQUENCE: 7
```
taagagacag aca            13

<210> SEQ ID NO 8
<211> LENGTH: 13
<212> TYPE: DNA
<213> ORGANISM: Artificial
<220> FEATURE:
<223> OTHER INFORMATION: synthetic

<400> SEQUENCE: 8
taagagacag acc            13

<210> SEQ ID NO 9
<211> LENGTH: 13
<212> TYPE: DNA
<213> ORGANISM: Artificial
<220> FEATURE:
<223> OTHER INFORMATION: synthetic

<400> SEQUENCE: 9
taagagacag acg            13

<210> SEQ ID NO 10
<211> LENGTH: 13
<212> TYPE: DNA
<213> ORGANISM: Artificial
<220> FEATURE:
<223> OTHER INFORMATION: synthetic

<400> SEQUENCE: 10
taagagacag act            13

<210> SEQ ID NO 11
<211> LENGTH: 13
<212> TYPE: DNA
<213> ORGANISM: Artificial
<220> FEATURE:
<223> OTHER INFORMATION: synthetic

<400> SEQUENCE: 11
taagagacag aga            13

<210> SEQ ID NO 12
<211> LENGTH: 13
<212> TYPE: DNA
<213> ORGANISM: Artificial
<220> FEATURE:
<223> OTHER INFORMATION: synthetic

<400> SEQUENCE: 12
taagagacag agc            13

<210> SEQ ID NO 13
<211> LENGTH: 13
<212> TYPE: DNA
<213> ORGANISM: Artificial
<220> FEATURE:
<223> OTHER INFORMATION: synthetic

<400> SEQUENCE: 13
taagagacag agg            13

<210> SEQ ID NO 14
<211> LENGTH: 13
<212> TYPE: DNA

```
<213> ORGANISM: Artificial
<220> FEATURE:
<223> OTHER INFORMATION: synthetic

<400> SEQUENCE: 14
taagagacag agt                                                          13

<210> SEQ ID NO 15
<211> LENGTH: 13
<212> TYPE: DNA
<213> ORGANISM: Artificial
<220> FEATURE:
<223> OTHER INFORMATION: synthetic

<400> SEQUENCE: 15
taagagacag ata                                                          13

<210> SEQ ID NO 16
<211> LENGTH: 13
<212> TYPE: DNA
<213> ORGANISM: Artificial
<220> FEATURE:
<223> OTHER INFORMATION: synthetic

<400> SEQUENCE: 16
taagagacag atc                                                          13

<210> SEQ ID NO 17
<211> LENGTH: 13
<212> TYPE: DNA
<213> ORGANISM: Artificial
<220> FEATURE:
<223> OTHER INFORMATION: synthetic

<400> SEQUENCE: 17
taagagacag atg                                                          13

<210> SEQ ID NO 18
<211> LENGTH: 13
<212> TYPE: DNA
<213> ORGANISM: Artificial
<220> FEATURE:
<223> OTHER INFORMATION: synthetic

<400> SEQUENCE: 18
taagagacag att                                                          13

<210> SEQ ID NO 19
<211> LENGTH: 13
<212> TYPE: DNA
<213> ORGANISM: Artificial
<220> FEATURE:
<223> OTHER INFORMATION: synthetic

<400> SEQUENCE: 19
taagagacag caa                                                          13

<210> SEQ ID NO 20
<211> LENGTH: 13
<212> TYPE: DNA
<213> ORGANISM: Artificial
<220> FEATURE:
<223> OTHER INFORMATION: synthetic

<400> SEQUENCE: 20
taagagacag cac                                                          13
```

<210> SEQ ID NO 21
<211> LENGTH: 13
<212> TYPE: DNA
<213> ORGANISM: Artificial
<220> FEATURE:
<223> OTHER INFORMATION: synthetic

<400> SEQUENCE: 21
taagagacag cag                                                     13

<210> SEQ ID NO 22
<211> LENGTH: 13
<212> TYPE: DNA
<213> ORGANISM: Artificial
<220> FEATURE:
<223> OTHER INFORMATION: synthetic

<400> SEQUENCE: 22
taagagacag cat                                                     13

<210> SEQ ID NO 23
<211> LENGTH: 13
<212> TYPE: DNA
<213> ORGANISM: Artificial
<220> FEATURE:
<223> OTHER INFORMATION: synthetic

<400> SEQUENCE: 23
taagagacag cca                                                     13

<210> SEQ ID NO 24
<211> LENGTH: 13
<212> TYPE: DNA
<213> ORGANISM: Artificial
<220> FEATURE:
<223> OTHER INFORMATION: synthetic

<400> SEQUENCE: 24
taagagacag ccc                                                     13

<210> SEQ ID NO 25
<211> LENGTH: 13
<212> TYPE: DNA
<213> ORGANISM: Artificial
<220> FEATURE:
<223> OTHER INFORMATION: synthetic

<400> SEQUENCE: 25
taagagacag ccg                                                     13

<210> SEQ ID NO 26
<211> LENGTH: 13
<212> TYPE: DNA
<213> ORGANISM: Artificial
<220> FEATURE:
<223> OTHER INFORMATION: synthetic

<400> SEQUENCE: 26
taagagacag cct                                                     13

<210> SEQ ID NO 27
<211> LENGTH: 13
<212> TYPE: DNA
<213> ORGANISM: Artificial
<220> FEATURE:

-continued

<223> OTHER INFORMATION: synthetic

<400> SEQUENCE: 27
taagagacag cga                                                      13

<210> SEQ ID NO 28
<211> LENGTH: 13
<212> TYPE: DNA
<213> ORGANISM: Artificial
<220> FEATURE:
<223> OTHER INFORMATION: synthetic

<400> SEQUENCE: 28
taagagacag cgc                                                      13

<210> SEQ ID NO 29
<211> LENGTH: 13
<212> TYPE: DNA
<213> ORGANISM: Artificial
<220> FEATURE:
<223> OTHER INFORMATION: synthetic

<400> SEQUENCE: 29
taagagacag cgg                                                      13

<210> SEQ ID NO 30
<211> LENGTH: 13
<212> TYPE: DNA
<213> ORGANISM: Artificial
<220> FEATURE:
<223> OTHER INFORMATION: synthetic

<400> SEQUENCE: 30
taagagacag cgt                                                      13

<210> SEQ ID NO 31
<211> LENGTH: 13
<212> TYPE: DNA
<213> ORGANISM: Artificial
<220> FEATURE:
<223> OTHER INFORMATION: synthetic

<400> SEQUENCE: 31
taagagacag cta                                                      13

<210> SEQ ID NO 32
<211> LENGTH: 13
<212> TYPE: DNA
<213> ORGANISM: Artificial
<220> FEATURE:
<223> OTHER INFORMATION: synthetic

<400> SEQUENCE: 32
taagagacag ctc                                                      13

<210> SEQ ID NO 33
<211> LENGTH: 13
<212> TYPE: DNA
<213> ORGANISM: Artificial
<220> FEATURE:
<223> OTHER INFORMATION: synthetic

<400> SEQUENCE: 33
taagagacag ctg                                                      13

```
<210> SEQ ID NO 34
<211> LENGTH: 13
<212> TYPE: DNA
<213> ORGANISM: Artificial
<220> FEATURE:
<223> OTHER INFORMATION: synthetic

<400> SEQUENCE: 34
taagagacag ctt                                                          13

<210> SEQ ID NO 35
<211> LENGTH: 13
<212> TYPE: DNA
<213> ORGANISM: Artificial
<220> FEATURE:
<223> OTHER INFORMATION: synthetic

<400> SEQUENCE: 35
taagagacag gaa                                                          13

<210> SEQ ID NO 36
<211> LENGTH: 13
<212> TYPE: DNA
<213> ORGANISM: Artificial
<220> FEATURE:
<223> OTHER INFORMATION: synthetic

<400> SEQUENCE: 36
taagagacag gac                                                          13

<210> SEQ ID NO 37
<211> LENGTH: 13
<212> TYPE: DNA
<213> ORGANISM: Artificial
<220> FEATURE:
<223> OTHER INFORMATION: synthetic

<400> SEQUENCE: 37
taagagacag gag                                                          13

<210> SEQ ID NO 38
<211> LENGTH: 13
<212> TYPE: DNA
<213> ORGANISM: Artificial
<220> FEATURE:
<223> OTHER INFORMATION: synthetic

<400> SEQUENCE: 38
taagagacag gat                                                          13

<210> SEQ ID NO 39
<211> LENGTH: 13
<212> TYPE: DNA
<213> ORGANISM: Artificial
<220> FEATURE:
<223> OTHER INFORMATION: synthetic

<400> SEQUENCE: 39
taagagacag gca                                                          13

<210> SEQ ID NO 40
<211> LENGTH: 13
<212> TYPE: DNA
<213> ORGANISM: Artificial
<220> FEATURE:
<223> OTHER INFORMATION: synthetic
```

```
<400> SEQUENCE: 40
taagagacag gcc                                                        13

<210> SEQ ID NO 41
<211> LENGTH: 13
<212> TYPE: DNA
<213> ORGANISM: Artificial
<220> FEATURE:
<223> OTHER INFORMATION: synthetic

<400> SEQUENCE: 41
taagagacag gcg                                                        13

<210> SEQ ID NO 42
<211> LENGTH: 13
<212> TYPE: DNA
<213> ORGANISM: Artificial
<220> FEATURE:
<223> OTHER INFORMATION: synthetic

<400> SEQUENCE: 42
taagagacag gct                                                        13

<210> SEQ ID NO 43
<211> LENGTH: 13
<212> TYPE: DNA
<213> ORGANISM: Artificial
<220> FEATURE:
<223> OTHER INFORMATION: synthetic

<400> SEQUENCE: 43
taagagacag gga                                                        13

<210> SEQ ID NO 44
<211> LENGTH: 13
<212> TYPE: DNA
<213> ORGANISM: Artificial
<220> FEATURE:
<223> OTHER INFORMATION: synthetic

<400> SEQUENCE: 44
taagagacag ggc                                                        13

<210> SEQ ID NO 45
<211> LENGTH: 13
<212> TYPE: DNA
<213> ORGANISM: Artificial
<220> FEATURE:
<223> OTHER INFORMATION: synthetic

<400> SEQUENCE: 45
taagagacag ggg                                                        13

<210> SEQ ID NO 46
<211> LENGTH: 13
<212> TYPE: DNA
<213> ORGANISM: Artificial
<220> FEATURE:
<223> OTHER INFORMATION: synthetic

<400> SEQUENCE: 46
taagagacag ggt                                                        13

<210> SEQ ID NO 47
<211> LENGTH: 13
```

```
<212> TYPE: DNA
<213> ORGANISM: Artificial
<220> FEATURE:
<223> OTHER INFORMATION: synthetic

<400> SEQUENCE: 47
taagagacag gta                                                       13

<210> SEQ ID NO 48
<211> LENGTH: 13
<212> TYPE: DNA
<213> ORGANISM: Artificial
<220> FEATURE:
<223> OTHER INFORMATION: synthetic

<400> SEQUENCE: 48
taagagacag gtc                                                       13

<210> SEQ ID NO 49
<211> LENGTH: 13
<212> TYPE: DNA
<213> ORGANISM: Artificial
<220> FEATURE:
<223> OTHER INFORMATION: synthetic

<400> SEQUENCE: 49
taagagacag gtg                                                       13

<210> SEQ ID NO 50
<211> LENGTH: 13
<212> TYPE: DNA
<213> ORGANISM: Artificial
<220> FEATURE:
<223> OTHER INFORMATION: synthetic

<400> SEQUENCE: 50
taagagacag gtt                                                       13

<210> SEQ ID NO 51
<211> LENGTH: 13
<212> TYPE: DNA
<213> ORGANISM: Artificial
<220> FEATURE:
<223> OTHER INFORMATION: synthetic

<400> SEQUENCE: 51
taagagacag taa                                                       13

<210> SEQ ID NO 52
<211> LENGTH: 13
<212> TYPE: DNA
<213> ORGANISM: Artificial
<220> FEATURE:
<223> OTHER INFORMATION: synthetic

<400> SEQUENCE: 52
taagagacag tac                                                       13

<210> SEQ ID NO 53
<211> LENGTH: 13
<212> TYPE: DNA
<213> ORGANISM: Artificial
<220> FEATURE:
<223> OTHER INFORMATION: synthetic

<400> SEQUENCE: 53
```
taagagacag tag                                           13

<210> SEQ ID NO 54
<211> LENGTH: 13
<212> TYPE: DNA
<213> ORGANISM: Artificial
<220> FEATURE:
<223> OTHER INFORMATION: synthetic

<400> SEQUENCE: 54
taagagacag tat                                           13

<210> SEQ ID NO 55
<211> LENGTH: 13
<212> TYPE: DNA
<213> ORGANISM: Artificial
<220> FEATURE:
<223> OTHER INFORMATION: synthetic

<400> SEQUENCE: 55
taagagacag tca                                           13

<210> SEQ ID NO 56
<211> LENGTH: 13
<212> TYPE: DNA
<213> ORGANISM: Artificial
<220> FEATURE:
<223> OTHER INFORMATION: synthetic

<400> SEQUENCE: 56
taagagacag tcc                                           13

<210> SEQ ID NO 57
<211> LENGTH: 13
<212> TYPE: DNA
<213> ORGANISM: Artificial
<220> FEATURE:
<223> OTHER INFORMATION: synthetic

<400> SEQUENCE: 57
taagagacag tcg                                           13

<210> SEQ ID NO 58
<211> LENGTH: 13
<212> TYPE: DNA
<213> ORGANISM: Artificial
<220> FEATURE:
<223> OTHER INFORMATION: synthetic

<400> SEQUENCE: 58
taagagacag tct                                           13

<210> SEQ ID NO 59
<211> LENGTH: 13
<212> TYPE: DNA
<213> ORGANISM: Artificial
<220> FEATURE:
<223> OTHER INFORMATION: synthetic

<400> SEQUENCE: 59
taagagacag tga                                           13

<210> SEQ ID NO 60
<211> LENGTH: 13
<212> TYPE: DNA
<213> ORGANISM: Artificial

```
<220> FEATURE:
<223> OTHER INFORMATION: synthetic

<400> SEQUENCE: 60
taagagacag tgg                                                              13

<210> SEQ ID NO 61
<211> LENGTH: 13
<212> TYPE: DNA
<213> ORGANISM: Artificial
<220> FEATURE:
<223> OTHER INFORMATION: synthetic

<400> SEQUENCE: 61
taagagacag tgt                                                              13

<210> SEQ ID NO 62
<211> LENGTH: 13
<212> TYPE: DNA
<213> ORGANISM: Artificial
<220> FEATURE:
<223> OTHER INFORMATION: synthetic

<400> SEQUENCE: 62
taagagacag tta                                                              13

<210> SEQ ID NO 63
<211> LENGTH: 13
<212> TYPE: DNA
<213> ORGANISM: Artificial
<220> FEATURE:
<223> OTHER INFORMATION: synthetic

<400> SEQUENCE: 63
taagagacag ttc                                                              13

<210> SEQ ID NO 64
<211> LENGTH: 13
<212> TYPE: DNA
<213> ORGANISM: Artificial
<220> FEATURE:
<223> OTHER INFORMATION: synthetic

<400> SEQUENCE: 64
taagagacag ttg                                                              13

<210> SEQ ID NO 65
<211> LENGTH: 13
<212> TYPE: DNA
<213> ORGANISM: Artificial
<220> FEATURE:
<223> OTHER INFORMATION: synthetic

<400> SEQUENCE: 65
taagagacag ttt                                                              13

<210> SEQ ID NO 66
<211> LENGTH: 70
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (30)..(37)
<223> OTHER INFORMATION: n is a, c, g, or t
```

<400> SEQUENCE: 66
aatgatacgg cgaccaccga gatctacacn nnnnnnntcg tcggcagcgt cagatgtgta    60
taagagacag    70

<210> SEQ ID NO 67
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(32)
<223> OTHER INFORMATION: n is a, c, g, or t

<400> SEQUENCE: 67
caagcagaag acggcatacg agatnnnnnn nngtctcgtg ggctcggaga tgtgtataag    60
agacag    66

<210> SEQ ID NO 68
<211> LENGTH: 66
<212> TYPE: DNA
<213> ORGANISM: Artificial
<220> FEATURE:
<223> OTHER INFORMATION: synthetic

<400> SEQUENCE: 68
caagcagaag acggcatacg agatgtgata ctgtctcgtg ggctcggaga tgtgtataag    60
agacag    66

<210> SEQ ID NO 69
<211> LENGTH: 66
<212> TYPE: DNA
<213> ORGANISM: Artificial
<220> FEATURE:
<223> OTHER INFORMATION: synthetic

<400> SEQUENCE: 69
caagcagaag acggcatacg agatgagcgc gtgtctcgtg ggctcggaga tgtgtataag    60
agacag    66

<210> SEQ ID NO 70
<211> LENGTH: 66
<212> TYPE: DNA
<213> ORGANISM: Artificial
<220> FEATURE:
<223> OTHER INFORMATION: synthetic

<400> SEQUENCE: 70
caagcagaag acggcatacg agatgcatct cggtctcgtg ggctcggaga tgtgtataag    60
agacag    66

<210> SEQ ID NO 71
<211> LENGTH: 66
<212> TYPE: DNA
<213> ORGANISM: Artificial
<220> FEATURE:
<223> OTHER INFORMATION: synthetic

<400> SEQUENCE: 71
caagcagaag acggcatacg agattcgtac gtgtctcgtg ggctcggaga tgtgtataag    60
agacag    66

```
<210> SEQ ID NO 72
<211> LENGTH: 66
<212> TYPE: DNA
<213> ORGANISM: Artificial
<220> FEATURE:
<223> OTHER INFORMATION: synthetic

<400> SEQUENCE: 72
caagcagaag acggcatacg agattatcgt cggtctcgtg ggctcggaga tgtgtataag    60
agacag                                                              66

<210> SEQ ID NO 73
<211> LENGTH: 66
<212> TYPE: DNA
<213> ORGANISM: Artificial
<220> FEATURE:
<223> OTHER INFORMATION: synthetic

<400> SEQUENCE: 73
caagcagaag acggcatacg agattgcaca gagtctcgtg ggctcggaga tgtgtataag    60
agacag                                                              66

<210> SEQ ID NO 74
<211> LENGTH: 66
<212> TYPE: DNA
<213> ORGANISM: Artificial
<220> FEATURE:
<223> OTHER INFORMATION: synthetic

<400> SEQUENCE: 74
caagcagaag acggcatacg agatcgtatg acgtctcgtg ggctcggaga tgtgtataag    60
agacag                                                              66

<210> SEQ ID NO 75
<211> LENGTH: 66
<212> TYPE: DNA
<213> ORGANISM: Artificial
<220> FEATURE:
<223> OTHER INFORMATION: synthetic

<400> SEQUENCE: 75
caagcagaag acggcatacg agattcgatc tcgtctcgtg ggctcggaga tgtgtataag    60
agacag                                                              66

<210> SEQ ID NO 76
<211> LENGTH: 66
<212> TYPE: DNA
<213> ORGANISM: Artificial
<220> FEATURE:
<223> OTHER INFORMATION: synthetic

<400> SEQUENCE: 76
caagcagaag acggcatacg agatatatga cagtctcgtg ggctcggaga tgtgtataag    60
agacag                                                              66

<210> SEQ ID NO 77
<211> LENGTH: 66
<212> TYPE: DNA
<213> ORGANISM: Artificial
<220> FEATURE:
<223> OTHER INFORMATION: synthetic
```

```
<400> SEQUENCE: 77
caagcagaag acggcatacg agatgctatc gtgtctcgtg ggctcggaga tgtgtataag    60
agacag                                                                66

<210> SEQ ID NO 78
<211> LENGTH: 66
<212> TYPE: DNA
<213> ORGANISM: Artificial
<220> FEATURE:
<223> OTHER INFORMATION: synthetic

<400> SEQUENCE: 78
caagcagaag acggcatacg agatctgtgt gtgtctcgtg ggctcggaga tgtgtataag    60
agacag                                                                66

<210> SEQ ID NO 79
<211> LENGTH: 66
<212> TYPE: DNA
<213> ORGANISM: Artificial
<220> FEATURE:
<223> OTHER INFORMATION: synthetic

<400> SEQUENCE: 79
caagcagaag acggcatacg agattatact gcgtctcgtg ggctcggaga tgtgtataag    60
agacag                                                                66

<210> SEQ ID NO 80
<211> LENGTH: 66
<212> TYPE: DNA
<213> ORGANISM: Artificial
<220> FEATURE:
<223> OTHER INFORMATION: synthetic

<400> SEQUENCE: 80
caagcagaag acggcatacg agatactgtc gtgtctcgtg ggctcggaga tgtgtataag    60
agacag                                                                66

<210> SEQ ID NO 81
<211> LENGTH: 66
<212> TYPE: DNA
<213> ORGANISM: Artificial
<220> FEATURE:
<223> OTHER INFORMATION: synthetic

<400> SEQUENCE: 81
caagcagaag acggcatacg agatgagcta tagtctcgtg ggctcggaga tgtgtataag    60
agacag                                                                66

<210> SEQ ID NO 82
<211> LENGTH: 66
<212> TYPE: DNA
<213> ORGANISM: Artificial
<220> FEATURE:
<223> OTHER INFORMATION: synthetic

<400> SEQUENCE: 82
caagcagaag acggcatacg agattgtgtc gtgtctcgtg ggctcggaga tgtgtataag    60
agacag                                                                66

<210> SEQ ID NO 83
<211> LENGTH: 66
```

```
<212> TYPE: DNA
<213> ORGANISM: Artificial
<220> FEATURE:
<223> OTHER INFORMATION: synthetic

<400> SEQUENCE: 83
caagcagaag acggcatacg agatgtgact atgtctcgtg ggctcggaga tgtgtataag    60
agacag                                                              66

<210> SEQ ID NO 84
<211> LENGTH: 66
<212> TYPE: DNA
<213> ORGANISM: Artificial
<220> FEATURE:
<223> OTHER INFORMATION: synthetic

<400> SEQUENCE: 84
caagcagaag acggcatacg agattataca gtgtctcgtg ggctcggaga tgtgtataag    60
agacag                                                              66

<210> SEQ ID NO 85
<211> LENGTH: 66
<212> TYPE: DNA
<213> ORGANISM: Artificial
<220> FEATURE:
<223> OTHER INFORMATION: synthetic

<400> SEQUENCE: 85
caagcagaag acggcatacg agatatgagc gagtctcgtg ggctcggaga tgtgtataag    60
agacag                                                              66

<210> SEQ ID NO 86
<211> LENGTH: 66
<212> TYPE: DNA
<213> ORGANISM: Artificial
<220> FEATURE:
<223> OTHER INFORMATION: synthetic

<400> SEQUENCE: 86
caagcagaag acggcatacg agatagatca gagtctcgtg ggctcggaga tgtgtataag    60
agacag                                                              66

<210> SEQ ID NO 87
<211> LENGTH: 66
<212> TYPE: DNA
<213> ORGANISM: Artificial
<220> FEATURE:
<223> OTHER INFORMATION: synthetic

<400> SEQUENCE: 87
caagcagaag acggcatacg agatagtctg cagtctcgtg ggctcggaga tgtgtataag    60
agacag                                                              66

<210> SEQ ID NO 88
<211> LENGTH: 66
<212> TYPE: DNA
<213> ORGANISM: Artificial
<220> FEATURE:
<223> OTHER INFORMATION: synthetic

<400> SEQUENCE: 88
caagcagaag acggcatacg agatcgctgt gagtctcgtg ggctcggaga tgtgtataag    60
``` agacag 66

<210> SEQ ID NO 89
<211> LENGTH: 66
<212> TYPE: DNA
<213> ORGANISM: Artificial
<220> FEATURE:
<223> OTHER INFORMATION: synthetic

<400> SEQUENCE: 89
caagcagaag acggcatacg agatgtctat gtgtctcgtg ggctcggaga tgtgtataag   60
agacag   66

<210> SEQ ID NO 90
<211> LENGTH: 66
<212> TYPE: DNA
<213> ORGANISM: Artificial
<220> FEATURE:
<223> OTHER INFORMATION: synthetic

<400> SEQUENCE: 90
caagcagaag acggcatacg agatctgatg tggtctcgtg ggctcggaga tgtgtataag   60
agacag   66

<210> SEQ ID NO 91
<211> LENGTH: 66
<212> TYPE: DNA
<213> ORGANISM: Artificial
<220> FEATURE:
<223> OTHER INFORMATION: synthetic

<400> SEQUENCE: 91
caagcagaag acggcatacg agatcgcact atgtctcgtg ggctcggaga tgtgtataag   60
agacag   66

<210> SEQ ID NO 92
<211> LENGTH: 66
<212> TYPE: DNA
<213> ORGANISM: Artificial
<220> FEATURE:
<223> OTHER INFORMATION: synthetic

<400> SEQUENCE: 92
caagcagaag acggcatacg agatagtgtg cggtctcgtg ggctcggaga tgtgtataag   60
agacag   66

<210> SEQ ID NO 93
<211> LENGTH: 66
<212> TYPE: DNA
<213> ORGANISM: Artificial
<220> FEATURE:
<223> OTHER INFORMATION: synthetic

<400> SEQUENCE: 93
caagcagaag acggcatacg agatcgtatc gcgtctcgtg ggctcggaga tgtgtataag   60
agacag   66

<210> SEQ ID NO 94
<211> LENGTH: 66
<212> TYPE: DNA
<213> ORGANISM: Artificial
<220> FEATURE:
<223> OTHER INFORMATION: synthetic

```
<400> SEQUENCE: 94
caagcagaag acggcatacg agatgcactc tagtctcgtg ggctcggaga tgtgtataag    60
agacag                                                                66

<210> SEQ ID NO 95
<211> LENGTH: 66
<212> TYPE: DNA
<213> ORGANISM: Artificial
<220> FEATURE:
<223> OTHER INFORMATION: synthetic

<400> SEQUENCE: 95
caagcagaag acggcatacg agattacgac acgtctcgtg ggctcggaga tgtgtataag    60
agacag                                                                66

<210> SEQ ID NO 96
<211> LENGTH: 66
<212> TYPE: DNA
<213> ORGANISM: Artificial
<220> FEATURE:
<223> OTHER INFORMATION: synthetic

<400> SEQUENCE: 96
caagcagaag acggcatacg agattctgct cagtctcgtg ggctcggaga tgtgtataag    60
agacag                                                                66

<210> SEQ ID NO 97
<211> LENGTH: 66
<212> TYPE: DNA
<213> ORGANISM: Artificial
<220> FEATURE:
<223> OTHER INFORMATION: synthetic

<400> SEQUENCE: 97
caagcagaag acggcatacg agattcgtga ctgtctcgtg ggctcggaga tgtgtataag    60
agacag                                                                66

<210> SEQ ID NO 98
<211> LENGTH: 66
<212> TYPE: DNA
<213> ORGANISM: Artificial
<220> FEATURE:
<223> OTHER INFORMATION: synthetic

<400> SEQUENCE: 98
caagcagaag acggcatacg agattgtatc tagtctcgtg ggctcggaga tgtgtataag    60
agacag                                                                66

<210> SEQ ID NO 99
<211> LENGTH: 66
<212> TYPE: DNA
<213> ORGANISM: Artificial
<220> FEATURE:
<223> OTHER INFORMATION: synthetic

<400> SEQUENCE: 99
caagcagaag acggcatacg agatgtgcgt acgtctcgtg ggctcggaga tgtgtataag    60
agacag                                                                66

<210> SEQ ID NO 100
```

```
-continued

<211> LENGTH: 66
<212> TYPE: DNA
<213> ORGANISM: Artificial
<220> FEATURE:
<223> OTHER INFORMATION: synthetic

<400> SEQUENCE: 100
caagcagaag acggcatacg agatcactac tcgtctcgtg ggctcggaga tgtgtataag    60
agacag                                                               66

<210> SEQ ID NO 101
<211> LENGTH: 66
<212> TYPE: DNA
<213> ORGANISM: Artificial
<220> FEATURE:
<223> OTHER INFORMATION: synthetic

<400> SEQUENCE: 101
caagcagaag acggcatacg agattgagcg tcgtctcgtg ggctcggaga tgtgtataag    60
agacag                                                               66

<210> SEQ ID NO 102
<211> LENGTH: 66
<212> TYPE: DNA
<213> ORGANISM: Artificial
<220> FEATURE:
<223> OTHER INFORMATION: synthetic

<400> SEQUENCE: 102
caagcagaag acggcatacg agattgacgt ctgtctcgtg ggctcggaga tgtgtataag    60
agacag                                                               66

<210> SEQ ID NO 103
<211> LENGTH: 66
<212> TYPE: DNA
<213> ORGANISM: Artificial
<220> FEATURE:
<223> OTHER INFORMATION: synthetic

<400> SEQUENCE: 103
caagcagaag acggcatacg agatacagtg aggtctcgtg ggctcggaga tgtgtataag    60
agacag                                                               66

<210> SEQ ID NO 104
<211> LENGTH: 66
<212> TYPE: DNA
<213> ORGANISM: Artificial
<220> FEATURE:
<223> OTHER INFORMATION: synthetic

<400> SEQUENCE: 104
caagcagaag acggcatacg agatgactct cagtctcgtg ggctcggaga tgtgtataag    60
agacag                                                               66

<210> SEQ ID NO 105
<211> LENGTH: 66
<212> TYPE: DNA
<213> ORGANISM: Artificial
<220> FEATURE:
<223> OTHER INFORMATION: synthetic

<400> SEQUENCE: 105
caagcagaag acggcatacg agatagcgcg ctgtctcgtg ggctcggaga tgtgtataag    60
```

-continued agacag                                                              66

<210> SEQ ID NO 106
<211> LENGTH: 66
<212> TYPE: DNA
<213> ORGANISM: Artificial
<220> FEATURE:
<223> OTHER INFORMATION: synthetic

<400> SEQUENCE: 106
caagcagaag acggcatacg agatctgtag aggtctcgtg ggctcggaga tgtgtataag    60
agacag                                                              66

<210> SEQ ID NO 107
<211> LENGTH: 66
<212> TYPE: DNA
<213> ORGANISM: Artificial
<220> FEATURE:
<223> OTHER INFORMATION: synthetic

<400> SEQUENCE: 107
caagcagaag acggcatacg agatatgcga tagtctcgtg ggctcggaga tgtgtataag    60
agacag                                                              66

<210> SEQ ID NO 108
<211> LENGTH: 66
<212> TYPE: DNA
<213> ORGANISM: Artificial
<220> FEATURE:
<223> OTHER INFORMATION: synthetic

<400> SEQUENCE: 108
caagcagaag acggcatacg agatgagaca tggtctcgtg ggctcggaga tgtgtataag    60
agacag                                                              66

<210> SEQ ID NO 109
<211> LENGTH: 66
<212> TYPE: DNA
<213> ORGANISM: Artificial
<220> FEATURE:
<223> OTHER INFORMATION: synthetic

<400> SEQUENCE: 109
caagcagaag acggcatacg agatgtcatg tggtctcgtg ggctcggaga tgtgtataag    60
agacag                                                              66

<210> SEQ ID NO 110
<211> LENGTH: 66
<212> TYPE: DNA
<213> ORGANISM: Artificial
<220> FEATURE:
<223> OTHER INFORMATION: synthetic

<400> SEQUENCE: 110
caagcagaag acggcatacg agattcatga tagtctcgtg ggctcggaga tgtgtataag    60
agacag                                                              66

<210> SEQ ID NO 111
<211> LENGTH: 66
<212> TYPE: DNA
<213> ORGANISM: Artificial
<220> FEATURE:

<223> OTHER INFORMATION: synthetic

<400> SEQUENCE: 111
caagcagaag acggcatacg agatgtcatc tcgtctcgtg ggctcggaga tgtgtataag    60
agacag                                                              66

<210> SEQ ID NO 112
<211> LENGTH: 66
<212> TYPE: DNA
<213> ORGANISM: Artificial
<220> FEATURE:
<223> OTHER INFORMATION: synthetic

<400> SEQUENCE: 112
caagcagaag acggcatacg agatagtgtc gcgtctcgtg ggctcggaga tgtgtataag    60
agacag                                                              66

<210> SEQ ID NO 113
<211> LENGTH: 66
<212> TYPE: DNA
<213> ORGANISM: Artificial
<220> FEATURE:
<223> OTHER INFORMATION: synthetic

<400> SEQUENCE: 113
caagcagaag acggcatacg agatgctgac gtgtctcgtg ggctcggaga tgtgtataag    60
agacag                                                              66

<210> SEQ ID NO 114
<211> LENGTH: 66
<212> TYPE: DNA
<213> ORGANISM: Artificial
<220> FEATURE:
<223> OTHER INFORMATION: synthetic

<400> SEQUENCE: 114
caagcagaag acggcatacg agatgatcag ctgtctcgtg ggctcggaga tgtgtataag    60
agacag                                                              66

<210> SEQ ID NO 115
<211> LENGTH: 66
<212> TYPE: DNA
<213> ORGANISM: Artificial
<220> FEATURE:
<223> OTHER INFORMATION: synthetic

<400> SEQUENCE: 115
caagcagaag acggcatacg agattatctc tagtctcgtg ggctcggaga tgtgtataag    60
agacag                                                              66

<210> SEQ ID NO 116
<211> LENGTH: 66
<212> TYPE: DNA
<213> ORGANISM: Artificial
<220> FEATURE:
<223> OTHER INFORMATION: synthetic

<400> SEQUENCE: 116
caagcagaag acggcatacg agatgcagag ctgtctcgtg ggctcggaga tgtgtataag    60
agacag                                                              66

```
<210> SEQ ID NO 117
<211> LENGTH: 66
<212> TYPE: DNA
<213> ORGANISM: Artificial
<220> FEATURE:
<223> OTHER INFORMATION: synthetic

<400> SEQUENCE: 117
caagcagaag acggcatacg agattgctag cggtctcgtg ggctcggaga tgtgtataag    60
agacag                                                                66

<210> SEQ ID NO 118
<211> LENGTH: 66
<212> TYPE: DNA
<213> ORGANISM: Artificial
<220> FEATURE:
<223> OTHER INFORMATION: synthetic

<400> SEQUENCE: 118
caagcagaag acggcatacg agatcgtatc tcgtctcgtg ggctcggaga tgtgtataag    60
agacag                                                                66

<210> SEQ ID NO 119
<211> LENGTH: 66
<212> TYPE: DNA
<213> ORGANISM: Artificial
<220> FEATURE:
<223> OTHER INFORMATION: synthetic

<400> SEQUENCE: 119
caagcagaag acggcatacg agatctgata tagtctcgtg ggctcggaga tgtgtataag    60
agacag                                                                66

<210> SEQ ID NO 120
<211> LENGTH: 66
<212> TYPE: DNA
<213> ORGANISM: Artificial
<220> FEATURE:
<223> OTHER INFORMATION: synthetic

<400> SEQUENCE: 120
caagcagaag acggcatacg agattagtgc gcgtctcgtg ggctcggaga tgtgtataag    60
agacag                                                                66

<210> SEQ ID NO 121
<211> LENGTH: 66
<212> TYPE: DNA
<213> ORGANISM: Artificial
<220> FEATURE:
<223> OTHER INFORMATION: synthetic

<400> SEQUENCE: 121
caagcagaag acggcatacg agatctagtg cagtctcgtg ggctcggaga tgtgtataag    60
agacag                                                                66

<210> SEQ ID NO 122
<211> LENGTH: 66
<212> TYPE: DNA
<213> ORGANISM: Artificial
<220> FEATURE:
<223> OTHER INFORMATION: synthetic

<400> SEQUENCE: 122
```

```
caagcagaag acggcatacg agatgatgtc acgtctcgtg ggctcggaga tgtgtataag    60
agacag                                                               66

<210> SEQ ID NO 123
<211> LENGTH: 66
<212> TYPE: DNA
<213> ORGANISM: Artificial
<220> FEATURE:
<223> OTHER INFORMATION: synthetic

<400> SEQUENCE: 123
caagcagaag acggcatacg agatatagag cggtctcgtg ggctcggaga tgtgtataag    60
agacag                                                               66

<210> SEQ ID NO 124
<211> LENGTH: 66
<212> TYPE: DNA
<213> ORGANISM: Artificial
<220> FEATURE:
<223> OTHER INFORMATION: synthetic

<400> SEQUENCE: 124
caagcagaag acggcatacg agatagacat atgtctcgtg ggctcggaga tgtgtataag    60
agacag                                                               66

<210> SEQ ID NO 125
<211> LENGTH: 66
<212> TYPE: DNA
<213> ORGANISM: Artificial
<220> FEATURE:
<223> OTHER INFORMATION: synthetic

<400> SEQUENCE: 125
caagcagaag acggcatacg agatcgatca tggtctcgtg ggctcggaga tgtgtataag    60
agacag                                                               66

<210> SEQ ID NO 126
<211> LENGTH: 66
<212> TYPE: DNA
<213> ORGANISM: Artificial
<220> FEATURE:
<223> OTHER INFORMATION: synthetic

<400> SEQUENCE: 126
caagcagaag acggcatacg agatacatag cggtctcgtg ggctcggaga tgtgtataag    60
agacag                                                               66

<210> SEQ ID NO 127
<211> LENGTH: 66
<212> TYPE: DNA
<213> ORGANISM: Artificial
<220> FEATURE:
<223> OTHER INFORMATION: synthetic

<400> SEQUENCE: 127
caagcagaag acggcatacg agatatcgac acgtctcgtg ggctcggaga tgtgtataag    60
agacag                                                               66

<210> SEQ ID NO 128
<211> LENGTH: 66
<212> TYPE: DNA
<213> ORGANISM: Artificial
```

-continued

```
<220> FEATURE:
<223> OTHER INFORMATION: synthetic

<400> SEQUENCE: 128
caagcagaag acggcatacg agattacaca cggtctcgtg ggctcggaga tgtgtataag      60
agacag                                                                 66

<210> SEQ ID NO 129
<211> LENGTH: 66
<212> TYPE: DNA
<213> ORGANISM: Artificial
<220> FEATURE:
<223> OTHER INFORMATION: synthetic

<400> SEQUENCE: 129
caagcagaag acggcatacg agattacgca tggtctcgtg ggctcggaga tgtgtataag      60
agacag                                                                 66

<210> SEQ ID NO 130
<211> LENGTH: 66
<212> TYPE: DNA
<213> ORGANISM: Artificial
<220> FEATURE:
<223> OTHER INFORMATION: synthetic

<400> SEQUENCE: 130
caagcagaag acggcatacg agatcgtgag tggtctcgtg ggctcggaga tgtgtataag      60
agacag                                                                 66

<210> SEQ ID NO 131
<211> LENGTH: 66
<212> TYPE: DNA
<213> ORGANISM: Artificial
<220> FEATURE:
<223> OTHER INFORMATION: synthetic

<400> SEQUENCE: 131
caagcagaag acggcatacg agatgtctgc atgtctcgtg ggctcggaga tgtgtataag      60
agacag                                                                 66

<210> SEQ ID NO 132
<211> LENGTH: 66
<212> TYPE: DNA
<213> ORGANISM: Artificial
<220> FEATURE:
<223> OTHER INFORMATION: synthetic

<400> SEQUENCE: 132
caagcagaag acggcatacg agatgcatat gagtctcgtg ggctcggaga tgtgtataag      60
agacag                                                                 66

<210> SEQ ID NO 133
<211> LENGTH: 66
<212> TYPE: DNA
<213> ORGANISM: Artificial
<220> FEATURE:
<223> OTHER INFORMATION: synthetic

<400> SEQUENCE: 133
caagcagaag acggcatacg agattgctct ctgtctcgtg ggctcggaga tgtgtataag      60
agacag                                                                 66
```

```
<210> SEQ ID NO 134
<211> LENGTH: 66
<212> TYPE: DNA
<213> ORGANISM: Artificial
<220> FEATURE:
<223> OTHER INFORMATION: synthetic

<400> SEQUENCE: 134
caagcagaag acggcatacg agatgacaca tggtctcgtg ggctcggaga tgtgtataag    60
agacag                                                               66

<210> SEQ ID NO 135
<211> LENGTH: 66
<212> TYPE: DNA
<213> ORGANISM: Artificial
<220> FEATURE:
<223> OTHER INFORMATION: synthetic

<400> SEQUENCE: 135
caagcagaag acggcatacg agatctgagc aggtctcgtg ggctcggaga tgtgtataag    60
agacag                                                               66

<210> SEQ ID NO 136
<211> LENGTH: 66
<212> TYPE: DNA
<213> ORGANISM: Artificial
<220> FEATURE:
<223> OTHER INFORMATION: synthetic

<400> SEQUENCE: 136
caagcagaag acggcatacg agatgacatg cggtctcgtg ggctcggaga tgtgtataag    60
agacag                                                               66

<210> SEQ ID NO 137
<211> LENGTH: 66
<212> TYPE: DNA
<213> ORGANISM: Artificial
<220> FEATURE:
<223> OTHER INFORMATION: synthetic

<400> SEQUENCE: 137
caagcagaag acggcatacg agattctgac gagtctcgtg ggctcggaga tgtgtataag    60
agacag                                                               66

<210> SEQ ID NO 138
<211> LENGTH: 66
<212> TYPE: DNA
<213> ORGANISM: Artificial
<220> FEATURE:
<223> OTHER INFORMATION: synthetic

<400> SEQUENCE: 138
caagcagaag acggcatacg agattacagt gtgtctcgtg ggctcggaga tgtgtataag    60
agacag                                                               66

<210> SEQ ID NO 139
<211> LENGTH: 66
<212> TYPE: DNA
<213> ORGANISM: Artificial
<220> FEATURE:
<223> OTHER INFORMATION: synthetic

<400> SEQUENCE: 139
```

-continued caagcagaag acggcatacg agatgatcgc aggtctcgtg ggctcggaga tgtgtataag    60
agacag    66

<210> SEQ ID NO 140
<211> LENGTH: 66
<212> TYPE: DNA
<213> ORGANISM: Artificial
<220> FEATURE:
<223> OTHER INFORMATION: synthetic

<400> SEQUENCE: 140
caagcagaag acggcatacg agatacatga cggtctcgtg ggctcggaga tgtgtataag    60
agacag    66

<210> SEQ ID NO 141
<211> LENGTH: 66
<212> TYPE: DNA
<213> ORGANISM: Artificial
<220> FEATURE:
<223> OTHER INFORMATION: synthetic

<400> SEQUENCE: 141
caagcagaag acggcatacg agatctagat gagtctcgtg ggctcggaga tgtgtataag    60
agacag    66

<210> SEQ ID NO 142
<211> LENGTH: 66
<212> TYPE: DNA
<213> ORGANISM: Artificial
<220> FEATURE:
<223> OTHER INFORMATION: synthetic

<400> SEQUENCE: 142
caagcagaag acggcatacg agatgcgtct aggtctcgtg ggctcggaga tgtgtataag    60
agacag    66

<210> SEQ ID NO 143
<211> LENGTH: 66
<212> TYPE: DNA
<213> ORGANISM: Artificial
<220> FEATURE:
<223> OTHER INFORMATION: synthetic

<400> SEQUENCE: 143
caagcagaag acggcatacg agatactcgt gcgtctcgtg ggctcggaga tgtgtataag    60
agacag    66

<210> SEQ ID NO 144
<211> LENGTH: 66
<212> TYPE: DNA
<213> ORGANISM: Artificial
<220> FEATURE:
<223> OTHER INFORMATION: synthetic

<400> SEQUENCE: 144
caagcagaag acggcatacg agattcacgc tggtctcgtg ggctcggaga tgtgtataag    60
agacag    66

<210> SEQ ID NO 145
<211> LENGTH: 66
<212> TYPE: DNA

```
<213> ORGANISM: Artificial
<220> FEATURE:
<223> OTHER INFORMATION: synthetic

<400> SEQUENCE: 145
caagcagaag acggcatacg agatctagat ctgtctcgtg ggctcggaga tgtgtataag      60
agacag                                                                66

<210> SEQ ID NO 146
<211> LENGTH: 66
<212> TYPE: DNA
<213> ORGANISM: Artificial
<220> FEATURE:
<223> OTHER INFORMATION: synthetic

<400> SEQUENCE: 146
caagcagaag acggcatacg agatcgatag cagtctcgtg ggctcggaga tgtgtataag      60
agacag                                                                66

<210> SEQ ID NO 147
<211> LENGTH: 66
<212> TYPE: DNA
<213> ORGANISM: Artificial
<220> FEATURE:
<223> OTHER INFORMATION: synthetic

<400> SEQUENCE: 147
caagcagaag acggcatacg agatatcgta ctgtctcgtg ggctcggaga tgtgtataag      60
agacag                                                                66

<210> SEQ ID NO 148
<211> LENGTH: 66
<212> TYPE: DNA
<213> ORGANISM: Artificial
<220> FEATURE:
<223> OTHER INFORMATION: synthetic

<400> SEQUENCE: 148
caagcagaag acggcatacg agattcatgt acgtctcgtg ggctcggaga tgtgtataag      60
agacag                                                                66

<210> SEQ ID NO 149
<211> LENGTH: 66
<212> TYPE: DNA
<213> ORGANISM: Artificial
<220> FEATURE:
<223> OTHER INFORMATION: synthetic

<400> SEQUENCE: 149
caagcagaag acggcatacg agattagtga cggtctcgtg ggctcggaga tgtgtataag      60
agacag                                                                66

<210> SEQ ID NO 150
<211> LENGTH: 66
<212> TYPE: DNA
<213> ORGANISM: Artificial
<220> FEATURE:
<223> OTHER INFORMATION: synthetic

<400> SEQUENCE: 150
caagcagaag acggcatacg agatcacgat aggtctcgtg ggctcggaga tgtgtataag      60
agacag                                                                66
```

<210> SEQ ID NO 151
<211> LENGTH: 66
<212> TYPE: DNA
<213> ORGANISM: Artificial
<220> FEATURE:
<223> OTHER INFORMATION: synthetic

<400> SEQUENCE: 151
caagcagaag acggcatacg agatacacac tggtctcgtg ggctcggaga tgtgtataag      60
agacag                                                                66

<210> SEQ ID NO 152
<211> LENGTH: 66
<212> TYPE: DNA
<213> ORGANISM: Artificial
<220> FEATURE:
<223> OTHER INFORMATION: synthetic

<400> SEQUENCE: 152
caagcagaag acggcatacg agatcgtcta gcgtctcgtg ggctcggaga tgtgtataag      60
agacag                                                                66

<210> SEQ ID NO 153
<211> LENGTH: 66
<212> TYPE: DNA
<213> ORGANISM: Artificial
<220> FEATURE:
<223> OTHER INFORMATION: synthetic

<400> SEQUENCE: 153
caagcagaag acggcatacg agattagcta gcgtctcgtg ggctcggaga tgtgtataag      60
agacag                                                                66

<210> SEQ ID NO 154
<211> LENGTH: 66
<212> TYPE: DNA
<213> ORGANISM: Artificial
<220> FEATURE:
<223> OTHER INFORMATION: synthetic

<400> SEQUENCE: 154
caagcagaag acggcatacg agattcgacg tcgtctcgtg ggctcggaga tgtgtataag      60
agacag                                                                66

<210> SEQ ID NO 155
<211> LENGTH: 66
<212> TYPE: DNA
<213> ORGANISM: Artificial
<220> FEATURE:
<223> OTHER INFORMATION: synthetic

<400> SEQUENCE: 155
caagcagaag acggcatacg agatagcatc acgtctcgtg ggctcggaga tgtgtataag      60
agacag                                                                66

<210> SEQ ID NO 156
<211> LENGTH: 66
<212> TYPE: DNA
<213> ORGANISM: Artificial
<220> FEATURE:
<223> OTHER INFORMATION: synthetic

```
<400> SEQUENCE: 156
caagcagaag acggcatacg agatcgagac gcgtctcgtg ggctcggaga tgtgtataag    60
agacag                                                               66

<210> SEQ ID NO 157
<211> LENGTH: 66
<212> TYPE: DNA
<213> ORGANISM: Artificial
<220> FEATURE:
<223> OTHER INFORMATION: synthetic

<400> SEQUENCE: 157
caagcagaag acggcatacg agatcgcgag cagtctcgtg ggctcggaga tgtgtataag    60
agacag                                                               66

<210> SEQ ID NO 158
<211> LENGTH: 66
<212> TYPE: DNA
<213> ORGANISM: Artificial
<220> FEATURE:
<223> OTHER INFORMATION: synthetic

<400> SEQUENCE: 158
caagcagaag acggcatacg agattagtcg tagtctcgtg ggctcggaga tgtgtataag    60
agacag                                                               66

<210> SEQ ID NO 159
<211> LENGTH: 66
<212> TYPE: DNA
<213> ORGANISM: Artificial
<220> FEATURE:
<223> OTHER INFORMATION: synthetic

<400> SEQUENCE: 159
caagcagaag acggcatacg agatcgtagt atgtctcgtg ggctcggaga tgtgtataag    60
agacag                                                               66

<210> SEQ ID NO 160
<211> LENGTH: 66
<212> TYPE: DNA
<213> ORGANISM: Artificial
<220> FEATURE:
<223> OTHER INFORMATION: synthetic

<400> SEQUENCE: 160
caagcagaag acggcatacg agattcacgt acgtctcgtg ggctcggaga tgtgtataag    60
agacag                                                               66

<210> SEQ ID NO 161
<211> LENGTH: 66
<212> TYPE: DNA
<213> ORGANISM: Artificial
<220> FEATURE:
<223> OTHER INFORMATION: synthetic

<400> SEQUENCE: 161
caagcagaag acggcatacg agatgcatcg cggtctcgtg ggctcggaga tgtgtataag    60
agacag                                                               66

<210> SEQ ID NO 162
<211> LENGTH: 66
```

```
<212> TYPE: DNA
<213> ORGANISM: Artificial
<220> FEATURE:
<223> OTHER INFORMATION: synthetic

<400> SEQUENCE: 162
caagcagaag acggcatacg agatatcatg tcgtctcgtg ggctcggaga tgtgtataag    60
agacag                                                               66

<210> SEQ ID NO 163
<211> LENGTH: 66
<212> TYPE: DNA
<213> ORGANISM: Artificial
<220> FEATURE:
<223> OTHER INFORMATION: synthetic

<400> SEQUENCE: 163
caagcagaag acggcatacg agatctatgc atgtctcgtg ggctcggaga tgtgtataag    60
agacag                                                               66

<210> SEQ ID NO 164
<211> LENGTH: 70
<212> TYPE: DNA
<213> ORGANISM: Artificial
<220> FEATURE:
<223> OTHER INFORMATION: synthetic

<400> SEQUENCE: 164
aatgatacgg cgaccaccga gatctacacc tgctcgttcg tcggcagcgt cagatgtgta    60
taagagacag                                                           70

<210> SEQ ID NO 165
<211> LENGTH: 70
<212> TYPE: DNA
<213> ORGANISM: Artificial
<220> FEATURE:
<223> OTHER INFORMATION: synthetic

<400> SEQUENCE: 165
aatgatacgg cgaccaccga gatctacact gcgacgatcg tcggcagcgt cagatgtgta    60
taagagacag                                                           70

<210> SEQ ID NO 166
<211> LENGTH: 70
<212> TYPE: DNA
<213> ORGANISM: Artificial
<220> FEATURE:
<223> OTHER INFORMATION: synthetic

<400> SEQUENCE: 166
aatgatacgg cgaccaccga gatctacacc acatgcttcg tcggcagcgt cagatgtgta    60
taagagacag                                                           70

<210> SEQ ID NO 167
<211> LENGTH: 70
<212> TYPE: DNA
<213> ORGANISM: Artificial
<220> FEATURE:
<223> OTHER INFORMATION: synthetic

<400> SEQUENCE: 167
aatgatacgg cgaccaccga gatctacaca tactcattcg tcggcagcgt cagatgtgta    60
```
taagagacag 70

<210> SEQ ID NO 168
<211> LENGTH: 70
<212> TYPE: DNA
<213> ORGANISM: Artificial
<220> FEATURE:
<223> OTHER INFORMATION: synthetic

<400> SEQUENCE: 168
aatgatacgg cgaccaccga gatctacacg atgcacgtcg tcggcagcgt cagatgtgta    60
taagagacag                                                          70

<210> SEQ ID NO 169
<211> LENGTH: 70
<212> TYPE: DNA
<213> ORGANISM: Artificial
<220> FEATURE:
<223> OTHER INFORMATION: synthetic

<400> SEQUENCE: 169
aatgatacgg cgaccaccga gatctacacg tagtgcttcg tcggcagcgt cagatgtgta    60
taagagacag                                                          70

<210> SEQ ID NO 170
<211> LENGTH: 70
<212> TYPE: DNA
<213> ORGANISM: Artificial
<220> FEATURE:
<223> OTHER INFORMATION: synthetic

<400> SEQUENCE: 170
aatgatacgg cgaccaccga gatctacaca tgatagttcg tcggcagcgt cagatgtgta    60
taagagacag                                                          70

<210> SEQ ID NO 171
<211> LENGTH: 70
<212> TYPE: DNA
<213> ORGANISM: Artificial
<220> FEATURE:
<223> OTHER INFORMATION: synthetic

<400> SEQUENCE: 171
aatgatacgg cgaccaccga gatctacacc tcgctagtcg tcggcagcgt cagatgtgta    60
taagagacag                                                          70

<210> SEQ ID NO 172
<211> LENGTH: 70
<212> TYPE: DNA
<213> ORGANISM: Artificial
<220> FEATURE:
<223> OTHER INFORMATION: synthetic

<400> SEQUENCE: 172
aatgatacgg cgaccaccga gatctacacg ctgagagtcg tcggcagcgt cagatgtgta    60
taagagacag                                                          70

<210> SEQ ID NO 173
<211> LENGTH: 70
<212> TYPE: DNA
<213> ORGANISM: Artificial
<220> FEATURE:
<223> OTHER INFORMATION: synthetic

<400> SEQUENCE: 173
aatgatacgg cgaccaccga gatctacaca gcacgagtcg tcggcagcgt cagatgtgta    60
taagagacag    70

<210> SEQ ID NO 174
<211> LENGTH: 70
<212> TYPE: DNA
<213> ORGANISM: Artificial
<220> FEATURE:
<223> OTHER INFORMATION: synthetic

<400> SEQUENCE: 174
aatgatacgg cgaccaccga gatctacact gtcagagtcg tcggcagcgt cagatgtgta    60
taagagacag    70

<210> SEQ ID NO 175
<211> LENGTH: 70
<212> TYPE: DNA
<213> ORGANISM: Artificial
<220> FEATURE:
<223> OTHER INFORMATION: synthetic

<400> SEQUENCE: 175
aatgatacgg cgaccaccga gatctacacg cgcagtatcg tcggcagcgt cagatgtgta    60
taagagacag    70

<210> SEQ ID NO 176
<211> LENGTH: 70
<212> TYPE: DNA
<213> ORGANISM: Artificial
<220> FEATURE:
<223> OTHER INFORMATION: synthetic

<400> SEQUENCE: 176
aatgatacgg cgaccaccga gatctacacc atcagcgtcg tcggcagcgt cagatgtgta    60
taagagacag    70

<210> SEQ ID NO 177
<211> LENGTH: 70
<212> TYPE: DNA
<213> ORGANISM: Artificial
<220> FEATURE:
<223> OTHER INFORMATION: synthetic

<400> SEQUENCE: 177
aatgatacgg cgaccaccga gatctacact acgagcatcg tcggcagcgt cagatgtgta    60
taagagacag    70

<210> SEQ ID NO 178
<211> LENGTH: 70
<212> TYPE: DNA
<213> ORGANISM: Artificial
<220> FEATURE:
<223> OTHER INFORMATION: synthetic

<400> SEQUENCE: 178
aatgatacgg cgaccaccga gatctacaca gcagacttcg tcggcagcgt cagatgtgta    60
taagagacag    70

<210> SEQ ID NO 179

```
<211> LENGTH: 70
<212> TYPE: DNA
<213> ORGANISM: Artificial
<220> FEATURE:
<223> OTHER INFORMATION: synthetic

<400> SEQUENCE: 179
aatgatacgg cgaccaccga gatctacacc agtacattcg tcggcagcgt cagatgtgta      60
taagagacag                                                             70

<210> SEQ ID NO 180
<211> LENGTH: 70
<212> TYPE: DNA
<213> ORGANISM: Artificial
<220> FEATURE:
<223> OTHER INFORMATION: synthetic

<400> SEQUENCE: 180
aatgatacgg cgaccaccga gatctacacg agtatgatcg tcggcagcgt cagatgtgta      60
taagagacag                                                             70

<210> SEQ ID NO 181
<211> LENGTH: 70
<212> TYPE: DNA
<213> ORGANISM: Artificial
<220> FEATURE:
<223> OTHER INFORMATION: synthetic

<400> SEQUENCE: 181
aatgatacgg cgaccaccga gatctacact atcacattcg tcggcagcgt cagatgtgta      60
taagagacag                                                             70

<210> SEQ ID NO 182
<211> LENGTH: 70
<212> TYPE: DNA
<213> ORGANISM: Artificial
<220> FEATURE:
<223> OTHER INFORMATION: synthetic

<400> SEQUENCE: 182
aatgatacgg cgaccaccga gatctacacc acagtcatcg tcggcagcgt cagatgtgta      60
taagagacag                                                             70

<210> SEQ ID NO 183
<211> LENGTH: 70
<212> TYPE: DNA
<213> ORGANISM: Artificial
<220> FEATURE:
<223> OTHER INFORMATION: synthetic

<400> SEQUENCE: 183
aatgatacgg cgaccaccga gatctacact gcagctatcg tcggcagcgt cagatgtgta      60
taagagacag                                                             70

<210> SEQ ID NO 184
<211> LENGTH: 70
<212> TYPE: DNA
<213> ORGANISM: Artificial
<220> FEATURE:
<223> OTHER INFORMATION: synthetic

<400> SEQUENCE: 184
aatgatacgg cgaccaccga gatctacacg cgagcagtcg tcggcagcgt cagatgtgta      60
```
taagagacag 70

<210> SEQ ID NO 185
<211> LENGTH: 70
<212> TYPE: DNA
<213> ORGANISM: Artificial
<220> FEATURE:
<223> OTHER INFORMATION: synthetic

<400> SEQUENCE: 185
aatgatacgg cgaccaccga gatctacacg acagcgttcg tcggcagcgt cagatgtgta    60
taagagacag    70

<210> SEQ ID NO 186
<211> LENGTH: 70
<212> TYPE: DNA
<213> ORGANISM: Artificial
<220> FEATURE:
<223> OTHER INFORMATION: synthetic

<400> SEQUENCE: 186
aatgatacgg cgaccaccga gatctacaca gctcgagtcg tcggcagcgt cagatgtgta    60
taagagacag    70

<210> SEQ ID NO 187
<211> LENGTH: 70
<212> TYPE: DNA
<213> ORGANISM: Artificial
<220> FEATURE:
<223> OTHER INFORMATION: synthetic

<400> SEQUENCE: 187
aatgatacgg cgaccaccga gatctacact agatcattcg tcggcagcgt cagatgtgta    60
taagagacag    70

<210> SEQ ID NO 188
<211> LENGTH: 70
<212> TYPE: DNA
<213> ORGANISM: Artificial
<220> FEATURE:
<223> OTHER INFORMATION: synthetic

<400> SEQUENCE: 188
aatgatacgg cgaccaccga gatctacacc gcagtgatcg tcggcagcgt cagatgtgta    60
taagagacag    70

<210> SEQ ID NO 189
<211> LENGTH: 70
<212> TYPE: DNA
<213> ORGANISM: Artificial
<220> FEATURE:
<223> OTHER INFORMATION: synthetic

<400> SEQUENCE: 189
aatgatacgg cgaccaccga gatctacacc gtactgatcg tcggcagcgt cagatgtgta    60
taagagacag    70

<210> SEQ ID NO 190
<211> LENGTH: 70
<212> TYPE: DNA
<213> ORGANISM: Artificial
<220> FEATURE:

<223> OTHER INFORMATION: synthetic

<400> SEQUENCE: 190
aatgatacgg cgaccaccga gatctacact cagatgttcg tcggcagcgt cagatgtgta    60
taagagacag                                                            70

<210> SEQ ID NO 191
<211> LENGTH: 70
<212> TYPE: DNA
<213> ORGANISM: Artificial
<220> FEATURE:
<223> OTHER INFORMATION: synthetic

<400> SEQUENCE: 191
aatgatacgg cgaccaccga gatctacacc tctctgatcg tcggcagcgt cagatgtgta    60
taagagacag                                                            70

<210> SEQ ID NO 192
<211> LENGTH: 70
<212> TYPE: DNA
<213> ORGANISM: Artificial
<220> FEATURE:
<223> OTHER INFORMATION: synthetic

<400> SEQUENCE: 192
aatgatacgg cgaccaccga gatctacact cagcatatcg tcggcagcgt cagatgtgta    60
taagagacag                                                            70

<210> SEQ ID NO 193
<211> LENGTH: 70
<212> TYPE: DNA
<213> ORGANISM: Artificial
<220> FEATURE:
<223> OTHER INFORMATION: synthetic

<400> SEQUENCE: 193
aatgatacgg cgaccaccga gatctacacc atacagatcg tcggcagcgt cagatgtgta    60
taagagacag                                                            70

<210> SEQ ID NO 194
<211> LENGTH: 70
<212> TYPE: DNA
<213> ORGANISM: Artificial
<220> FEATURE:
<223> OTHER INFORMATION: synthetic

<400> SEQUENCE: 194
aatgatacgg cgaccaccga gatctacacc gagacgatcg tcggcagcgt cagatgtgta    60
taagagacag                                                            70

<210> SEQ ID NO 195
<211> LENGTH: 70
<212> TYPE: DNA
<213> ORGANISM: Artificial
<220> FEATURE:
<223> OTHER INFORMATION: synthetic

<400> SEQUENCE: 195
aatgatacgg cgaccaccga gatctacacc tcgacagtcg tcggcagcgt cagatgtgta    60
taagagacag                                                            70

```
<210> SEQ ID NO 196
<211> LENGTH: 70
<212> TYPE: DNA
<213> ORGANISM: Artificial
<220> FEATURE:
<223> OTHER INFORMATION: synthetic

<400> SEQUENCE: 196
aatgatacgg cgaccaccga gatctacacg tagatgatcg tcggcagcgt cagatgtgta    60
taagagacag                                                          70

<210> SEQ ID NO 197
<211> LENGTH: 70
<212> TYPE: DNA
<213> ORGANISM: Artificial
<220> FEATURE:
<223> OTHER INFORMATION: synthetic

<400> SEQUENCE: 197
aatgatacgg cgaccaccga gatctacacc atctcagtcg tcggcagcgt cagatgtgta    60
taagagacag                                                          70

<210> SEQ ID NO 198
<211> LENGTH: 70
<212> TYPE: DNA
<213> ORGANISM: Artificial
<220> FEATURE:
<223> OTHER INFORMATION: synthetic

<400> SEQUENCE: 198
aatgatacgg cgaccaccga gatctacact gagctcatcg tcggcagcgt cagatgtgta    60
taagagacag                                                          70

<210> SEQ ID NO 199
<211> LENGTH: 70
<212> TYPE: DNA
<213> ORGANISM: Artificial
<220> FEATURE:
<223> OTHER INFORMATION: synthetic

<400> SEQUENCE: 199
aatgatacgg cgaccaccga gatctacact agagcgttcg tcggcagcgt cagatgtgta    60
taagagacag                                                          70

<210> SEQ ID NO 200
<211> LENGTH: 70
<212> TYPE: DNA
<213> ORGANISM: Artificial
<220> FEATURE:
<223> OTHER INFORMATION: synthetic

<400> SEQUENCE: 200
aatgatacgg cgaccaccga gatctacaca gatagcatcg tcggcagcgt cagatgtgta    60
taagagacag                                                          70

<210> SEQ ID NO 201
<211> LENGTH: 70
<212> TYPE: DNA
<213> ORGANISM: Artificial
<220> FEATURE:
<223> OTHER INFORMATION: synthetic

<400> SEQUENCE: 201
```
aatgatacgg cgaccaccga gatctacaca gactgagtcg tcggcagcgt cagatgtgta    60
taagagacag                                                          70

<210> SEQ ID NO 202
<211> LENGTH: 70
<212> TYPE: DNA
<213> ORGANISM: Artificial
<220> FEATURE:
<223> OTHER INFORMATION: synthetic

<400> SEQUENCE: 202
aatgatacgg cgaccaccga gatctacacg ctacatatcg tcggcagcgt cagatgtgta    60
taagagacag                                                          70

<210> SEQ ID NO 203
<211> LENGTH: 70
<212> TYPE: DNA
<213> ORGANISM: Artificial
<220> FEATURE:
<223> OTHER INFORMATION: synthetic

<400> SEQUENCE: 203
aatgatacgg cgaccaccga gatctacaca tagctattcg tcggcagcgt cagatgtgta    60
taagagacag                                                          70

<210> SEQ ID NO 204
<211> LENGTH: 70
<212> TYPE: DNA
<213> ORGANISM: Artificial
<220> FEATURE:
<223> OTHER INFORMATION: synthetic

<400> SEQUENCE: 204
aatgatacgg cgaccaccga gatctacaca tcgagtatcg tcggcagcgt cagatgtgta    60
taagagacag                                                          70

<210> SEQ ID NO 205
<211> LENGTH: 70
<212> TYPE: DNA
<213> ORGANISM: Artificial
<220> FEATURE:
<223> OTHER INFORMATION: synthetic

<400> SEQUENCE: 205
aatgatacgg cgaccaccga gatctacacg atgtgattcg tcggcagcgt cagatgtgta    60
taagagacag                                                          70

<210> SEQ ID NO 206
<211> LENGTH: 70
<212> TYPE: DNA
<213> ORGANISM: Artificial
<220> FEATURE:
<223> OTHER INFORMATION: synthetic

<400> SEQUENCE: 206
aatgatacgg cgaccaccga gatctacacg atcagtatcg tcggcagcgt cagatgtgta    60
taagagacag                                                          70

<210> SEQ ID NO 207
<211> LENGTH: 70
<212> TYPE: DNA
<213> ORGANISM: Artificial

```
<220> FEATURE:
<223> OTHER INFORMATION: synthetic

<400> SEQUENCE: 207
aatgatacgg cgaccaccga gatctacact atgtacttcg tcggcagcgt cagatgtgta    60
taagagacag                                                           70

<210> SEQ ID NO 208
<211> LENGTH: 70
<212> TYPE: DNA
<213> ORGANISM: Artificial
<220> FEATURE:
<223> OTHER INFORMATION: synthetic

<400> SEQUENCE: 208
aatgatacgg cgaccaccga gatctacact cactgcatcg tcggcagcgt cagatgtgta    60
taagagacag                                                           70

<210> SEQ ID NO 209
<211> LENGTH: 70
<212> TYPE: DNA
<213> ORGANISM: Artificial
<220> FEATURE:
<223> OTHER INFORMATION: synthetic

<400> SEQUENCE: 209
aatgatacgg cgaccaccga gatctacaca cacatattcg tcggcagcgt cagatgtgta    60
taagagacag                                                           70

<210> SEQ ID NO 210
<211> LENGTH: 70
<212> TYPE: DNA
<213> ORGANISM: Artificial
<220> FEATURE:
<223> OTHER INFORMATION: synthetic

<400> SEQUENCE: 210
aatgatacgg cgaccaccga gatctacacc tctctagtcg tcggcagcgt cagatgtgta    60
taagagacag                                                           70

<210> SEQ ID NO 211
<211> LENGTH: 70
<212> TYPE: DNA
<213> ORGANISM: Artificial
<220> FEATURE:
<223> OTHER INFORMATION: synthetic

<400> SEQUENCE: 211
aatgatacgg cgaccaccga gatctacacg tgagtgttcg tcggcagcgt cagatgtgta    60
taagagacag                                                           70

<210> SEQ ID NO 212
<211> LENGTH: 70
<212> TYPE: DNA
<213> ORGANISM: Artificial
<220> FEATURE:
<223> OTHER INFORMATION: synthetic

<400> SEQUENCE: 212
aatgatacgg cgaccaccga gatctacacc atcgatgtcg tcggcagcgt cagatgtgta    60
taagagacag                                                           70
```

<210> SEQ ID NO 213
<211> LENGTH: 70
<212> TYPE: DNA
<213> ORGANISM: Artificial
<220> FEATURE:
<223> OTHER INFORMATION: synthetic

<400> SEQUENCE: 213
aatgatacgg cgaccaccga gatctacacg atgcacttcg tcggcagcgt cagatgtgta    60
taagagacag                                                           70

<210> SEQ ID NO 214
<211> LENGTH: 70
<212> TYPE: DNA
<213> ORGANISM: Artificial
<220> FEATURE:
<223> OTHER INFORMATION: synthetic

<400> SEQUENCE: 214
aatgatacgg cgaccaccga gatctacacc gtactcgtcg tcggcagcgt cagatgtgta    60
taagagacag                                                           70

<210> SEQ ID NO 215
<211> LENGTH: 70
<212> TYPE: DNA
<213> ORGANISM: Artificial
<220> FEATURE:
<223> OTHER INFORMATION: synthetic

<400> SEQUENCE: 215
aatgatacgg cgaccaccga gatctacact gagtgcatcg tcggcagcgt cagatgtgta    60
taagagacag                                                           70

<210> SEQ ID NO 216
<211> LENGTH: 70
<212> TYPE: DNA
<213> ORGANISM: Artificial
<220> FEATURE:
<223> OTHER INFORMATION: synthetic

<400> SEQUENCE: 216
aatgatacgg cgaccaccga gatctacacc gcgatgatcg tcggcagcgt cagatgtgta    60
taagagacag                                                           70

<210> SEQ ID NO 217
<211> LENGTH: 70
<212> TYPE: DNA
<213> ORGANISM: Artificial
<220> FEATURE:
<223> OTHER INFORMATION: synthetic

<400> SEQUENCE: 217
aatgatacgg cgaccaccga gatctacact gatcgcatcg tcggcagcgt cagatgtgta    60
taagagacag                                                           70

<210> SEQ ID NO 218
<211> LENGTH: 70
<212> TYPE: DNA
<213> ORGANISM: Artificial
<220> FEATURE:
<223> OTHER INFORMATION: synthetic

<400> SEQUENCE: 218

```
aatgatacgg cgaccaccga gatctacacc gcgactatcg tcggcagcgt cagatgtgta    60
taagagacag                                                          70

<210> SEQ ID NO 219
<211> LENGTH: 70
<212> TYPE: DNA
<213> ORGANISM: Artificial
<220> FEATURE:
<223> OTHER INFORMATION: synthetic

<400> SEQUENCE: 219
aatgatacgg cgaccaccga gatctacaca tacgcattcg tcggcagcgt cagatgtgta    60
taagagacag                                                          70

<210> SEQ ID NO 220
<211> LENGTH: 70
<212> TYPE: DNA
<213> ORGANISM: Artificial
<220> FEATURE:
<223> OTHER INFORMATION: synthetic

<400> SEQUENCE: 220
aatgatacgg cgaccaccga gatctacacc gagcgcttcg tcggcagcgt cagatgtgta    60
taagagacag                                                          70

<210> SEQ ID NO 221
<211> LENGTH: 70
<212> TYPE: DNA
<213> ORGANISM: Artificial
<220> FEATURE:
<223> OTHER INFORMATION: synthetic

<400> SEQUENCE: 221
aatgatacgg cgaccaccga gatctacaca ctacgattcg tcggcagcgt cagatgtgta    60
taagagacag                                                          70

<210> SEQ ID NO 222
<211> LENGTH: 70
<212> TYPE: DNA
<213> ORGANISM: Artificial
<220> FEATURE:
<223> OTHER INFORMATION: synthetic

<400> SEQUENCE: 222
aatgatacgg cgaccaccga gatctacact gcagcagtcg tcggcagcgt cagatgtgta    60
taagagacag                                                          70

<210> SEQ ID NO 223
<211> LENGTH: 70
<212> TYPE: DNA
<213> ORGANISM: Artificial
<220> FEATURE:
<223> OTHER INFORMATION: synthetic

<400> SEQUENCE: 223
aatgatacgg cgaccaccga gatctacaca gtactcgtcg tcggcagcgt cagatgtgta    60
taagagacag                                                          70

<210> SEQ ID NO 224
<211> LENGTH: 70
<212> TYPE: DNA
```

```
<213> ORGANISM: Artificial
<220> FEATURE:
<223> OTHER INFORMATION: synthetic

<400> SEQUENCE: 224
aatgatacgg cgaccaccga gatctacacc tgagtgttcg tcggcagcgt cagatgtgta      60
taagagacag                                                            70

<210> SEQ ID NO 225
<211> LENGTH: 70
<212> TYPE: DNA
<213> ORGANISM: Artificial
<220> FEATURE:
<223> OTHER INFORMATION: synthetic

<400> SEQUENCE: 225
aatgatacgg cgaccaccga gatctacacg tgagtgatcg tcggcagcgt cagatgtgta      60
taagagacag                                                            70

<210> SEQ ID NO 226
<211> LENGTH: 70
<212> TYPE: DNA
<213> ORGANISM: Artificial
<220> FEATURE:
<223> OTHER INFORMATION: synthetic

<400> SEQUENCE: 226
aatgatacgg cgaccaccga gatctacact gtcgtcatcg tcggcagcgt cagatgtgta      60
taagagacag                                                            70

<210> SEQ ID NO 227
<211> LENGTH: 70
<212> TYPE: DNA
<213> ORGANISM: Artificial
<220> FEATURE:
<223> OTHER INFORMATION: synthetic

<400> SEQUENCE: 227
aatgatacgg cgaccaccga gatctacacc acgagcttcg tcggcagcgt cagatgtgta      60
taagagacag                                                            70

<210> SEQ ID NO 228
<211> LENGTH: 70
<212> TYPE: DNA
<213> ORGANISM: Artificial
<220> FEATURE:
<223> OTHER INFORMATION: synthetic

<400> SEQUENCE: 228
aatgatacgg cgaccaccga gatctacacg agactcttcg tcggcagcgt cagatgtgta      60
taagagacag                                                            70

<210> SEQ ID NO 229
<211> LENGTH: 70
<212> TYPE: DNA
<213> ORGANISM: Artificial
<220> FEATURE:
<223> OTHER INFORMATION: synthetic

<400> SEQUENCE: 229
aatgatacgg cgaccaccga gatctacacc atgtcactcg tcggcagcgt cagatgtgta      60
taagagacag                                                            70
```

<210> SEQ ID NO 230
<211> LENGTH: 70
<212> TYPE: DNA
<213> ORGANISM: Artificial
<220> FEATURE:
<223> OTHER INFORMATION: synthetic

<400> SEQUENCE: 230
aatgatacgg cgaccaccga gatctacacc gtgtacgtcg tcggcagcgt cagatgtgta      60
taagagacag                                                            70

<210> SEQ ID NO 231
<211> LENGTH: 70
<212> TYPE: DNA
<213> ORGANISM: Artificial
<220> FEATURE:
<223> OTHER INFORMATION: synthetic

<400> SEQUENCE: 231
aatgatacgg cgaccaccga gatctacact cgtagattcg tcggcagcgt cagatgtgta      60
taagagacag                                                            70

<210> SEQ ID NO 232
<211> LENGTH: 70
<212> TYPE: DNA
<213> ORGANISM: Artificial
<220> FEATURE:
<223> OTHER INFORMATION: synthetic

<400> SEQUENCE: 232
aatgatacgg cgaccaccga gatctacaca gctgacatcg tcggcagcgt cagatgtgta      60
taagagacag                                                            70

<210> SEQ ID NO 233
<211> LENGTH: 70
<212> TYPE: DNA
<213> ORGANISM: Artificial
<220> FEATURE:
<223> OTHER INFORMATION: synthetic

<400> SEQUENCE: 233
aatgatacgg cgaccaccga gatctacacc gtcatcatcg tcggcagcgt cagatgtgta      60
taagagacag                                                            70

<210> SEQ ID NO 234
<211> LENGTH: 70
<212> TYPE: DNA
<213> ORGANISM: Artificial
<220> FEATURE:
<223> OTHER INFORMATION: synthetic

<400> SEQUENCE: 234
aatgatacgg cgaccaccga gatctacact actcacgtcg tcggcagcgt cagatgtgta      60
taagagacag                                                            70

<210> SEQ ID NO 235
<211> LENGTH: 70
<212> TYPE: DNA
<213> ORGANISM: Artificial
<220> FEATURE:
<223> OTHER INFORMATION: synthetic

<400> SEQUENCE: 235
aatgatacgg cgaccaccga gatctacacc agtagcgtcg tcggcagcgt cagatgtgta    60
taagagacag                                                            70

<210> SEQ ID NO 236
<211> LENGTH: 70
<212> TYPE: DNA
<213> ORGANISM: Artificial
<220> FEATURE:
<223> OTHER INFORMATION: synthetic

<400> SEQUENCE: 236
aatgatacgg cgaccaccga gatctacacc atgtagttcg tcggcagcgt cagatgtgta    60
taagagacag                                                            70

<210> SEQ ID NO 237
<211> LENGTH: 70
<212> TYPE: DNA
<213> ORGANISM: Artificial
<220> FEATURE:
<223> OTHER INFORMATION: synthetic

<400> SEQUENCE: 237
aatgatacgg cgaccaccga gatctacact agagacgtcg tcggcagcgt cagatgtgta    60
taagagacag                                                            70

<210> SEQ ID NO 238
<211> LENGTH: 70
<212> TYPE: DNA
<213> ORGANISM: Artificial
<220> FEATURE:
<223> OTHER INFORMATION: synthetic

<400> SEQUENCE: 238
aatgatacgg cgaccaccga gatctacacc gtctcagtcg tcggcagcgt cagatgtgta    60
taagagacag                                                            70

<210> SEQ ID NO 239
<211> LENGTH: 70
<212> TYPE: DNA
<213> ORGANISM: Artificial
<220> FEATURE:
<223> OTHER INFORMATION: synthetic

<400> SEQUENCE: 239
aatgatacgg cgaccaccga gatctacact acatgcatcg tcggcagcgt cagatgtgta    60
taagagacag                                                            70

<210> SEQ ID NO 240
<211> LENGTH: 70
<212> TYPE: DNA
<213> ORGANISM: Artificial
<220> FEATURE:
<223> OTHER INFORMATION: synthetic

<400> SEQUENCE: 240
aatgatacgg cgaccaccga gatctacact actagcatcg tcggcagcgt cagatgtgta    60
taagagacag                                                            70

<210> SEQ ID NO 241
<211> LENGTH: 70

```
<212> TYPE: DNA
<213> ORGANISM: Artificial
<220> FEATURE:
<223> OTHER INFORMATION: synthetic

<400> SEQUENCE: 241
aatgatacgg cgaccaccga gatctacaca tgacagatcg tcggcagcgt cagatgtgta    60
taagagacag                                                          70

<210> SEQ ID NO 242
<211> LENGTH: 70
<212> TYPE: DNA
<213> ORGANISM: Artificial
<220> FEATURE:
<223> OTHER INFORMATION: synthetic

<400> SEQUENCE: 242
aatgatacgg cgaccaccga gatctacaca cagcgtatcg tcggcagcgt cagatgtgta    60
taagagacag                                                          70

<210> SEQ ID NO 243
<211> LENGTH: 70
<212> TYPE: DNA
<213> ORGANISM: Artificial
<220> FEATURE:
<223> OTHER INFORMATION: synthetic

<400> SEQUENCE: 243
aatgatacgg cgaccaccga gatctacacc atgcacttcg tcggcagcgt cagatgtgta    60
taagagacag                                                          70

<210> SEQ ID NO 244
<211> LENGTH: 70
<212> TYPE: DNA
<213> ORGANISM: Artificial
<220> FEATURE:
<223> OTHER INFORMATION: synthetic

<400> SEQUENCE: 244
aatgatacgg cgaccaccga gatctacact cgagcgttcg tcggcagcgt cagatgtgta    60
taagagacag                                                          70

<210> SEQ ID NO 245
<211> LENGTH: 70
<212> TYPE: DNA
<213> ORGANISM: Artificial
<220> FEATURE:
<223> OTHER INFORMATION: synthetic

<400> SEQUENCE: 245
aatgatacgg cgaccaccga gatctacacc gcacgagtcg tcggcagcgt cagatgtgta    60
taagagacag                                                          70

<210> SEQ ID NO 246
<211> LENGTH: 70
<212> TYPE: DNA
<213> ORGANISM: Artificial
<220> FEATURE:
<223> OTHER INFORMATION: synthetic

<400> SEQUENCE: 246
aatgatacgg cgaccaccga gatctacacc acagtattcg tcggcagcgt cagatgtgta    60
```

-continued taagagacag                                                              70

<210> SEQ ID NO 247
<211> LENGTH: 70
<212> TYPE: DNA
<213> ORGANISM: Artificial
<220> FEATURE:
<223> OTHER INFORMATION: synthetic

<400> SEQUENCE: 247
aatgatacgg cgaccaccga gatctacaca gtcatcatcg tcggcagcgt cagatgtgta      60
taagagacag                                                              70

<210> SEQ ID NO 248
<211> LENGTH: 70
<212> TYPE: DNA
<213> ORGANISM: Artificial
<220> FEATURE:
<223> OTHER INFORMATION: synthetic

<400> SEQUENCE: 248
aatgatacgg cgaccaccga gatctacact gactatatcg tcggcagcgt cagatgtgta      60
taagagacag                                                              70

<210> SEQ ID NO 249
<211> LENGTH: 70
<212> TYPE: DNA
<213> ORGANISM: Artificial
<220> FEATURE:
<223> OTHER INFORMATION: synthetic

<400> SEQUENCE: 249
aatgatacgg cgaccaccga gatctacact cgcatattcg tcggcagcgt cagatgtgta      60
taagagacag                                                              70

<210> SEQ ID NO 250
<211> LENGTH: 70
<212> TYPE: DNA
<213> ORGANISM: Artificial
<220> FEATURE:
<223> OTHER INFORMATION: synthetic

<400> SEQUENCE: 250
aatgatacgg cgaccaccga gatctacaca tcgatgttcg tcggcagcgt cagatgtgta      60
taagagacag                                                              70

<210> SEQ ID NO 251
<211> LENGTH: 70
<212> TYPE: DNA
<213> ORGANISM: Artificial
<220> FEATURE:
<223> OTHER INFORMATION: synthetic

<400> SEQUENCE: 251
aatgatacgg cgaccaccga gatctacacc gacagcgtcg tcggcagcgt cagatgtgta      60
taagagacag                                                              70

<210> SEQ ID NO 252
<211> LENGTH: 70
<212> TYPE: DNA
<213> ORGANISM: Artificial
<220> FEATURE:
<223> OTHER INFORMATION: synthetic

<400> SEQUENCE: 252
aatgatacgg cgaccaccga gatctacaca tcgtgtatcg tcggcagcgt cagatgtgta    60
taagagacag    70

<210> SEQ ID NO 253
<211> LENGTH: 70
<212> TYPE: DNA
<213> ORGANISM: Artificial
<220> FEATURE:
<223> OTHER INFORMATION: synthetic

<400> SEQUENCE: 253
aatgatacgg cgaccaccga gatctacacg catgtagtcg tcggcagcgt cagatgtgta    60
taagagacag    70

<210> SEQ ID NO 254
<211> LENGTH: 70
<212> TYPE: DNA
<213> ORGANISM: Artificial
<220> FEATURE:
<223> OTHER INFORMATION: synthetic

<400> SEQUENCE: 254
aatgatacgg cgaccaccga gatctacaca gagatcatcg tcggcagcgt cagatgtgta    60
taagagacag    70

<210> SEQ ID NO 255
<211> LENGTH: 70
<212> TYPE: DNA
<213> ORGANISM: Artificial
<220> FEATURE:
<223> OTHER INFORMATION: synthetic

<400> SEQUENCE: 255
aatgatacgg cgaccaccga gatctacacc gtcagtatcg tcggcagcgt cagatgtgta    60
taagagacag    70

<210> SEQ ID NO 256
<211> LENGTH: 70
<212> TYPE: DNA
<213> ORGANISM: Artificial
<220> FEATURE:
<223> OTHER INFORMATION: synthetic

<400> SEQUENCE: 256
aatgatacgg cgaccaccga gatctacacg cgtagattcg tcggcagcgt cagatgtgta    60
taagagacag    70

<210> SEQ ID NO 257
<211> LENGTH: 70
<212> TYPE: DNA
<213> ORGANISM: Artificial
<220> FEATURE:
<223> OTHER INFORMATION: synthetic

<400> SEQUENCE: 257
aatgatacgg cgaccaccga gatctacacg tactacatcg tcggcagcgt cagatgtgta    60
taagagacag    70

<210> SEQ ID NO 258

```
<211> LENGTH: 70
<212> TYPE: DNA
<213> ORGANISM: Artificial
<220> FEATURE:
<223> OTHER INFORMATION: synthetic

<400> SEQUENCE: 258
aatgatacgg cgaccaccga gatctacacg cgagacatcg tcggcagcgt cagatgtgta      60
taagagacag                                                            70

<210> SEQ ID NO 259
<211> LENGTH: 70
<212> TYPE: DNA
<213> ORGANISM: Artificial
<220> FEATURE:
<223> OTHER INFORMATION: synthetic

<400> SEQUENCE: 259
aatgatacgg cgaccaccga gatctacacg atagacgtcg tcggcagcgt cagatgtgta      60
taagagacag                                                            70

<210> SEQ ID NO 260
<211> LENGTH: 70
<212> TYPE: DNA
<213> ORGANISM: Artificial
<220> FEATURE:
<223> OTHER INFORMATION: synthetic

<400> SEQUENCE: 260
aatgatacgg cgaccaccga gatctacact atactagtcg tcggcagcgt cagatgtgta      60
taagagacag                                                            70

<210> SEQ ID NO 261
<211> LENGTH: 70
<212> TYPE: DNA
<213> ORGANISM: Artificial
<220> FEATURE:
<223> OTHER INFORMATION: synthetic

<400> SEQUENCE: 261
aatgatacgg cgaccaccga gatctacact gctcgcatcg tcggcagcgt cagatgtgta      60
taagagacag                                                            70

<210> SEQ ID NO 262
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 262
caagcagaag acggcatacg agatcnnctt ttgtctcgtg ggctcggaga tgtgtataag      60
agacag                                                                66

<210> SEQ ID NO 263
<211> LENGTH: 66
<212> TYPE: DNA
<213> ORGANISM: Artificial
<220> FEATURE:
<223> OTHER INFORMATION: synthetic
```

<400> SEQUENCE: 263
caagcagaag acggcatacg agatcctcgt ttgtctcgtg ggctcggaga tgtgtataag    60
agacag    66

<210> SEQ ID NO 264
<211> LENGTH: 66
<212> TYPE: DNA
<213> ORGANISM: Artificial
<220> FEATURE:
<223> OTHER INFORMATION: synthetic

<400> SEQUENCE: 264
caagcagaag acggcatacg agatcccgt ttgtctcgtg ggctcggaga tgtgtataag    60
agacag    66

<210> SEQ ID NO 265
<211> LENGTH: 66
<212> TYPE: DNA
<213> ORGANISM: Artificial
<220> FEATURE:
<223> OTHER INFORMATION: synthetic

<400> SEQUENCE: 265
caagcagaag acggcatacg agatccacgt ttgtctcgtg ggctcggaga tgtgtataag    60
agacag    66

<210> SEQ ID NO 266
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 266
caagcagaag acggcatacg agatnnntnt ttgtctcgtg ggctcggaga tgtgtataag    60
agacag    66

<210> SEQ ID NO 267
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 267
caagcagaag acggcatacg agatnnngnt ttgtctcgtg ggctcggaga tgtgtataag    60
agacag    66

<210> SEQ ID NO 268
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 268
caagcagaag acggcatacg agattnncnt tgtctcgtg ggctcggaga tgtgtataag      60
agacag                                                                66

<210> SEQ ID NO 269
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 269
caagcagaag acggcatacg agatgnncnt tgtctcgtg ggctcggaga tgtgtataag      60
agacag                                                                66

<210> SEQ ID NO 270
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 270
caagcagaag acggcatacg agatanncnt tgtctcgtg ggctcggaga tgtgtataag      60
agacag                                                                66

<210> SEQ ID NO 271
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature -continued
<222> LOCATION: (29)..(29)
<223> OTHER INFORMATION: n is a, c, g, or t

<400> SEQUENCE: 271
caagcagaag acggcatacg agatnnnant tgtctcgtg ggctcggaga tgtgtataag    60
agacag                                                              66

<210> SEQ ID NO 272
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 272
caagcagaag acggcatacg agatcnncat tgtctcgtg ggctcggaga tgtgtataag    60
agacag                                                              66

<210> SEQ ID NO 273
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 273
caagcagaag acggcatacg agatcnnttg tgtctcgtg ggctcggaga tgtgtataag    60
agacag                                                              66

<210> SEQ ID NO 274
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 274
caagcagaag acggcatacg agattnngtg tgtctcgtg ggctcggaga tgtgtataag    60
agacag                                                              66

<210> SEQ ID NO 275
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 275
caagcagaag acggcatacg agatgnngtg tgtctcgtg ggctcggaga tgtgtataag    60
agacag                                                              66

<210> SEQ ID NO 276
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 276
caagcagaag acggcatacg agatcnngtg ttgtctcgtg ggctcggaga tgtgtataag    60
agacag                                                              66

<210> SEQ ID NO 277
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 277
caagcagaag acggcatacg agatccnctg ttgtctcgtg ggctcggaga tgtgtataag    60
agacag                                                              66

<210> SEQ ID NO 278
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 278
caagcagaag acggcatacg agattnnctg ttgtctcgtg ggctcggaga tgtgtataag    60
agacag                                                              66

<210> SEQ ID NO 279
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 279
caagcagaag acggcatacg agatgnnctg ttgtctcgtg ggctcggaga tgtgtataag    60
agacag                                                              66

<210> SEQ ID NO 280
<211> LENGTH: 66
<212> TYPE: DNA
<213> ORGANISM: Artificial

```
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 280
caagcagaag acggcatacg agatannctg ttgtctcgtg ggctcggaga tgtgtataag    60
agacag                                                               66

<210> SEQ ID NO 281
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 281
caagcagaag acggcatacg agattnnatg ttgtctcgtg ggctcggaga tgtgtataag    60
agacag                                                               66

<210> SEQ ID NO 282
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 282
caagcagaag acggcatacg agatgnnatg ttgtctcgtg ggctcggaga tgtgtataag    60
agacag                                                               66

<210> SEQ ID NO 283
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 283
caagcagaag acggcatacg agatcnnatg ttgtctcgtg ggctcggaga tgtgtataag    60
agacag                                                               66

<210> SEQ ID NO 284
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t
```

<400> SEQUENCE: 284
caagcagaag acggcatacg agatcgntgg ttgtctcgtg ggctcggaga tgtgtataag    60
agacag                                                              66

<210> SEQ ID NO 285
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 285
caagcagaag acggcatacg agatccntgg ttgtctcgtg ggctcggaga tgtgtataag    60
agacag                                                              66

<210> SEQ ID NO 286
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 286
caagcagaag acggcatacg agatcantgg ttgtctcgtg ggctcggaga tgtgtataag    60
agacag                                                              66

<210> SEQ ID NO 287
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 287
caagcagaag acggcatacg agattgnggg ttgtctcgtg ggctcggaga tgtgtataag    60
agacag                                                              66

<210> SEQ ID NO 288
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 288
caagcagaag acggcatacg agatggnggg ttgtctcgtg ggctcggaga tgtgtataag    60
agacag                                                              66

```
<210> SEQ ID NO 289
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 289
caagcagaag acggcatacg agattcnggg ttgtctcgtg ggctcggaga tgtgtataag      60
agacag                                                                 66

<210> SEQ ID NO 290
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 290
caagcagaag acggcatacg agatgcnggg ttgtctcgtg ggctcggaga tgtgtataag      60
agacag                                                                 66

<210> SEQ ID NO 291
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 291
caagcagaag acggcatacg agattanggg ttgtctcgtg ggctcggaga tgtgtataag      60
agacag                                                                 66

<210> SEQ ID NO 292
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 292
caagcagaag acggcatacg agatganggg ttgtctcgtg ggctcggaga tgtgtataag      60
agacag                                                                 66

<210> SEQ ID NO 293
<211> LENGTH: 66
<212> TYPE: DNA
<213> ORGANISM: Artificial
<220> FEATURE:
<223> OTHER INFORMATION: synthetic
<220> FEATURE:
```

```
<221> NAME/KEY: misc_feature
<222> LOCATION: (27)..(27)
<223> OTHER INFORMATION: n is a, c, g, or t

<400> SEQUENCE: 293
caagcagaag acggcatacg agatagncgg ttgtctcgtg ggctcggaga tgtgtataag    60
agacag                                                              66

<210> SEQ ID NO 294
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 294
caagcagaag acggcatacg agatacncgg ttgtctcgtg ggctcggaga tgtgtataag    60
agacag                                                              66

<210> SEQ ID NO 295
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 295
caagcagaag acggcatacg agataancgg ttgtctcgtg ggctcggaga tgtgtataag    60
agacag                                                              66

<210> SEQ ID NO 296
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 296
caagcagaag acggcatacg agattgnagg ttgtctcgtg ggctcggaga tgtgtataag    60
agacag                                                              66

<210> SEQ ID NO 297
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 297
caagcagaag acggcatacg agatggnagg ttgtctcgtg ggctcggaga tgtgtataag    60
```

```
agacag                                                              66

<210> SEQ ID NO 298
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 298
caagcagaag acggcatacg agattcnagg ttgtctcgtg ggctcggaga tgtgtataag    60
agacag                                                              66

<210> SEQ ID NO 299
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 299
caagcagaag acggcatacg agatgcnagg ttgtctcgtg ggctcggaga tgtgtataag    60
agacag                                                              66

<210> SEQ ID NO 300
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 300
caagcagaag acggcatacg agattanagg ttgtctcgtg ggctcggaga tgtgtataag    60
agacag                                                              66

<210> SEQ ID NO 301
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 301
caagcagaag acggcatacg agatganagg ttgtctcgtg ggctcggaga tgtgtataag    60
agacag                                                              66

<210> SEQ ID NO 302
<211> LENGTH: 66
<212> TYPE: DNA
```

<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 302
caagcagaag acggcatacg agatcgntcg ttgtctcgtg ggctcggaga tgtgtataag    60
agacag                                                               66

<210> SEQ ID NO 303
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 303
caagcagaag acggcatacg agatccntcg ttgtctcgtg ggctcggaga tgtgtataag    60
agacag                                                               66

<210> SEQ ID NO 304
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 304
caagcagaag acggcatacg agatcantcg ttgtctcgtg ggctcggaga tgtgtataag    60
agacag                                                               66

<210> SEQ ID NO 305
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 305
caagcagaag acggcatacg agattgngcg ttgtctcgtg ggctcggaga tgtgtataag    60
agacag                                                               66

<210> SEQ ID NO 306
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 306
caagcagaag acggcatacg agatggngcg ttgtctcgtg ggctcggaga tgtgtataag    60
agacag                                                              66

<210> SEQ ID NO 307
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 307
caagcagaag acggcatacg agattcngcg ttgtctcgtg ggctcggaga tgtgtataag    60
agacag                                                              66

<210> SEQ ID NO 308
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 308
caagcagaag acggcatacg agatgcngcg ttgtctcgtg ggctcggaga tgtgtataag    60
agacag                                                              66

<210> SEQ ID NO 309
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 309
caagcagaag acggcatacg agattangcg ttgtctcgtg ggctcggaga tgtgtataag    60
agacag                                                              66

<210> SEQ ID NO 310
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 310
caagcagaag acggcatacg agatgangcg ttgtctcgtg ggctcggaga tgtgtataag    60
agacag                                                              66

<210> SEQ ID NO 311
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 311
caagcagaag acggcatacg agatagnccg ttgtctcgtg ggctcggaga tgtgtataag     60
agacag                                                                66

<210> SEQ ID NO 312
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 312
caagcagaag acggcatacg agatacnccg ttgtctcgtg ggctcggaga tgtgtataag     60
agacag                                                                66

<210> SEQ ID NO 313
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 313
caagcagaag acggcatacg agataanccg ttgtctcgtg ggctcggaga tgtgtataag     60
agacag                                                                66

<210> SEQ ID NO 314
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 314
caagcagaag acggcatacg agattgnacg ttgtctcgtg ggctcggaga tgtgtataag     60
agacag                                                                66

<210> SEQ ID NO 315
<211> LENGTH: 66
<212> TYPE: DNA
<213> ORGANISM: Artificial
<220> FEATURE:
<223> OTHER INFORMATION: synthetic -continued
<220> FEATURE:
<221> NAME/KEY: misc_feature
<222> LOCATION: (27)..(27)
<223> OTHER INFORMATION: n is a, c, g, or t

<400> SEQUENCE: 315
caagcagaag acggcatacg agatggnacg ttgtctcgtg ggctcggaga tgtgtataag    60
agacag                                                              66

<210> SEQ ID NO 316
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 316
caagcagaag acggcatacg agattcnacg ttgtctcgtg ggctcggaga tgtgtataag    60
agacag                                                              66

<210> SEQ ID NO 317
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 317
caagcagaag acggcatacg agatgcnacg ttgtctcgtg ggctcggaga tgtgtataag    60
agacag                                                              66

<210> SEQ ID NO 318
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 318
caagcagaag acggcatacg agattanacg ttgtctcgtg ggctcggaga tgtgtataag    60
agacag                                                              66

<210> SEQ ID NO 319
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 319

```
caagcagaag acggcatacg agatganacg ttgtctcgtg ggctcggaga tgtgtataag    60
agacag                                                              66

<210> SEQ ID NO 320
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 320
caagcagaag acggcatacg agattnntng ttgtctcgtg ggctcggaga tgtgtataag    60
agacag                                                              66

<210> SEQ ID NO 321
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 321
caagcagaag acggcatacg agatgnntng ttgtctcgtg ggctcggaga tgtgtataag    60
agacag                                                              66

<210> SEQ ID NO 322
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 322
caagcagaag acggcatacg agatanntng ttgtctcgtg ggctcggaga tgtgtataag    60
agacag                                                              66

<210> SEQ ID NO 323
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 323
caagcagaag acggcatacg agatanngng ttgtctcgtg ggctcggaga tgtgtataag    60
agacag    66

<210> SEQ ID NO 324
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 324
caagcagaag acggcatacg agatannang ttgtctcgtg ggctcggaga tgtgtataag    60
agacag    66

<210> SEQ ID NO 325
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 325
caagcagaag acggcatacg agatcnntag ttgtctcgtg ggctcggaga tgtgtataag    60
agacag    66

<210> SEQ ID NO 326
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 326
caagcagaag acggcatacg agattnngag ttgtctcgtg ggctcggaga tgtgtataag    60
agacag    66

<210> SEQ ID NO 327
<211> LENGTH: 66
<212> TYPE: DNA
<213> ORGANISM: Artificial
<220> FEATURE:
<223> OTHER INFORMATION: synthetic
<220> FEATURE:

<221> NAME/KEY: misc_feature
<222> LOCATION: (26)..(27)
<223> OTHER INFORMATION: n is a, c, g, or t

<400> SEQUENCE: 327
caagcagaag acggcatacg agatgnngag ttgtctcgtg ggctcggaga tgtgtataag    60
agacag                                                               66

<210> SEQ ID NO 328
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 328
caagcagaag acggcatacg agattgncag ttgtctcgtg ggctcggaga tgtgtataag    60
agacag                                                               66

<210> SEQ ID NO 329
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 329
caagcagaag acggcatacg agatggncag ttgtctcgtg ggctcggaga tgtgtataag    60
agacag                                                               66

<210> SEQ ID NO 330
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 330
caagcagaag acggcatacg agattcncag ttgtctcgtg ggctcggaga tgtgtataag    60
agacag                                                               66

<210> SEQ ID NO 331
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 331
caagcagaag acggcatacg agatgcncag ttgtctcgtg ggctcggaga tgtgtataag    60
agacag 66

<210> SEQ ID NO 332
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 332
caagcagaag acggcatacg agatanncag ttgtctcgtg ggctcggaga tgtgtataag    60
agacag    66

<210> SEQ ID NO 333
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 333
caagcagaag acggcatacg agattancag ttgtctcgtg ggctcggaga tgtgtataag    60
agacag    66

<210> SEQ ID NO 334
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 334
caagcagaag acggcatacg agatgancag ttgtctcgtg ggctcggaga tgtgtataag    60
agacag    66

<210> SEQ ID NO 335
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 335
caagcagaag acggcatacg agattnnaag ttgtctcgtg ggctcggaga tgtgtataag    60
agacag    66

<210> SEQ ID NO 336
<211> LENGTH: 66
<212> TYPE: DNA

```
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 336
caagcagaag acggcatacg agatgnnaag ttgtctcgtg ggctcggaga tgtgtataag    60
agacag                                                               66

<210> SEQ ID NO 337
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 337
caagcagaag acggcatacg agatcnnttc ttgtctcgtg ggctcggaga tgtgtataag    60
agacag                                                               66

<210> SEQ ID NO 338
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 338
caagcagaag acggcatacg agattnngtc ttgtctcgtg ggctcggaga tgtgtataag    60
agacag                                                               66

<210> SEQ ID NO 339
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 339
caagcagaag acggcatacg agatgnngtc ttgtctcgtg ggctcggaga tgtgtataag    60
agacag                                                               66

<210> SEQ ID NO 340
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
```

<400> SEQUENCE: 340
caagcagaag acggcatacg agatcnngtc ttgtctcgtg ggctcggaga tgtgtataag        60
agacag        66

<210> SEQ ID NO 341
<211> LENGTH: 66
<212> TYPE: DNA
<213> ORGANISM: Artificial
<220> FEATURE:
<223> OTHER INFORMATION: synthetic

<400> SEQUENCE: 341
caagcagaag acggcatacg agatcctctc ttgtctcgtg ggctcggaga tgtgtataag        60
agacag        66

<210> SEQ ID NO 342
<211> LENGTH: 66
<212> TYPE: DNA
<213> ORGANISM: Artificial
<220> FEATURE:
<223> OTHER INFORMATION: synthetic

<400> SEQUENCE: 342
caagcagaag acggcatacg agatccctc ttgtctcgtg ggctcggaga tgtgtataag        60
agacag        66

<210> SEQ ID NO 343
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 343
caagcagaag acggcatacg agattnnctc ttgtctcgtg ggctcggaga tgtgtataag        60
agacag        66

<210> SEQ ID NO 344
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 344
caagcagaag acggcatacg agatgnnctc ttgtctcgtg ggctcggaga tgtgtataag        60
agacag        66

<210> SEQ ID NO 345
<211> LENGTH: 66
<212> TYPE: DNA
<213> ORGANISM: Artificial
<220> FEATURE:
<223> OTHER INFORMATION: synthetic
<220> FEATURE:

```
<221> NAME/KEY: misc_feature
<222> LOCATION: (26)..(27)
<223> OTHER INFORMATION: n is a, c, g, or t

<400> SEQUENCE: 345
caagcagaag acggcatacg agatannctc ttgtctcgtg ggctcggaga tgtgtataag    60
agacag                                                               66

<210> SEQ ID NO 346
<211> LENGTH: 66
<212> TYPE: DNA
<213> ORGANISM: Artificial
<220> FEATURE:
<223> OTHER INFORMATION: synthetic

<400> SEQUENCE: 346
caagcagaag acggcatacg agatccactc ttgtctcgtg ggctcggaga tgtgtataag    60
agacag                                                               66

<210> SEQ ID NO 347
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 347
caagcagaag acggcatacg agattnnatc ttgtctcgtg ggctcggaga tgtgtataag    60
agacag                                                               66

<210> SEQ ID NO 348
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 348
caagcagaag acggcatacg agatgnnatc ttgtctcgtg ggctcggaga tgtgtataag    60
agacag                                                               66

<210> SEQ ID NO 349
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 349
caagcagaag acggcatacg agatcnnatc ttgtctcgtg ggctcggaga tgtgtataag    60
agacag                                                               66
```

```
<210> SEQ ID NO 350
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 350
caagcagaag acggcatacg agatcgntgc ttgtctcgtg ggctcggaga tgtgtataag      60
agacag                                                                66

<210> SEQ ID NO 351
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 351
caagcagaag acggcatacg agatccntgc ttgtctcgtg ggctcggaga tgtgtataag      60
agacag                                                                66

<210> SEQ ID NO 352
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 352
caagcagaag acggcatacg agatcantgc ttgtctcgtg ggctcggaga tgtgtataag      60
agacag                                                                66

<210> SEQ ID NO 353
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 353
caagcagaag acggcatacg agattgnggc ttgtctcgtg ggctcggaga tgtgtataag      60
agacag                                                                66

<210> SEQ ID NO 354
<211> LENGTH: 66
<212> TYPE: DNA
<213> ORGANISM: Artificial
<220> FEATURE:
<223> OTHER INFORMATION: synthetic
<220> FEATURE:
```

```
<221> NAME/KEY: misc_feature
<222> LOCATION: (27)..(27)
<223> OTHER INFORMATION: n is a, c, g, or t

<400> SEQUENCE: 354
caagcagaag acggcatacg agatggnggc ttgtctcgtg ggctcggaga tgtgtataag      60
agacag                                                                66

<210> SEQ ID NO 355
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 355
caagcagaag acggcatacg agattcnggc ttgtctcgtg ggctcggaga tgtgtataag      60
agacag                                                                66

<210> SEQ ID NO 356
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 356
caagcagaag acggcatacg agatgcnggc ttgtctcgtg ggctcggaga tgtgtataag      60
agacag                                                                66

<210> SEQ ID NO 357
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 357
caagcagaag acggcatacg agattanggc ttgtctcgtg ggctcggaga tgtgtataag      60
agacag                                                                66

<210> SEQ ID NO 358
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 358
caagcagaag acggcatacg agatganggc ttgtctcgtg ggctcggaga tgtgtataag      60
```

```
agacag                                                                 66

<210> SEQ ID NO 359
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 359
caagcagaag acggcatacg agatagncgc ttgtctcgtg ggctcggaga tgtgtataag      60
agacag                                                                 66

<210> SEQ ID NO 360
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 360
caagcagaag acggcatacg agatacncgc ttgtctcgtg ggctcggaga tgtgtataag      60
agacag                                                                 66

<210> SEQ ID NO 361
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 361
caagcagaag acggcatacg agataancgc ttgtctcgtg ggctcggaga tgtgtataag      60
agacag                                                                 66

<210> SEQ ID NO 362
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 362
caagcagaag acggcatacg agattgnagc ttgtctcgtg ggctcggaga tgtgtataag      60
agacag                                                                 66

<210> SEQ ID NO 363
<211> LENGTH: 66
<212> TYPE: DNA
```

```
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 363
caagcagaag acggcatacg agatggnagc ttgtctcgtg ggctcggaga tgtgtataag    60
agacag                                                              66

<210> SEQ ID NO 364
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 364
caagcagaag acggcatacg agattcnagc ttgtctcgtg ggctcggaga tgtgtataag    60
agacag                                                              66

<210> SEQ ID NO 365
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 365
caagcagaag acggcatacg agatgcnagc ttgtctcgtg ggctcggaga tgtgtataag    60
agacag                                                              66

<210> SEQ ID NO 366
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 366
caagcagaag acggcatacg agattanagc ttgtctcgtg ggctcggaga tgtgtataag    60
agacag                                                              66

<210> SEQ ID NO 367
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t
```

```
<400> SEQUENCE: 367
caagcagaag acggcatacg agatganagc ttgtctcgtg ggctcggaga tgtgtataag    60
agacag                                                               66

<210> SEQ ID NO 368
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 368
caagcagaag acggcatacg agatcgntcc ttgtctcgtg ggctcggaga tgtgtataag    60
agacag                                                               66

<210> SEQ ID NO 369
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 369
caagcagaag acggcatacg agatccntcc ttgtctcgtg ggctcggaga tgtgtataag    60
agacag                                                               66

<210> SEQ ID NO 370
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 370
caagcagaag acggcatacg agatcantcc ttgtctcgtg ggctcggaga tgtgtataag    60
agacag                                                               66

<210> SEQ ID NO 371
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 371
caagcagaag acggcatacg agattgngcc ttgtctcgtg ggctcggaga tgtgtataag    60
agacag                                                               66
```

<210> SEQ ID NO 372
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 372
caagcagaag acggcatacg agatggngcc ttgtctcgtg ggctcggaga tgtgtataag    60
agacag    66

<210> SEQ ID NO 373
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 373
caagcagaag acggcatacg agattcngcc ttgtctcgtg ggctcggaga tgtgtataag    60
agacag    66

<210> SEQ ID NO 374
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 374
caagcagaag acggcatacg agatgcngcc ttgtctcgtg ggctcggaga tgtgtataag    60
agacag    66

<210> SEQ ID NO 375
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 375
caagcagaag acggcatacg agattangcc ttgtctcgtg ggctcggaga tgtgtataag    60
agacag    66

<210> SEQ ID NO 376
<211> LENGTH: 66
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (27)..(27)
<223> OTHER INFORMATION: n is a, c, g, or t

<400> SEQUENCE: 376
caagcagaag acggcatacg agatgangcc ttgtctcgtg ggctcggaga tgtgtataag      60
agacag                                                                66

<210> SEQ ID NO 377
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 377
caagcagaag acggcatacg agatagnccc ttgtctcgtg ggctcggaga tgtgtataag      60
agacag                                                                66

<210> SEQ ID NO 378
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 378
caagcagaag acggcatacg agatacnccc ttgtctcgtg ggctcggaga tgtgtataag      60
agacag                                                                66

<210> SEQ ID NO 379
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 379
caagcagaag acggcatacg agataanccc ttgtctcgtg ggctcggaga tgtgtataag      60
agacag                                                                66

<210> SEQ ID NO 380
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 380
```
caagcagaag acggcatacg agattgnacc ttgtctcgtg ggctcggaga tgtgtataag        60
agacag                                                                  66

<210> SEQ ID NO 381
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 381
caagcagaag acggcatacg agatggnacc ttgtctcgtg ggctcggaga tgtgtataag        60
agacag                                                                  66

<210> SEQ ID NO 382
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 382
caagcagaag acggcatacg agattcnacc ttgtctcgtg ggctcggaga tgtgtataag        60
agacag                                                                  66

<210> SEQ ID NO 383
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 383
caagcagaag acggcatacg agatgcnacc ttgtctcgtg ggctcggaga tgtgtataag        60
agacag                                                                  66

<210> SEQ ID NO 384
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 384
caagcagaag acggcatacg agattanacc ttgtctcgtg ggctcggaga tgtgtataag        60
agacag                                                                  66

<210> SEQ ID NO 385
<211> LENGTH: 66

<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 385
caagcagaag acggcatacg agatganacc ttgtctcgtg ggctcggaga tgtgtataag    60
agacag                                                               66

<210> SEQ ID NO 386
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 386
caagcagaag acggcatacg agattnntnc ttgtctcgtg ggctcggaga tgtgtataag    60
agacag                                                               66

<210> SEQ ID NO 387
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 387
caagcagaag acggcatacg agatgnntnc ttgtctcgtg ggctcggaga tgtgtataag    60
agacag                                                               66

<210> SEQ ID NO 388
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 388
caagcagaag acggcatacg agatanntnc ttgtctcgtg ggctcggaga tgtgtataag    60

```
agacag                                                              66

<210> SEQ ID NO 389
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 389
caagcagaag acggcatacg agatanngnc ttgtctcgtg ggctcggaga tgtgtataag    60
agacag                                                              66

<210> SEQ ID NO 390
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 390
caagcagaag acggcatacg agatannanc ttgtctcgtg ggctcggaga tgtgtataag    60
agacag                                                              66

<210> SEQ ID NO 391
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 391
caagcagaag acggcatacg agatcnntac ttgtctcgtg ggctcggaga tgtgtataag    60
agacag                                                              66

<210> SEQ ID NO 392
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 392
caagcagaag acggcatacg agattnngac ttgtctcgtg ggctcggaga tgtgtataag    60
```

-continued agacag                                                              66

<210> SEQ ID NO 393
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 393
caagcagaag acggcatacg agatgnngac ttgtctcgtg ggctcggaga tgtgtataag    60
agacag                                                              66

<210> SEQ ID NO 394
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 394
caagcagaag acggcatacg agattgncac ttgtctcgtg ggctcggaga tgtgtataag    60
agacag                                                              66

<210> SEQ ID NO 395
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 395
caagcagaag acggcatacg agatggncac ttgtctcgtg ggctcggaga tgtgtataag    60
agacag                                                              66

<210> SEQ ID NO 396
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 396
caagcagaag acggcatacg agattcncac ttgtctcgtg ggctcggaga tgtgtataag    60
agacag                                                              66

<210> SEQ ID NO 397
<211> LENGTH: 66
<212> TYPE: DNA

-continued

```
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 397
caagcagaag acggcatacg agatgcncac ttgtctcgtg ggctcggaga tgtgtataag      60
agacag                                                                66

<210> SEQ ID NO 398
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 398
caagcagaag acggcatacg agatanncac ttgtctcgtg ggctcggaga tgtgtataag      60
agacag                                                                66

<210> SEQ ID NO 399
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 399
caagcagaag acggcatacg agattancac ttgtctcgtg ggctcggaga tgtgtataag      60
agacag                                                                66

<210> SEQ ID NO 400
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 400
caagcagaag acggcatacg agatgancac ttgtctcgtg ggctcggaga tgtgtataag      60
agacag                                                                66

<210> SEQ ID NO 401
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
```

<400> SEQUENCE: 401
caagcagaag acggcatacg agattnnaac ttgtctcgtg ggctcggaga tgtgtataag    60
agacag                                                                66

<210> SEQ ID NO 402
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 402
caagcagaag acggcatacg agatgnnaac ttgtctcgtg ggctcggaga tgtgtataag    60
agacag                                                                66

<210> SEQ ID NO 403
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 403
caagcagaag acggcatacg agatcnngta ttgtctcgtg ggctcggaga tgtgtataag    60
agacag                                                                66

<210> SEQ ID NO 404
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 404
caagcagaag acggcatacg agattnncta ttgtctcgtg ggctcggaga tgtgtataag    60
agacag                                                                66

<210> SEQ ID NO 405
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 405
caagcagaag acggcatacg agatgnncta ttgtctcgtg ggctcggaga tgtgtataag    60
agacag                                                                66

```
<210> SEQ ID NO 406
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 406
caagcagaag acggcatacg agatcnncta ttgtctcgtg ggctcggaga tgtgtataag      60
agacag                                                                66

<210> SEQ ID NO 407
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 407
caagcagaag acggcatacg agatcnnata ttgtctcgtg ggctcggaga tgtgtataag      60
agacag                                                                66

<210> SEQ ID NO 408
<211> LENGTH: 66
<212> TYPE: DNA
<213> ORGANISM: Artificial
<220> FEATURE:
<223> OTHER INFORMATION: synthetic

<400> SEQUENCE: 408
caagcagaag acggcatacg agatcctgga ttgtctcgtg ggctcggaga tgtgtataag      60
agacag                                                                66

<210> SEQ ID NO 409
<211> LENGTH: 66
<212> TYPE: DNA
<213> ORGANISM: Artificial
<220> FEATURE:
<223> OTHER INFORMATION: synthetic

<400> SEQUENCE: 409
caagcagaag acggcatacg agatcccgga ttgtctcgtg ggctcggaga tgtgtataag      60
agacag                                                                66

<210> SEQ ID NO 410
<211> LENGTH: 66
<212> TYPE: DNA
<213> ORGANISM: Artificial
<220> FEATURE:
<223> OTHER INFORMATION: synthetic

<400> SEQUENCE: 410
caagcagaag acggcatacg agatccagga ttgtctcgtg ggctcggaga tgtgtataag      60
agacag                                                                66
```

```
<210> SEQ ID NO 411
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 411
caagcagaag acggcatacg agattgncga ttgtctcgtg ggctcggaga tgtgtataag    60
agacag                                                              66

<210> SEQ ID NO 412
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 412
caagcagaag acggcatacg agatggncga ttgtctcgtg ggctcggaga tgtgtataag    60
agacag                                                              66

<210> SEQ ID NO 413
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 413
caagcagaag acggcatacg agattcncga ttgtctcgtg ggctcggaga tgtgtataag    60
agacag                                                              66

<210> SEQ ID NO 414
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 414
caagcagaag acggcatacg agatgcncga ttgtctcgtg ggctcggaga tgtgtataag    60
agacag                                                              66

<210> SEQ ID NO 415
<211> LENGTH: 66
<212> TYPE: DNA
<213> ORGANISM: Artificial
<220> FEATURE:
<223> OTHER INFORMATION: synthetic
<220> FEATURE:
```

```
<221> NAME/KEY: misc_feature
<222> LOCATION: (27)..(27)
<223> OTHER INFORMATION: n is a, c, g, or t

<400> SEQUENCE: 415
caagcagaag acggcatacg agattancga ttgtctcgtg ggctcggaga tgtgtataag    60
agacag                                                              66

<210> SEQ ID NO 416
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 416
caagcagaag acggcatacg agatgancga ttgtctcgtg ggctcggaga tgtgtataag    60
agacag                                                              66

<210> SEQ ID NO 417
<211> LENGTH: 66
<212> TYPE: DNA
<213> ORGANISM: Artificial
<220> FEATURE:
<223> OTHER INFORMATION: synthetic

<400> SEQUENCE: 417
caagcagaag acggcatacg agatcctaga ttgtctcgtg ggctcggaga tgtgtataag    60
agacag                                                              66

<210> SEQ ID NO 418
<211> LENGTH: 66
<212> TYPE: DNA
<213> ORGANISM: Artificial
<220> FEATURE:
<223> OTHER INFORMATION: synthetic

<400> SEQUENCE: 418
caagcagaag acggcatacg agatcccaga ttgtctcgtg ggctcggaga tgtgtataag    60
agacag                                                              66

<210> SEQ ID NO 419
<211> LENGTH: 66
<212> TYPE: DNA
<213> ORGANISM: Artificial
<220> FEATURE:
<223> OTHER INFORMATION: synthetic

<400> SEQUENCE: 419
caagcagaag acggcatacg agatccaaga ttgtctcgtg ggctcggaga tgtgtataag    60
agacag                                                              66

<210> SEQ ID NO 420
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

```
<222> LOCATION: (27)..(27)
<223> OTHER INFORMATION: n is a, c, g, or t

<400> SEQUENCE: 420
caagcagaag acggcatacg agattgncca ttgtctcgtg ggctcggaga tgtgtataag    60
agacag                                                               66

<210> SEQ ID NO 421
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 421
caagcagaag acggcatacg agatggncca ttgtctcgtg ggctcggaga tgtgtataag    60
agacag                                                               66

<210> SEQ ID NO 422
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 422
caagcagaag acggcatacg agattcncca ttgtctcgtg ggctcggaga tgtgtataag    60
agacag                                                               66

<210> SEQ ID NO 423
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 423
caagcagaag acggcatacg agatgcncca ttgtctcgtg ggctcggaga tgtgtataag    60
agacag                                                               66

<210> SEQ ID NO 424
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 424
caagcagaag acggcatacg agattancca ttgtctcgtg ggctcggaga tgtgtataag    60
``` agacag                                                               66

<210> SEQ ID NO 425
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 425
caagcagaag acggcatacg agatgancca ttgtctcgtg ggctcggaga tgtgtataag      60
agacag                                                               66

<210> SEQ ID NO 426
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 426
caagcagaag acggcatacg agatnnntna ttgtctcgtg ggctcggaga tgtgtataag      60
agacag                                                               66

<210> SEQ ID NO 427
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 427
caagcagaag acggcatacg agattnngna ttgtctcgtg ggctcggaga tgtgtataag      60
agacag                                                               66

<210> SEQ ID NO 428
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 428
caagcagaag acggcatacg agatgnngna ttgtctcgtg ggctcggaga tgtgtataag      60
agacag                                                                66

<210> SEQ ID NO 429
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 429
caagcagaag acggcatacg agatanngna ttgtctcgtg ggctcggaga tgtgtataag      60
agacag                                                                66

<210> SEQ ID NO 430
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 430
caagcagaag acggcatacg agatanncna ttgtctcgtg ggctcggaga tgtgtataag      60
agacag                                                                66

<210> SEQ ID NO 431
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 431
caagcagaag acggcatacg agattnnana ttgtctcgtg ggctcggaga tgtgtataag      60
agacag                                                                66

<210> SEQ ID NO 432
<211> LENGTH: 66
<212> TYPE: DNA
<213> ORGANISM: Artificial
<220> FEATURE:

<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 432
caagcagaag acggcatacg agatgnnana ttgtctcgtg ggctcggaga tgtgtataag    60
agacag    66

<210> SEQ ID NO 433
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 433
caagcagaag acggcatacg agatannana ttgtctcgtg ggctcggaga tgtgtataag    60
agacag    66

<210> SEQ ID NO 434
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 434
caagcagaag acggcatacg agatcnngaa ttgtctcgtg ggctcggaga tgtgtataag    60
agacag    66

<210> SEQ ID NO 435
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 435
caagcagaag acggcatacg agattnncaa ttgtctcgtg ggctcggaga tgtgtataag    60
agacag    66

<210> SEQ ID NO 436
<211> LENGTH: 66
<212> TYPE: DNA
<213> ORGANISM: Artificial

<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 436
caagcagaag acggcatacg agatgnncaa ttgtctcgtg ggctcggaga tgtgtataag    60
agacag    66

<210> SEQ ID NO 437
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 437
caagcagaag acggcatacg agatcnnaaa ttgtctcgtg ggctcggaga tgtgtataag    60
agacag    66

<210> SEQ ID NO 438
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 438
caagcagaag acggcatacg agatcnntttt gtgtctcgtg ggctcggaga tgtgtataag    60
agacag    66

<210> SEQ ID NO 439
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 439
caagcagaag acggcatacg agattnngtt gtgtctcgtg ggctcggaga tgtgtataag    60
agacag    66

<210> SEQ ID NO 440
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

```
<400> SEQUENCE: 440
caagcagaag acggcatacg agatgnngtt gtgtctcgtg ggctcggaga tgtgtataag    60
agacag                                                              66

<210> SEQ ID NO 441
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 441
caagcagaag acggcatacg agatcnngtt gtgtctcgtg ggctcggaga tgtgtataag    60
agacag                                                              66

<210> SEQ ID NO 442
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 442
caagcagaag acggcatacg agatcgnctt gtgtctcgtg ggctcggaga tgtgtataag    60
agacag                                                              66

<210> SEQ ID NO 443
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 443
caagcagaag acggcatacg agatccnctt gtgtctcgtg ggctcggaga tgtgtataag    60
agacag                                                              66

<210> SEQ ID NO 444
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 444
caagcagaag acggcatacg agattnnctt gtgtctcgtg ggctcggaga tgtgtataag    60
agacag                                                              66
```

```
<210> SEQ ID NO 445
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 445
caagcagaag acggcatacg agatgnnctt gtgtctcgtg ggctcggaga tgtgtataag    60
agacag                                                               66

<210> SEQ ID NO 446
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 446
caagcagaag acggcatacg agatannctt gtgtctcgtg ggctcggaga tgtgtataag    60
agacag                                                               66

<210> SEQ ID NO 447
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 447
caagcagaag acggcatacg agatcanctt gtgtctcgtg ggctcggaga tgtgtataag    60
agacag                                                               66

<210> SEQ ID NO 448
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 448
caagcagaag acggcatacg agattnnatt gtgtctcgtg ggctcggaga tgtgtataag    60
agacag                                                               66

<210> SEQ ID NO 449
<211> LENGTH: 66
<212> TYPE: DNA
<213> ORGANISM: Artificial
<220> FEATURE:
<223> OTHER INFORMATION: synthetic
<220> FEATURE:
```

<221> NAME/KEY: misc_feature
<222> LOCATION: (26)..(27)
<223> OTHER INFORMATION: n is a, c, g, or t

<400> SEQUENCE: 449
caagcagaag acggcatacg agatgnnatt gtgtctcgtg ggctcggaga tgtgtataag    60
agacag    66

<210> SEQ ID NO 450
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 450
caagcagaag acggcatacg agatcnnatt gtgtctcgtg ggctcggaga tgtgtataag    60
agacag    66

<210> SEQ ID NO 451
<211> LENGTH: 66
<212> TYPE: DNA
<213> ORGANISM: Artificial
<220> FEATURE:
<223> OTHER INFORMATION: synthetic

<400> SEQUENCE: 451
caagcagaag acggcatacg agatctttgt gtgtctcgtg ggctcggaga tgtgtataag    60
agacag    66

<210> SEQ ID NO 452
<211> LENGTH: 66
<212> TYPE: DNA
<213> ORGANISM: Artificial
<220> FEATURE:
<223> OTHER INFORMATION: synthetic

<400> SEQUENCE: 452
caagcagaag acggcatacg agatctctgt gtgtctcgtg ggctcggaga tgtgtataag    60
agacag    66

<210> SEQ ID NO 453
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 453
caagcagaag acggcatacg agatcgntgt gtgtctcgtg ggctcggaga tgtgtataag    60
agacag    66

<210> SEQ ID NO 454
<211> LENGTH: 66
<212> TYPE: DNA
<213> ORGANISM: Artificial

```
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 454
caagcagaag acggcatacg agatccntgt gtgtctcgtg ggctcggaga tgtgtataag     60
agacag                                                               66

<210> SEQ ID NO 455
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 455
caagcagaag acggcatacg agatcantgt gtgtctcgtg ggctcggaga tgtgtataag     60
agacag                                                               66

<210> SEQ ID NO 456
<211> LENGTH: 66
<212> TYPE: DNA
<213> ORGANISM: Artificial
<220> FEATURE:
<223> OTHER INFORMATION: synthetic

<400> SEQUENCE: 456
caagcagaag acggcatacg agatctatgt gtgtctcgtg ggctcggaga tgtgtataag     60
agacag                                                               66

<210> SEQ ID NO 457
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 457
caagcagaag acggcatacg agattgnggt gtgtctcgtg ggctcggaga tgtgtataag     60
agacag                                                               66

<210> SEQ ID NO 458
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 458
caagcagaag acggcatacg agatggnggt gtgtctcgtg ggctcggaga tgtgtataag     60
``` agacag                                                              66

<210> SEQ ID NO 459
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 459
caagcagaag acggcatacg agattcnggt gtgtctcgtg ggctcggaga tgtgtataag      60
agacag                                                              66

<210> SEQ ID NO 460
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 460
caagcagaag acggcatacg agatgcnggt gtgtctcgtg ggctcggaga tgtgtataag      60
agacag                                                              66

<210> SEQ ID NO 461
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 461
caagcagaag acggcatacg agattanggt gtgtctcgtg ggctcggaga tgtgtataag      60
agacag                                                              66

<210> SEQ ID NO 462
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 462
caagcagaag acggcatacg agatganggt gtgtctcgtg ggctcggaga tgtgtataag      60
agacag                                                              66

<210> SEQ ID NO 463
<211> LENGTH: 66
<212> TYPE: DNA
<213> ORGANISM: Artificial

<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 463
caagcagaag acggcatacg agatagncgt gtgtctcgtg ggctcggaga tgtgtataag    60
agacag    66

<210> SEQ ID NO 464
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 464
caagcagaag acggcatacg agatacncgt gtgtctcgtg ggctcggaga tgtgtataag    60
agacag    66

<210> SEQ ID NO 465
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 465
caagcagaag acggcatacg agataancgt gtgtctcgtg ggctcggaga tgtgtataag    60
agacag    66

<210> SEQ ID NO 466
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 466
caagcagaag acggcatacg agattgnagt gtgtctcgtg ggctcggaga tgtgtataag    60
agacag    66

<210> SEQ ID NO 467
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 467
caagcagaag acggcatacg agatggnagt gtgtctcgtg ggctcggaga tgtgtataag    60
agacag                                                              66

<210> SEQ ID NO 468
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 468
caagcagaag acggcatacg agattcnagt gtgtctcgtg ggctcggaga tgtgtataag    60
agacag                                                              66

<210> SEQ ID NO 469
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 469
caagcagaag acggcatacg agatgcnagt gtgtctcgtg ggctcggaga tgtgtataag    60
agacag                                                              66

<210> SEQ ID NO 470
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 470
caagcagaag acggcatacg agattanagt gtgtctcgtg ggctcggaga tgtgtataag    60
agacag                                                              66

<210> SEQ ID NO 471
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 471
caagcagaag acggcatacg agatganagt gtgtctcgtg ggctcggaga tgtgtataag    60
agacag                                                              66

```
<210> SEQ ID NO 472
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 472
caagcagaag acggcatacg agatcgntct gtgtctcgtg ggctcggaga tgtgtataag    60
agacag                                                               66

<210> SEQ ID NO 473
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 473
caagcagaag acggcatacg agatccntct gtgtctcgtg ggctcggaga tgtgtataag    60
agacag                                                               66

<210> SEQ ID NO 474
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 474
caagcagaag acggcatacg agatcantct gtgtctcgtg ggctcggaga tgtgtataag    60
agacag                                                               66

<210> SEQ ID NO 475
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 475
caagcagaag acggcatacg agattgngct gtgtctcgtg ggctcggaga tgtgtataag    60
agacag                                                               66

<210> SEQ ID NO 476
<211> LENGTH: 66
<212> TYPE: DNA
<213> ORGANISM: Artificial
<220> FEATURE:
<223> OTHER INFORMATION: synthetic
<220> FEATURE:
```

<221> NAME/KEY: misc_feature
<222> LOCATION: (27)..(27)
<223> OTHER INFORMATION: n is a, c, g, or t

<400> SEQUENCE: 476
caagcagaag acggcatacg agatggngct gtgtctcgtg ggctcggaga tgtgtataag    60
agacag                                                              66

<210> SEQ ID NO 477
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 477
caagcagaag acggcatacg agattcngct gtgtctcgtg ggctcggaga tgtgtataag    60
agacag                                                              66

<210> SEQ ID NO 478
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 478
caagcagaag acggcatacg agatgcngct gtgtctcgtg ggctcggaga tgtgtataag    60
agacag                                                              66

<210> SEQ ID NO 479
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 479
caagcagaag acggcatacg agattangct gtgtctcgtg ggctcggaga tgtgtataag    60
agacag                                                              66

<210> SEQ ID NO 480
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 480
caagcagaag acggcatacg agatgangct gtgtctcgtg ggctcggaga tgtgtataag    60
agacag 66

<210> SEQ ID NO 481
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 481
caagcagaag acggcatacg agatagncct gtgtctcgtg ggctcggaga tgtgtataag 60
agacag 66

<210> SEQ ID NO 482
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 482
caagcagaag acggcatacg agatacncct gtgtctcgtg ggctcggaga tgtgtataag 60
agacag 66

<210> SEQ ID NO 483
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 483
caagcagaag acggcatacg agataancct gtgtctcgtg ggctcggaga tgtgtataag 60
agacag 66

<210> SEQ ID NO 484
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 484
caagcagaag acggcatacg agattgnact gtgtctcgtg ggctcggaga tgtgtataag 60
agacag 66

<210> SEQ ID NO 485
<211> LENGTH: 66
<212> TYPE: DNA

```
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 485
caagcagaag acggcatacg agatggnact gtgtctcgtg ggctcggaga tgtgtataag    60
agacag                                                               66

<210> SEQ ID NO 486
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 486
caagcagaag acggcatacg agattcnact gtgtctcgtg ggctcggaga tgtgtataag    60
agacag                                                               66

<210> SEQ ID NO 487
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 487
caagcagaag acggcatacg agatgcnact gtgtctcgtg ggctcggaga tgtgtataag    60
agacag                                                               66

<210> SEQ ID NO 488
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 488
caagcagaag acggcatacg agattanact gtgtctcgtg ggctcggaga tgtgtataag    60
agacag                                                               66

<210> SEQ ID NO 489
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t
```

<400> SEQUENCE: 489
caagcagaag acggcatacg agatganact gtgtctcgtg ggctcggaga tgtgtataag    60
agacag    66

<210> SEQ ID NO 490
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 490
caagcagaag acggcatacg agattnntnt gtgtctcgtg ggctcggaga tgtgtataag    60
agacag    66

<210> SEQ ID NO 491
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 491
caagcagaag acggcatacg agatgnntnt gtgtctcgtg ggctcggaga tgtgtataag    60
agacag    66

<210> SEQ ID NO 492
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 492
caagcagaag acggcatacg agatanngnt gtgtctcgtg ggctcggaga tgtgtataag    60
agacag    66

<210> SEQ ID NO 493
<211> LENGTH: 66
<212> TYPE: DNA
<213> ORGANISM: Artificial
<220> FEATURE:

<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 493
caagcagaag acggcatacg agatannant gtgtctcgtg ggctcggaga tgtgtataag    60
agacag                                                              66

<210> SEQ ID NO 494
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 494
caagcagaag acggcatacg agatcnntat gtgtctcgtg ggctcggaga tgtgtataag    60
agacag                                                              66

<210> SEQ ID NO 495
<211> LENGTH: 66
<212> TYPE: DNA
<213> ORGANISM: Artificial
<220> FEATURE:
<223> OTHER INFORMATION: synthetic

<400> SEQUENCE: 495
caagcagaag acggcatacg agatcgtgat gtgtctcgtg ggctcggaga tgtgtataag    60
agacag                                                              66

<210> SEQ ID NO 496
<211> LENGTH: 66
<212> TYPE: DNA
<213> ORGANISM: Artificial
<220> FEATURE:
<223> OTHER INFORMATION: synthetic

<400> SEQUENCE: 496
caagcagaag acggcatacg agatcatgat gtgtctcgtg ggctcggaga tgtgtataag    60
agacag                                                              66

<210> SEQ ID NO 497
<211> LENGTH: 66
<212> TYPE: DNA
<213> ORGANISM: Artificial
<220> FEATURE:
<223> OTHER INFORMATION: synthetic

<400> SEQUENCE: 497
caagcagaag acggcatacg agatcgcgat gtgtctcgtg ggctcggaga tgtgtataag    60
agacag                                                              66

<210> SEQ ID NO 498
<211> LENGTH: 66

```
<212> TYPE: DNA
<213> ORGANISM: Artificial
<220> FEATURE:
<223> OTHER INFORMATION: synthetic

<400> SEQUENCE: 498
caagcagaag acggcatacg agatcacgat gtgtctcgtg ggctcggaga tgtgtataag      60
agacag                                                                66

<210> SEQ ID NO 499
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 499
caagcagaag acggcatacg agatccngat gtgtctcgtg ggctcggaga tgtgtataag      60
agacag                                                                66

<210> SEQ ID NO 500
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 500
caagcagaag acggcatacg agattnngat gtgtctcgtg ggctcggaga tgtgtataag      60
agacag                                                                66

<210> SEQ ID NO 501
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 501
caagcagaag acggcatacg agatgnngat gtgtctcgtg ggctcggaga tgtgtataag      60
agacag                                                                66

<210> SEQ ID NO 502
<211> LENGTH: 66
<212> TYPE: DNA
<213> ORGANISM: Artificial
<220> FEATURE:
<223> OTHER INFORMATION: synthetic

<400> SEQUENCE: 502
caagcagaag acggcatacg agatcgagat gtgtctcgtg ggctcggaga tgtgtataag      60
agacag                                                                66
```

-continued

```
<210> SEQ ID NO 503
<211> LENGTH: 66
<212> TYPE: DNA
<213> ORGANISM: Artificial
<220> FEATURE:
<223> OTHER INFORMATION: synthetic

<400> SEQUENCE: 503
caagcagaag acggcatacg agatcaagat gtgtctcgtg ggctcggaga tgtgtataag    60
agacag                                                              66

<210> SEQ ID NO 504
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 504
caagcagaag acggcatacg agattgncat gtgtctcgtg ggctcggaga tgtgtataag    60
agacag                                                              66

<210> SEQ ID NO 505
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 505
caagcagaag acggcatacg agatggncat gtgtctcgtg ggctcggaga tgtgtataag    60
agacag                                                              66

<210> SEQ ID NO 506
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 506
caagcagaag acggcatacg agattcncat gtgtctcgtg ggctcggaga tgtgtataag    60
agacag                                                              66

<210> SEQ ID NO 507
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t
```

<400> SEQUENCE: 507
caagcagaag acggcatacg agatgcncat gtgtctcgtg ggctcggaga tgtgtataag    60
agacag                                                              66

<210> SEQ ID NO 508
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 508
caagcagaag acggcatacg agatanncat gtgtctcgtg ggctcggaga tgtgtataag    60
agacag                                                              66

<210> SEQ ID NO 509
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 509
caagcagaag acggcatacg agattancat gtgtctcgtg ggctcggaga tgtgtataag    60
agacag                                                              66

<210> SEQ ID NO 510
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 510
caagcagaag acggcatacg agatgancat gtgtctcgtg ggctcggaga tgtgtataag    60
agacag                                                              66

<210> SEQ ID NO 511
<211> LENGTH: 66
<212> TYPE: DNA
<213> ORGANISM: Artificial
<220> FEATURE:
<223> OTHER INFORMATION: synthetic

<400> SEQUENCE: 511
caagcagaag acggcatacg agatcgtaat gtgtctcgtg ggctcggaga tgtgtataag    60
agacag                                                              66

<210> SEQ ID NO 512
<211> LENGTH: 66
<212> TYPE: DNA

<213> ORGANISM: Artificial
<220> FEATURE:
<223> OTHER INFORMATION: synthetic

<400> SEQUENCE: 512
caagcagaag acggcatacg agatcataat gtgtctcgtg ggctcggaga tgtgtataag     60
agacag                                                               66

<210> SEQ ID NO 513
<211> LENGTH: 66
<212> TYPE: DNA
<213> ORGANISM: Artificial
<220> FEATURE:
<223> OTHER INFORMATION: synthetic

<400> SEQUENCE: 513
caagcagaag acggcatacg agatcgcaat gtgtctcgtg ggctcggaga tgtgtataag     60
agacag                                                               66

<210> SEQ ID NO 514
<211> LENGTH: 66
<212> TYPE: DNA
<213> ORGANISM: Artificial
<220> FEATURE:
<223> OTHER INFORMATION: synthetic

<400> SEQUENCE: 514
caagcagaag acggcatacg agatcacaat gtgtctcgtg ggctcggaga tgtgtataag     60
agacag                                                               66

<210> SEQ ID NO 515
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 515
caagcagaag acggcatacg agatccnaat gtgtctcgtg ggctcggaga tgtgtataag     60
agacag                                                               66

<210> SEQ ID NO 516
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 516
caagcagaag acggcatacg agattnnaat gtgtctcgtg ggctcggaga tgtgtataag     60
agacag                                                               66

<210> SEQ ID NO 517
<211> LENGTH: 66
<212> TYPE: DNA
<213> ORGANISM: Artificial

```
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 517
caagcagaag acggcatacg agatgnnaat gtgtctcgtg ggctcggaga tgtgtataag      60
agacag                                                                66

<210> SEQ ID NO 518
<211> LENGTH: 66
<212> TYPE: DNA
<213> ORGANISM: Artificial
<220> FEATURE:
<223> OTHER INFORMATION: synthetic

<400> SEQUENCE: 518
caagcagaag acggcatacg agatcgaaat gtgtctcgtg ggctcggaga tgtgtataag      60
agacag                                                                66

<210> SEQ ID NO 519
<211> LENGTH: 66
<212> TYPE: DNA
<213> ORGANISM: Artificial
<220> FEATURE:
<223> OTHER INFORMATION: synthetic

<400> SEQUENCE: 519
caagcagaag acggcatacg agatcaaaat gtgtctcgtg ggctcggaga tgtgtataag      60
agacag                                                                66

<210> SEQ ID NO 520
<211> LENGTH: 66
<212> TYPE: DNA
<213> ORGANISM: Artificial
<220> FEATURE:
<223> OTHER INFORMATION: synthetic

<400> SEQUENCE: 520
caagcagaag acggcatacg agatcttttg gtgtctcgtg ggctcggaga tgtgtataag      60
agacag                                                                66

<210> SEQ ID NO 521
<211> LENGTH: 66
<212> TYPE: DNA
<213> ORGANISM: Artificial
<220> FEATURE:
<223> OTHER INFORMATION: synthetic

<400> SEQUENCE: 521
caagcagaag acggcatacg agatctcttg gtgtctcgtg ggctcggaga tgtgtataag      60
agacag                                                                66

<210> SEQ ID NO 522
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
```

-continued

<223> OTHER INFORMATION: n is a, c, g, or t

<400> SEQUENCE: 522
caagcagaag acggcatacg agatcgnttg gtgtctcgtg ggctcggaga tgtgtataag    60
agacag    66

<210> SEQ ID NO 523
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 523
caagcagaag acggcatacg agatccnttg gtgtctcgtg ggctcggaga tgtgtataag    60
agacag    66

<210> SEQ ID NO 524
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 524
caagcagaag acggcatacg agattnnttg gtgtctcgtg ggctcggaga tgtgtataag    60
agacag    66

<210> SEQ ID NO 525
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 525
caagcagaag acggcatacg agatgnnttg gtgtctcgtg ggctcggaga tgtgtataag    60
agacag    66

<210> SEQ ID NO 526
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 526
caagcagaag acggcatacg agatcanttg gtgtctcgtg ggctcggaga tgtgtataag    60
agacag    66

<210> SEQ ID NO 527
<211> LENGTH: 66
<212> TYPE: DNA
<213> ORGANISM: Artificial
<220> FEATURE:
<223> OTHER INFORMATION: synthetic

<400> SEQUENCE: 527
caagcagaag acggcatacg agatctattg gtgtctcgtg ggctcggaga tgtgtataag    60
agacag    66

<210> SEQ ID NO 528
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 528
caagcagaag acggcatacg agattgngtg gtgtctcgtg ggctcggaga tgtgtataag    60
agacag    66

<210> SEQ ID NO 529
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 529
caagcagaag acggcatacg agatggngtg gtgtctcgtg ggctcggaga tgtgtataag    60
agacag    66

<210> SEQ ID NO 530
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 530
caagcagaag acggcatacg agattcngtg gtgtctcgtg ggctcggaga tgtgtataag    60
agacag    66

<210> SEQ ID NO 531
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)

<223> OTHER INFORMATION: n is a, c, g, or t

<400> SEQUENCE: 531
caagcagaag acggcatacg agatgcngtg gtgtctcgtg ggctcggaga tgtgtataag    60
agacag    66

<210> SEQ ID NO 532
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 532
caagcagaag acggcatacg agatanngtg gtgtctcgtg ggctcggaga tgtgtataag    60
agacag    66

<210> SEQ ID NO 533
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 533
caagcagaag acggcatacg agattangtg gtgtctcgtg ggctcggaga tgtgtataag    60
agacag    66

<210> SEQ ID NO 534
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 534
caagcagaag acggcatacg agatgangtg gtgtctcgtg ggctcggaga tgtgtataag    60
agacag    66

<210> SEQ ID NO 535
<211> LENGTH: 66
<212> TYPE: DNA
<213> ORGANISM: Artificial
<220> FEATURE:
<223> OTHER INFORMATION: synthetic

<400> SEQUENCE: 535
caagcagaag acggcatacg agatattctg gtgtctcgtg ggctcggaga tgtgtataag    60
agacag    66

<210> SEQ ID NO 536
<211> LENGTH: 66

```
<212> TYPE: DNA
<213> ORGANISM: Artificial
<220> FEATURE:
<223> OTHER INFORMATION: synthetic

<400> SEQUENCE: 536
caagcagaag acggcatacg agatatcctg gtgtctcgtg ggctcggaga tgtgtataag    60
agacag                                                               66

<210> SEQ ID NO 537
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 537
caagcagaag acggcatacg agatagnctg gtgtctcgtg ggctcggaga tgtgtataag    60
agacag                                                               66

<210> SEQ ID NO 538
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 538
caagcagaag acggcatacg agatacnctg gtgtctcgtg ggctcggaga tgtgtataag    60
agacag                                                               66

<210> SEQ ID NO 539
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 539
caagcagaag acggcatacg agataanctg gtgtctcgtg ggctcggaga tgtgtataag    60
agacag                                                               66

<210> SEQ ID NO 540
<211> LENGTH: 66
<212> TYPE: DNA
<213> ORGANISM: Artificial
<220> FEATURE:
<223> OTHER INFORMATION: synthetic

<400> SEQUENCE: 540
caagcagaag acggcatacg agatatactg gtgtctcgtg ggctcggaga tgtgtataag    60
agacag                                                               66
```

<210> SEQ ID NO 541
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 541
caagcagaag acggcatacg agattgnatg gtgtctcgtg ggctcggaga tgtgtataag    60
agacag    66

<210> SEQ ID NO 542
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 542
caagcagaag acggcatacg agatggnatg gtgtctcgtg ggctcggaga tgtgtataag    60
agacag    66

<210> SEQ ID NO 543
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 543
caagcagaag acggcatacg agattcnatg gtgtctcgtg ggctcggaga tgtgtataag    60
agacag    66

<210> SEQ ID NO 544
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 544
caagcagaag acggcatacg agatgcnatg gtgtctcgtg ggctcggaga tgtgtataag    60
agacag    66

<210> SEQ ID NO 545
<211> LENGTH: 66
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (26)..(27)
<223> OTHER INFORMATION: n is a, c, g, or t

<400> SEQUENCE: 545
caagcagaag acggcatacg agatannatg gtgtctcgtg ggctcggaga tgtgtataag    60
agacag                                                              66

<210> SEQ ID NO 546
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 546
caagcagaag acggcatacg agattanatg gtgtctcgtg ggctcggaga tgtgtataag    60
agacag                                                              66

<210> SEQ ID NO 547
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 547
caagcagaag acggcatacg agatganatg gtgtctcgtg ggctcggaga tgtgtataag    60
agacag                                                              66

<210> SEQ ID NO 548
<211> LENGTH: 66
<212> TYPE: DNA
<213> ORGANISM: Artificial
<220> FEATURE:
<223> OTHER INFORMATION: synthetic

<400> SEQUENCE: 548
caagcagaag acggcatacg agattgttgg gtgtctcgtg ggctcggaga tgtgtataag    60
agacag                                                              66

<210> SEQ ID NO 549
<211> LENGTH: 66
<212> TYPE: DNA
<213> ORGANISM: Artificial
<220> FEATURE:
<223> OTHER INFORMATION: synthetic

<400> SEQUENCE: 549
caagcagaag acggcatacg agatggttgg gtgtctcgtg ggctcggaga tgtgtataag    60
agacag                                                              66

<210> SEQ ID NO 550
<211> LENGTH: 66
<212> TYPE: DNA
```

```
<213> ORGANISM: Artificial
<220> FEATURE:
<223> OTHER INFORMATION: synthetic

<400> SEQUENCE: 550
caagcagaag acggcatacg agattattgg gtgtctcgtg ggctcggaga tgtgtataag    60
agacag                                                               66

<210> SEQ ID NO 551
<211> LENGTH: 66
<212> TYPE: DNA
<213> ORGANISM: Artificial
<220> FEATURE:
<223> OTHER INFORMATION: synthetic

<400> SEQUENCE: 551
caagcagaag acggcatacg agatgattgg gtgtctcgtg ggctcggaga tgtgtataag    60
agacag                                                               66

<210> SEQ ID NO 552
<211> LENGTH: 66
<212> TYPE: DNA
<213> ORGANISM: Artificial
<220> FEATURE:
<223> OTHER INFORMATION: synthetic

<400> SEQUENCE: 552
caagcagaag acggcatacg agattgctgg gtgtctcgtg ggctcggaga tgtgtataag    60
agacag                                                               66

<210> SEQ ID NO 553
<211> LENGTH: 66
<212> TYPE: DNA
<213> ORGANISM: Artificial
<220> FEATURE:
<223> OTHER INFORMATION: synthetic

<400> SEQUENCE: 553
caagcagaag acggcatacg agatggctgg gtgtctcgtg ggctcggaga tgtgtataag    60
agacag                                                               66

<210> SEQ ID NO 554
<211> LENGTH: 66
<212> TYPE: DNA
<213> ORGANISM: Artificial
<220> FEATURE:
<223> OTHER INFORMATION: synthetic

<400> SEQUENCE: 554
caagcagaag acggcatacg agattactgg gtgtctcgtg ggctcggaga tgtgtataag    60
agacag                                                               66

<210> SEQ ID NO 555
<211> LENGTH: 66
<212> TYPE: DNA
<213> ORGANISM: Artificial
<220> FEATURE:
<223> OTHER INFORMATION: synthetic

<400> SEQUENCE: 555
caagcagaag acggcatacg agatgactgg gtgtctcgtg ggctcggaga tgtgtataag    60
agacag                                                               66
```

<210> SEQ ID NO 556
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 556
caagcagaag acggcatacg agattcntgg gtgtctcgtg ggctcggaga tgtgtataag    60
agacag                                                              66

<210> SEQ ID NO 557
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 557
caagcagaag acggcatacg agatgcntgg gtgtctcgtg ggctcggaga tgtgtataag    60
agacag                                                              66

<210> SEQ ID NO 558
<211> LENGTH: 66
<212> TYPE: DNA
<213> ORGANISM: Artificial
<220> FEATURE:
<223> OTHER INFORMATION: synthetic

<400> SEQUENCE: 558
caagcagaag acggcatacg agattgatgg gtgtctcgtg ggctcggaga tgtgtataag    60
agacag                                                              66

<210> SEQ ID NO 559
<211> LENGTH: 66
<212> TYPE: DNA
<213> ORGANISM: Artificial
<220> FEATURE:
<223> OTHER INFORMATION: synthetic

<400> SEQUENCE: 559
caagcagaag acggcatacg agatggatgg gtgtctcgtg ggctcggaga tgtgtataag    60
agacag                                                              66

<210> SEQ ID NO 560
<211> LENGTH: 66
<212> TYPE: DNA
<213> ORGANISM: Artificial
<220> FEATURE:
<223> OTHER INFORMATION: synthetic

<400> SEQUENCE: 560
caagcagaag acggcatacg agattaatgg gtgtctcgtg ggctcggaga tgtgtataag    60
agacag                                                              66

<210> SEQ ID NO 561
<211> LENGTH: 66
<212> TYPE: DNA
<213> ORGANISM: Artificial
<220> FEATURE:
<223> OTHER INFORMATION: synthetic

<400> SEQUENCE: 561
caagcagaag acggcatacg agatgaatgg gtgtctcgtg ggctcggaga tgtgtataag    60
agacag                                                              66

<210> SEQ ID NO 562
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 562
caagcagaag acggcatacg agattcntcg gtgtctcgtg ggctcggaga tgtgtataag    60
agacag                                                              66

<210> SEQ ID NO 563
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 563
caagcagaag acggcatacg agatgcntcg gtgtctcgtg ggctcggaga tgtgtataag    60
agacag                                                              66

<210> SEQ ID NO 564
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 564
caagcagaag acggcatacg agattnntag gtgtctcgtg ggctcggaga tgtgtataag    60
agacag                                                              66

<210> SEQ ID NO 565
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 565
caagcagaag acggcatacg agatgnntag gtgtctcgtg ggctcggaga tgtgtataag    60
agacag                                                                66

<210> SEQ ID NO 566
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 566
caagcagaag acggcatacg agatagngag gtgtctcgtg ggctcggaga tgtgtataag    60
agacag                                                                66

<210> SEQ ID NO 567
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 567
caagcagaag acggcatacg agatacngag gtgtctcgtg ggctcggaga tgtgtataag    60
agacag                                                                66

<210> SEQ ID NO 568
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 568
caagcagaag acggcatacg agataangag gtgtctcgtg ggctcggaga tgtgtataag    60
agacag                                                                66

<210> SEQ ID NO 569
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 569
caagcagaag acggcatacg agatagnaag gtgtctcgtg ggctcggaga tgtgtataag    60
agacag                                                                66

<210> SEQ ID NO 570
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 570
caagcagaag acggcatacg agatacnaag gtgtctcgtg ggctcggaga tgtgtataag    60
agacag                                                               66

<210> SEQ ID NO 571
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 571
caagcagaag acggcatacg agataanaag gtgtctcgtg ggctcggaga tgtgtataag    60
agacag                                                               66

<210> SEQ ID NO 572
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 572
caagcagaag acggcatacg agatcgnttc gtgtctcgtg ggctcggaga tgtgtataag    60
agacag                                                               66

<210> SEQ ID NO 573
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 573
caagcagaag acggcatacg agatccnttc gtgtctcgtg ggctcggaga tgtgtataag    60
agacag                                                               66

<210> SEQ ID NO 574
<211> LENGTH: 66
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (26)..(27)
<223> OTHER INFORMATION: n is a, c, g, or t

<400> SEQUENCE: 574
caagcagaag acggcatacg agattnnttc gtgtctcgtg ggctcggaga tgtgtataag    60
agacag                                                              66

<210> SEQ ID NO 575
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 575
caagcagaag acggcatacg agatgnnttc gtgtctcgtg ggctcggaga tgtgtataag    60
agacag                                                              66

<210> SEQ ID NO 576
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 576
caagcagaag acggcatacg agatcanttc gtgtctcgtg ggctcggaga tgtgtataag    60
agacag                                                              66

<210> SEQ ID NO 577
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 577
caagcagaag acggcatacg agattgngtc gtgtctcgtg ggctcggaga tgtgtataag    60
agacag                                                              66

<210> SEQ ID NO 578
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 578
```

```
caagcagaag acggcatacg agatggngtc gtgtctcgtg ggctcggaga tgtgtataag    60
agacag                                                              66

<210> SEQ ID NO 579
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 579
caagcagaag acggcatacg agattcngtc gtgtctcgtg ggctcggaga tgtgtataag    60
agacag                                                              66

<210> SEQ ID NO 580
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 580
caagcagaag acggcatacg agatgcngtc gtgtctcgtg ggctcggaga tgtgtataag    60
agacag                                                              66

<210> SEQ ID NO 581
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 581
caagcagaag acggcatacg agatanngtc gtgtctcgtg ggctcggaga tgtgtataag    60
agacag                                                              66

<210> SEQ ID NO 582
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 582
caagcagaag acggcatacg agattangtc gtgtctcgtg ggctcggaga tgtgtataag    60
agacag                                                              66

<210> SEQ ID NO 583
<211> LENGTH: 66
```

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 583
caagcagaag acggcatacg agatgangtc gtgtctcgtg ggctcggaga tgtgtataag    60
agacag                                                              66

<210> SEQ ID NO 584
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 584
caagcagaag acggcatacg agatagnctc gtgtctcgtg ggctcggaga tgtgtataag    60
agacag                                                              66

<210> SEQ ID NO 585
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 585
caagcagaag acggcatacg agatacnctc gtgtctcgtg ggctcggaga tgtgtataag    60
agacag                                                              66

<210> SEQ ID NO 586
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 586
caagcagaag acggcatacg agataanctc gtgtctcgtg ggctcggaga tgtgtataag    60
agacag                                                              66

<210> SEQ ID NO 587
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
```

<223> OTHER INFORMATION: n is a, c, g, or t

<400> SEQUENCE: 587
caagcagaag acggcatacg agattgnatc gtgtctcgtg ggctcggaga tgtgtataag    60
agacag    66

<210> SEQ ID NO 588
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 588
caagcagaag acggcatacg agatggnatc gtgtctcgtg ggctcggaga tgtgtataag    60
agacag    66

<210> SEQ ID NO 589
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 589
caagcagaag acggcatacg agattcnatc gtgtctcgtg ggctcggaga tgtgtataag    60
agacag    66

<210> SEQ ID NO 590
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 590
caagcagaag acggcatacg agatgcnatc gtgtctcgtg ggctcggaga tgtgtataag    60
agacag    66

<210> SEQ ID NO 591
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 591
caagcagaag acggcatacg agatannatc gtgtctcgtg ggctcggaga tgtgtataag    60
agacag    66

<210> SEQ ID NO 592
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 592
caagcagaag acggcatacg agattanatc gtgtctcgtg ggctcggaga tgtgtataag    60
agacag                                                               66

<210> SEQ ID NO 593
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 593
caagcagaag acggcatacg agatganatc gtgtctcgtg ggctcggaga tgtgtataag    60
agacag                                                               66

<210> SEQ ID NO 594
<211> LENGTH: 66
<212> TYPE: DNA
<213> ORGANISM: Artificial
<220> FEATURE:
<223> OTHER INFORMATION: synthetic

<400> SEQUENCE: 594
caagcagaag acggcatacg agattcttgc gtgtctcgtg ggctcggaga tgtgtataag    60
agacag                                                               66

<210> SEQ ID NO 595
<211> LENGTH: 66
<212> TYPE: DNA
<213> ORGANISM: Artificial
<220> FEATURE:
<223> OTHER INFORMATION: synthetic

<400> SEQUENCE: 595
caagcagaag acggcatacg agatgcttgc gtgtctcgtg ggctcggaga tgtgtataag    60
agacag                                                               66

<210> SEQ ID NO 596
<211> LENGTH: 66
<212> TYPE: DNA
<213> ORGANISM: Artificial
<220> FEATURE:
<223> OTHER INFORMATION: synthetic

<400> SEQUENCE: 596
caagcagaag acggcatacg agattcctgc gtgtctcgtg ggctcggaga tgtgtataag    60
agacag                                                               66

<210> SEQ ID NO 597
<211> LENGTH: 66
<212> TYPE: DNA
<213> ORGANISM: Artificial
<220> FEATURE:
<223> OTHER INFORMATION: synthetic

<400> SEQUENCE: 597
caagcagaag acggcatacg agatgcctgc gtgtctcgtg ggctcggaga tgtgtataag      60
agacag                                                                66

<210> SEQ ID NO 598
<211> LENGTH: 66
<212> TYPE: DNA
<213> ORGANISM: Artificial
<220> FEATURE:
<223> OTHER INFORMATION: synthetic

<400> SEQUENCE: 598
caagcagaag acggcatacg agattcatgc gtgtctcgtg ggctcggaga tgtgtataag      60
agacag                                                                66

<210> SEQ ID NO 599
<211> LENGTH: 66
<212> TYPE: DNA
<213> ORGANISM: Artificial
<220> FEATURE:
<223> OTHER INFORMATION: synthetic

<400> SEQUENCE: 599
caagcagaag acggcatacg agatgcatgc gtgtctcgtg ggctcggaga tgtgtataag      60
agacag                                                                66

<210> SEQ ID NO 600
<211> LENGTH: 66
<212> TYPE: DNA
<213> ORGANISM: Artificial
<220> FEATURE:
<223> OTHER INFORMATION: synthetic

<400> SEQUENCE: 600
caagcagaag acggcatacg agattcttcc gtgtctcgtg ggctcggaga tgtgtataag      60
agacag                                                                66

<210> SEQ ID NO 601
<211> LENGTH: 66
<212> TYPE: DNA
<213> ORGANISM: Artificial
<220> FEATURE:
<223> OTHER INFORMATION: synthetic

<400> SEQUENCE: 601
caagcagaag acggcatacg agatgcttcc gtgtctcgtg ggctcggaga tgtgtataag      60
agacag                                                                66

<210> SEQ ID NO 602
<211> LENGTH: 66
<212> TYPE: DNA
<213> ORGANISM: Artificial
<220> FEATURE:
<223> OTHER INFORMATION: synthetic

<400> SEQUENCE: 602

```
caagcagaag acggcatacg agattcctcc gtgtctcgtg ggctcggaga tgtgtataag    60
agacag                                                               66

<210> SEQ ID NO 603
<211> LENGTH: 66
<212> TYPE: DNA
<213> ORGANISM: Artificial
<220> FEATURE:
<223> OTHER INFORMATION: synthetic

<400> SEQUENCE: 603
caagcagaag acggcatacg agatgcctcc gtgtctcgtg ggctcggaga tgtgtataag    60
agacag                                                               66

<210> SEQ ID NO 604
<211> LENGTH: 66
<212> TYPE: DNA
<213> ORGANISM: Artificial
<220> FEATURE:
<223> OTHER INFORMATION: synthetic

<400> SEQUENCE: 604
caagcagaag acggcatacg agattcatcc gtgtctcgtg ggctcggaga tgtgtataag    60
agacag                                                               66

<210> SEQ ID NO 605
<211> LENGTH: 66
<212> TYPE: DNA
<213> ORGANISM: Artificial
<220> FEATURE:
<223> OTHER INFORMATION: synthetic

<400> SEQUENCE: 605
caagcagaag acggcatacg agatgcatcc gtgtctcgtg ggctcggaga tgtgtataag    60
agacag                                                               66

<210> SEQ ID NO 606
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 606
caagcagaag acggcatacg agattnntac gtgtctcgtg ggctcggaga tgtgtataag    60
agacag                                                               66

<210> SEQ ID NO 607
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 607
```
caagcagaag acggcatacg agatgnntac gtgtctcgtg ggctcggaga tgtgtataag    60
agacag    66

<210> SEQ ID NO 608
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 608
caagcagaag acggcatacg agatagngac gtgtctcgtg ggctcggaga tgtgtataag    60
agacag    66

<210> SEQ ID NO 609
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 609
caagcagaag acggcatacg agatacngac gtgtctcgtg ggctcggaga tgtgtataag    60
agacag    66

<210> SEQ ID NO 610
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 610
caagcagaag acggcatacg agataangac gtgtctcgtg ggctcggaga tgtgtataag    60
agacag    66

<210> SEQ ID NO 611
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 611
caagcagaag acggcatacg agatagnaac gtgtctcgtg ggctcggaga tgtgtataag    60
agacag    66

<210> SEQ ID NO 612
<211> LENGTH: 66

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 612
caagcagaag acggcatacg agatacnaac gtgtctcgtg ggctcggaga tgtgtataag    60
agacag                                                               66

<210> SEQ ID NO 613
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 613
caagcagaag acggcatacg agataanaac gtgtctcgtg ggctcggaga tgtgtataag    60
agacag                                                               66

<210> SEQ ID NO 614
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 614
caagcagaag acggcatacg agatanntnn gtgtctcgtg ggctcggaga tgtgtataag    60
agacag                                                               66

<210> SEQ ID NO 615
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 615
caagcagaag acggcatacg agatcnntta gtgtctcgtg ggctcggaga tgtgtataag    60
agacag                                                               66

<210> SEQ ID NO 616
<211> LENGTH: 66
<212> TYPE: DNA
<213> ORGANISM: Artificial
<220> FEATURE:
```

<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 616
caagcagaag acggcatacg agatcgngta gtgtctcgtg ggctcggaga tgtgtataag    60
agacag    66

<210> SEQ ID NO 617
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 617
caagcagaag acggcatacg agatccngta gtgtctcgtg ggctcggaga tgtgtataag    60
agacag    66

<210> SEQ ID NO 618
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 618
caagcagaag acggcatacg agattnngta gtgtctcgtg ggctcggaga tgtgtataag    60
agacag    66

<210> SEQ ID NO 619
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 619
caagcagaag acggcatacg agatgnngta gtgtctcgtg ggctcggaga tgtgtataag    60
agacag    66

<210> SEQ ID NO 620
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 620
caagcagaag acggcatacg agatanngta gtgtctcgtg ggctcggaga tgtgtataag    60
agacag    66

<210> SEQ ID NO 621
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 621
caagcagaag acggcatacg agatcangta gtgtctcgtg ggctcggaga tgtgtataag    60
agacag    66

<210> SEQ ID NO 622
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 622
caagcagaag acggcatacg agattgncta gtgtctcgtg ggctcggaga tgtgtataag    60
agacag    66

<210> SEQ ID NO 623
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 623
caagcagaag acggcatacg agatggncta gtgtctcgtg ggctcggaga tgtgtataag    60
agacag    66

<210> SEQ ID NO 624
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 624
caagcagaag acggcatacg agattcncta gtgtctcgtg ggctcggaga tgtgtataag    60
agacag    66

<210> SEQ ID NO 625

<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 625
caagcagaag acggcatacg agatgcncta gtgtctcgtg ggctcggaga tgtgtataag      60
agacag                                                                66

<210> SEQ ID NO 626
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 626
caagcagaag acggcatacg agatanncta gtgtctcgtg ggctcggaga tgtgtataag      60
agacag                                                                66

<210> SEQ ID NO 627
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 627
caagcagaag acggcatacg agattancta gtgtctcgtg ggctcggaga tgtgtataag      60
agacag                                                                66

<210> SEQ ID NO 628
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 628
caagcagaag acggcatacg agatgancta gtgtctcgtg ggctcggaga tgtgtataag      60
agacag                                                                66

<210> SEQ ID NO 629
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature

```
<222> LOCATION: (27)..(27)
<223> OTHER INFORMATION: n is a, c, g, or t

<400> SEQUENCE: 629
caagcagaag acggcatacg agatcgnata gtgtctcgtg ggctcggaga tgtgtataag    60
agacag                                                              66

<210> SEQ ID NO 630
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 630
caagcagaag acggcatacg agatccnata gtgtctcgtg ggctcggaga tgtgtataag    60
agacag                                                              66

<210> SEQ ID NO 631
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 631
caagcagaag acggcatacg agattnnata gtgtctcgtg ggctcggaga tgtgtataag    60
agacag                                                              66

<210> SEQ ID NO 632
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 632
caagcagaag acggcatacg agatgnnata gtgtctcgtg ggctcggaga tgtgtataag    60
agacag                                                              66

<210> SEQ ID NO 633
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 633
caagcagaag acggcatacg agatannata gtgtctcgtg ggctcggaga tgtgtataag    60
```

```
agacag                                                              66

<210> SEQ ID NO 634
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 634
caagcagaag acggcatacg agatcanata gtgtctcgtg ggctcggaga tgtgtataag    60
agacag                                                              66

<210> SEQ ID NO 635
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 635
caagcagaag acggcatacg agatagngga gtgtctcgtg ggctcggaga tgtgtataag    60
agacag                                                              66

<210> SEQ ID NO 636
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 636
caagcagaag acggcatacg agatacngga gtgtctcgtg ggctcggaga tgtgtataag    60
agacag                                                              66

<210> SEQ ID NO 637
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 637
caagcagaag acggcatacg agataangga gtgtctcgtg ggctcggaga tgtgtataag    60
agacag                                                              66

<210> SEQ ID NO 638
<211> LENGTH: 66
<212> TYPE: DNA
<213> ORGANISM: Artificial
```

```
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 638
caagcagaag acggcatacg agatagnaga gtgtctcgtg ggctcggaga tgtgtataag    60
agacag                                                               66

<210> SEQ ID NO 639
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 639
caagcagaag acggcatacg agatacnaga gtgtctcgtg ggctcggaga tgtgtataag    60
agacag                                                               66

<210> SEQ ID NO 640
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 640
caagcagaag acggcatacg agataanaga gtgtctcgtg ggctcggaga tgtgtataag    60
agacag                                                               66

<210> SEQ ID NO 641
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 641
caagcagaag acggcatacg agatagngca gtgtctcgtg ggctcggaga tgtgtataag    60
agacag                                                               66

<210> SEQ ID NO 642
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t
```

```
<400> SEQUENCE: 642
caagcagaag acggcatacg agatacngca gtgtctcgtg ggctcggaga tgtgtataag    60
agacag                                                              66

<210> SEQ ID NO 643
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 643
caagcagaag acggcatacg agataangca gtgtctcgtg ggctcggaga tgtgtataag    60
agacag                                                              66

<210> SEQ ID NO 644
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 644
caagcagaag acggcatacg agatagnaca gtgtctcgtg ggctcggaga tgtgtataag    60
agacag                                                              66

<210> SEQ ID NO 645
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 645
caagcagaag acggcatacg agatacnaca gtgtctcgtg ggctcggaga tgtgtataag    60
agacag                                                              66

<210> SEQ ID NO 646
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 646
caagcagaag acggcatacg agataanaca gtgtctcgtg ggctcggaga tgtgtataag    60
agacag                                                              66
```

<210> SEQ ID NO 647
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 647
caagcagaag acggcatacg agattnntna gtgtctcgtg ggctcggaga tgtgtataag    60
agacag                                                              66

<210> SEQ ID NO 648
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 648
caagcagaag acggcatacg agatgnntna gtgtctcgtg ggctcggaga tgtgtataag    60
agacag                                                              66

<210> SEQ ID NO 649
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 649
caagcagaag acggcatacg agatcgntaa gtgtctcgtg ggctcggaga tgtgtataag    60
agacag                                                              66

<210> SEQ ID NO 650
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 650
caagcagaag acggcatacg agatccntaa gtgtctcgtg ggctcggaga tgtgtataag    60
agacag                                                              66

<210> SEQ ID NO 651
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 651
caagcagaag acggcatacg agatcantaa gtgtctcgtg ggctcggaga tgtgtataag    60
agacag                                                              66

<210> SEQ ID NO 652
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 652
caagcagaag acggcatacg agattgngaa gtgtctcgtg ggctcggaga tgtgtataag    60
agacag                                                              66

<210> SEQ ID NO 653
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 653
caagcagaag acggcatacg agatggngaa gtgtctcgtg ggctcggaga tgtgtataag    60
agacag                                                              66

<210> SEQ ID NO 654
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 654
caagcagaag acggcatacg agattcngaa gtgtctcgtg ggctcggaga tgtgtataag    60
agacag                                                              66

<210> SEQ ID NO 655
<211> LENGTH: 66
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (27)..(27)
<223> OTHER INFORMATION: n is a, c, g, or t

<400> SEQUENCE: 655
caagcagaag acggcatacg agatgcngaa gtgtctcgtg ggctcggaga tgtgtataag    60
agacag                                                               66

<210> SEQ ID NO 656
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 656
caagcagaag acggcatacg agatanngaa gtgtctcgtg ggctcggaga tgtgtataag    60
agacag                                                               66

<210> SEQ ID NO 657
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 657
caagcagaag acggcatacg agattangaa gtgtctcgtg ggctcggaga tgtgtataag    60
agacag                                                               66

<210> SEQ ID NO 658
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 658
caagcagaag acggcatacg agatgangaa gtgtctcgtg ggctcggaga tgtgtataag    60
agacag                                                               66

<210> SEQ ID NO 659
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 659
```

```
caagcagaag acggcatacg agatagncaa gtgtctcgtg ggctcggaga tgtgtataag    60
agacag                                                               66

<210> SEQ ID NO 660
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 660
caagcagaag acggcatacg agatacncaa gtgtctcgtg ggctcggaga tgtgtataag    60
agacag                                                               66

<210> SEQ ID NO 661
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 661
caagcagaag acggcatacg agataancaa gtgtctcgtg ggctcggaga tgtgtataag    60
agacag                                                               66

<210> SEQ ID NO 662
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 662
caagcagaag acggcatacg agattgnaaa gtgtctcgtg ggctcggaga tgtgtataag    60
agacag                                                               66

<210> SEQ ID NO 663
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 663
caagcagaag acggcatacg agatggnaaa gtgtctcgtg ggctcggaga tgtgtataag    60
agacag                                                               66

<210> SEQ ID NO 664
<211> LENGTH: 66
```

<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 664
caagcagaag acggcatacg agattcnaaa gtgtctcgtg ggctcggaga tgtgtataag    60
agacag    66

<210> SEQ ID NO 665
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 665
caagcagaag acggcatacg agatgcnaaa gtgtctcgtg ggctcggaga tgtgtataag    60
agacag    66

<210> SEQ ID NO 666
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 666
caagcagaag acggcatacg agatannaaa gtgtctcgtg ggctcggaga tgtgtataag    60
agacag    66

<210> SEQ ID NO 667
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 667
caagcagaag acggcatacg agattanaaa gtgtctcgtg ggctcggaga tgtgtataag    60
agacag    66

<210> SEQ ID NO 668
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)

<223> OTHER INFORMATION: n is a, c, g, or t

<400> SEQUENCE: 668
caagcagaag acggcatacg agatganaaa gtgtctcgtg ggctcggaga tgtgtataag    60
agacag    66

<210> SEQ ID NO 669
<211> LENGTH: 66
<212> TYPE: DNA
<213> ORGANISM: Artificial
<220> FEATURE:
<223> OTHER INFORMATION: synthetic

<400> SEQUENCE: 669
caagcagaag acggcatacg agatctttt ctgtctcgtg ggctcggaga tgtgtataag    60
agacag    66

<210> SEQ ID NO 670
<211> LENGTH: 66
<212> TYPE: DNA
<213> ORGANISM: Artificial
<220> FEATURE:
<223> OTHER INFORMATION: synthetic

<400> SEQUENCE: 670
caagcagaag acggcatacg agatctcttt ctgtctcgtg ggctcggaga tgtgtataag    60
agacag    66

<210> SEQ ID NO 671
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 671
caagcagaag acggcatacg agatcgnttt ctgtctcgtg ggctcggaga tgtgtataag    60
agacag    66

<210> SEQ ID NO 672
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 672
caagcagaag acggcatacg agatccnttt ctgtctcgtg ggctcggaga tgtgtataag    60
agacag    66

<210> SEQ ID NO 673
<211> LENGTH: 66
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (26)..(27)
<223> OTHER INFORMATION: n is a, c, g, or t

<400> SEQUENCE: 673
caagcagaag acggcatacg agattnnttt ctgtctcgtg ggctcggaga tgtgtataag    60
agacag                                                               66

<210> SEQ ID NO 674
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 674
caagcagaag acggcatacg agatgnnttt ctgtctcgtg ggctcggaga tgtgtataag    60
agacag                                                               66

<210> SEQ ID NO 675
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 675
caagcagaag acggcatacg agatcanttt ctgtctcgtg ggctcggaga tgtgtataag    60
agacag                                                               66

<210> SEQ ID NO 676
<211> LENGTH: 66
<212> TYPE: DNA
<213> ORGANISM: Artificial
<220> FEATURE:
<223> OTHER INFORMATION: synthetic

<400> SEQUENCE: 676
caagcagaag acggcatacg agatctattt ctgtctcgtg ggctcggaga tgtgtataag    60
agacag                                                               66

<210> SEQ ID NO 677
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 677
caagcagaag acggcatacg agattgngtt ctgtctcgtg ggctcggaga tgtgtataag    60
agacag                                                               66
```

<210> SEQ ID NO 678
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 678
caagcagaag acggcatacg agatggngtt ctgtctcgtg ggctcggaga tgtgtataag     60
agacag                                                                66

<210> SEQ ID NO 679
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 679
caagcagaag acggcatacg agattcngtt ctgtctcgtg ggctcggaga tgtgtataag     60
agacag                                                                66

<210> SEQ ID NO 680
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 680
caagcagaag acggcatacg agatgcngtt ctgtctcgtg ggctcggaga tgtgtataag     60
agacag                                                                66

<210> SEQ ID NO 681
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 681
caagcagaag acggcatacg agatanngtt ctgtctcgtg ggctcggaga tgtgtataag     60
agacag                                                                66

<210> SEQ ID NO 682
<211> LENGTH: 66
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (27)..(27)
<223> OTHER INFORMATION: n is a, c, g, or t

<400> SEQUENCE: 682
caagcagaag acggcatacg agattangtt ctgtctcgtg ggctcggaga tgtgtataag    60
agacag                                                              66

<210> SEQ ID NO 683
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 683
caagcagaag acggcatacg agatgangtt ctgtctcgtg ggctcggaga tgtgtataag    60
agacag                                                              66

<210> SEQ ID NO 684
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 684
caagcagaag acggcatacg agatagnctt ctgtctcgtg ggctcggaga tgtgtataag    60
agacag                                                              66

<210> SEQ ID NO 685
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 685
caagcagaag acggcatacg agatacnctt ctgtctcgtg ggctcggaga tgtgtataag    60
agacag                                                              66

<210> SEQ ID NO 686
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 686
```
caagcagaag acggcatacg agataanctt ctgtctcgtg ggctcggaga tgtgtataag    60
agacag                                                              66

<210> SEQ ID NO 687
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 687
caagcagaag acggcatacg agattgnatt ctgtctcgtg ggctcggaga tgtgtataag    60
agacag                                                              66

<210> SEQ ID NO 688
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 688
caagcagaag acggcatacg agatggnatt ctgtctcgtg ggctcggaga tgtgtataag    60
agacag                                                              66

<210> SEQ ID NO 689
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 689
caagcagaag acggcatacg agattcnatt ctgtctcgtg ggctcggaga tgtgtataag    60
agacag                                                              66

<210> SEQ ID NO 690
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 690
caagcagaag acggcatacg agatgcnatt ctgtctcgtg ggctcggaga tgtgtataag    60
agacag                                                              66

<210> SEQ ID NO 691
<211> LENGTH: 66

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 691
caagcagaag acggcatacg agatannatt ctgtctcgtg ggctcggaga tgtgtataag    60
agacag                                                              66

<210> SEQ ID NO 692
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 692
caagcagaag acggcatacg agattanatt ctgtctcgtg ggctcggaga tgtgtataag    60
agacag                                                              66

<210> SEQ ID NO 693
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 693
caagcagaag acggcatacg agatganatt ctgtctcgtg ggctcggaga tgtgtataag    60
agacag                                                              66

<210> SEQ ID NO 694
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 694
caagcagaag acggcatacg agattcntgt ctgtctcgtg ggctcggaga tgtgtataag    60
agacag                                                              66

<210> SEQ ID NO 695
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
```

<223> OTHER INFORMATION: n is a, c, g, or t

<400> SEQUENCE: 695
caagcagaag acggcatacg agatgcntgt ctgtctcgtg ggctcggaga tgtgtataag    60
agacag    66

<210> SEQ ID NO 696
<211> LENGTH: 66
<212> TYPE: DNA
<213> ORGANISM: Artificial
<220> FEATURE:
<223> OTHER INFORMATION: synthetic

<400> SEQUENCE: 696
caagcagaag acggcatacg agattcttct ctgtctcgtg ggctcggaga tgtgtataag    60
agacag    66

<210> SEQ ID NO 697
<211> LENGTH: 66
<212> TYPE: DNA
<213> ORGANISM: Artificial
<220> FEATURE:
<223> OTHER INFORMATION: synthetic

<400> SEQUENCE: 697
caagcagaag acggcatacg agatgcttct ctgtctcgtg ggctcggaga tgtgtataag    60
agacag    66

<210> SEQ ID NO 698
<211> LENGTH: 66
<212> TYPE: DNA
<213> ORGANISM: Artificial
<220> FEATURE:
<223> OTHER INFORMATION: synthetic

<400> SEQUENCE: 698
caagcagaag acggcatacg agattcctct ctgtctcgtg ggctcggaga tgtgtataag    60
agacag    66

<210> SEQ ID NO 699
<211> LENGTH: 66
<212> TYPE: DNA
<213> ORGANISM: Artificial
<220> FEATURE:
<223> OTHER INFORMATION: synthetic

<400> SEQUENCE: 699
caagcagaag acggcatacg agatgcctct ctgtctcgtg ggctcggaga tgtgtataag    60
agacag    66

<210> SEQ ID NO 700
<211> LENGTH: 66
<212> TYPE: DNA
<213> ORGANISM: Artificial
<220> FEATURE:
<223> OTHER INFORMATION: synthetic

<400> SEQUENCE: 700
caagcagaag acggcatacg agattcatct ctgtctcgtg ggctcggaga tgtgtataag    60
agacag    66

```
<210> SEQ ID NO 701
<211> LENGTH: 66
<212> TYPE: DNA
<213> ORGANISM: Artificial
<220> FEATURE:
<223> OTHER INFORMATION: synthetic

<400> SEQUENCE: 701
caagcagaag acggcatacg agatgcatct ctgtctcgtg ggctcggaga tgtgtataag    60
agacag                                                              66

<210> SEQ ID NO 702
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 702
caagcagaag acggcatacg agatanntnt ctgtctcgtg ggctcggaga tgtgtataag    60
agacag                                                              66

<210> SEQ ID NO 703
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 703
caagcagaag acggcatacg agattnntat ctgtctcgtg ggctcggaga tgtgtataag    60
agacag                                                              66

<210> SEQ ID NO 704
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 704
caagcagaag acggcatacg agatgnntat ctgtctcgtg ggctcggaga tgtgtataag    60
agacag                                                              66

<210> SEQ ID NO 705
<211> LENGTH: 66
<212> TYPE: DNA
<213> ORGANISM: Artificial
<220> FEATURE:
<223> OTHER INFORMATION: synthetic
<220> FEATURE:
```

```
<221> NAME/KEY: misc_feature
<222> LOCATION: (27)..(27)
<223> OTHER INFORMATION: n is a, c, g, or t

<400> SEQUENCE: 705
caagcagaag acggcatacg agatagngat ctgtctcgtg ggctcggaga tgtgtataag    60
agacag                                                              66

<210> SEQ ID NO 706
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 706
caagcagaag acggcatacg agatacngat ctgtctcgtg ggctcggaga tgtgtataag    60
agacag                                                              66

<210> SEQ ID NO 707
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 707
caagcagaag acggcatacg agataangat ctgtctcgtg ggctcggaga tgtgtataag    60
agacag                                                              66

<210> SEQ ID NO 708
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 708
caagcagaag acggcatacg agatagnaat ctgtctcgtg ggctcggaga tgtgtataag    60
agacag                                                              66

<210> SEQ ID NO 709
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 709
caagcagaag acggcatacg agatacnaat ctgtctcgtg ggctcggaga tgtgtataag    60
``` agacag 66

<210> SEQ ID NO 710
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 710
caagcagaag acggcatacg agataanaat ctgtctcgtg ggctcggaga tgtgtataag    60
agacag                                                              66

<210> SEQ ID NO 711
<211> LENGTH: 66
<212> TYPE: DNA
<213> ORGANISM: Artificial
<220> FEATURE:
<223> OTHER INFORMATION: synthetic

<400> SEQUENCE: 711
caagcagaag acggcatacg agattgtttg ctgtctcgtg ggctcggaga tgtgtataag    60
agacag                                                              66

<210> SEQ ID NO 712
<211> LENGTH: 66
<212> TYPE: DNA
<213> ORGANISM: Artificial
<220> FEATURE:
<223> OTHER INFORMATION: synthetic

<400> SEQUENCE: 712
caagcagaag acggcatacg agatggtttg ctgtctcgtg ggctcggaga tgtgtataag    60
agacag                                                              66

<210> SEQ ID NO 713
<211> LENGTH: 66
<212> TYPE: DNA
<213> ORGANISM: Artificial
<220> FEATURE:
<223> OTHER INFORMATION: synthetic

<400> SEQUENCE: 713
caagcagaag acggcatacg agattatttg ctgtctcgtg ggctcggaga tgtgtataag    60
agacag                                                              66

<210> SEQ ID NO 714
<211> LENGTH: 66
<212> TYPE: DNA
<213> ORGANISM: Artificial
<220> FEATURE:
<223> OTHER INFORMATION: synthetic

<400> SEQUENCE: 714
caagcagaag acggcatacg agatgatttg ctgtctcgtg ggctcggaga tgtgtataag    60
agacag                                                              66

<210> SEQ ID NO 715

```
<211> LENGTH: 66
<212> TYPE: DNA
<213> ORGANISM: Artificial
<220> FEATURE:
<223> OTHER INFORMATION: synthetic

<400> SEQUENCE: 715
caagcagaag acggcatacg agattgcttg ctgtctcgtg ggctcggaga tgtgtataag    60
agacag                                                              66

<210> SEQ ID NO 716
<211> LENGTH: 66
<212> TYPE: DNA
<213> ORGANISM: Artificial
<220> FEATURE:
<223> OTHER INFORMATION: synthetic

<400> SEQUENCE: 716
caagcagaag acggcatacg agatggcttg ctgtctcgtg ggctcggaga tgtgtataag    60
agacag                                                              66

<210> SEQ ID NO 717
<211> LENGTH: 66
<212> TYPE: DNA
<213> ORGANISM: Artificial
<220> FEATURE:
<223> OTHER INFORMATION: synthetic

<400> SEQUENCE: 717
caagcagaag acggcatacg agattacttg ctgtctcgtg ggctcggaga tgtgtataag    60
agacag                                                              66

<210> SEQ ID NO 718
<211> LENGTH: 66
<212> TYPE: DNA
<213> ORGANISM: Artificial
<220> FEATURE:
<223> OTHER INFORMATION: synthetic

<400> SEQUENCE: 718
caagcagaag acggcatacg agatgacttg ctgtctcgtg ggctcggaga tgtgtataag    60
agacag                                                              66

<210> SEQ ID NO 719
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 719
caagcagaag acggcatacg agattcnttg ctgtctcgtg ggctcggaga tgtgtataag    60
agacag                                                              66

<210> SEQ ID NO 720
<211> LENGTH: 66
<212> TYPE: DNA
<213> ORGANISM: Artificial
<220> FEATURE:
<223> OTHER INFORMATION: synthetic
```

```
<220> FEATURE:
<221> NAME/KEY: misc_feature
<222> LOCATION: (27)..(27)
<223> OTHER INFORMATION: n is a, c, g, or t

<400> SEQUENCE: 720
caagcagaag acggcatacg agatgcnttg ctgtctcgtg ggctcggaga tgtgtataag    60
agacag                                                               66

<210> SEQ ID NO 721
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 721
caagcagaag acggcatacg agatannttg ctgtctcgtg ggctcggaga tgtgtataag    60
agacag                                                               66

<210> SEQ ID NO 722
<211> LENGTH: 66
<212> TYPE: DNA
<213> ORGANISM: Artificial
<220> FEATURE:
<223> OTHER INFORMATION: synthetic

<400> SEQUENCE: 722
caagcagaag acggcatacg agattgattg ctgtctcgtg ggctcggaga tgtgtataag    60
agacag                                                               66

<210> SEQ ID NO 723
<211> LENGTH: 66
<212> TYPE: DNA
<213> ORGANISM: Artificial
<220> FEATURE:
<223> OTHER INFORMATION: synthetic

<400> SEQUENCE: 723
caagcagaag acggcatacg agatggattg ctgtctcgtg ggctcggaga tgtgtataag    60
agacag                                                               66

<210> SEQ ID NO 724
<211> LENGTH: 66
<212> TYPE: DNA
<213> ORGANISM: Artificial
<220> FEATURE:
<223> OTHER INFORMATION: synthetic

<400> SEQUENCE: 724
caagcagaag acggcatacg agattaattg ctgtctcgtg ggctcggaga tgtgtataag    60
agacag                                                               66

<210> SEQ ID NO 725
<211> LENGTH: 66
<212> TYPE: DNA
<213> ORGANISM: Artificial
<220> FEATURE:
<223> OTHER INFORMATION: synthetic
```

<400> SEQUENCE: 725
caagcagaag acggcatacg agatgaattg ctgtctcgtg ggctcggaga tgtgtataag    60
agacag                                                               66

<210> SEQ ID NO 726
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 726
caagcagaag acggcatacg agatacntag ctgtctcgtg ggctcggaga tgtgtataag    60
agacag                                                               66

<210> SEQ ID NO 727
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 727
caagcagaag acggcatacg agattcnttc ctgtctcgtg ggctcggaga tgtgtataag    60
agacag                                                               66

<210> SEQ ID NO 728
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 728
caagcagaag acggcatacg agatgcnttc ctgtctcgtg ggctcggaga tgtgtataag    60
agacag                                                               66

<210> SEQ ID NO 729
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 729
caagcagaag acggcatacg agatannttc ctgtctcgtg ggctcggaga tgtgtataag    60
agacag                                                               66

```
<210> SEQ ID NO 730
<211> LENGTH: 66
<212> TYPE: DNA
<213> ORGANISM: Artificial
<220> FEATURE:
<223> OTHER INFORMATION: synthetic

<400> SEQUENCE: 730
caagcagaag acggcatacg agatacttac ctgtctcgtg ggctcggaga tgtgtataag    60
agacag                                                                66

<210> SEQ ID NO 731
<211> LENGTH: 66
<212> TYPE: DNA
<213> ORGANISM: Artificial
<220> FEATURE:
<223> OTHER INFORMATION: synthetic

<400> SEQUENCE: 731
caagcagaag acggcatacg agatacctac ctgtctcgtg ggctcggaga tgtgtataag    60
agacag                                                                66

<210> SEQ ID NO 732
<211> LENGTH: 66
<212> TYPE: DNA
<213> ORGANISM: Artificial
<220> FEATURE:
<223> OTHER INFORMATION: synthetic

<400> SEQUENCE: 732
caagcagaag acggcatacg agatacatac ctgtctcgtg ggctcggaga tgtgtataag    60
agacag                                                                66

<210> SEQ ID NO 733
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 733
caagcagaag acggcatacg agattnntta ctgtctcgtg ggctcggaga tgtgtataag    60
agacag                                                                66

<210> SEQ ID NO 734
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 734
caagcagaag acggcatacg agatgnntta ctgtctcgtg ggctcggaga tgtgtataag    60
agacag                                                                66

<210> SEQ ID NO 735
```

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 735
caagcagaag acggcatacg agatanntta ctgtctcgtg ggctcggaga tgtgtataag       60
agacag                                                                 66

<210> SEQ ID NO 736
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 736
caagcagaag acggcatacg agatagngta ctgtctcgtg ggctcggaga tgtgtataag       60
agacag                                                                 66

<210> SEQ ID NO 737
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 737
caagcagaag acggcatacg agatacngta ctgtctcgtg ggctcggaga tgtgtataag       60
agacag                                                                 66

<210> SEQ ID NO 738
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 738
caagcagaag acggcatacg agataangta ctgtctcgtg ggctcggaga tgtgtataag       60
agacag                                                                 66

<210> SEQ ID NO 739
<211> LENGTH: 66
<212> TYPE: DNA
<213> ORGANISM: Artificial
<220> FEATURE:
<223> OTHER INFORMATION: synthetic

<400> SEQUENCE: 739
```
caagcagaag acggcatacg agatatagta ctgtctcgtg ggctcggaga tgtgtataag   60
agacag                                                              66

<210> SEQ ID NO 740
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 740
caagcagaag acggcatacg agatagnata ctgtctcgtg ggctcggaga tgtgtataag   60
agacag                                                              66

<210> SEQ ID NO 741
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 741
caagcagaag acggcatacg agatacnata ctgtctcgtg ggctcggaga tgtgtataag   60
agacag                                                              66

<210> SEQ ID NO 742
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 742
caagcagaag acggcatacg agataanata ctgtctcgtg ggctcggaga tgtgtataag   60
agacag                                                              66

<210> SEQ ID NO 743
<211> LENGTH: 66
<212> TYPE: DNA
<213> ORGANISM: Artificial
<220> FEATURE:
<223> OTHER INFORMATION: synthetic

<400> SEQUENCE: 743
caagcagaag acggcatacg agatataata ctgtctcgtg ggctcggaga tgtgtataag   60
agacag                                                              66

<210> SEQ ID NO 744
<211> LENGTH: 66
<212> TYPE: DNA
<213> ORGANISM: Artificial
<220> FEATURE:

<223> OTHER INFORMATION: synthetic

<400> SEQUENCE: 744
caagcagaag acggcatacg agatagttga ctgtctcgtg ggctcggaga tgtgtataag    60
agacag    66

<210> SEQ ID NO 745
<211> LENGTH: 66
<212> TYPE: DNA
<213> ORGANISM: Artificial
<220> FEATURE:
<223> OTHER INFORMATION: synthetic

<400> SEQUENCE: 745
caagcagaag acggcatacg agataattga ctgtctcgtg ggctcggaga tgtgtataag    60
agacag    66

<210> SEQ ID NO 746
<211> LENGTH: 66
<212> TYPE: DNA
<213> ORGANISM: Artificial
<220> FEATURE:
<223> OTHER INFORMATION: synthetic

<400> SEQUENCE: 746
caagcagaag acggcatacg agatagctga ctgtctcgtg ggctcggaga tgtgtataag    60
agacag    66

<210> SEQ ID NO 747
<211> LENGTH: 66
<212> TYPE: DNA
<213> ORGANISM: Artificial
<220> FEATURE:
<223> OTHER INFORMATION: synthetic

<400> SEQUENCE: 747
caagcagaag acggcatacg agataactga ctgtctcgtg ggctcggaga tgtgtataag    60
agacag    66

<210> SEQ ID NO 748
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 748
caagcagaag acggcatacg agatacntga ctgtctcgtg ggctcggaga tgtgtataag    60
agacag    66

<210> SEQ ID NO 749
<211> LENGTH: 66
<212> TYPE: DNA
<213> ORGANISM: Artificial
<220> FEATURE:
<223> OTHER INFORMATION: synthetic

<400> SEQUENCE: 749
caagcagaag acggcatacg agatagatga ctgtctcgtg ggctcggaga tgtgtataag    60
agacag                                                             66

<210> SEQ ID NO 750
<211> LENGTH: 66
<212> TYPE: DNA
<213> ORGANISM: Artificial
<220> FEATURE:
<223> OTHER INFORMATION: synthetic

<400> SEQUENCE: 750
caagcagaag acggcatacg agataaatga ctgtctcgtg ggctcggaga tgtgtataag    60
agacag                                                             66

<210> SEQ ID NO 751
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 751
caagcagaag acggcatacg agatacntca ctgtctcgtg ggctcggaga tgtgtataag    60
agacag                                                             66

<210> SEQ ID NO 752
<211> LENGTH: 66
<212> TYPE: DNA
<213> ORGANISM: Artificial
<220> FEATURE:
<223> OTHER INFORMATION: synthetic

<400> SEQUENCE: 752
caagcagaag acggcatacg agattcttaa ctgtctcgtg ggctcggaga tgtgtataag    60
agacag                                                             66

<210> SEQ ID NO 753
<211> LENGTH: 66
<212> TYPE: DNA
<213> ORGANISM: Artificial
<220> FEATURE:
<223> OTHER INFORMATION: synthetic

<400> SEQUENCE: 753
caagcagaag acggcatacg agatgcttaa ctgtctcgtg ggctcggaga tgtgtataag    60
agacag                                                             66

<210> SEQ ID NO 754
<211> LENGTH: 66
<212> TYPE: DNA
<213> ORGANISM: Artificial
<220> FEATURE:
<223> OTHER INFORMATION: synthetic

<400> SEQUENCE: 754
caagcagaag acggcatacg agattcctaa ctgtctcgtg ggctcggaga tgtgtataag    60
agacag                                                             66

<210> SEQ ID NO 755

```
<211> LENGTH: 66
<212> TYPE: DNA
<213> ORGANISM: Artificial
<220> FEATURE:
<223> OTHER INFORMATION: synthetic

<400> SEQUENCE: 755
caagcagaag acggcatacg agatgcctaa ctgtctcgtg ggctcggaga tgtgtataag    60
agacag                                                              66

<210> SEQ ID NO 756
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 756
caagcagaag acggcatacg agatanntaa ctgtctcgtg ggctcggaga tgtgtataag    60
agacag                                                              66

<210> SEQ ID NO 757
<211> LENGTH: 66
<212> TYPE: DNA
<213> ORGANISM: Artificial
<220> FEATURE:
<223> OTHER INFORMATION: synthetic

<400> SEQUENCE: 757
caagcagaag acggcatacg agattcataa ctgtctcgtg ggctcggaga tgtgtataag    60
agacag                                                              66

<210> SEQ ID NO 758
<211> LENGTH: 66
<212> TYPE: DNA
<213> ORGANISM: Artificial
<220> FEATURE:
<223> OTHER INFORMATION: synthetic

<400> SEQUENCE: 758
caagcagaag acggcatacg agatgcataa ctgtctcgtg ggctcggaga tgtgtataag    60
agacag                                                              66

<210> SEQ ID NO 759
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 759
caagcagaag acggcatacg agatcnnctt atgtctcgtg ggctcggaga tgtgtataag    60
agacag                                                              66

<210> SEQ ID NO 760
<211> LENGTH: 66
```

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 760
caagcagaag acggcatacg agatccncgt atgtctcgtg ggctcggaga tgtgtataag      60
agacag                                                                66

<210> SEQ ID NO 761
<211> LENGTH: 66
<212> TYPE: DNA
<213> ORGANISM: Artificial
<220> FEATURE:
<223> OTHER INFORMATION: synthetic

<400> SEQUENCE: 761
caagcagaag acggcatacg agatcctcct atgtctcgtg ggctcggaga tgtgtataag      60
agacag                                                                66

<210> SEQ ID NO 762
<211> LENGTH: 66
<212> TYPE: DNA
<213> ORGANISM: Artificial
<220> FEATURE:
<223> OTHER INFORMATION: synthetic

<400> SEQUENCE: 762
caagcagaag acggcatacg agatccccct atgtctcgtg ggctcggaga tgtgtataag      60
agacag                                                                66

<210> SEQ ID NO 763
<211> LENGTH: 66
<212> TYPE: DNA
<213> ORGANISM: Artificial
<220> FEATURE:
<223> OTHER INFORMATION: synthetic

<400> SEQUENCE: 763
caagcagaag acggcatacg agatccacct atgtctcgtg ggctcggaga tgtgtataag      60
agacag                                                                66

<210> SEQ ID NO 764
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 764
caagcagaag acggcatacg agatnnntnt atgtctcgtg ggctcggaga tgtgtataag      60
agacag                                                                66
```

<210> SEQ ID NO 765
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 765
caagcagaag acggcatacg agatnnngnt atgtctcgtg ggctcggaga tgtgtataag    60
agacag                                                              66

<210> SEQ ID NO 766
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 766
caagcagaag acggcatacg agattnncnt atgtctcgtg ggctcggaga tgtgtataag    60
agacag                                                              66

<210> SEQ ID NO 767
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 767
caagcagaag acggcatacg agatgnncnt atgtctcgtg ggctcggaga tgtgtataag    60
agacag                                                              66

<210> SEQ ID NO 768
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 768
caagcagaag acggcatacg agatanncnt atgtctcgtg ggctcggaga tgtgtataag    60
agacag    66

<210> SEQ ID NO 769
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 769
caagcagaag acggcatacg agatnnnant atgtctcgtg ggctcggaga tgtgtataag    60
agacag    66

<210> SEQ ID NO 770
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 770
caagcagaag acggcatacg agatcnncat atgtctcgtg ggctcggaga tgtgtataag    60
agacag    66

<210> SEQ ID NO 771
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 771
caagcagaag acggcatacg agatcnnttg atgtctcgtg ggctcggaga tgtgtataag    60
agacag    66

<210> SEQ ID NO 772
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

```
<400> SEQUENCE: 772
caagcagaag acggcatacg agattnngtg atgtctcgtg ggctcggaga tgtgtataag    60
agacag                                                               66

<210> SEQ ID NO 773
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 773
caagcagaag acggcatacg agatgnngtg atgtctcgtg ggctcggaga tgtgtataag    60
agacag                                                               66

<210> SEQ ID NO 774
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 774
caagcagaag acggcatacg agatcnngtg atgtctcgtg ggctcggaga tgtgtataag    60
agacag                                                               66

<210> SEQ ID NO 775
<211> LENGTH: 66
<212> TYPE: DNA
<213> ORGANISM: Artificial
<220> FEATURE:
<223> OTHER INFORMATION: synthetic

<400> SEQUENCE: 775
caagcagaag acggcatacg agatcgtctg atgtctcgtg ggctcggaga tgtgtataag    60
agacag                                                               66

<210> SEQ ID NO 776
<211> LENGTH: 66
<212> TYPE: DNA
<213> ORGANISM: Artificial
<220> FEATURE:
<223> OTHER INFORMATION: synthetic

<400> SEQUENCE: 776
caagcagaag acggcatacg agatcatctg atgtctcgtg ggctcggaga tgtgtataag    60
agacag                                                               66

<210> SEQ ID NO 777
<211> LENGTH: 66
<212> TYPE: DNA
<213> ORGANISM: Artificial
<220> FEATURE:
<223> OTHER INFORMATION: synthetic

<400> SEQUENCE: 777
```

```
caagcagaag acggcatacg agatcgcctg atgtctcgtg ggctcggaga tgtgtataag    60
agacag                                                               66

<210> SEQ ID NO 778
<211> LENGTH: 66
<212> TYPE: DNA
<213> ORGANISM: Artificial
<220> FEATURE:
<223> OTHER INFORMATION: synthetic

<400> SEQUENCE: 778
caagcagaag acggcatacg agatcacctg atgtctcgtg ggctcggaga tgtgtataag    60
agacag                                                               66

<210> SEQ ID NO 779
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 779
caagcagaag acggcatacg agatccnctg atgtctcgtg ggctcggaga tgtgtataag    60
agacag                                                               66

<210> SEQ ID NO 780
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 780
caagcagaag acggcatacg agattnnctg atgtctcgtg ggctcggaga tgtgtataag    60
agacag                                                               66

<210> SEQ ID NO 781
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 781
caagcagaag acggcatacg agatgnnctg atgtctcgtg ggctcggaga tgtgtataag    60
agacag                                                               66

<210> SEQ ID NO 782
<211> LENGTH: 66
<212> TYPE: DNA
<213> ORGANISM: Artificial
<220> FEATURE:
```

<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 782
caagcagaag acggcatacg agatannctg atgtctcgtg ggctcggaga tgtgtataag    60
agacag                                                              66

<210> SEQ ID NO 783
<211> LENGTH: 66
<212> TYPE: DNA
<213> ORGANISM: Artificial
<220> FEATURE:
<223> OTHER INFORMATION: synthetic

<400> SEQUENCE: 783
caagcagaag acggcatacg agatcgactg atgtctcgtg ggctcggaga tgtgtataag    60
agacag                                                              66

<210> SEQ ID NO 784
<211> LENGTH: 66
<212> TYPE: DNA
<213> ORGANISM: Artificial
<220> FEATURE:
<223> OTHER INFORMATION: synthetic

<400> SEQUENCE: 784
caagcagaag acggcatacg agatcaactg atgtctcgtg ggctcggaga tgtgtataag    60
agacag                                                              66

<210> SEQ ID NO 785
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 785
caagcagaag acggcatacg agattnnatg atgtctcgtg ggctcggaga tgtgtataag    60
agacag                                                              66

<210> SEQ ID NO 786
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 786
caagcagaag acggcatacg agatgnnatg atgtctcgtg ggctcggaga tgtgtataag    60
agacag                                                              66

<210> SEQ ID NO 787
<211> LENGTH: 66

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 787
caagcagaag acggcatacg agatcnnatg atgtctcgtg ggctcggaga tgtgtataag      60
agacag                                                                66

<210> SEQ ID NO 788
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 788
caagcagaag acggcatacg agatcgntgg atgtctcgtg ggctcggaga tgtgtataag      60
agacag                                                                66

<210> SEQ ID NO 789
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 789
caagcagaag acggcatacg agatccntgg atgtctcgtg ggctcggaga tgtgtataag      60
agacag                                                                66

<210> SEQ ID NO 790
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 790
caagcagaag acggcatacg agatcantgg atgtctcgtg ggctcggaga tgtgtataag      60
agacag                                                                66

<210> SEQ ID NO 791
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
```

<223> OTHER INFORMATION: n is a, c, g, or t

<400> SEQUENCE: 791
caagcagaag acggcatacg agattgnggg atgtctcgtg ggctcggaga tgtgtataag    60
agacag    66

<210> SEQ ID NO 792
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 792
caagcagaag acggcatacg agatggnggg atgtctcgtg ggctcggaga tgtgtataag    60
agacag    66

<210> SEQ ID NO 793
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 793
caagcagaag acggcatacg agattcnggg atgtctcgtg ggctcggaga tgtgtataag    60
agacag    66

<210> SEQ ID NO 794
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 794
caagcagaag acggcatacg agatgcnggg atgtctcgtg ggctcggaga tgtgtataag    60
agacag    66

<210> SEQ ID NO 795
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 795
caagcagaag acggcatacg agattanggg atgtctcgtg ggctcggaga tgtgtataag    60
agacag    66

```
<210> SEQ ID NO 796
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 796
caagcagaag acggcatacg agatganggg atgtctcgtg ggctcggaga tgtgtataag    60
agacag                                                              66

<210> SEQ ID NO 797
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 797
caagcagaag acggcatacg agatagncgg atgtctcgtg ggctcggaga tgtgtataag    60
agacag                                                              66

<210> SEQ ID NO 798
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 798
caagcagaag acggcatacg agatacncgg atgtctcgtg ggctcggaga tgtgtataag    60
agacag                                                              66

<210> SEQ ID NO 799
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 799
caagcagaag acggcatacg agataancgg atgtctcgtg ggctcggaga tgtgtataag    60
agacag                                                              66

<210> SEQ ID NO 800
<211> LENGTH: 66
<212> TYPE: DNA
<213> ORGANISM: Artificial
<220> FEATURE:
```

```
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 800
caagcagaag acggcatacg agattgnagg atgtctcgtg ggctcggaga tgtgtataag    60
agacag                                                               66

<210> SEQ ID NO 801
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 801
caagcagaag acggcatacg agatggnagg atgtctcgtg ggctcggaga tgtgtataag    60
agacag                                                               66

<210> SEQ ID NO 802
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 802
caagcagaag acggcatacg agattcnagg atgtctcgtg ggctcggaga tgtgtataag    60
agacag                                                               66

<210> SEQ ID NO 803
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 803
caagcagaag acggcatacg agatgcnagg atgtctcgtg ggctcggaga tgtgtataag    60
agacag                                                               66

<210> SEQ ID NO 804
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 804
```

-continued

```
caagcagaag acggcatacg agattanagg atgtctcgtg ggctcggaga tgtgtataag    60
agacag                                                               66

<210> SEQ ID NO 805
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 805
caagcagaag acggcatacg agatganagg atgtctcgtg ggctcggaga tgtgtataag    60
agacag                                                               66

<210> SEQ ID NO 806
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 806
caagcagaag acggcatacg agatcgntcg atgtctcgtg ggctcggaga tgtgtataag    60
agacag                                                               66

<210> SEQ ID NO 807
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 807
caagcagaag acggcatacg agatccntcg atgtctcgtg ggctcggaga tgtgtataag    60
agacag                                                               66

<210> SEQ ID NO 808
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 808
caagcagaag acggcatacg agatcantcg atgtctcgtg ggctcggaga tgtgtataag    60
agacag                                                               66

<210> SEQ ID NO 809
```

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 809
caagcagaag acggcatacg agattgngcg atgtctcgtg ggctcggaga tgtgtataag    60
agacag                                                               66

<210> SEQ ID NO 810
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 810
caagcagaag acggcatacg agatggngcg atgtctcgtg ggctcggaga tgtgtataag    60
agacag                                                               66

<210> SEQ ID NO 811
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 811
caagcagaag acggcatacg agattcngcg atgtctcgtg ggctcggaga tgtgtataag    60
agacag                                                               66

<210> SEQ ID NO 812
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 812
caagcagaag acggcatacg agatgcngcg atgtctcgtg ggctcggaga tgtgtataag    60
agacag                                                               66

<210> SEQ ID NO 813
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

-continued

<222> LOCATION: (27)..(27)
<223> OTHER INFORMATION: n is a, c, g, or t

<400> SEQUENCE: 813
caagcagaag acggcatacg agattangcg atgtctcgtg ggctcggaga tgtgtataag    60
agacag                                                               66

<210> SEQ ID NO 814
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 814
caagcagaag acggcatacg agatgangcg atgtctcgtg ggctcggaga tgtgtataag    60
agacag                                                               66

<210> SEQ ID NO 815
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 815
caagcagaag acggcatacg agatagnccg atgtctcgtg ggctcggaga tgtgtataag    60
agacag                                                               66

<210> SEQ ID NO 816
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 816
caagcagaag acggcatacg agatacnccg atgtctcgtg ggctcggaga tgtgtataag    60
agacag                                                               66

<210> SEQ ID NO 817
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 817
caagcagaag acggcatacg agataanccg atgtctcgtg ggctcggaga tgtgtataag    60
agacag 66

<210> SEQ ID NO 818
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 818
caagcagaag acggcatacg agattgnacg atgtctcgtg ggctcggaga tgtgtataag    60
agacag    66

<210> SEQ ID NO 819
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 819
caagcagaag acggcatacg agatggnacg atgtctcgtg ggctcggaga tgtgtataag    60
agacag    66

<210> SEQ ID NO 820
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 820
caagcagaag acggcatacg agattcnacg atgtctcgtg ggctcggaga tgtgtataag    60
agacag    66

<210> SEQ ID NO 821
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 821
caagcagaag acggcatacg agatgcnacg atgtctcgtg ggctcggaga tgtgtataag    60
agacag    66

<210> SEQ ID NO 822
<211> LENGTH: 66
<212> TYPE: DNA
<213> ORGANISM: Artificial

```
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 822
caagcagaag acggcatacg agattanacg atgtctcgtg ggctcggaga tgtgtataag    60
agacag                                                               66

<210> SEQ ID NO 823
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 823
caagcagaag acggcatacg agatganacg atgtctcgtg ggctcggaga tgtgtataag    60
agacag                                                               66

<210> SEQ ID NO 824
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 824
caagcagaag acggcatacg agattnntng atgtctcgtg ggctcggaga tgtgtataag    60
agacag                                                               66

<210> SEQ ID NO 825
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 825
caagcagaag acggcatacg agatgnntng atgtctcgtg ggctcggaga tgtgtataag    60
agacag                                                               66

<210> SEQ ID NO 826
<211> LENGTH: 66
<212> TYPE: DNA
```

```
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 826
caagcagaag acggcatacg agatanntng atgtctcgtg ggctcggaga tgtgtataag    60
agacag                                                              66

<210> SEQ ID NO 827
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 827
caagcagaag acggcatacg agatanngng atgtctcgtg ggctcggaga tgtgtataag    60
agacag                                                              66

<210> SEQ ID NO 828
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 828
caagcagaag acggcatacg agatannang atgtctcgtg ggctcggaga tgtgtataag    60
agacag                                                              66

<210> SEQ ID NO 829
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 829
caagcagaag acggcatacg agatcnntag atgtctcgtg ggctcggaga tgtgtataag    60
agacag                                                              66
```

<210> SEQ ID NO 830
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 830
caagcagaag acggcatacg agatccngag atgtctcgtg ggctcggaga tgtgtataag    60
agacag                                                                66

<210> SEQ ID NO 831
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 831
caagcagaag acggcatacg agattnngag atgtctcgtg ggctcggaga tgtgtataag    60
agacag                                                                66

<210> SEQ ID NO 832
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 832
caagcagaag acggcatacg agatgnngag atgtctcgtg ggctcggaga tgtgtataag    60
agacag                                                                66

<210> SEQ ID NO 833
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 833
caagcagaag acggcatacg agattgncag atgtctcgtg ggctcggaga tgtgtataag    60
agacag                                                                66

<210> SEQ ID NO 834
<211> LENGTH: 66
<212> TYPE: DNA
<213> ORGANISM: Artificial
<220> FEATURE:

<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 834
caagcagaag acggcatacg agatggncag atgtctcgtg ggctcggaga tgtgtataag    60
agacag                                                              66

<210> SEQ ID NO 835
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 835
caagcagaag acggcatacg agattcncag atgtctcgtg ggctcggaga tgtgtataag    60
agacag                                                              66

<210> SEQ ID NO 836
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 836
caagcagaag acggcatacg agatgcncag atgtctcgtg ggctcggaga tgtgtataag    60
agacag                                                              66

<210> SEQ ID NO 837
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 837
caagcagaag acggcatacg agatanncag atgtctcgtg ggctcggaga tgtgtataag    60
agacag                                                              66

<210> SEQ ID NO 838
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 838

```
caagcagaag acggcatacg agattancag atgtctcgtg ggctcggaga tgtgtataag    60
agacag                                                                66

<210> SEQ ID NO 839
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 839
caagcagaag acggcatacg agatgancag atgtctcgtg ggctcggaga tgtgtataag    60
agacag                                                                66

<210> SEQ ID NO 840
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 840
caagcagaag acggcatacg agatccnaag atgtctcgtg ggctcggaga tgtgtataag    60
agacag                                                                66

<210> SEQ ID NO 841
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 841
caagcagaag acggcatacg agattnnaag atgtctcgtg ggctcggaga tgtgtataag    60
agacag                                                                66

<210> SEQ ID NO 842
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 842
caagcagaag acggcatacg agatgnnaag atgtctcgtg ggctcggaga tgtgtataag    60
agacag                                                                66

<210> SEQ ID NO 843
```

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 843
caagcagaag acggcatacg agatcnnttc atgtctcgtg ggctcggaga tgtgtataag    60
agacag                                                              66

<210> SEQ ID NO 844
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 844
caagcagaag acggcatacg agattnngtc atgtctcgtg ggctcggaga tgtgtataag    60
agacag                                                              66

<210> SEQ ID NO 845
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 845
caagcagaag acggcatacg agatgnngtc atgtctcgtg ggctcggaga tgtgtataag    60
agacag                                                              66

<210> SEQ ID NO 846
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 846
caagcagaag acggcatacg agatcnngtc atgtctcgtg ggctcggaga tgtgtataag    60
agacag                                                              66

<210> SEQ ID NO 847
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

```
<222> LOCATION: (27)..(27)
<223> OTHER INFORMATION: n is a, c, g, or t

<400> SEQUENCE: 847
caagcagaag acggcatacg agatccnctc atgtctcgtg ggctcggaga tgtgtataag    60
agacag                                                               66

<210> SEQ ID NO 848
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 848
caagcagaag acggcatacg agattnnctc atgtctcgtg ggctcggaga tgtgtataag    60
agacag                                                               66

<210> SEQ ID NO 849
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 849
caagcagaag acggcatacg agatgnnctc atgtctcgtg ggctcggaga tgtgtataag    60
agacag                                                               66

<210> SEQ ID NO 850
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 850
caagcagaag acggcatacg agatannctc atgtctcgtg ggctcggaga tgtgtataag    60
agacag                                                               66

<210> SEQ ID NO 851
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 851
caagcagaag acggcatacg agattnnatc atgtctcgtg ggctcggaga tgtgtataag    60
``` agacag 66

<210> SEQ ID NO 852
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 852
caagcagaag acggcatacg agatgnnatc atgtctcgtg ggctcggaga tgtgtataag    60
agacag    66

<210> SEQ ID NO 853
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 853
caagcagaag acggcatacg agatcnnatc atgtctcgtg ggctcggaga tgtgtataag    60
agacag    66

<210> SEQ ID NO 854
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 854
caagcagaag acggcatacg agatcgntgc atgtctcgtg ggctcggaga tgtgtataag    60
agacag    66

<210> SEQ ID NO 855
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 855
caagcagaag acggcatacg agatccntgc atgtctcgtg ggctcggaga tgtgtataag    60
agacag    66

<210> SEQ ID NO 856
<211> LENGTH: 66
<212> TYPE: DNA
<213> ORGANISM: Artificial

<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 856
caagcagaag acggcatacg agatcantgc atgtctcgtg ggctcggaga tgtgtataag    60
agacag                                                              66

<210> SEQ ID NO 857
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 857
caagcagaag acggcatacg agattgnggc atgtctcgtg ggctcggaga tgtgtataag    60
agacag                                                              66

<210> SEQ ID NO 858
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 858
caagcagaag acggcatacg agatggnggc atgtctcgtg ggctcggaga tgtgtataag    60
agacag                                                              66

<210> SEQ ID NO 859
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 859
caagcagaag acggcatacg agattcnggc atgtctcgtg ggctcggaga tgtgtataag    60
agacag                                                              66

<210> SEQ ID NO 860
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

```
<400> SEQUENCE: 860
caagcagaag acggcatacg agatgcnggc atgtctcgtg ggctcggaga tgtgtataag    60
agacag                                                               66

<210> SEQ ID NO 861
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 861
caagcagaag acggcatacg agattanggc atgtctcgtg ggctcggaga tgtgtataag    60
agacag                                                               66

<210> SEQ ID NO 862
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 862
caagcagaag acggcatacg agatganggc atgtctcgtg ggctcggaga tgtgtataag    60
agacag                                                               66

<210> SEQ ID NO 863
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 863
caagcagaag acggcatacg agatagncgc atgtctcgtg ggctcggaga tgtgtataag    60
agacag                                                               66

<210> SEQ ID NO 864
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 864
caagcagaag acggcatacg agatacncgc atgtctcgtg ggctcggaga tgtgtataag    60
agacag                                                               66
```

```
<210> SEQ ID NO 865
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 865
caagcagaag acggcatacg agataancgc atgtctcgtg ggctcggaga tgtgtataag    60
agacag                                                              66

<210> SEQ ID NO 866
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 866
caagcagaag acggcatacg agattgnagc atgtctcgtg ggctcggaga tgtgtataag    60
agacag                                                              66

<210> SEQ ID NO 867
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 867
caagcagaag acggcatacg agatggnagc atgtctcgtg ggctcggaga tgtgtataag    60
agacag                                                              66

<210> SEQ ID NO 868
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 868
caagcagaag acggcatacg agattcnagc atgtctcgtg ggctcggaga tgtgtataag    60
agacag                                                              66

<210> SEQ ID NO 869
<211> LENGTH: 66
<212> TYPE: DNA
<213> ORGANISM: Artificial
<220> FEATURE:
<223> OTHER INFORMATION: synthetic
<220> FEATURE:
```

```
<221> NAME/KEY: misc_feature
<222> LOCATION: (27)..(27)
<223> OTHER INFORMATION: n is a, c, g, or t

<400> SEQUENCE: 869
caagcagaag acggcatacg agatgcnagc atgtctcgtg ggctcggaga tgtgtataag    60
agacag                                                              66

<210> SEQ ID NO 870
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 870
caagcagaag acggcatacg agattanagc atgtctcgtg ggctcggaga tgtgtataag    60
agacag                                                              66

<210> SEQ ID NO 871
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 871
caagcagaag acggcatacg agatganagc atgtctcgtg ggctcggaga tgtgtataag    60
agacag                                                              66

<210> SEQ ID NO 872
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 872
caagcagaag acggcatacg agatcgntcc atgtctcgtg ggctcggaga tgtgtataag    60
agacag                                                              66

<210> SEQ ID NO 873
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 873
caagcagaag acggcatacg agatccntcc atgtctcgtg ggctcggaga tgtgtataag    60
```

```
agacag                                                              66

<210> SEQ ID NO 874
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 874
caagcagaag acggcatacg agatcantcc atgtctcgtg ggctcggaga tgtgtataag    60
agacag                                                              66

<210> SEQ ID NO 875
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 875
caagcagaag acggcatacg agattgngcc atgtctcgtg ggctcggaga tgtgtataag    60
agacag                                                              66

<210> SEQ ID NO 876
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 876
caagcagaag acggcatacg agatggngcc atgtctcgtg ggctcggaga tgtgtataag    60
agacag                                                              66

<210> SEQ ID NO 877
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 877
caagcagaag acggcatacg agattcngcc atgtctcgtg ggctcggaga tgtgtataag    60
agacag                                                              66

<210> SEQ ID NO 878
<211> LENGTH: 66
<212> TYPE: DNA
```

```
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 878
caagcagaag acggcatacg agatgcngcc atgtctcgtg ggctcggaga tgtgtataag    60
agacag                                                                66

<210> SEQ ID NO 879
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 879
caagcagaag acggcatacg agattangcc atgtctcgtg ggctcggaga tgtgtataag    60
agacag                                                                66

<210> SEQ ID NO 880
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 880
caagcagaag acggcatacg agatgangcc atgtctcgtg ggctcggaga tgtgtataag    60
agacag                                                                66

<210> SEQ ID NO 881
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 881
caagcagaag acggcatacg agatagnccc atgtctcgtg ggctcggaga tgtgtataag    60
agacag                                                                66

<210> SEQ ID NO 882
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t
```

<400> SEQUENCE: 882
caagcagaag acggcatacg agatacnccc atgtctcgtg ggctcggaga tgtgtataag    60
agacag                                                                66

<210> SEQ ID NO 883
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 883
caagcagaag acggcatacg agataanccc atgtctcgtg ggctcggaga tgtgtataag    60
agacag                                                                66

<210> SEQ ID NO 884
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 884
caagcagaag acggcatacg agattgnacc atgtctcgtg ggctcggaga tgtgtataag    60
agacag                                                                66

<210> SEQ ID NO 885
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 885
caagcagaag acggcatacg agatggnacc atgtctcgtg ggctcggaga tgtgtataag    60
agacag                                                                66

<210> SEQ ID NO 886
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 886
caagcagaag acggcatacg agattcnacc atgtctcgtg ggctcggaga tgtgtataag    60
agacag                                                                66

<210> SEQ ID NO 887
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 887
caagcagaag acggcatacg agatgcnacc atgtctcgtg ggctcggaga tgtgtataag      60
agacag                                                                66

<210> SEQ ID NO 888
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 888
caagcagaag acggcatacg agattanacc atgtctcgtg ggctcggaga tgtgtataag      60
agacag                                                                66

<210> SEQ ID NO 889
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 889
caagcagaag acggcatacg agatganacc atgtctcgtg ggctcggaga tgtgtataag      60
agacag                                                                66

<210> SEQ ID NO 890
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 890
caagcagaag acggcatacg agattnntnc atgtctcgtg ggctcggaga tgtgtataag      60
agacag                                                                66

<210> SEQ ID NO 891
<211> LENGTH: 66

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 891
caagcagaag acggcatacg agatgnntnc atgtctcgtg ggctcggaga tgtgtataag    60
agacag                                                               66

<210> SEQ ID NO 892
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 892
caagcagaag acggcatacg agatanntnc atgtctcgtg ggctcggaga tgtgtataag    60
agacag                                                               66

<210> SEQ ID NO 893
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 893
caagcagaag acggcatacg agatanngnc atgtctcgtg ggctcggaga tgtgtataag    60
agacag                                                               66

<210> SEQ ID NO 894
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
```

-continued

<400> SEQUENCE: 894
caagcagaag acggcatacg agatannanc atgtctcgtg ggctcggaga tgtgtataag    60
agacag                                                              66

<210> SEQ ID NO 895
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 895
caagcagaag acggcatacg agatcnntac atgtctcgtg ggctcggaga tgtgtataag    60
agacag                                                              66

<210> SEQ ID NO 896
<211> LENGTH: 66
<212> TYPE: DNA
<213> ORGANISM: Artificial
<220> FEATURE:
<223> OTHER INFORMATION: synthetic

<400> SEQUENCE: 896
caagcagaag acggcatacg agatcctgac atgtctcgtg ggctcggaga tgtgtataag    60
agacag                                                              66

<210> SEQ ID NO 897
<211> LENGTH: 66
<212> TYPE: DNA
<213> ORGANISM: Artificial
<220> FEATURE:
<223> OTHER INFORMATION: synthetic

<400> SEQUENCE: 897
caagcagaag acggcatacg agatcccgac atgtctcgtg ggctcggaga tgtgtataag    60
agacag                                                              66

<210> SEQ ID NO 898
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 898
caagcagaag acggcatacg agattnngac atgtctcgtg ggctcggaga tgtgtataag    60
agacag                                                              66

<210> SEQ ID NO 899
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 899
caagcagaag acggcatacg agatgnngac atgtctcgtg ggctcggaga tgtgtataag    60
agacag                                                              66

<210> SEQ ID NO 900
<211> LENGTH: 66
<212> TYPE: DNA
<213> ORGANISM: Artificial
<220> FEATURE:
<223> OTHER INFORMATION: synthetic

<400> SEQUENCE: 900
caagcagaag acggcatacg agatccagac atgtctcgtg ggctcggaga tgtgtataag    60
agacag                                                              66

<210> SEQ ID NO 901
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 901
caagcagaag acggcatacg agattgncac atgtctcgtg ggctcggaga tgtgtataag    60
agacag                                                              66

<210> SEQ ID NO 902
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 902
caagcagaag acggcatacg agatggncac atgtctcgtg ggctcggaga tgtgtataag    60
agacag                                                              66

<210> SEQ ID NO 903
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 903
caagcagaag acggcatacg agattcncac atgtctcgtg ggctcggaga tgtgtataag    60
agacag                                                              66

<210> SEQ ID NO 904

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 904
caagcagaag acggcatacg agatgcncac atgtctcgtg ggctcggaga tgtgtataag      60
agacag                                                                66

<210> SEQ ID NO 905
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 905
caagcagaag acggcatacg agatanncac atgtctcgtg ggctcggaga tgtgtataag      60
agacag                                                                66

<210> SEQ ID NO 906
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 906
caagcagaag acggcatacg agattancac atgtctcgtg ggctcggaga tgtgtataag      60
agacag                                                                66

<210> SEQ ID NO 907
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 907
caagcagaag acggcatacg agatgancac atgtctcgtg ggctcggaga tgtgtataag      60
agacag                                                                66

<210> SEQ ID NO 908
<211> LENGTH: 66
<212> TYPE: DNA
<213> ORGANISM: Artificial
<220> FEATURE:
<223> OTHER INFORMATION: synthetic

<400> SEQUENCE: 908
```

```
caagcagaag acggcatacg agatcctaac atgtctcgtg ggctcggaga tgtgtataag    60
agacag                                                               66

<210> SEQ ID NO 909
<211> LENGTH: 66
<212> TYPE: DNA
<213> ORGANISM: Artificial
<220> FEATURE:
<223> OTHER INFORMATION: synthetic

<400> SEQUENCE: 909
caagcagaag acggcatacg agatcccaac atgtctcgtg ggctcggaga tgtgtataag    60
agacag                                                               66

<210> SEQ ID NO 910
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 910
caagcagaag acggcatacg agattnnaac atgtctcgtg ggctcggaga tgtgtataag    60
agacag                                                               66

<210> SEQ ID NO 911
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 911
caagcagaag acggcatacg agatgnnaac atgtctcgtg ggctcggaga tgtgtataag    60
agacag                                                               66

<210> SEQ ID NO 912
<211> LENGTH: 66
<212> TYPE: DNA
<213> ORGANISM: Artificial
<220> FEATURE:
<223> OTHER INFORMATION: synthetic

<400> SEQUENCE: 912
caagcagaag acggcatacg agatccaaac atgtctcgtg ggctcggaga tgtgtataag    60
agacag                                                               66

<210> SEQ ID NO 913
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
```

```
<223> OTHER INFORMATION: n is a, c, g, or t

<400> SEQUENCE: 913
caagcagaag acggcatacg agatcnngta atgtctcgtg ggctcggaga tgtgtataag    60
agacag                                                              66

<210> SEQ ID NO 914
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 914
caagcagaag acggcatacg agattnncta atgtctcgtg ggctcggaga tgtgtataag    60
agacag                                                              66

<210> SEQ ID NO 915
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 915
caagcagaag acggcatacg agatgnncta atgtctcgtg ggctcggaga tgtgtataag    60
agacag                                                              66

<210> SEQ ID NO 916
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 916
caagcagaag acggcatacg agatcnncta atgtctcgtg ggctcggaga tgtgtataag    60
agacag                                                              66

<210> SEQ ID NO 917
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 917
caagcagaag acggcatacg agatcnnata atgtctcgtg ggctcggaga tgtgtataag    60
agacag                                                              66
```

<210> SEQ ID NO 918
<211> LENGTH: 66
<212> TYPE: DNA
<213> ORGANISM: Artificial
<220> FEATURE:
<223> OTHER INFORMATION: synthetic

<400> SEQUENCE: 918
caagcagaag acggcatacg agatcgtgga atgtctcgtg ggctcggaga tgtgtataag    60
agacag                                                              66

<210> SEQ ID NO 919
<211> LENGTH: 66
<212> TYPE: DNA
<213> ORGANISM: Artificial
<220> FEATURE:
<223> OTHER INFORMATION: synthetic

<400> SEQUENCE: 919
caagcagaag acggcatacg agatcatgga atgtctcgtg ggctcggaga tgtgtataag    60
agacag                                                              66

<210> SEQ ID NO 920
<211> LENGTH: 66
<212> TYPE: DNA
<213> ORGANISM: Artificial
<220> FEATURE:
<223> OTHER INFORMATION: synthetic

<400> SEQUENCE: 920
caagcagaag acggcatacg agatcgcgga atgtctcgtg ggctcggaga tgtgtataag    60
agacag                                                              66

<210> SEQ ID NO 921
<211> LENGTH: 66
<212> TYPE: DNA
<213> ORGANISM: Artificial
<220> FEATURE:
<223> OTHER INFORMATION: synthetic

<400> SEQUENCE: 921
caagcagaag acggcatacg agatcacgga atgtctcgtg ggctcggaga tgtgtataag    60
agacag                                                              66

<210> SEQ ID NO 922
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 922
caagcagaag acggcatacg agatccngga atgtctcgtg ggctcggaga tgtgtataag    60
agacag                                                              66

<210> SEQ ID NO 923
<211> LENGTH: 66
<212> TYPE: DNA

<213> ORGANISM: Artificial
<220> FEATURE:
<223> OTHER INFORMATION: synthetic

<400> SEQUENCE: 923
caagcagaag acggcatacg agatcgagga atgtctcgtg ggctcggaga tgtgtataag    60
agacag                                                               66

<210> SEQ ID NO 924
<211> LENGTH: 66
<212> TYPE: DNA
<213> ORGANISM: Artificial
<220> FEATURE:
<223> OTHER INFORMATION: synthetic

<400> SEQUENCE: 924
caagcagaag acggcatacg agatcaagga atgtctcgtg ggctcggaga tgtgtataag    60
agacag                                                               66

<210> SEQ ID NO 925
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 925
caagcagaag acggcatacg agattgncga atgtctcgtg ggctcggaga tgtgtataag    60
agacag                                                               66

<210> SEQ ID NO 926
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 926
caagcagaag acggcatacg agatggncga atgtctcgtg ggctcggaga tgtgtataag    60
agacag                                                               66

<210> SEQ ID NO 927
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 927
caagcagaag acggcatacg agattcncga atgtctcgtg ggctcggaga tgtgtataag    60
agacag                                                               66

```
<210> SEQ ID NO 928
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 928
caagcagaag acggcatacg agatgcncga atgtctcgtg ggctcggaga tgtgtataag      60
agacag                                                                 66

<210> SEQ ID NO 929
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 929
caagcagaag acggcatacg agattancga atgtctcgtg ggctcggaga tgtgtataag      60
agacag                                                                 66

<210> SEQ ID NO 930
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 930
caagcagaag acggcatacg agatgancga atgtctcgtg ggctcggaga tgtgtataag      60
agacag                                                                 66

<210> SEQ ID NO 931
<211> LENGTH: 66
<212> TYPE: DNA
<213> ORGANISM: Artificial
<220> FEATURE:
<223> OTHER INFORMATION: synthetic

<400> SEQUENCE: 931
caagcagaag acggcatacg agatcgtaga atgtctcgtg ggctcggaga tgtgtataag      60
agacag                                                                 66

<210> SEQ ID NO 932
<211> LENGTH: 66
<212> TYPE: DNA
<213> ORGANISM: Artificial
<220> FEATURE:
<223> OTHER INFORMATION: synthetic

<400> SEQUENCE: 932
caagcagaag acggcatacg agatcataga atgtctcgtg ggctcggaga tgtgtataag      60
```

```
agacag                                                              66

<210> SEQ ID NO 933
<211> LENGTH: 66
<212> TYPE: DNA
<213> ORGANISM: Artificial
<220> FEATURE:
<223> OTHER INFORMATION: synthetic

<400> SEQUENCE: 933
caagcagaag acggcatacg agatcgcaga atgtctcgtg ggctcggaga tgtgtataag      60
agacag                                                              66

<210> SEQ ID NO 934
<211> LENGTH: 66
<212> TYPE: DNA
<213> ORGANISM: Artificial
<220> FEATURE:
<223> OTHER INFORMATION: synthetic

<400> SEQUENCE: 934
caagcagaag acggcatacg agatcacaga atgtctcgtg ggctcggaga tgtgtataag      60
agacag                                                              66

<210> SEQ ID NO 935
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 935
caagcagaag acggcatacg agatccnaga atgtctcgtg ggctcggaga tgtgtataag      60
agacag                                                              66

<210> SEQ ID NO 936
<211> LENGTH: 66
<212> TYPE: DNA
<213> ORGANISM: Artificial
<220> FEATURE:
<223> OTHER INFORMATION: synthetic

<400> SEQUENCE: 936
caagcagaag acggcatacg agatcgaaga atgtctcgtg ggctcggaga tgtgtataag      60
agacag                                                              66

<210> SEQ ID NO 937
<211> LENGTH: 66
<212> TYPE: DNA
<213> ORGANISM: Artificial
<220> FEATURE:
<223> OTHER INFORMATION: synthetic

<400> SEQUENCE: 937
caagcagaag acggcatacg agatcaaaga atgtctcgtg ggctcggaga tgtgtataag      60
agacag                                                              66

<210> SEQ ID NO 938
<211> LENGTH: 66
```

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 938
caagcagaag acggcatacg agatccngca atgtctcgtg ggctcggaga tgtgtataag    60
agacag                                                               66

<210> SEQ ID NO 939
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 939
caagcagaag acggcatacg agattgncca atgtctcgtg ggctcggaga tgtgtataag    60
agacag                                                               66

<210> SEQ ID NO 940
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 940
caagcagaag acggcatacg agatggncca atgtctcgtg ggctcggaga tgtgtataag    60
agacag                                                               66

<210> SEQ ID NO 941
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 941
caagcagaag acggcatacg agattcncca atgtctcgtg ggctcggaga tgtgtataag    60
agacag                                                               66

<210> SEQ ID NO 942
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
```

<223> OTHER INFORMATION: n is a, c, g, or t

<400> SEQUENCE: 942
caagcagaag acggcatacg agatgcncca atgtctcgtg ggctcggaga tgtgtataag    60
agacag    66

<210> SEQ ID NO 943
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 943
caagcagaag acggcatacg agattancca atgtctcgtg ggctcggaga tgtgtataag    60
agacag    66

<210> SEQ ID NO 944
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 944
caagcagaag acggcatacg agatgancca atgtctcgtg ggctcggaga tgtgtataag    60
agacag    66

<210> SEQ ID NO 945
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 945
caagcagaag acggcatacg agatccnaca atgtctcgtg ggctcggaga tgtgtataag    60
agacag    66

<210> SEQ ID NO 946
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 946

```
caagcagaag acggcatacg agatnnntna atgtctcgtg ggctcggaga tgtgtataag    60
agacag                                                               66

<210> SEQ ID NO 947
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 947
caagcagaag acggcatacg agattnngna atgtctcgtg ggctcggaga tgtgtataag    60
agacag                                                               66

<210> SEQ ID NO 948
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 948
caagcagaag acggcatacg agatgnngna atgtctcgtg ggctcggaga tgtgtataag    60
agacag                                                               66

<210> SEQ ID NO 949
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 949
caagcagaag acggcatacg agatanngna atgtctcgtg ggctcggaga tgtgtataag    60
agacag                                                               66

<210> SEQ ID NO 950
<211> LENGTH: 66
<212> TYPE: DNA
<213> ORGANISM: Artificial
<220> FEATURE:
<223> OTHER INFORMATION: synthetic
<220> FEATURE:
```

```
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 950
caagcagaag acggcatacg agatanncna atgtctcgtg ggctcggaga tgtgtataag    60
agacag                                                               66

<210> SEQ ID NO 951
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 951
caagcagaag acggcatacg agattnnana atgtctcgtg ggctcggaga tgtgtataag    60
agacag                                                               66

<210> SEQ ID NO 952
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 952
caagcagaag acggcatacg agatgnnana atgtctcgtg ggctcggaga tgtgtataag    60
agacag                                                               66

<210> SEQ ID NO 953
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 953
caagcagaag acggcatacg agatannana atgtctcgtg ggctcggaga tgtgtataag    60
agacag                                                               66
```

<210> SEQ ID NO 954
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 954
caagcagaag acggcatacg agatcnngaa atgtctcgtg ggctcggaga tgtgtataag    60
agacag                                                               66

<210> SEQ ID NO 955
<211> LENGTH: 66
<212> TYPE: DNA
<213> ORGANISM: Artificial
<220> FEATURE:
<223> OTHER INFORMATION: synthetic

<400> SEQUENCE: 955
caagcagaag acggcatacg agatcctcaa atgtctcgtg ggctcggaga tgtgtataag    60
agacag                                                               66

<210> SEQ ID NO 956
<211> LENGTH: 66
<212> TYPE: DNA
<213> ORGANISM: Artificial
<220> FEATURE:
<223> OTHER INFORMATION: synthetic

<400> SEQUENCE: 956
caagcagaag acggcatacg agatccccaa atgtctcgtg ggctcggaga tgtgtataag    60
agacag                                                               66

<210> SEQ ID NO 957
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 957
caagcagaag acggcatacg agattnncaa atgtctcgtg ggctcggaga tgtgtataag    60
agacag                                                               66

<210> SEQ ID NO 958
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 958

```
caagcagaag acggcatacg agatgnncaa atgtctcgtg ggctcggaga tgtgtataag    60
agacag                                                                66

<210> SEQ ID NO 959
<211> LENGTH: 66
<212> TYPE: DNA
<213> ORGANISM: Artificial
<220> FEATURE:
<223> OTHER INFORMATION: synthetic

<400> SEQUENCE: 959
caagcagaag acggcatacg agatccacaa atgtctcgtg ggctcggaga tgtgtataag    60
agacag                                                                66

<210> SEQ ID NO 960
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 960
caagcagaag acggcatacg agatcnnaaa atgtctcgtg ggctcggaga tgtgtataag    60
agacag                                                                66

<210> SEQ ID NO 961
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(31)
<223> OTHER INFORMATION: n is a, c, g, or t

<400> SEQUENCE: 961
caagcagaag acggcatacg agatnnnnnn nggtctcgtg ggctcggaga tgtgtataag    60
agacag                                                                66

<210> SEQ ID NO 962
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(31)
<223> OTHER INFORMATION: n is a, c, g, or t

<400> SEQUENCE: 962
caagcagaag acggcatacg agatnnnnnn ncgtctcgtg ggctcggaga tgtgtataag    60
agacag                                                                66

<210> SEQ ID NO 963
<211> LENGTH: 66
<212> TYPE: DNA
<213> ORGANISM: Artificial
<220> FEATURE:
<223> OTHER INFORMATION: synthetic
```

<220> FEATURE:
<221> NAME/KEY: misc_feature
<222> LOCATION: (25)..(31)
<223> OTHER INFORMATION: n is a, c, g, or t

<400> SEQUENCE: 963
caagcagaag acggcatacg agatnnnnnn nagtctcgtg ggctcggaga tgtgtataag    60
agacag                                                              66

<210> SEQ ID NO 964
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 964
caagcagaag acggcatacg agattnnttt tgtctcgtg ggctcggaga tgtgtataag    60
agacag                                                              66

<210> SEQ ID NO 965
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 965
caagcagaag acggcatacg agatgnnttt tgtctcgtg ggctcggaga tgtgtataag    60
agacag                                                              66

<210> SEQ ID NO 966
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 966
caagcagaag acggcatacg agatannttt tgtctcgtg ggctcggaga tgtgtataag    60
agacag                                                              66

<210> SEQ ID NO 967
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 967

```
caagcagaag acggcatacg agatagngtt ttgtctcgtg ggctcggaga tgtgtataag    60
agacag                                                                66

<210> SEQ ID NO 968
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 968
caagcagaag acggcatacg agatacngtt ttgtctcgtg ggctcggaga tgtgtataag    60
agacag                                                                66

<210> SEQ ID NO 969
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 969
caagcagaag acggcatacg agataangtt ttgtctcgtg ggctcggaga tgtgtataag    60
agacag                                                                66

<210> SEQ ID NO 970
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 970
caagcagaag acggcatacg agatagnatt ttgtctcgtg ggctcggaga tgtgtataag    60
agacag                                                                66

<210> SEQ ID NO 971
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 971
caagcagaag acggcatacg agatacnatt ttgtctcgtg ggctcggaga tgtgtataag    60
agacag                                                                66

<210> SEQ ID NO 972
<211> LENGTH: 66
```

<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 972
caagcagaag acggcatacg agataanatt ttgtctcgtg ggctcggaga tgtgtataag      60
agacag                                                                66

<210> SEQ ID NO 973
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 973
caagcagaag acggcatacg agatacntgt ttgtctcgtg ggctcggaga tgtgtataag      60
agacag                                                                66

<210> SEQ ID NO 974
<211> LENGTH: 66
<212> TYPE: DNA
<213> ORGANISM: Artificial
<220> FEATURE:
<223> OTHER INFORMATION: synthetic

<400> SEQUENCE: 974
caagcagaag acggcatacg agatacttct ttgtctcgtg ggctcggaga tgtgtataag      60
agacag                                                                66

<210> SEQ ID NO 975
<211> LENGTH: 66
<212> TYPE: DNA
<213> ORGANISM: Artificial
<220> FEATURE:
<223> OTHER INFORMATION: synthetic

<400> SEQUENCE: 975
caagcagaag acggcatacg agatacctct ttgtctcgtg ggctcggaga tgtgtataag      60
agacag                                                                66

<210> SEQ ID NO 976
<211> LENGTH: 66
<212> TYPE: DNA
<213> ORGANISM: Artificial
<220> FEATURE:
<223> OTHER INFORMATION: synthetic

<400> SEQUENCE: 976
caagcagaag acggcatacg agatacatct ttgtctcgtg ggctcggaga tgtgtataag      60
agacag                                                                66

<210> SEQ ID NO 977
<211> LENGTH: 66
<212> TYPE: DNA

```
<213> ORGANISM: Artificial
<220> FEATURE:
<223> OTHER INFORMATION: synthetic

<400> SEQUENCE: 977
caagcagaag acggcatacg agattcttat ttgtctcgtg ggctcggaga tgtgtataag     60
agacag                                                               66

<210> SEQ ID NO 978
<211> LENGTH: 66
<212> TYPE: DNA
<213> ORGANISM: Artificial
<220> FEATURE:
<223> OTHER INFORMATION: synthetic

<400> SEQUENCE: 978
caagcagaag acggcatacg agatgcttat ttgtctcgtg ggctcggaga tgtgtataag     60
agacag                                                               66

<210> SEQ ID NO 979
<211> LENGTH: 66
<212> TYPE: DNA
<213> ORGANISM: Artificial
<220> FEATURE:
<223> OTHER INFORMATION: synthetic

<400> SEQUENCE: 979
caagcagaag acggcatacg agattcctat ttgtctcgtg ggctcggaga tgtgtataag     60
agacag                                                               66

<210> SEQ ID NO 980
<211> LENGTH: 66
<212> TYPE: DNA
<213> ORGANISM: Artificial
<220> FEATURE:
<223> OTHER INFORMATION: synthetic

<400> SEQUENCE: 980
caagcagaag acggcatacg agatgcctat ttgtctcgtg ggctcggaga tgtgtataag     60
agacag                                                               66

<210> SEQ ID NO 981
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 981
caagcagaag acggcatacg agatanntat ttgtctcgtg ggctcggaga tgtgtataag     60
agacag                                                               66

<210> SEQ ID NO 982
<211> LENGTH: 66
<212> TYPE: DNA
<213> ORGANISM: Artificial
<220> FEATURE:
<223> OTHER INFORMATION: synthetic

<400> SEQUENCE: 982
```

```
caagcagaag acggcatacg agattcatat ttgtctcgtg ggctcggaga tgtgtataag    60
agacag                                                              66

<210> SEQ ID NO 983
<211> LENGTH: 66
<212> TYPE: DNA
<213> ORGANISM: Artificial
<220> FEATURE:
<223> OTHER INFORMATION: synthetic

<400> SEQUENCE: 983
caagcagaag acggcatacg agatgcatat ttgtctcgtg ggctcggaga tgtgtataag    60
agacag                                                              66

<210> SEQ ID NO 984
<211> LENGTH: 66
<212> TYPE: DNA
<213> ORGANISM: Artificial
<220> FEATURE:
<223> OTHER INFORMATION: synthetic

<400> SEQUENCE: 984
caagcagaag acggcatacg agatagtttg ttgtctcgtg ggctcggaga tgtgtataag    60
agacag                                                              66

<210> SEQ ID NO 985
<211> LENGTH: 66
<212> TYPE: DNA
<213> ORGANISM: Artificial
<220> FEATURE:
<223> OTHER INFORMATION: synthetic

<400> SEQUENCE: 985
caagcagaag acggcatacg agataatttg ttgtctcgtg ggctcggaga tgtgtataag    60
agacag                                                              66

<210> SEQ ID NO 986
<211> LENGTH: 66
<212> TYPE: DNA
<213> ORGANISM: Artificial
<220> FEATURE:
<223> OTHER INFORMATION: synthetic

<400> SEQUENCE: 986
caagcagaag acggcatacg agatagcttg ttgtctcgtg ggctcggaga tgtgtataag    60
agacag                                                              66

<210> SEQ ID NO 987
<211> LENGTH: 66
<212> TYPE: DNA
<213> ORGANISM: Artificial
<220> FEATURE:
<223> OTHER INFORMATION: synthetic

<400> SEQUENCE: 987
caagcagaag acggcatacg agataacttg ttgtctcgtg ggctcggaga tgtgtataag    60
agacag                                                              66

<210> SEQ ID NO 988
<211> LENGTH: 66
<212> TYPE: DNA
```

```
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 988
caagcagaag acggcatacg agatacnttg ttgtctcgtg ggctcggaga tgtgtataag    60
agacag                                                                66

<210> SEQ ID NO 989
<211> LENGTH: 66
<212> TYPE: DNA
<213> ORGANISM: Artificial
<220> FEATURE:
<223> OTHER INFORMATION: synthetic

<400> SEQUENCE: 989
caagcagaag acggcatacg agatagattg ttgtctcgtg ggctcggaga tgtgtataag    60
agacag                                                                66

<210> SEQ ID NO 990
<211> LENGTH: 66
<212> TYPE: DNA
<213> ORGANISM: Artificial
<220> FEATURE:
<223> OTHER INFORMATION: synthetic

<400> SEQUENCE: 990
caagcagaag acggcatacg agataaattg ttgtctcgtg ggctcggaga tgtgtataag    60
agacag                                                                66

<210> SEQ ID NO 991
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 991
caagcagaag acggcatacg agatacnttc ttgtctcgtg ggctcggaga tgtgtataag    60
agacag                                                                66

<210> SEQ ID NO 992
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 992
caagcagaag acggcatacg agattcntta ttgtctcgtg ggctcggaga tgtgtataag    60
agacag                                                                66
```

```
<210> SEQ ID NO 993
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 993
caagcagaag acggcatacg agatgcntta ttgtctcgtg ggctcggaga tgtgtataag      60
agacag                                                                66

<210> SEQ ID NO 994
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 994
caagcagaag acggcatacg agatanntta ttgtctcgtg ggctcggaga tgtgtataag      60
agacag                                                                66

<210> SEQ ID NO 995
<211> LENGTH: 66
<212> TYPE: DNA
<213> ORGANISM: Artificial
<220> FEATURE:
<223> OTHER INFORMATION: synthetic

<400> SEQUENCE: 995
caagcagaag acggcatacg agatacttaa ttgtctcgtg ggctcggaga tgtgtataag      60
agacag                                                                66

<210> SEQ ID NO 996
<211> LENGTH: 66
<212> TYPE: DNA
<213> ORGANISM: Artificial
<220> FEATURE:
<223> OTHER INFORMATION: synthetic

<400> SEQUENCE: 996
caagcagaag acggcatacg agatacctaa ttgtctcgtg ggctcggaga tgtgtataag      60
agacag                                                                66

<210> SEQ ID NO 997
<211> LENGTH: 66
<212> TYPE: DNA
<213> ORGANISM: Artificial
<220> FEATURE:
<223> OTHER INFORMATION: synthetic

<400> SEQUENCE: 997
caagcagaag acggcatacg agatacataa ttgtctcgtg ggctcggaga tgtgtataag      60
agacag                                                                66

<210> SEQ ID NO 998
```

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 998
caagcagaag acggcatacg agatagnttt gtgtctcgtg ggctcggaga tgtgtataag    60
agacag                                                              66

<210> SEQ ID NO 999
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 999
caagcagaag acggcatacg agatacnttt gtgtctcgtg ggctcggaga tgtgtataag    60
agacag                                                              66

<210> SEQ ID NO 1000
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1000
caagcagaag acggcatacg agataanttt gtgtctcgtg ggctcggaga tgtgtataag    60
agacag                                                              66

<210> SEQ ID NO 1001
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1001
caagcagaag acggcatacg agattnnttt atgtctcgtg ggctcggaga tgtgtataag    60
agacag                                                              66

<210> SEQ ID NO 1002
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

<222> LOCATION: (26)..(27)
<223> OTHER INFORMATION: n is a, c, g, or t

<400> SEQUENCE: 1002
caagcagaag acggcatacg agatgnnttt atgtctcgtg ggctcggaga tgtgtataag    60
agacag    66

<210> SEQ ID NO 1003
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1003
caagcagaag acggcatacg agatannttt atgtctcgtg ggctcggaga tgtgtataag    60
agacag    66

<210> SEQ ID NO 1004
<211> LENGTH: 66
<212> TYPE: DNA
<213> ORGANISM: Artificial
<220> FEATURE:
<223> OTHER INFORMATION: synthetic

<400> SEQUENCE: 1004
caagcagaag acggcatacg agatattgtt atgtctcgtg ggctcggaga tgtgtataag    60
agacag    66

<210> SEQ ID NO 1005
<211> LENGTH: 66
<212> TYPE: DNA
<213> ORGANISM: Artificial
<220> FEATURE:
<223> OTHER INFORMATION: synthetic

<400> SEQUENCE: 1005
caagcagaag acggcatacg agatatcgtt atgtctcgtg ggctcggaga tgtgtataag    60
agacag    66

<210> SEQ ID NO 1006
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1006
caagcagaag acggcatacg agatagngtt atgtctcgtg ggctcggaga tgtgtataag    60
agacag    66

<210> SEQ ID NO 1007
<211> LENGTH: 66
<212> TYPE: DNA
<213> ORGANISM: Artificial
<220> FEATURE:

<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1007
caagcagaag acggcatacg agatacngtt atgtctcgtg ggctcggaga tgtgtataag     60
agacag                                                                66

<210> SEQ ID NO 1008
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1008
caagcagaag acggcatacg agataangtt atgtctcgtg ggctcggaga tgtgtataag     60
agacag                                                                66

<210> SEQ ID NO 1009
<211> LENGTH: 66
<212> TYPE: DNA
<213> ORGANISM: Artificial
<220> FEATURE:
<223> OTHER INFORMATION: synthetic

<400> SEQUENCE: 1009
caagcagaag acggcatacg agatatagtt atgtctcgtg ggctcggaga tgtgtataag     60
agacag                                                                66

<210> SEQ ID NO 1010
<211> LENGTH: 66
<212> TYPE: DNA
<213> ORGANISM: Artificial
<220> FEATURE:
<223> OTHER INFORMATION: synthetic

<400> SEQUENCE: 1010
caagcagaag acggcatacg agatattatt atgtctcgtg ggctcggaga tgtgtataag     60
agacag                                                                66

<210> SEQ ID NO 1011
<211> LENGTH: 66
<212> TYPE: DNA
<213> ORGANISM: Artificial
<220> FEATURE:
<223> OTHER INFORMATION: synthetic

<400> SEQUENCE: 1011
caagcagaag acggcatacg agatatcatt atgtctcgtg ggctcggaga tgtgtataag     60
agacag                                                                66

<210> SEQ ID NO 1012
<211> LENGTH: 66
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (27)..(27)
<223> OTHER INFORMATION: n is a, c, g, or t

<400> SEQUENCE: 1012
caagcagaag acggcatacg agatagnatt atgtctcgtg ggctcggaga tgtgtataag    60
agacag                                                               66

<210> SEQ ID NO 1013
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1013
caagcagaag acggcatacg agatacnatt atgtctcgtg ggctcggaga tgtgtataag    60
agacag                                                               66

<210> SEQ ID NO 1014
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1014
caagcagaag acggcatacg agataanatt atgtctcgtg ggctcggaga tgtgtataag    60
agacag                                                               66

<210> SEQ ID NO 1015
<211> LENGTH: 66
<212> TYPE: DNA
<213> ORGANISM: Artificial
<220> FEATURE:
<223> OTHER INFORMATION: synthetic

<400> SEQUENCE: 1015
caagcagaag acggcatacg agatataatt atgtctcgtg ggctcggaga tgtgtataag    60
agacag                                                               66

<210> SEQ ID NO 1016
<211> LENGTH: 66
<212> TYPE: DNA
<213> ORGANISM: Artificial
<220> FEATURE:
<223> OTHER INFORMATION: synthetic

<400> SEQUENCE: 1016
caagcagaag acggcatacg agatagttgt atgtctcgtg ggctcggaga tgtgtataag    60
agacag                                                               66

<210> SEQ ID NO 1017
<211> LENGTH: 66
<212> TYPE: DNA
```

```
<213> ORGANISM: Artificial
<220> FEATURE:
<223> OTHER INFORMATION: synthetic

<400> SEQUENCE: 1017
caagcagaag acggcatacg agataattgt atgtctcgtg ggctcggaga tgtgtataag      60
agacag                                                                66

<210> SEQ ID NO 1018
<211> LENGTH: 66
<212> TYPE: DNA
<213> ORGANISM: Artificial
<220> FEATURE:
<223> OTHER INFORMATION: synthetic

<400> SEQUENCE: 1018
caagcagaag acggcatacg agatagctgt atgtctcgtg ggctcggaga tgtgtataag      60
agacag                                                                66

<210> SEQ ID NO 1019
<211> LENGTH: 66
<212> TYPE: DNA
<213> ORGANISM: Artificial
<220> FEATURE:
<223> OTHER INFORMATION: synthetic

<400> SEQUENCE: 1019
caagcagaag acggcatacg agataactgt atgtctcgtg ggctcggaga tgtgtataag      60
agacag                                                                66

<210> SEQ ID NO 1020
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1020
caagcagaag acggcatacg agatacntgt atgtctcgtg ggctcggaga tgtgtataag      60
agacag                                                                66

<210> SEQ ID NO 1021
<211> LENGTH: 66
<212> TYPE: DNA
<213> ORGANISM: Artificial
<220> FEATURE:
<223> OTHER INFORMATION: synthetic

<400> SEQUENCE: 1021
caagcagaag acggcatacg agatagatgt atgtctcgtg ggctcggaga tgtgtataag      60
agacag                                                                66

<210> SEQ ID NO 1022
<211> LENGTH: 66
<212> TYPE: DNA
<213> ORGANISM: Artificial
<220> FEATURE:
<223> OTHER INFORMATION: synthetic

<400> SEQUENCE: 1022
```

-continued

```
caagcagaag acggcatacg agataaatgt atgtctcgtg ggctcggaga tgtgtataag    60
agacag                                                               66

<210> SEQ ID NO 1023
<211> LENGTH: 66
<212> TYPE: DNA
<213> ORGANISM: Artificial
<220> FEATURE:
<223> OTHER INFORMATION: synthetic

<400> SEQUENCE: 1023
caagcagaag acggcatacg agatagttct atgtctcgtg ggctcggaga tgtgtataag    60
agacag                                                               66

<210> SEQ ID NO 1024
<211> LENGTH: 66
<212> TYPE: DNA
<213> ORGANISM: Artificial
<220> FEATURE:
<223> OTHER INFORMATION: synthetic

<400> SEQUENCE: 1024
caagcagaag acggcatacg agataattct atgtctcgtg ggctcggaga tgtgtataag    60
agacag                                                               66

<210> SEQ ID NO 1025
<211> LENGTH: 66
<212> TYPE: DNA
<213> ORGANISM: Artificial
<220> FEATURE:
<223> OTHER INFORMATION: synthetic

<400> SEQUENCE: 1025
caagcagaag acggcatacg agatagctct atgtctcgtg ggctcggaga tgtgtataag    60
agacag                                                               66

<210> SEQ ID NO 1026
<211> LENGTH: 66
<212> TYPE: DNA
<213> ORGANISM: Artificial
<220> FEATURE:
<223> OTHER INFORMATION: synthetic

<400> SEQUENCE: 1026
caagcagaag acggcatacg agataactct atgtctcgtg ggctcggaga tgtgtataag    60
agacag                                                               66

<210> SEQ ID NO 1027
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1027
caagcagaag acggcatacg agatacntct atgtctcgtg ggctcggaga tgtgtataag    60
agacag                                                               66
```

<210> SEQ ID NO 1028
<211> LENGTH: 66
<212> TYPE: DNA
<213> ORGANISM: Artificial
<220> FEATURE:
<223> OTHER INFORMATION: synthetic

<400> SEQUENCE: 1028
caagcagaag acggcatacg agatagatct atgtctcgtg ggctcggaga tgtgtataag    60
agacag                                                               66

<210> SEQ ID NO 1029
<211> LENGTH: 66
<212> TYPE: DNA
<213> ORGANISM: Artificial
<220> FEATURE:
<223> OTHER INFORMATION: synthetic

<400> SEQUENCE: 1029
caagcagaag acggcatacg agataaatct atgtctcgtg ggctcggaga tgtgtataag    60
agacag                                                               66

<210> SEQ ID NO 1030
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1030
caagcagaag acggcatacg agattcntat atgtctcgtg ggctcggaga tgtgtataag    60
agacag                                                               66

<210> SEQ ID NO 1031
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1031
caagcagaag acggcatacg agatgcntat atgtctcgtg ggctcggaga tgtgtataag    60
agacag                                                               66

<210> SEQ ID NO 1032
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1032
caagcagaag acggcatacg agatanntat atgtctcgtg ggctcggaga tgtgtataag    60
agacag 66

<210> SEQ ID NO 1033
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1033
caagcagaag acggcatacg agatagnttg atgtctcgtg ggctcggaga tgtgtataag    60
agacag    66

<210> SEQ ID NO 1034
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1034
caagcagaag acggcatacg agatacnttg atgtctcgtg ggctcggaga tgtgtataag    60
agacag    66

<210> SEQ ID NO 1035
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1035
caagcagaag acggcatacg agataanttg atgtctcgtg ggctcggaga tgtgtataag    60
agacag    66

<210> SEQ ID NO 1036
<211> LENGTH: 66
<212> TYPE: DNA
<213> ORGANISM: Artificial
<220> FEATURE:
<223> OTHER INFORMATION: synthetic

<400> SEQUENCE: 1036
caagcagaag acggcatacg agatagtttc atgtctcgtg ggctcggaga tgtgtataag    60
agacag    66

<210> SEQ ID NO 1037
<211> LENGTH: 66
<212> TYPE: DNA
<213> ORGANISM: Artificial
<220> FEATURE:
<223> OTHER INFORMATION: synthetic

```
<400> SEQUENCE: 1037
caagcagaag acggcatacg agataatttc atgtctcgtg ggctcggaga tgtgtataag    60
agacag                                                                66

<210> SEQ ID NO 1038
<211> LENGTH: 66
<212> TYPE: DNA
<213> ORGANISM: Artificial
<220> FEATURE:
<223> OTHER INFORMATION: synthetic

<400> SEQUENCE: 1038
caagcagaag acggcatacg agatagcttc atgtctcgtg ggctcggaga tgtgtataag    60
agacag                                                                66

<210> SEQ ID NO 1039
<211> LENGTH: 66
<212> TYPE: DNA
<213> ORGANISM: Artificial
<220> FEATURE:
<223> OTHER INFORMATION: synthetic

<400> SEQUENCE: 1039
caagcagaag acggcatacg agataacttc atgtctcgtg ggctcggaga tgtgtataag    60
agacag                                                                66

<210> SEQ ID NO 1040
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1040
caagcagaag acggcatacg agatacnttc atgtctcgtg ggctcggaga tgtgtataag    60
agacag                                                                66

<210> SEQ ID NO 1041
<211> LENGTH: 66
<212> TYPE: DNA
<213> ORGANISM: Artificial
<220> FEATURE:
<223> OTHER INFORMATION: synthetic

<400> SEQUENCE: 1041
caagcagaag acggcatacg agatagattc atgtctcgtg ggctcggaga tgtgtataag    60
agacag                                                                66

<210> SEQ ID NO 1042
<211> LENGTH: 66
<212> TYPE: DNA
<213> ORGANISM: Artificial
<220> FEATURE:
<223> OTHER INFORMATION: synthetic

<400> SEQUENCE: 1042
caagcagaag acggcatacg agataaattc atgtctcgtg ggctcggaga tgtgtataag    60
agacag                                                                66
```

<210> SEQ ID NO 1043
<211> LENGTH: 66
<212> TYPE: DNA
<213> ORGANISM: Artificial
<220> FEATURE:
<223> OTHER INFORMATION: synthetic

<400> SEQUENCE: 1043
caagcagaag acggcatacg agattgttta atgtctcgtg ggctcggaga tgtgtataag    60
agacag                                                                66

<210> SEQ ID NO 1044
<211> LENGTH: 66
<212> TYPE: DNA
<213> ORGANISM: Artificial
<220> FEATURE:
<223> OTHER INFORMATION: synthetic

<400> SEQUENCE: 1044
caagcagaag acggcatacg agatggttta atgtctcgtg ggctcggaga tgtgtataag    60
agacag                                                                66

<210> SEQ ID NO 1045
<211> LENGTH: 66
<212> TYPE: DNA
<213> ORGANISM: Artificial
<220> FEATURE:
<223> OTHER INFORMATION: synthetic

<400> SEQUENCE: 1045
caagcagaag acggcatacg agattattta atgtctcgtg ggctcggaga tgtgtataag    60
agacag                                                                66

<210> SEQ ID NO 1046
<211> LENGTH: 66
<212> TYPE: DNA
<213> ORGANISM: Artificial
<220> FEATURE:
<223> OTHER INFORMATION: synthetic

<400> SEQUENCE: 1046
caagcagaag acggcatacg agatgattta atgtctcgtg ggctcggaga tgtgtataag    60
agacag                                                                66

<210> SEQ ID NO 1047
<211> LENGTH: 66
<212> TYPE: DNA
<213> ORGANISM: Artificial
<220> FEATURE:
<223> OTHER INFORMATION: synthetic

<400> SEQUENCE: 1047
caagcagaag acggcatacg agattgctta atgtctcgtg ggctcggaga tgtgtataag    60
agacag                                                                66

<210> SEQ ID NO 1048
<211> LENGTH: 66
<212> TYPE: DNA
<213> ORGANISM: Artificial
<220> FEATURE:
<223> OTHER INFORMATION: synthetic

<400> SEQUENCE: 1048
caagcagaag acggcatacg agatggctta atgtctcgtg ggctcggaga tgtgtataag    60
agacag                                                               66

<210> SEQ ID NO 1049
<211> LENGTH: 66
<212> TYPE: DNA
<213> ORGANISM: Artificial
<220> FEATURE:
<223> OTHER INFORMATION: synthetic

<400> SEQUENCE: 1049
caagcagaag acggcatacg agattactta atgtctcgtg ggctcggaga tgtgtataag    60
agacag                                                               66

<210> SEQ ID NO 1050
<211> LENGTH: 66
<212> TYPE: DNA
<213> ORGANISM: Artificial
<220> FEATURE:
<223> OTHER INFORMATION: synthetic

<400> SEQUENCE: 1050
caagcagaag acggcatacg agatgactta atgtctcgtg ggctcggaga tgtgtataag    60
agacag                                                               66

<210> SEQ ID NO 1051
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1051
caagcagaag acggcatacg agattcntta atgtctcgtg ggctcggaga tgtgtataag    60
agacag                                                               66

<210> SEQ ID NO 1052
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1052
caagcagaag acggcatacg agatgcntta atgtctcgtg ggctcggaga tgtgtataag    60
agacag                                                               66

<210> SEQ ID NO 1053
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature

```
<222> LOCATION: (26)..(27)
<223> OTHER INFORMATION: n is a, c, g, or t

<400> SEQUENCE: 1053
caagcagaag acggcatacg agatannttta atgtctcgtg ggctcggaga tgtgtataag    60
agacag                                                                66

<210> SEQ ID NO 1054
<211> LENGTH: 66
<212> TYPE: DNA
<213> ORGANISM: Artificial
<220> FEATURE:
<223> OTHER INFORMATION: synthetic

<400> SEQUENCE: 1054
caagcagaag acggcatacg agattgatta atgtctcgtg ggctcggaga tgtgtataag    60
agacag                                                                66

<210> SEQ ID NO 1055
<211> LENGTH: 66
<212> TYPE: DNA
<213> ORGANISM: Artificial
<220> FEATURE:
<223> OTHER INFORMATION: synthetic

<400> SEQUENCE: 1055
caagcagaag acggcatacg agatggatta atgtctcgtg ggctcggaga tgtgtataag    60
agacag                                                                66

<210> SEQ ID NO 1056
<211> LENGTH: 66
<212> TYPE: DNA
<213> ORGANISM: Artificial
<220> FEATURE:
<223> OTHER INFORMATION: synthetic

<400> SEQUENCE: 1056
caagcagaag acggcatacg agattaatta atgtctcgtg ggctcggaga tgtgtataag    60
agacag                                                                66

<210> SEQ ID NO 1057
<211> LENGTH: 66
<212> TYPE: DNA
<213> ORGANISM: Artificial
<220> FEATURE:
<223> OTHER INFORMATION: synthetic

<400> SEQUENCE: 1057
caagcagaag acggcatacg agatgaatta atgtctcgtg ggctcggaga tgtgtataag    60
agacag                                                                66

<210> SEQ ID NO 1058
<211> LENGTH: 66
<212> TYPE: DNA
<213> ORGANISM: Artificial
<220> FEATURE:
<223> OTHER INFORMATION: synthetic

<400> SEQUENCE: 1058
caagcagaag acggcatacg agatagttaa atgtctcgtg ggctcggaga tgtgtataag    60
agacag                                                                66
```

<210> SEQ ID NO 1059
<211> LENGTH: 66
<212> TYPE: DNA
<213> ORGANISM: Artificial
<220> FEATURE:
<223> OTHER INFORMATION: synthetic

<400> SEQUENCE: 1059
caagcagaag acggcatacg agataattaa atgtctcgtg ggctcggaga tgtgtataag    60
agacag                                                                66

<210> SEQ ID NO 1060
<211> LENGTH: 66
<212> TYPE: DNA
<213> ORGANISM: Artificial
<220> FEATURE:
<223> OTHER INFORMATION: synthetic

<400> SEQUENCE: 1060
caagcagaag acggcatacg agatagctaa atgtctcgtg ggctcggaga tgtgtataag    60
agacag                                                                66

<210> SEQ ID NO 1061
<211> LENGTH: 66
<212> TYPE: DNA
<213> ORGANISM: Artificial
<220> FEATURE:
<223> OTHER INFORMATION: synthetic

<400> SEQUENCE: 1061
caagcagaag acggcatacg agataactaa atgtctcgtg ggctcggaga tgtgtataag    60
agacag                                                                66

<210> SEQ ID NO 1062
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1062
caagcagaag acggcatacg agatacntaa atgtctcgtg ggctcggaga tgtgtataag    60
agacag                                                                66

<210> SEQ ID NO 1063
<211> LENGTH: 66
<212> TYPE: DNA
<213> ORGANISM: Artificial
<220> FEATURE:
<223> OTHER INFORMATION: synthetic

<400> SEQUENCE: 1063
caagcagaag acggcatacg agatagataa atgtctcgtg ggctcggaga tgtgtataag    60
agacag                                                                66

<210> SEQ ID NO 1064
<211> LENGTH: 66
<212> TYPE: DNA
<213> ORGANISM: Artificial -continued
<220> FEATURE:
<223> OTHER INFORMATION: synthetic

<400> SEQUENCE: 1064
caagcagaag acggcatacg agataaataa atgtctcgtg ggctcggaga tgtgtataag    60
agacag                                                               66

<210> SEQ ID NO 1065
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(30)
<223> OTHER INFORMATION: n is a, c, g, or t

<400> SEQUENCE: 1065
caagcagaag acggcatacg agatnnnnnn tggtctcgtg ggctcggaga tgtgtataag    60
agacag                                                               66

<210> SEQ ID NO 1066
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(30)
<223> OTHER INFORMATION: n is a, c, g, or t

<400> SEQUENCE: 1066
caagcagaag acggcatacg agatnnnnnn gggtctcgtg ggctcggaga tgtgtataag    60
agacag                                                               66

<210> SEQ ID NO 1067
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(29)
<223> OTHER INFORMATION: n is a, c, g, or t

<400> SEQUENCE: 1067
caagcagaag acggcatacg agatnnnnnt cggtctcgtg ggctcggaga tgtgtataag    60
agacag                                                               66

<210> SEQ ID NO 1068
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1068
caagcagaag acggcatacg agatcnnctg cggtctcgtg ggctcggaga tgtgtataag    60

<210> SEQ ID NO 1069
<211> LENGTH: 66
<212> TYPE: DNA
<213> ORGANISM: Artificial
<220> FEATURE:
<223> OTHER INFORMATION: synthetic

<400> SEQUENCE: 1069
caagcagaag acggcatacg agatcgtcgg cggtctcgtg ggctcggaga tgtgtataag    60
agacag                                                              66

<210> SEQ ID NO 1070
<211> LENGTH: 66
<212> TYPE: DNA
<213> ORGANISM: Artificial
<220> FEATURE:
<223> OTHER INFORMATION: synthetic

<400> SEQUENCE: 1070
caagcagaag acggcatacg agatcatcgg cggtctcgtg ggctcggaga tgtgtataag    60
agacag                                                              66

<210> SEQ ID NO 1071
<211> LENGTH: 66
<212> TYPE: DNA
<213> ORGANISM: Artificial
<220> FEATURE:
<223> OTHER INFORMATION: synthetic

<400> SEQUENCE: 1071
caagcagaag acggcatacg agatcgccgg cggtctcgtg ggctcggaga tgtgtataag    60
agacag                                                              66

<210> SEQ ID NO 1072
<211> LENGTH: 66
<212> TYPE: DNA
<213> ORGANISM: Artificial
<220> FEATURE:
<223> OTHER INFORMATION: synthetic

<400> SEQUENCE: 1072
caagcagaag acggcatacg agatcaccgg cggtctcgtg ggctcggaga tgtgtataag    60
agacag                                                              66

<210> SEQ ID NO 1073
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1073
caagcagaag acggcatacg agatccncgg cggtctcgtg ggctcggaga tgtgtataag    60
agacag                                                              66

<210> SEQ ID NO 1074
<211> LENGTH: 66

```
<212> TYPE: DNA
<213> ORGANISM: Artificial
<220> FEATURE:
<223> OTHER INFORMATION: synthetic

<400> SEQUENCE: 1074
caagcagaag acggcatacg agatcgacgg cggtctcgtg ggctcggaga tgtgtataag    60
agacag                                                               66

<210> SEQ ID NO 1075
<211> LENGTH: 66
<212> TYPE: DNA
<213> ORGANISM: Artificial
<220> FEATURE:
<223> OTHER INFORMATION: synthetic

<400> SEQUENCE: 1075
caagcagaag acggcatacg agatcaacgg cggtctcgtg ggctcggaga tgtgtataag    60
agacag                                                               66

<210> SEQ ID NO 1076
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1076
caagcagaag acggcatacg agatccnccg cggtctcgtg ggctcggaga tgtgtataag    60
agacag                                                               66

<210> SEQ ID NO 1077
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1077
caagcagaag acggcatacg agatnnntng cggtctcgtg ggctcggaga tgtgtataag    60
agacag                                                               66

<210> SEQ ID NO 1078
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
```

```
<223> OTHER INFORMATION: n is a, c, g, or t

<400> SEQUENCE: 1078
caagcagaag acggcatacg agatnnngng cggtctcgtg ggctcggaga tgtgtataag    60
agacag                                                               66

<210> SEQ ID NO 1079
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1079
caagcagaag acggcatacg agattnncng cggtctcgtg ggctcggaga tgtgtataag    60
agacag                                                               66

<210> SEQ ID NO 1080
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1080
caagcagaag acggcatacg agatgnncng cggtctcgtg ggctcggaga tgtgtataag    60
agacag                                                               66

<210> SEQ ID NO 1081
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1081
caagcagaag acggcatacg agatanncng cggtctcgtg ggctcggaga tgtgtataag    60
agacag                                                               66

<210> SEQ ID NO 1082
<211> LENGTH: 66
<212> TYPE: DNA
<213> ORGANISM: Artificial
```

```
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1082
caagcagaag acggcatacg agatnnnang cggtctcgtg ggctcggaga tgtgtataag    60
agacag                                                              66

<210> SEQ ID NO 1083
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1083
caagcagaag acggcatacg agatcnncag cggtctcgtg ggctcggaga tgtgtataag    60
agacag                                                              66

<210> SEQ ID NO 1084
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1084
caagcagaag acggcatacg agatcnnctc cggtctcgtg ggctcggaga tgtgtataag    60
agacag                                                              66

<210> SEQ ID NO 1085
<211> LENGTH: 66
<212> TYPE: DNA
<213> ORGANISM: Artificial
<220> FEATURE:
<223> OTHER INFORMATION: synthetic

<400> SEQUENCE: 1085
caagcagaag acggcatacg agatcctcgc cggtctcgtg ggctcggaga tgtgtataag    60
agacag                                                              66

<210> SEQ ID NO 1086
<211> LENGTH: 66
<212> TYPE: DNA
<213> ORGANISM: Artificial
<220> FEATURE:
<223> OTHER INFORMATION: synthetic

<400> SEQUENCE: 1086
caagcagaag acggcatacg agatccccgc cggtctcgtg ggctcggaga tgtgtataag    60
```

```
agacag                                                                  66

<210> SEQ ID NO 1087
<211> LENGTH: 66
<212> TYPE: DNA
<213> ORGANISM: Artificial
<220> FEATURE:
<223> OTHER INFORMATION: synthetic

<400> SEQUENCE: 1087
caagcagaag acggcatacg agatccacgc cggtctcgtg ggctcggaga tgtgtataag       60
agacag                                                                  66

<210> SEQ ID NO 1088
<211> LENGTH: 66
<212> TYPE: DNA
<213> ORGANISM: Artificial
<220> FEATURE:
<223> OTHER INFORMATION: synthetic

<400> SEQUENCE: 1088
caagcagaag acggcatacg agatcctccc cggtctcgtg ggctcggaga tgtgtataag       60
agacag                                                                  66

<210> SEQ ID NO 1089
<211> LENGTH: 66
<212> TYPE: DNA
<213> ORGANISM: Artificial
<220> FEATURE:
<223> OTHER INFORMATION: synthetic

<400> SEQUENCE: 1089
caagcagaag acggcatacg agatccccccc cggtctcgtg ggctcggaga tgtgtataag      60
agacag                                                                  66

<210> SEQ ID NO 1090
<211> LENGTH: 66
<212> TYPE: DNA
<213> ORGANISM: Artificial
<220> FEATURE:
<223> OTHER INFORMATION: synthetic

<400> SEQUENCE: 1090
caagcagaag acggcatacg agatccaccc cggtctcgtg ggctcggaga tgtgtataag       60
agacag                                                                  66

<210> SEQ ID NO 1091
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1091
caagcagaag acggcatacg agatnnntnc cggtctcgtg ggctcggaga tgtgtataag       60
agacag                                                                  66
```

<210> SEQ ID NO 1092
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1092
caagcagaag acggcatacg agatnnngnc cggtctcgtg ggctcggaga tgtgtataag    60
agacag                                                              66

<210> SEQ ID NO 1093
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1093
caagcagaag acggcatacg agattnncnc cggtctcgtg ggctcggaga tgtgtataag    60
agacag                                                              66

<210> SEQ ID NO 1094
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1094
caagcagaag acggcatacg agatgnncnc cggtctcgtg ggctcggaga tgtgtataag    60
agacag                                                              66

<210> SEQ ID NO 1095
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:

```
<221> NAME/KEY: misc_feature
<222> LOCATION: (29)..(29)
<223> OTHER INFORMATION: n is a, c, g, or t

<400> SEQUENCE: 1095
caagcagaag acggcatacg agatanncnc cggtctcgtg ggctcggaga tgtgtataag    60
agacag                                                              66

<210> SEQ ID NO 1096
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1096
caagcagaag acggcatacg agatnnnanc cggtctcgtg ggctcggaga tgtgtataag    60
agacag                                                              66

<210> SEQ ID NO 1097
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1097
caagcagaag acggcatacg agatcnncac cggtctcgtg ggctcggaga tgtgtataag    60
agacag                                                              66

<210> SEQ ID NO 1098
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(29)
<223> OTHER INFORMATION: n is a, c, g, or t

<400> SEQUENCE: 1098
caagcagaag acggcatacg agatnnnnna cggtctcgtg ggctcggaga tgtgtataag    60
agacag                                                              66

<210> SEQ ID NO 1099
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(30)
<223> OTHER INFORMATION: n is a, c, g, or t
```

<400> SEQUENCE: 1099
caagcagaag acggcatacg agatnnnnnnn aggtctcgtg ggctcggaga tgtgtataag     60
agacag                                                                66

<210> SEQ ID NO 1100
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(29)
<223> OTHER INFORMATION: n is a, c, g, or t

<400> SEQUENCE: 1100
caagcagaag acggcatacg agatnnnnnt tcgtctcgtg ggctcggaga tgtgtataag     60
agacag                                                                66

<210> SEQ ID NO 1101
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(29)
<223> OTHER INFORMATION: n is a, c, g, or t

<400> SEQUENCE: 1101
caagcagaag acggcatacg agatnnnnng tcgtctcgtg ggctcggaga tgtgtataag     60
agacag                                                                66

<210> SEQ ID NO 1102
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1102
caagcagaag acggcatacg agatcnnctc tcgtctcgtg ggctcggaga tgtgtataag     60
agacag                                                                66

<210> SEQ ID NO 1103
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1103
caagcagaag acggcatacg agatcnncgc tcgtctcgtg ggctcggaga tgtgtataag     60
agacag                                                                66

<210> SEQ ID NO 1104
<211> LENGTH: 66
<212> TYPE: DNA
<213> ORGANISM: Artificial
<220> FEATURE:
<223> OTHER INFORMATION: synthetic

<400> SEQUENCE: 1104
caagcagaag acggcatacg agatcttccc tcgtctcgtg ggctcggaga tgtgtataag     60
agacag                                                                66

<210> SEQ ID NO 1105
<211> LENGTH: 66
<212> TYPE: DNA
<213> ORGANISM: Artificial
<220> FEATURE:
<223> OTHER INFORMATION: synthetic

<400> SEQUENCE: 1105
caagcagaag acggcatacg agatctcccc tcgtctcgtg ggctcggaga tgtgtataag     60
agacag                                                                66

<210> SEQ ID NO 1106
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1106
caagcagaag acggcatacg agatcgnccc tcgtctcgtg ggctcggaga tgtgtataag     60
agacag                                                                66

<210> SEQ ID NO 1107
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1107
caagcagaag acggcatacg agatccnccc tcgtctcgtg ggctcggaga tgtgtataag     60
agacag                                                                66

<210> SEQ ID NO 1108
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1108
caagcagaag acggcatacg agatcanccc tcgtctcgtg ggctcggaga tgtgtataag     60
agacag                                                              66

<210> SEQ ID NO 1109
<211> LENGTH: 66
<212> TYPE: DNA
<213> ORGANISM: Artificial
<220> FEATURE:
<223> OTHER INFORMATION: synthetic

<400> SEQUENCE: 1109
caagcagaag acggcatacg agatctaccc tcgtctcgtg ggctcggaga tgtgtataag    60
agacag                                                              66

<210> SEQ ID NO 1110
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1110
caagcagaag acggcatacg agatnnntnc tcgtctcgtg ggctcggaga tgtgtataag    60
agacag                                                              66

<210> SEQ ID NO 1111
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1111
caagcagaag acggcatacg agatnnngnc tcgtctcgtg ggctcggaga tgtgtataag    60
agacag                                                              66

<210> SEQ ID NO 1112
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1112
caagcagaag acggcatacg agattnncnc tcgtctcgtg ggctcggaga tgtgtataag    60
agacag    66

<210> SEQ ID NO 1113
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1113
caagcagaag acggcatacg agatgnncnc tcgtctcgtg ggctcggaga tgtgtataag    60
agacag    66

<210> SEQ ID NO 1114
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1114
caagcagaag acggcatacg agatanncnc tcgtctcgtg ggctcggaga tgtgtataag    60
agacag    66

<210> SEQ ID NO 1115
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1115
caagcagaag acggcatacg agatnnnanc tcgtctcgtg ggctcggaga tgtgtataag    60
agacag    66

<210> SEQ ID NO 1116
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1116
caagcagaag acggcatacg agatcnncac tcgtctcgtg ggctcggaga tgtgtataag     60
agacag                                                               66

<210> SEQ ID NO 1117
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(29)
<223> OTHER INFORMATION: n is a, c, g, or t

<400> SEQUENCE: 1117
caagcagaag acggcatacg agatnnnnna tcgtctcgtg ggctcggaga tgtgtataag     60
agacag                                                               66

<210> SEQ ID NO 1118
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(29)
<223> OTHER INFORMATION: n is a, c, g, or t

<400> SEQUENCE: 1118
caagcagaag acggcatacg agatnnnnnt gcgtctcgtg ggctcggaga tgtgtataag     60
agacag                                                               66

<210> SEQ ID NO 1119
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1119
caagcagaag acggcatacg agatcnngtg gcgtctcgtg ggctcggaga tgtgtataag     60
agacag                                                               66

<210> SEQ ID NO 1120
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1120
caagcagaag acggcatacg agattnnctg gcgtctcgtg ggctcggaga tgtgtataag     60

-continued

```
agacag                                                              66

<210> SEQ ID NO 1121
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1121
caagcagaag acggcatacg agatgnnctg gcgtctcgtg ggctcggaga tgtgtataag      60
agacag                                                              66

<210> SEQ ID NO 1122
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1122
caagcagaag acggcatacg agatcnnctg gcgtctcgtg ggctcggaga tgtgtataag      60
agacag                                                              66

<210> SEQ ID NO 1123
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1123
caagcagaag acggcatacg agatcnnatg gcgtctcgtg ggctcggaga tgtgtataag      60
agacag                                                              66

<210> SEQ ID NO 1124
<211> LENGTH: 66
<212> TYPE: DNA
<213> ORGANISM: Artificial
<220> FEATURE:
<223> OTHER INFORMATION: synthetic

<400> SEQUENCE: 1124
caagcagaag acggcatacg agatcgtggg gcgtctcgtg ggctcggaga tgtgtataag      60
agacag                                                              66

<210> SEQ ID NO 1125
<211> LENGTH: 66
<212> TYPE: DNA
<213> ORGANISM: Artificial
<220> FEATURE:
<223> OTHER INFORMATION: synthetic

<400> SEQUENCE: 1125
```
caagcagaag acggcatacg agatcatggg gcgtctcgtg ggctcggaga tgtgtataag    60
agacag    66

<210> SEQ ID NO 1126
<211> LENGTH: 66
<212> TYPE: DNA
<213> ORGANISM: Artificial
<220> FEATURE:
<223> OTHER INFORMATION: synthetic

<400> SEQUENCE: 1126
caagcagaag acggcatacg agatcgcggg gcgtctcgtg ggctcggaga tgtgtataag    60
agacag    66

<210> SEQ ID NO 1127
<211> LENGTH: 66
<212> TYPE: DNA
<213> ORGANISM: Artificial
<220> FEATURE:
<223> OTHER INFORMATION: synthetic

<400> SEQUENCE: 1127
caagcagaag acggcatacg agatcacggg gcgtctcgtg ggctcggaga tgtgtataag    60
agacag    66

<210> SEQ ID NO 1128
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1128
caagcagaag acggcatacg agatccnggg gcgtctcgtg ggctcggaga tgtgtataag    60
agacag    66

<210> SEQ ID NO 1129
<211> LENGTH: 66
<212> TYPE: DNA
<213> ORGANISM: Artificial
<220> FEATURE:
<223> OTHER INFORMATION: synthetic

<400> SEQUENCE: 1129
caagcagaag acggcatacg agatcgaggg gcgtctcgtg ggctcggaga tgtgtataag    60
agacag    66

<210> SEQ ID NO 1130
<211> LENGTH: 66
<212> TYPE: DNA
<213> ORGANISM: Artificial
<220> FEATURE:
<223> OTHER INFORMATION: synthetic

<400> SEQUENCE: 1130
caagcagaag acggcatacg agatcaaggg gcgtctcgtg ggctcggaga tgtgtataag    60
agacag    66

<210> SEQ ID NO 1131
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1131
caagcagaag acggcatacg agattgncgg gcgtctcgtg ggctcggaga tgtgtataag     60
agacag                                                               66

<210> SEQ ID NO 1132
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1132
caagcagaag acggcatacg agatggncgg gcgtctcgtg ggctcggaga tgtgtataag     60
agacag                                                               66

<210> SEQ ID NO 1133
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1133
caagcagaag acggcatacg agattcncgg gcgtctcgtg ggctcggaga tgtgtataag     60
agacag                                                               66

<210> SEQ ID NO 1134
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1134
caagcagaag acggcatacg agatgcncgg gcgtctcgtg ggctcggaga tgtgtataag     60
agacag                                                               66

<210> SEQ ID NO 1135
<211> LENGTH: 66
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (27)..(27)
<223> OTHER INFORMATION: n is a, c, g, or t

<400> SEQUENCE: 1135
caagcagaag acggcatacg agattancgg gcgtctcgtg ggctcggaga tgtgtataag      60
agacag                                                                66

<210> SEQ ID NO 1136
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1136
caagcagaag acggcatacg agatgancgg gcgtctcgtg ggctcggaga tgtgtataag      60
agacag                                                                66

<210> SEQ ID NO 1137
<211> LENGTH: 66
<212> TYPE: DNA
<213> ORGANISM: Artificial
<220> FEATURE:
<223> OTHER INFORMATION: synthetic

<400> SEQUENCE: 1137
caagcagaag acggcatacg agatcgtagg gcgtctcgtg ggctcggaga tgtgtataag      60
agacag                                                                66

<210> SEQ ID NO 1138
<211> LENGTH: 66
<212> TYPE: DNA
<213> ORGANISM: Artificial
<220> FEATURE:
<223> OTHER INFORMATION: synthetic

<400> SEQUENCE: 1138
caagcagaag acggcatacg agatcatagg gcgtctcgtg ggctcggaga tgtgtataag      60
agacag                                                                66

<210> SEQ ID NO 1139
<211> LENGTH: 66
<212> TYPE: DNA
<213> ORGANISM: Artificial
<220> FEATURE:
<223> OTHER INFORMATION: synthetic

<400> SEQUENCE: 1139
caagcagaag acggcatacg agatcgcagg gcgtctcgtg ggctcggaga tgtgtataag      60
agacag                                                                66

<210> SEQ ID NO 1140
<211> LENGTH: 66
<212> TYPE: DNA
<213> ORGANISM: Artificial
<220> FEATURE:
<223> OTHER INFORMATION: synthetic
```

<400> SEQUENCE: 1140
caagcagaag acggcatacg agatcacagg gcgtctcgtg ggctcggaga tgtgtataag    60
agacag                                                              66

<210> SEQ ID NO 1141
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1141
caagcagaag acggcatacg agatccnagg gcgtctcgtg ggctcggaga tgtgtataag    60
agacag                                                              66

<210> SEQ ID NO 1142
<211> LENGTH: 66
<212> TYPE: DNA
<213> ORGANISM: Artificial
<220> FEATURE:
<223> OTHER INFORMATION: synthetic

<400> SEQUENCE: 1142
caagcagaag acggcatacg agatcgaagg gcgtctcgtg ggctcggaga tgtgtataag    60
agacag                                                              66

<210> SEQ ID NO 1143
<211> LENGTH: 66
<212> TYPE: DNA
<213> ORGANISM: Artificial
<220> FEATURE:
<223> OTHER INFORMATION: synthetic

<400> SEQUENCE: 1143
caagcagaag acggcatacg agatcaaagg gcgtctcgtg ggctcggaga tgtgtataag    60
agacag                                                              66

<210> SEQ ID NO 1144
<211> LENGTH: 66
<212> TYPE: DNA
<213> ORGANISM: Artificial
<220> FEATURE:
<223> OTHER INFORMATION: synthetic

<400> SEQUENCE: 1144
caagcagaag acggcatacg agatcgtgcg gcgtctcgtg ggctcggaga tgtgtataag    60
agacag                                                              66

<210> SEQ ID NO 1145
<211> LENGTH: 66
<212> TYPE: DNA
<213> ORGANISM: Artificial
<220> FEATURE:
<223> OTHER INFORMATION: synthetic

<400> SEQUENCE: 1145
caagcagaag acggcatacg agatcatgcg gcgtctcgtg ggctcggaga tgtgtataag    60
agacag                                                              66

<210> SEQ ID NO 1146
<211> LENGTH: 66
<212> TYPE: DNA
<213> ORGANISM: Artificial
<220> FEATURE:
<223> OTHER INFORMATION: synthetic

<400> SEQUENCE: 1146
caagcagaag acggcatacg agatcgcgcg gcgtctcgtg ggctcggaga tgtgtataag    60
agacag                                                              66

<210> SEQ ID NO 1147
<211> LENGTH: 66
<212> TYPE: DNA
<213> ORGANISM: Artificial
<220> FEATURE:
<223> OTHER INFORMATION: synthetic

<400> SEQUENCE: 1147
caagcagaag acggcatacg agatcacgcg gcgtctcgtg ggctcggaga tgtgtataag    60
agacag                                                              66

<210> SEQ ID NO 1148
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1148
caagcagaag acggcatacg agatccngcg gcgtctcgtg ggctcggaga tgtgtataag    60
agacag                                                              66

<210> SEQ ID NO 1149
<211> LENGTH: 66
<212> TYPE: DNA
<213> ORGANISM: Artificial
<220> FEATURE:
<223> OTHER INFORMATION: synthetic

<400> SEQUENCE: 1149
caagcagaag acggcatacg agatcgagcg gcgtctcgtg ggctcggaga tgtgtataag    60
agacag                                                              66

<210> SEQ ID NO 1150
<211> LENGTH: 66
<212> TYPE: DNA
<213> ORGANISM: Artificial
<220> FEATURE:
<223> OTHER INFORMATION: synthetic

<400> SEQUENCE: 1150
caagcagaag acggcatacg agatcaagcg gcgtctcgtg ggctcggaga tgtgtataag    60
agacag                                                              66

<210> SEQ ID NO 1151
<211> LENGTH: 66
<212> TYPE: DNA

```
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1151
caagcagaag acggcatacg agattgnccg gcgtctcgtg ggctcggaga tgtgtataag      60
agacag                                                                66

<210> SEQ ID NO 1152
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1152
caagcagaag acggcatacg agatggnccg gcgtctcgtg ggctcggaga tgtgtataag      60
agacag                                                                66

<210> SEQ ID NO 1153
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1153
caagcagaag acggcatacg agattcnccg gcgtctcgtg ggctcggaga tgtgtataag      60
agacag                                                                66

<210> SEQ ID NO 1154
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1154
caagcagaag acggcatacg agatgcnccg gcgtctcgtg ggctcggaga tgtgtataag      60
agacag                                                                66

<210> SEQ ID NO 1155
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t
```

<400> SEQUENCE: 1155
caagcagaag acggcatacg agattanccg gcgtctcgtg ggctcggaga tgtgtataag        60
agacag        66

<210> SEQ ID NO 1156
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1156
caagcagaag acggcatacg agatganccg gcgtctcgtg ggctcggaga tgtgtataag        60
agacag        66

<210> SEQ ID NO 1157
<211> LENGTH: 66
<212> TYPE: DNA
<213> ORGANISM: Artificial
<220> FEATURE:
<223> OTHER INFORMATION: synthetic

<400> SEQUENCE: 1157
caagcagaag acggcatacg agatcgtacg gcgtctcgtg ggctcggaga tgtgtataag        60
agacag        66

<210> SEQ ID NO 1158
<211> LENGTH: 66
<212> TYPE: DNA
<213> ORGANISM: Artificial
<220> FEATURE:
<223> OTHER INFORMATION: synthetic

<400> SEQUENCE: 1158
caagcagaag acggcatacg agatcatacg gcgtctcgtg ggctcggaga tgtgtataag        60
agacag        66

<210> SEQ ID NO 1159
<211> LENGTH: 66
<212> TYPE: DNA
<213> ORGANISM: Artificial
<220> FEATURE:
<223> OTHER INFORMATION: synthetic

<400> SEQUENCE: 1159
caagcagaag acggcatacg agatcgcacg gcgtctcgtg ggctcggaga tgtgtataag        60
agacag        66

<210> SEQ ID NO 1160
<211> LENGTH: 66
<212> TYPE: DNA
<213> ORGANISM: Artificial
<220> FEATURE:
<223> OTHER INFORMATION: synthetic

<400> SEQUENCE: 1160
caagcagaag acggcatacg agatcacacg gcgtctcgtg ggctcggaga tgtgtataag        60

-continued agacag                                                                66

<210> SEQ ID NO 1161
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1161
caagcagaag acggcatacg agatccnacg gcgtctcgtg ggctcggaga tgtgtataag      60
agacag                                                                66

<210> SEQ ID NO 1162
<211> LENGTH: 66
<212> TYPE: DNA
<213> ORGANISM: Artificial
<220> FEATURE:
<223> OTHER INFORMATION: synthetic

<400> SEQUENCE: 1162
caagcagaag acggcatacg agatcgaacg gcgtctcgtg ggctcggaga tgtgtataag      60
agacag                                                                66

<210> SEQ ID NO 1163
<211> LENGTH: 66
<212> TYPE: DNA
<213> ORGANISM: Artificial
<220> FEATURE:
<223> OTHER INFORMATION: synthetic

<400> SEQUENCE: 1163
caagcagaag acggcatacg agatcaaacg gcgtctcgtg ggctcggaga tgtgtataag      60
agacag                                                                66

<210> SEQ ID NO 1164
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1164
caagcagaag acggcatacg agatnnntng gcgtctcgtg ggctcggaga tgtgtataag      60
agacag                                                                66

<210> SEQ ID NO 1165
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature

```
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1165
caagcagaag acggcatacg agattnngng gcgtctcgtg ggctcggaga tgtgtataag    60
agacag                                                              66

<210> SEQ ID NO 1166
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1166
caagcagaag acggcatacg agatgnngng gcgtctcgtg ggctcggaga tgtgtataag    60
agacag                                                              66

<210> SEQ ID NO 1167
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1167
caagcagaag acggcatacg agatanngng gcgtctcgtg ggctcggaga tgtgtataag    60
agacag                                                              66

<210> SEQ ID NO 1168
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1168
caagcagaag acggcatacg agatanncng gcgtctcgtg ggctcggaga tgtgtataag    60
agacag                                                              66
```

<210> SEQ ID NO 1169
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1169
caagcagaag acggcatacg agattnnang gcgtctcgtg ggctcggaga tgtgtataag    60
agacag                                                               66

<210> SEQ ID NO 1170
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1170
caagcagaag acggcatacg agatgnnang gcgtctcgtg ggctcggaga tgtgtataag    60
agacag                                                               66

<210> SEQ ID NO 1171
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1171
caagcagaag acggcatacg agatannang gcgtctcgtg ggctcggaga tgtgtataag    60
agacag                                                               66

<210> SEQ ID NO 1172
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1172
caagcagaag acggcatacg agatcnngag gcgtctcgtg ggctcggaga tgtgtataag    60
agacag                                                              66

<210> SEQ ID NO 1173
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1173
caagcagaag acggcatacg agatccncag gcgtctcgtg ggctcggaga tgtgtataag    60
agacag                                                              66

<210> SEQ ID NO 1174
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1174
caagcagaag acggcatacg agattnncag gcgtctcgtg ggctcggaga tgtgtataag    60
agacag                                                              66

<210> SEQ ID NO 1175
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1175
caagcagaag acggcatacg agatgnncag gcgtctcgtg ggctcggaga tgtgtataag    60
agacag                                                              66

<210> SEQ ID NO 1176
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1176
caagcagaag acggcatacg agatcnnaag gcgtctcgtg ggctcggaga tgtgtataag    60
agacag                                                              66

<210> SEQ ID NO 1177

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1177
caagcagaag acggcatacg agatcnngtc gcgtctcgtg ggctcggaga tgtgtataag    60
agacag                                                              66

<210> SEQ ID NO 1178
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1178
caagcagaag acggcatacg agattnnctc gcgtctcgtg ggctcggaga tgtgtataag    60
agacag                                                              66

<210> SEQ ID NO 1179
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1179
caagcagaag acggcatacg agatgnnctc gcgtctcgtg ggctcggaga tgtgtataag    60
agacag                                                              66

<210> SEQ ID NO 1180
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1180
caagcagaag acggcatacg agatcnnctc gcgtctcgtg ggctcggaga tgtgtataag    60
agacag                                                              66

<210> SEQ ID NO 1181
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

```
<222> LOCATION: (26)..(27)
<223> OTHER INFORMATION: n is a, c, g, or t

<400> SEQUENCE: 1181
caagcagaag acggcatacg agatcnnatc gcgtctcgtg ggctcggaga tgtgtataag     60
agacag                                                                66

<210> SEQ ID NO 1182
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1182
caagcagaag acggcatacg agatccnggc gcgtctcgtg ggctcggaga tgtgtataag     60
agacag                                                                66

<210> SEQ ID NO 1183
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1183
caagcagaag acggcatacg agattgncgc gcgtctcgtg ggctcggaga tgtgtataag     60
agacag                                                                66

<210> SEQ ID NO 1184
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1184
caagcagaag acggcatacg agatggncgc gcgtctcgtg ggctcggaga tgtgtataag     60
agacag                                                                66

<210> SEQ ID NO 1185
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1185
caagcagaag acggcatacg agattcncgc gcgtctcgtg ggctcggaga tgtgtataag     60
``` agacag 66

<210> SEQ ID NO 1186
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1186
caagcagaag acggcatacg agatgcncgc gcgtctcgtg ggctcggaga tgtgtataag    60
agacag    66

<210> SEQ ID NO 1187
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1187
caagcagaag acggcatacg agattancgc gcgtctcgtg ggctcggaga tgtgtataag    60
agacag    66

<210> SEQ ID NO 1188
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1188
caagcagaag acggcatacg agatgancgc gcgtctcgtg ggctcggaga tgtgtataag    60
agacag    66

<210> SEQ ID NO 1189
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1189
caagcagaag acggcatacg agatccnagc gcgtctcgtg ggctcggaga tgtgtataag    60
agacag    66

<210> SEQ ID NO 1190
<211> LENGTH: 66
<212> TYPE: DNA
<213> ORGANISM: Artificial -continued

```
<220> FEATURE:
<223> OTHER INFORMATION: synthetic

<400> SEQUENCE: 1190
caagcagaag acggcatacg agatcctgcc gcgtctcgtg ggctcggaga tgtgtataag    60
agacag                                                                66

<210> SEQ ID NO 1191
<211> LENGTH: 66
<212> TYPE: DNA
<213> ORGANISM: Artificial
<220> FEATURE:
<223> OTHER INFORMATION: synthetic

<400> SEQUENCE: 1191
caagcagaag acggcatacg agatcccgcc gcgtctcgtg ggctcggaga tgtgtataag    60
agacag                                                                66

<210> SEQ ID NO 1192
<211> LENGTH: 66
<212> TYPE: DNA
<213> ORGANISM: Artificial
<220> FEATURE:
<223> OTHER INFORMATION: synthetic

<400> SEQUENCE: 1192
caagcagaag acggcatacg agatccagcc gcgtctcgtg ggctcggaga tgtgtataag    60
agacag                                                                66

<210> SEQ ID NO 1193
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1193
caagcagaag acggcatacg agattgnccc gcgtctcgtg ggctcggaga tgtgtataag    60
agacag                                                                66

<210> SEQ ID NO 1194
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1194
caagcagaag acggcatacg agatggnccc gcgtctcgtg ggctcggaga tgtgtataag    60
agacag                                                                66

<210> SEQ ID NO 1195
<211> LENGTH: 66
<212> TYPE: DNA
<213> ORGANISM: Artificial
<220> FEATURE:
```

```
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1195
caagcagaag acggcatacg agattcnccc gcgtctcgtg ggctcggaga tgtgtataag    60
agacag                                                              66

<210> SEQ ID NO 1196
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1196
caagcagaag acggcatacg agatgcnccc gcgtctcgtg ggctcggaga tgtgtataag    60
agacag                                                              66

<210> SEQ ID NO 1197
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1197
caagcagaag acggcatacg agattanccc gcgtctcgtg ggctcggaga tgtgtataag    60
agacag                                                              66

<210> SEQ ID NO 1198
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1198
caagcagaag acggcatacg agatganccc gcgtctcgtg ggctcggaga tgtgtataag    60
agacag                                                              66

<210> SEQ ID NO 1199
<211> LENGTH: 66
<212> TYPE: DNA
<213> ORGANISM: Artificial
<220> FEATURE:
<223> OTHER INFORMATION: synthetic

<400> SEQUENCE: 1199
caagcagaag acggcatacg agatcctacc gcgtctcgtg ggctcggaga tgtgtataag    60
agacag                                                              66
```

```
<210> SEQ ID NO 1200
<211> LENGTH: 66
<212> TYPE: DNA
<213> ORGANISM: Artificial
<220> FEATURE:
<223> OTHER INFORMATION: synthetic

<400> SEQUENCE: 1200
caagcagaag acggcatacg agatcccacc gcgtctcgtg ggctcggaga tgtgtataag      60
agacag                                                                66

<210> SEQ ID NO 1201
<211> LENGTH: 66
<212> TYPE: DNA
<213> ORGANISM: Artificial
<220> FEATURE:
<223> OTHER INFORMATION: synthetic

<400> SEQUENCE: 1201
caagcagaag acggcatacg agatccaacc gcgtctcgtg ggctcggaga tgtgtataag      60
agacag                                                                66

<210> SEQ ID NO 1202
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1202
caagcagaag acggcatacg agatnnntnc gcgtctcgtg ggctcggaga tgtgtataag      60
agacag                                                                66

<210> SEQ ID NO 1203
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1203
caagcagaag acggcatacg agattnngnc gcgtctcgtg ggctcggaga tgtgtataag      60
agacag                                                                66

<210> SEQ ID NO 1204
<211> LENGTH: 66
<212> TYPE: DNA
<213> ORGANISM: Artificial
<220> FEATURE:
```

```
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1204
caagcagaag acggcatacg agatgnngnc gcgtctcgtg ggctcggaga tgtgtataag    60
agacag                                                               66

<210> SEQ ID NO 1205
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1205
caagcagaag acggcatacg agatanngnc gcgtctcgtg ggctcggaga tgtgtataag    60
agacag                                                               66

<210> SEQ ID NO 1206
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1206
caagcagaag acggcatacg agatanncnc gcgtctcgtg ggctcggaga tgtgtataag    60
agacag                                                               66

<210> SEQ ID NO 1207
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1207
caagcagaag acggcatacg agattnnanc gcgtctcgtg ggctcggaga tgtgtataag    60
``` agacag 66

<210> SEQ ID NO 1208
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1208
caagcagaag acggcatacg agatgnnanc gcgtctcgtg ggctcggaga tgtgtataag       60
agacag                                                                66

<210> SEQ ID NO 1209
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1209
caagcagaag acggcatacg agatannanc gcgtctcgtg ggctcggaga tgtgtataag       60
agacag                                                                66

<210> SEQ ID NO 1210
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1210
caagcagaag acggcatacg agatcnngac gcgtctcgtg ggctcggaga tgtgtataag       60
agacag                                                                66

<210> SEQ ID NO 1211
<211> LENGTH: 66
<212> TYPE: DNA
<213> ORGANISM: Artificial
<220> FEATURE:
<223> OTHER INFORMATION: synthetic

<400> SEQUENCE: 1211
caagcagaag acggcatacg agatcctcac gcgtctcgtg ggctcggaga tgtgtataag       60
agacag                                                                66

<210> SEQ ID NO 1212
<211> LENGTH: 66
<212> TYPE: DNA
<213> ORGANISM: Artificial
<220> FEATURE:
<223> OTHER INFORMATION: synthetic

<400> SEQUENCE: 1212
caagcagaag acggcatacg agatccccac gcgtctcgtg ggctcggaga tgtgtataag    60
agacag                                                              66

<210> SEQ ID NO 1213
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1213
caagcagaag acggcatacg agattnncac gcgtctcgtg ggctcggaga tgtgtataag    60
agacag                                                              66

<210> SEQ ID NO 1214
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1214
caagcagaag acggcatacg agatgnncac gcgtctcgtg ggctcggaga tgtgtataag    60
agacag                                                              66

<210> SEQ ID NO 1215
<211> LENGTH: 66
<212> TYPE: DNA
<213> ORGANISM: Artificial
<220> FEATURE:
<223> OTHER INFORMATION: synthetic

<400> SEQUENCE: 1215
caagcagaag acggcatacg agatccacac gcgtctcgtg ggctcggaga tgtgtataag    60
agacag                                                              66

<210> SEQ ID NO 1216
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1216
caagcagaag acggcatacg agatcnnaac gcgtctcgtg ggctcggaga tgtgtataag    60

-continued agacag 66

<210> SEQ ID NO 1217
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1217
caagcagaag acggcatacg agatcnncta gcgtctcgtg ggctcggaga tgtgtataag    60
agacag                                                              66

<210> SEQ ID NO 1218
<211> LENGTH: 66
<212> TYPE: DNA
<213> ORGANISM: Artificial
<220> FEATURE:
<223> OTHER INFORMATION: synthetic

<400> SEQUENCE: 1218
caagcagaag acggcatacg agatcgtcga gcgtctcgtg ggctcggaga tgtgtataag    60
agacag                                                              66

<210> SEQ ID NO 1219
<211> LENGTH: 66
<212> TYPE: DNA
<213> ORGANISM: Artificial
<220> FEATURE:
<223> OTHER INFORMATION: synthetic

<400> SEQUENCE: 1219
caagcagaag acggcatacg agatcatcga gcgtctcgtg ggctcggaga tgtgtataag    60
agacag                                                              66

<210> SEQ ID NO 1220
<211> LENGTH: 66
<212> TYPE: DNA
<213> ORGANISM: Artificial
<220> FEATURE:
<223> OTHER INFORMATION: synthetic

<400> SEQUENCE: 1220
caagcagaag acggcatacg agatcgccga gcgtctcgtg ggctcggaga tgtgtataag    60
agacag                                                              66

<210> SEQ ID NO 1221
<211> LENGTH: 66
<212> TYPE: DNA
<213> ORGANISM: Artificial
<220> FEATURE:
<223> OTHER INFORMATION: synthetic

<400> SEQUENCE: 1221
caagcagaag acggcatacg agatcaccga gcgtctcgtg ggctcggaga tgtgtataag    60
agacag                                                              66

<210> SEQ ID NO 1222

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1222
caagcagaag acggcatacg agatccncga gcgtctcgtg ggctcggaga tgtgtataag    60
agacag                                                               66

<210> SEQ ID NO 1223
<211> LENGTH: 66
<212> TYPE: DNA
<213> ORGANISM: Artificial
<220> FEATURE:
<223> OTHER INFORMATION: synthetic

<400> SEQUENCE: 1223
caagcagaag acggcatacg agatcgacga gcgtctcgtg ggctcggaga tgtgtataag    60
agacag                                                               66

<210> SEQ ID NO 1224
<211> LENGTH: 66
<212> TYPE: DNA
<213> ORGANISM: Artificial
<220> FEATURE:
<223> OTHER INFORMATION: synthetic

<400> SEQUENCE: 1224
caagcagaag acggcatacg agatcaacga gcgtctcgtg ggctcggaga tgtgtataag    60
agacag                                                               66

<210> SEQ ID NO 1225
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1225
caagcagaag acggcatacg agatccncca gcgtctcgtg ggctcggaga tgtgtataag    60
agacag                                                               66

<210> SEQ ID NO 1226
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1226
```

```
caagcagaag acggcatacg agatnnntna gcgtctcgtg ggctcggaga tgtgtataag    60
agacag                                                                66

<210> SEQ ID NO 1227
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1227
caagcagaag acggcatacg agatnnngna gcgtctcgtg ggctcggaga tgtgtataag    60
agacag                                                                66

<210> SEQ ID NO 1228
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1228
caagcagaag acggcatacg agattnncna gcgtctcgtg ggctcggaga tgtgtataag    60
agacag                                                                66

<210> SEQ ID NO 1229
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1229
caagcagaag acggcatacg agatgnncna gcgtctcgtg ggctcggaga tgtgtataag    60
agacag                                                                66

<210> SEQ ID NO 1230
<211> LENGTH: 66
<212> TYPE: DNA
<213> ORGANISM: Artificial
<220> FEATURE:
<223> OTHER INFORMATION: synthetic
<220> FEATURE:
```

```
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1230
caagcagaag acggcatacg agatanncna gcgtctcgtg ggctcggaga tgtgtataag    60
agacag                                                              66

<210> SEQ ID NO 1231
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1231
caagcagaag acggcatacg agatnnnana gcgtctcgtg ggctcggaga tgtgtataag    60
agacag                                                              66

<210> SEQ ID NO 1232
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1232
caagcagaag acggcatacg agatcnncaa gcgtctcgtg ggctcggaga tgtgtataag    60
agacag                                                              66

<210> SEQ ID NO 1233
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1233
caagcagaag acggcatacg agatcnngtt ccgtctcgtg ggctcggaga tgtgtataag    60
agacag                                                              66

<210> SEQ ID NO 1234
<211> LENGTH: 66
<212> TYPE: DNA
<213> ORGANISM: Artificial
<220> FEATURE:
<223> OTHER INFORMATION: synthetic
```

```
<220> FEATURE:
<221> NAME/KEY: misc_feature
<222> LOCATION: (26)..(27)
<223> OTHER INFORMATION: n is a, c, g, or t

<400> SEQUENCE: 1234
caagcagaag acggcatacg agattnnctt ccgtctcgtg ggctcggaga tgtgtataag    60
agacag                                                               66

<210> SEQ ID NO 1235
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1235
caagcagaag acggcatacg agatgnnctt ccgtctcgtg ggctcggaga tgtgtataag    60
agacag                                                               66

<210> SEQ ID NO 1236
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1236
caagcagaag acggcatacg agatcnnctt ccgtctcgtg ggctcggaga tgtgtataag    60
agacag                                                               66

<210> SEQ ID NO 1237
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1237
caagcagaag acggcatacg agatcnnatt ccgtctcgtg ggctcggaga tgtgtataag    60
agacag                                                               66

<210> SEQ ID NO 1238
<211> LENGTH: 66
<212> TYPE: DNA
<213> ORGANISM: Artificial
<220> FEATURE:
<223> OTHER INFORMATION: synthetic

<400> SEQUENCE: 1238
caagcagaag acggcatacg agatcgtggt ccgtctcgtg ggctcggaga tgtgtataag    60
agacag                                                               66
```

<210> SEQ ID NO 1239
<211> LENGTH: 66
<212> TYPE: DNA
<213> ORGANISM: Artificial
<220> FEATURE:
<223> OTHER INFORMATION: synthetic

<400> SEQUENCE: 1239
caagcagaag acggcatacg agatcatggt ccgtctcgtg ggctcggaga tgtgtataag    60
agacag    66

<210> SEQ ID NO 1240
<211> LENGTH: 66
<212> TYPE: DNA
<213> ORGANISM: Artificial
<220> FEATURE:
<223> OTHER INFORMATION: synthetic

<400> SEQUENCE: 1240
caagcagaag acggcatacg agatcgcggt ccgtctcgtg ggctcggaga tgtgtataag    60
agacag    66

<210> SEQ ID NO 1241
<211> LENGTH: 66
<212> TYPE: DNA
<213> ORGANISM: Artificial
<220> FEATURE:
<223> OTHER INFORMATION: synthetic

<400> SEQUENCE: 1241
caagcagaag acggcatacg agatcacggt ccgtctcgtg ggctcggaga tgtgtataag    60
agacag    66

<210> SEQ ID NO 1242
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1242
caagcagaag acggcatacg agatccnggt ccgtctcgtg ggctcggaga tgtgtataag    60
agacag    66

<210> SEQ ID NO 1243
<211> LENGTH: 66
<212> TYPE: DNA
<213> ORGANISM: Artificial
<220> FEATURE:
<223> OTHER INFORMATION: synthetic

<400> SEQUENCE: 1243
caagcagaag acggcatacg agatcgaggt ccgtctcgtg ggctcggaga tgtgtataag    60
agacag    66

<210> SEQ ID NO 1244
<211> LENGTH: 66
<212> TYPE: DNA
<213> ORGANISM: Artificial

```
<220> FEATURE:
<223> OTHER INFORMATION: synthetic

<400> SEQUENCE: 1244
caagcagaag acggcatacg agatcaaggt ccgtctcgtg ggctcggaga tgtgtataag    60
agacag                                                               66

<210> SEQ ID NO 1245
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1245
caagcagaag acggcatacg agattgncgt ccgtctcgtg ggctcggaga tgtgtataag    60
agacag                                                               66

<210> SEQ ID NO 1246
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1246
caagcagaag acggcatacg agatggncgt ccgtctcgtg ggctcggaga tgtgtataag    60
agacag                                                               66

<210> SEQ ID NO 1247
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1247
caagcagaag acggcatacg agattcncgt ccgtctcgtg ggctcggaga tgtgtataag    60
agacag                                                               66

<210> SEQ ID NO 1248
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1248
caagcagaag acggcatacg agatgcncgt ccgtctcgtg ggctcggaga tgtgtataag    60
``` agacag 66

<210> SEQ ID NO 1249
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1249
caagcagaag acggcatacg agattancgt ccgtctcgtg ggctcggaga tgtgtataag    60
agacag    66

<210> SEQ ID NO 1250
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1250
caagcagaag acggcatacg agatgancgt ccgtctcgtg ggctcggaga tgtgtataag    60
agacag    66

<210> SEQ ID NO 1251
<211> LENGTH: 66
<212> TYPE: DNA
<213> ORGANISM: Artificial
<220> FEATURE:
<223> OTHER INFORMATION: synthetic

<400> SEQUENCE: 1251
caagcagaag acggcatacg agatcgtagt ccgtctcgtg ggctcggaga tgtgtataag    60
agacag    66

<210> SEQ ID NO 1252
<211> LENGTH: 66
<212> TYPE: DNA
<213> ORGANISM: Artificial
<220> FEATURE:
<223> OTHER INFORMATION: synthetic

<400> SEQUENCE: 1252
caagcagaag acggcatacg agatcatagt ccgtctcgtg ggctcggaga tgtgtataag    60
agacag    66

<210> SEQ ID NO 1253
<211> LENGTH: 66
<212> TYPE: DNA
<213> ORGANISM: Artificial
<220> FEATURE:
<223> OTHER INFORMATION: synthetic

<400> SEQUENCE: 1253
caagcagaag acggcatacg agatcgcagt ccgtctcgtg ggctcggaga tgtgtataag    60
agacag    66

<210> SEQ ID NO 1254
<211> LENGTH: 66
<212> TYPE: DNA
<213> ORGANISM: Artificial
<220> FEATURE:
<223> OTHER INFORMATION: synthetic

<400> SEQUENCE: 1254
caagcagaag acggcatacg agatcacagt ccgtctcgtg ggctcggaga tgtgtataag    60
agacag                                                               66

<210> SEQ ID NO 1255
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1255
caagcagaag acggcatacg agatccnagt ccgtctcgtg ggctcggaga tgtgtataag    60
agacag                                                               66

<210> SEQ ID NO 1256
<211> LENGTH: 66
<212> TYPE: DNA
<213> ORGANISM: Artificial
<220> FEATURE:
<223> OTHER INFORMATION: synthetic

<400> SEQUENCE: 1256
caagcagaag acggcatacg agatcgaagt ccgtctcgtg ggctcggaga tgtgtataag    60
agacag                                                               66

<210> SEQ ID NO 1257
<211> LENGTH: 66
<212> TYPE: DNA
<213> ORGANISM: Artificial
<220> FEATURE:
<223> OTHER INFORMATION: synthetic

<400> SEQUENCE: 1257
caagcagaag acggcatacg agatcaaagt ccgtctcgtg ggctcggaga tgtgtataag    60
agacag                                                               66

<210> SEQ ID NO 1258
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1258
caagcagaag acggcatacg agatccngct ccgtctcgtg ggctcggaga tgtgtataag    60
agacag                                                               66

<210> SEQ ID NO 1259
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1259
caagcagaag acggcatacg agattgncct ccgtctcgtg ggctcggaga tgtgtataag    60
agacag                                                              66

<210> SEQ ID NO 1260
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1260
caagcagaag acggcatacg agatggncct ccgtctcgtg ggctcggaga tgtgtataag    60
agacag                                                              66

<210> SEQ ID NO 1261
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1261
caagcagaag acggcatacg agattcncct ccgtctcgtg ggctcggaga tgtgtataag    60
agacag                                                              66

<210> SEQ ID NO 1262
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1262
caagcagaag acggcatacg agatgcncct ccgtctcgtg ggctcggaga tgtgtataag    60
agacag                                                              66

<210> SEQ ID NO 1263
<211> LENGTH: 66
<212> TYPE: DNA
<213> ORGANISM: Artificial
<220> FEATURE:
<223> OTHER INFORMATION: synthetic

```
<220> FEATURE:
<221> NAME/KEY: misc_feature
<222> LOCATION: (27)..(27)
<223> OTHER INFORMATION: n is a, c, g, or t

<400> SEQUENCE: 1263
caagcagaag acggcatacg agattancct ccgtctcgtg ggctcggaga tgtgtataag      60
agacag                                                                66

<210> SEQ ID NO 1264
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1264
caagcagaag acggcatacg agatgancct ccgtctcgtg ggctcggaga tgtgtataag      60
agacag                                                                66

<210> SEQ ID NO 1265
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1265
caagcagaag acggcatacg agatccnact ccgtctcgtg ggctcggaga tgtgtataag      60
agacag                                                                66

<210> SEQ ID NO 1266
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1266
caagcagaag acggcatacg agatnnntnt ccgtctcgtg ggctcggaga tgtgtataag      60
agacag                                                                66

<210> SEQ ID NO 1267
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
```

<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1267
caagcagaag acggcatacg agattnngnt ccgtctcgtg ggctcggaga tgtgtataag    60
agacag                                                              66

<210> SEQ ID NO 1268
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1268
caagcagaag acggcatacg agatgnngnt ccgtctcgtg ggctcggaga tgtgtataag    60
agacag                                                              66

<210> SEQ ID NO 1269
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1269
caagcagaag acggcatacg agatanngnt ccgtctcgtg ggctcggaga tgtgtataag    60
agacag                                                              66

<210> SEQ ID NO 1270
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1270
caagcagaag acggcatacg agatanncnt ccgtctcgtg ggctcggaga tgtgtataag    60
agacag                                                              66

```
<210> SEQ ID NO 1271
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1271
caagcagaag acggcatacg agattnnant ccgtctcgtg ggctcggaga tgtgtataag    60
agacag                                                              66

<210> SEQ ID NO 1272
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1272
caagcagaag acggcatacg agatgnnant ccgtctcgtg ggctcggaga tgtgtataag    60
agacag                                                              66

<210> SEQ ID NO 1273
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1273
caagcagaag acggcatacg agatannant ccgtctcgtg ggctcggaga tgtgtataag    60
agacag                                                              66

<210> SEQ ID NO 1274
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1274
```

```
caagcagaag acggcatacg agatcnngat ccgtctcgtg ggctcggaga tgtgtataag    60
agacag                                                               66
```

<210> SEQ ID NO 1275
<211> LENGTH: 66
<212> TYPE: DNA
<213> ORGANISM: Artificial
<220> FEATURE:
<223> OTHER INFORMATION: synthetic

<400> SEQUENCE: 1275

```
caagcagaag acggcatacg agatcctcat ccgtctcgtg ggctcggaga tgtgtataag    60
agacag                                                               66
```

<210> SEQ ID NO 1276
<211> LENGTH: 66
<212> TYPE: DNA
<213> ORGANISM: Artificial
<220> FEATURE:
<223> OTHER INFORMATION: synthetic

<400> SEQUENCE: 1276

```
caagcagaag acggcatacg agatccccat ccgtctcgtg ggctcggaga tgtgtataag    60
agacag                                                               66
```

<210> SEQ ID NO 1277
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1277

```
caagcagaag acggcatacg agattnncat ccgtctcgtg ggctcggaga tgtgtataag    60
agacag                                                               66
```

<210> SEQ ID NO 1278
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1278

```
caagcagaag acggcatacg agatgnncat ccgtctcgtg ggctcggaga tgtgtataag    60
agacag                                                               66
```

<210> SEQ ID NO 1279
<211> LENGTH: 66
<212> TYPE: DNA
<213> ORGANISM: Artificial
<220> FEATURE:
<223> OTHER INFORMATION: synthetic

<400> SEQUENCE: 1279

```
caagcagaag acggcatacg agatccacat ccgtctcgtg ggctcggaga tgtgtataag    60
``` agacag 66

<210> SEQ ID NO 1280
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1280
caagcagaag acggcatacg agatcnnaat ccgtctcgtg ggctcggaga tgtgtataag    60
agacag    66

<210> SEQ ID NO 1281
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1281
caagcagaag acggcatacg agatcnnttg ccgtctcgtg ggctcggaga tgtgtataag    60
agacag    66

<210> SEQ ID NO 1282
<211> LENGTH: 66
<212> TYPE: DNA
<213> ORGANISM: Artificial
<220> FEATURE:
<223> OTHER INFORMATION: synthetic

<400> SEQUENCE: 1282
caagcagaag acggcatacg agatcgtgtg ccgtctcgtg ggctcggaga tgtgtataag    60
agacag    66

<210> SEQ ID NO 1283
<211> LENGTH: 66
<212> TYPE: DNA
<213> ORGANISM: Artificial
<220> FEATURE:
<223> OTHER INFORMATION: synthetic

<400> SEQUENCE: 1283
caagcagaag acggcatacg agatcatgtg ccgtctcgtg ggctcggaga tgtgtataag    60
agacag    66

<210> SEQ ID NO 1284
<211> LENGTH: 66
<212> TYPE: DNA
<213> ORGANISM: Artificial
<220> FEATURE:
<223> OTHER INFORMATION: synthetic

<400> SEQUENCE: 1284
caagcagaag acggcatacg agatcgcgtg ccgtctcgtg ggctcggaga tgtgtataag    60

```
agacag                                                              66

<210> SEQ ID NO 1285
<211> LENGTH: 66
<212> TYPE: DNA
<213> ORGANISM: Artificial
<220> FEATURE:
<223> OTHER INFORMATION: synthetic

<400> SEQUENCE: 1285
caagcagaag acggcatacg agatcacgtg ccgtctcgtg ggctcggaga tgtgtataag      60
agacag                                                              66

<210> SEQ ID NO 1286
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1286
caagcagaag acggcatacg agatccngtg ccgtctcgtg ggctcggaga tgtgtataag      60
agacag                                                              66

<210> SEQ ID NO 1287
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1287
caagcagaag acggcatacg agattnngtg ccgtctcgtg ggctcggaga tgtgtataag      60
agacag                                                              66

<210> SEQ ID NO 1288
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1288
caagcagaag acggcatacg agatgnngtg ccgtctcgtg ggctcggaga tgtgtataag      60
agacag                                                              66

<210> SEQ ID NO 1289
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

<222> LOCATION: (26)..(27)
<223> OTHER INFORMATION: n is a, c, g, or t

<400> SEQUENCE: 1289
caagcagaag acggcatacg agatanngtg ccgtctcgtg ggctcggaga tgtgtataag    60
agacag                                                              66

<210> SEQ ID NO 1290
<211> LENGTH: 66
<212> TYPE: DNA
<213> ORGANISM: Artificial
<220> FEATURE:
<223> OTHER INFORMATION: synthetic

<400> SEQUENCE: 1290
caagcagaag acggcatacg agatcgagtg ccgtctcgtg ggctcggaga tgtgtataag    60
agacag                                                              66

<210> SEQ ID NO 1291
<211> LENGTH: 66
<212> TYPE: DNA
<213> ORGANISM: Artificial
<220> FEATURE:
<223> OTHER INFORMATION: synthetic

<400> SEQUENCE: 1291
caagcagaag acggcatacg agatcaagtg ccgtctcgtg ggctcggaga tgtgtataag    60
agacag                                                              66

<210> SEQ ID NO 1292
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1292
caagcagaag acggcatacg agattgnctg ccgtctcgtg ggctcggaga tgtgtataag    60
agacag                                                              66

<210> SEQ ID NO 1293
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1293
caagcagaag acggcatacg agatggnctg ccgtctcgtg ggctcggaga tgtgtataag    60
agacag                                                              66

<210> SEQ ID NO 1294
<211> LENGTH: 66
<212> TYPE: DNA
<213> ORGANISM: Artificial
<220> FEATURE:

```
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1294
caagcagaag acggcatacg agattcnctg ccgtctcgtg ggctcggaga tgtgtataag    60
agacag                                                                66

<210> SEQ ID NO 1295
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1295
caagcagaag acggcatacg agatgcnctg ccgtctcgtg ggctcggaga tgtgtataag    60
agacag                                                                66

<210> SEQ ID NO 1296
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1296
caagcagaag acggcatacg agatannctg ccgtctcgtg ggctcggaga tgtgtataag    60
agacag                                                                66

<210> SEQ ID NO 1297
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1297
caagcagaag acggcatacg agattanctg ccgtctcgtg ggctcggaga tgtgtataag    60
agacag                                                                66

<210> SEQ ID NO 1298
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1298
```

```
caagcagaag acggcatacg agatganctg ccgtctcgtg ggctcggaga tgtgtataag    60
agacag                                                               66

<210> SEQ ID NO 1299
<211> LENGTH: 66
<212> TYPE: DNA
<213> ORGANISM: Artificial
<220> FEATURE:
<223> OTHER INFORMATION: synthetic

<400> SEQUENCE: 1299
caagcagaag acggcatacg agatcgtatg ccgtctcgtg ggctcggaga tgtgtataag    60
agacag                                                               66

<210> SEQ ID NO 1300
<211> LENGTH: 66
<212> TYPE: DNA
<213> ORGANISM: Artificial
<220> FEATURE:
<223> OTHER INFORMATION: synthetic

<400> SEQUENCE: 1300
caagcagaag acggcatacg agatcatatg ccgtctcgtg ggctcggaga tgtgtataag    60
agacag                                                               66

<210> SEQ ID NO 1301
<211> LENGTH: 66
<212> TYPE: DNA
<213> ORGANISM: Artificial
<220> FEATURE:
<223> OTHER INFORMATION: synthetic

<400> SEQUENCE: 1301
caagcagaag acggcatacg agatcgcatg ccgtctcgtg ggctcggaga tgtgtataag    60
agacag                                                               66

<210> SEQ ID NO 1302
<211> LENGTH: 66
<212> TYPE: DNA
<213> ORGANISM: Artificial
<220> FEATURE:
<223> OTHER INFORMATION: synthetic

<400> SEQUENCE: 1302
caagcagaag acggcatacg agatcacatg ccgtctcgtg ggctcggaga tgtgtataag    60
agacag                                                               66

<210> SEQ ID NO 1303
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1303
caagcagaag acggcatacg agatccnatg ccgtctcgtg ggctcggaga tgtgtataag    60
agacag                                                               66
```

<210> SEQ ID NO 1304
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1304
caagcagaag acggcatacg agattnnatg ccgtctcgtg ggctcggaga tgtgtataag    60
agacag    66

<210> SEQ ID NO 1305
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1305
caagcagaag acggcatacg agatgnnatg ccgtctcgtg ggctcggaga tgtgtataag    60
agacag    66

<210> SEQ ID NO 1306
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1306
caagcagaag acggcatacg agatannatg ccgtctcgtg ggctcggaga tgtgtataag    60
agacag    66

<210> SEQ ID NO 1307
<211> LENGTH: 66
<212> TYPE: DNA
<213> ORGANISM: Artificial
<220> FEATURE:
<223> OTHER INFORMATION: synthetic

<400> SEQUENCE: 1307
caagcagaag acggcatacg agatcgaatg ccgtctcgtg ggctcggaga tgtgtataag    60
agacag    66

<210> SEQ ID NO 1308
<211> LENGTH: 66
<212> TYPE: DNA
<213> ORGANISM: Artificial
<220> FEATURE:
<223> OTHER INFORMATION: synthetic

<400> SEQUENCE: 1308
caagcagaag acggcatacg agatcaaatg ccgtctcgtg ggctcggaga tgtgtataag    60
agacag 66

<210> SEQ ID NO 1309
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1309
caagcagaag acggcatacg agatagnggg ccgtctcgtg ggctcggaga tgtgtataag    60
agacag                                                              66

<210> SEQ ID NO 1310
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1310
caagcagaag acggcatacg agatacnggg ccgtctcgtg ggctcggaga tgtgtataag    60
agacag                                                              66

<210> SEQ ID NO 1311
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1311
caagcagaag acggcatacg agataanggg ccgtctcgtg ggctcggaga tgtgtataag    60
agacag                                                              66

<210> SEQ ID NO 1312
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1312
caagcagaag acggcatacg agatagnagg ccgtctcgtg ggctcggaga tgtgtataag    60
agacag                                                              66

<210> SEQ ID NO 1313
<211> LENGTH: 66
<212> TYPE: DNA

```
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1313
caagcagaag acggcatacg agatacnagg ccgtctcgtg ggctcggaga tgtgtataag    60
agacag                                                              66

<210> SEQ ID NO 1314
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1314
caagcagaag acggcatacg agataanagg ccgtctcgtg ggctcggaga tgtgtataag    60
agacag                                                              66

<210> SEQ ID NO 1315
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1315
caagcagaag acggcatacg agatagngcg ccgtctcgtg ggctcggaga tgtgtataag    60
agacag                                                              66

<210> SEQ ID NO 1316
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1316
caagcagaag acggcatacg agatacngcg ccgtctcgtg ggctcggaga tgtgtataag    60
agacag                                                              66

<210> SEQ ID NO 1317
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t
```

<400> SEQUENCE: 1317
caagcagaag acggcatacg agataangcg ccgtctcgtg ggctcggaga tgtgtataag    60
agacag                                                                66

<210> SEQ ID NO 1318
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1318
caagcagaag acggcatacg agatagnacg ccgtctcgtg ggctcggaga tgtgtataag    60
agacag                                                                66

<210> SEQ ID NO 1319
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1319
caagcagaag acggcatacg agatacnacg ccgtctcgtg ggctcggaga tgtgtataag    60
agacag                                                                66

<210> SEQ ID NO 1320
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1320
caagcagaag acggcatacg agataanacg ccgtctcgtg ggctcggaga tgtgtataag    60
agacag                                                                66

<210> SEQ ID NO 1321
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1321
caagcagaag acggcatacg agattnntng ccgtctcgtg ggctcggaga tgtgtataag    60
agacag                                                              66

<210> SEQ ID NO 1322
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1322
caagcagaag acggcatacg agatgnntng ccgtctcgtg ggctcggaga tgtgtataag    60
agacag                                                              66

<210> SEQ ID NO 1323
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1323
caagcagaag acggcatacg agatanntng ccgtctcgtg ggctcggaga tgtgtataag    60
agacag                                                              66

<210> SEQ ID NO 1324
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1324
caagcagaag acggcatacg agatcgntag ccgtctcgtg ggctcggaga tgtgtataag    60
agacag                                                              66

<210> SEQ ID NO 1325
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1325

```
caagcagaag acggcatacg agatccntag ccgtctcgtg ggctcggaga tgtgtataag    60
agacag                                                               66

<210> SEQ ID NO 1326
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1326
caagcagaag acggcatacg agatcantag ccgtctcgtg ggctcggaga tgtgtataag    60
agacag                                                               66

<210> SEQ ID NO 1327
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1327
caagcagaag acggcatacg agattgngag ccgtctcgtg ggctcggaga tgtgtataag    60
agacag                                                               66

<210> SEQ ID NO 1328
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1328
caagcagaag acggcatacg agatggngag ccgtctcgtg ggctcggaga tgtgtataag    60
agacag                                                               66

<210> SEQ ID NO 1329
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1329
caagcagaag acggcatacg agattcngag ccgtctcgtg ggctcggaga tgtgtataag    60
agacag                                                               66

<210> SEQ ID NO 1330
```

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1330
caagcagaag acggcatacg agatgcngag ccgtctcgtg ggctcggaga tgtgtataag    60
agacag                                                              66

<210> SEQ ID NO 1331
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1331
caagcagaag acggcatacg agatanngag ccgtctcgtg ggctcggaga tgtgtataag    60
agacag                                                              66

<210> SEQ ID NO 1332
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1332
caagcagaag acggcatacg agattangag ccgtctcgtg ggctcggaga tgtgtataag    60
agacag                                                              66

<210> SEQ ID NO 1333
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1333
caagcagaag acggcatacg agatgangag ccgtctcgtg ggctcggaga tgtgtataag    60
agacag                                                              66

<210> SEQ ID NO 1334
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

-continued

<222> LOCATION: (27)..(27)
<223> OTHER INFORMATION: n is a, c, g, or t

<400> SEQUENCE: 1334
caagcagaag acggcatacg agatagncag ccgtctcgtg ggctcggaga tgtgtataag    60
agacag                                                              66

<210> SEQ ID NO 1335
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1335
caagcagaag acggcatacg agatacncag ccgtctcgtg ggctcggaga tgtgtataag    60
agacag                                                              66

<210> SEQ ID NO 1336
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1336
caagcagaag acggcatacg agataancag ccgtctcgtg ggctcggaga tgtgtataag    60
agacag                                                              66

<210> SEQ ID NO 1337
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1337
caagcagaag acggcatacg agattgnaag ccgtctcgtg ggctcggaga tgtgtataag    60
agacag                                                              66

<210> SEQ ID NO 1338
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1338
caagcagaag acggcatacg agatggnaag ccgtctcgtg ggctcggaga tgtgtataag    60
agacag                                                                66

<210> SEQ ID NO 1339
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1339
caagcagaag acggcatacg agattcnaag ccgtctcgtg ggctcggaga tgtgtataag    60
agacag                                                                66

<210> SEQ ID NO 1340
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1340
caagcagaag acggcatacg agatgcnaag ccgtctcgtg ggctcggaga tgtgtataag    60
agacag                                                                66

<210> SEQ ID NO 1341
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1341
caagcagaag acggcatacg agatannaag ccgtctcgtg ggctcggaga tgtgtataag    60
agacag                                                                66

<210> SEQ ID NO 1342
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1342
caagcagaag acggcatacg agattanaag ccgtctcgtg ggctcggaga tgtgtataag    60
agacag                                                                66

<210> SEQ ID NO 1343
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1343
caagcagaag acggcatacg agatganaag ccgtctcgtg ggctcggaga tgtgtataag    60
agacag                                                              66

<210> SEQ ID NO 1344
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1344
caagcagaag acggcatacg agatcnnttc ccgtctcgtg ggctcggaga tgtgtataag    60
agacag                                                              66

<210> SEQ ID NO 1345
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1345
caagcagaag acggcatacg agatccngtc ccgtctcgtg ggctcggaga tgtgtataag    60
agacag                                                              66

<210> SEQ ID NO 1346
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1346
caagcagaag acggcatacg agattnngtc ccgtctcgtg ggctcggaga tgtgtataag    60
agacag                                                              66

<210> SEQ ID NO 1347
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1347
caagcagaag acggcatacg agatgnngtc ccgtctcgtg ggctcggaga tgtgtataag    60
agacag                                                               66

<210> SEQ ID NO 1348
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1348
caagcagaag acggcatacg agatanngtc ccgtctcgtg ggctcggaga tgtgtataag    60
agacag                                                               66

<210> SEQ ID NO 1349
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1349
caagcagaag acggcatacg agattgnctc ccgtctcgtg ggctcggaga tgtgtataag    60
agacag                                                               66

<210> SEQ ID NO 1350
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1350
caagcagaag acggcatacg agatggnctc ccgtctcgtg ggctcggaga tgtgtataag    60
agacag                                                               66

<210> SEQ ID NO 1351
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1351
caagcagaag acggcatacg agattcnctc ccgtctcgtg ggctcggaga tgtgtataag    60
agacag                                                               66

-continued

```
<210> SEQ ID NO 1352
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1352
caagcagaag acggcatacg agatgcnctc ccgtctcgtg ggctcggaga tgtgtataag    60
agacag                                                              66

<210> SEQ ID NO 1353
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1353
caagcagaag acggcatacg agatannctc ccgtctcgtg ggctcggaga tgtgtataag    60
agacag                                                              66

<210> SEQ ID NO 1354
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1354
caagcagaag acggcatacg agattanctc ccgtctcgtg ggctcggaga tgtgtataag    60
agacag                                                              66

<210> SEQ ID NO 1355
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1355
caagcagaag acggcatacg agatganctc ccgtctcgtg ggctcggaga tgtgtataag    60
agacag                                                              66

<210> SEQ ID NO 1356
<211> LENGTH: 66
<212> TYPE: DNA
<213> ORGANISM: Artificial
<220> FEATURE:
<223> OTHER INFORMATION: synthetic
<220> FEATURE:
```

<221> NAME/KEY: misc_feature
<222> LOCATION: (27)..(27)
<223> OTHER INFORMATION: n is a, c, g, or t

<400> SEQUENCE: 1356
caagcagaag acggcatacg agatccnatc ccgtctcgtg ggctcggaga tgtgtataag    60
agacag    66

<210> SEQ ID NO 1357
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1357
caagcagaag acggcatacg agattnnatc ccgtctcgtg ggctcggaga tgtgtataag    60
agacag    66

<210> SEQ ID NO 1358
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1358
caagcagaag acggcatacg agatgnnatc ccgtctcgtg ggctcggaga tgtgtataag    60
agacag    66

<210> SEQ ID NO 1359
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1359
caagcagaag acggcatacg agatannatc ccgtctcgtg ggctcggaga tgtgtataag    60
agacag    66

<210> SEQ ID NO 1360
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1360
caagcagaag acggcatacg agatagnggc ccgtctcgtg ggctcggaga tgtgtataag    60

-continued agacag                                                               66

<210> SEQ ID NO 1361
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1361
caagcagaag acggcatacg agatacnggc ccgtctcgtg ggctcggaga tgtgtataag    60
agacag                                                               66

<210> SEQ ID NO 1362
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1362
caagcagaag acggcatacg agataanggc ccgtctcgtg ggctcggaga tgtgtataag    60
agacag                                                               66

<210> SEQ ID NO 1363
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1363
caagcagaag acggcatacg agatagnagc ccgtctcgtg ggctcggaga tgtgtataag    60
agacag                                                               66

<210> SEQ ID NO 1364
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1364
caagcagaag acggcatacg agatacnagc ccgtctcgtg ggctcggaga tgtgtataag    60
agacag                                                               66

<210> SEQ ID NO 1365
<211> LENGTH: 66
<212> TYPE: DNA

```
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1365
caagcagaag acggcatacg agataanagc ccgtctcgtg ggctcggaga tgtgtataag    60
agacag                                                                66

<210> SEQ ID NO 1366
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1366
caagcagaag acggcatacg agatagngcc ccgtctcgtg ggctcggaga tgtgtataag    60
agacag                                                                66

<210> SEQ ID NO 1367
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1367
caagcagaag acggcatacg agatacngcc ccgtctcgtg ggctcggaga tgtgtataag    60
agacag                                                                66

<210> SEQ ID NO 1368
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1368
caagcagaag acggcatacg agataangcc ccgtctcgtg ggctcggaga tgtgtataag    60
agacag                                                                66

<210> SEQ ID NO 1369
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t
```

<400> SEQUENCE: 1369
caagcagaag acggcatacg agatagnacc ccgtctcgtg ggctcggaga tgtgtataag    60
agacag                                                              66

<210> SEQ ID NO 1370
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1370
caagcagaag acggcatacg agatacnacc ccgtctcgtg ggctcggaga tgtgtataag    60
agacag                                                              66

<210> SEQ ID NO 1371
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1371
caagcagaag acggcatacg agataanacc ccgtctcgtg ggctcggaga tgtgtataag    60
agacag                                                              66

<210> SEQ ID NO 1372
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1372
caagcagaag acggcatacg agattnntnc ccgtctcgtg ggctcggaga tgtgtataag    60
agacag                                                              66

<210> SEQ ID NO 1373
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)

<223> OTHER INFORMATION: n is a, c, g, or t

<400> SEQUENCE: 1373
caagcagaag acggcatacg agatgnntnc ccgtctcgtg ggctcggaga tgtgtataag    60
agacag                                                              66

<210> SEQ ID NO 1374
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1374
caagcagaag acggcatacg agatanntnc ccgtctcgtg ggctcggaga tgtgtataag    60
agacag                                                              66

<210> SEQ ID NO 1375
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1375
caagcagaag acggcatacg agatcgntac ccgtctcgtg ggctcggaga tgtgtataag    60
agacag                                                              66

<210> SEQ ID NO 1376
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1376
caagcagaag acggcatacg agatccntac ccgtctcgtg ggctcggaga tgtgtataag    60
agacag                                                              66

<210> SEQ ID NO 1377
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1377

```
caagcagaag acggcatacg agatcantac ccgtctcgtg ggctcggaga tgtgtataag    60
agacag                                                              66

<210> SEQ ID NO 1378
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1378
caagcagaag acggcatacg agattgngac ccgtctcgtg ggctcggaga tgtgtataag    60
agacag                                                              66

<210> SEQ ID NO 1379
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1379
caagcagaag acggcatacg agatggngac ccgtctcgtg ggctcggaga tgtgtataag    60
agacag                                                              66

<210> SEQ ID NO 1380
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1380
caagcagaag acggcatacg agattcngac ccgtctcgtg ggctcggaga tgtgtataag    60
agacag                                                              66

<210> SEQ ID NO 1381
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1381
caagcagaag acggcatacg agatgcngac ccgtctcgtg ggctcggaga tgtgtataag    60
agacag                                                              66

<210> SEQ ID NO 1382
```

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1382
caagcagaag acggcatacg agatanngac ccgtctcgtg ggctcggaga tgtgtataag      60
agacag                                                                 66

<210> SEQ ID NO 1383
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1383
caagcagaag acggcatacg agattangac ccgtctcgtg ggctcggaga tgtgtataag      60
agacag                                                                 66

<210> SEQ ID NO 1384
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1384
caagcagaag acggcatacg agatgangac ccgtctcgtg ggctcggaga tgtgtataag      60
agacag                                                                 66

<210> SEQ ID NO 1385
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1385
caagcagaag acggcatacg agatagncac ccgtctcgtg ggctcggaga tgtgtataag      60
agacag                                                                 66

<210> SEQ ID NO 1386
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

```
<222> LOCATION: (27)..(27)
<223> OTHER INFORMATION: n is a, c, g, or t

<400> SEQUENCE: 1386
caagcagaag acggcatacg agatacncac ccgtctcgtg ggctcggaga tgtgtataag    60
agacag                                                              66

<210> SEQ ID NO 1387
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1387
caagcagaag acggcatacg agataancac ccgtctcgtg ggctcggaga tgtgtataag    60
agacag                                                              66

<210> SEQ ID NO 1388
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1388
caagcagaag acggcatacg agattgnaac ccgtctcgtg ggctcggaga tgtgtataag    60
agacag                                                              66

<210> SEQ ID NO 1389
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1389
caagcagaag acggcatacg agatggnaac ccgtctcgtg ggctcggaga tgtgtataag    60
agacag                                                              66

<210> SEQ ID NO 1390
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1390
caagcagaag acggcatacg agattcnaac ccgtctcgtg ggctcggaga tgtgtataag    60
```

```
agacag                                                               66

<210> SEQ ID NO 1391
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1391
caagcagaag acggcatacg agatgcnaac ccgtctcgtg ggctcggaga tgtgtataag    60
agacag                                                               66

<210> SEQ ID NO 1392
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1392
caagcagaag acggcatacg agatannaac ccgtctcgtg ggctcggaga tgtgtataag    60
agacag                                                               66

<210> SEQ ID NO 1393
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1393
caagcagaag acggcatacg agattanaac ccgtctcgtg ggctcggaga tgtgtataag    60
agacag                                                               66

<210> SEQ ID NO 1394
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1394
caagcagaag acggcatacg agatganaac ccgtctcgtg ggctcggaga tgtgtataag    60
agacag                                                               66

<210> SEQ ID NO 1395
<211> LENGTH: 66
<212> TYPE: DNA
<213> ORGANISM: Artificial
```

-continued

```
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1395
caagcagaag acggcatacg agatcnntta ccgtctcgtg ggctcggaga tgtgtataag     60
agacag                                                                66

<210> SEQ ID NO 1396
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1396
caagcagaag acggcatacg agattnngta ccgtctcgtg ggctcggaga tgtgtataag     60
agacag                                                                66

<210> SEQ ID NO 1397
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1397
caagcagaag acggcatacg agatgnngta ccgtctcgtg ggctcggaga tgtgtataag     60
agacag                                                                66

<210> SEQ ID NO 1398
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1398
caagcagaag acggcatacg agatcnngta ccgtctcgtg ggctcggaga tgtgtataag     60
agacag                                                                66

<210> SEQ ID NO 1399
<211> LENGTH: 66
<212> TYPE: DNA
<213> ORGANISM: Artificial
<220> FEATURE:
<223> OTHER INFORMATION: synthetic

<400> SEQUENCE: 1399
caagcagaag acggcatacg agatcgtcta ccgtctcgtg ggctcggaga tgtgtataag     60
```

-continued agacag                                                              66

<210> SEQ ID NO 1400
<211> LENGTH: 66
<212> TYPE: DNA
<213> ORGANISM: Artificial
<220> FEATURE:
<223> OTHER INFORMATION: synthetic

<400> SEQUENCE: 1400
caagcagaag acggcatacg agatcatcta ccgtctcgtg ggctcggaga tgtgtataag    60
agacag                                                              66

<210> SEQ ID NO 1401
<211> LENGTH: 66
<212> TYPE: DNA
<213> ORGANISM: Artificial
<220> FEATURE:
<223> OTHER INFORMATION: synthetic

<400> SEQUENCE: 1401
caagcagaag acggcatacg agatcgccta ccgtctcgtg ggctcggaga tgtgtataag    60
agacag                                                              66

<210> SEQ ID NO 1402
<211> LENGTH: 66
<212> TYPE: DNA
<213> ORGANISM: Artificial
<220> FEATURE:
<223> OTHER INFORMATION: synthetic

<400> SEQUENCE: 1402
caagcagaag acggcatacg agatcaccta ccgtctcgtg ggctcggaga tgtgtataag    60
agacag                                                              66

<210> SEQ ID NO 1403
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1403
caagcagaag acggcatacg agatccncta ccgtctcgtg ggctcggaga tgtgtataag    60
agacag                                                              66

<210> SEQ ID NO 1404
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1404
caagcagaag acggcatacg agattnncta ccgtctcgtg ggctcggaga tgtgtataag    60
agacag                                                              66

<210> SEQ ID NO 1405
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1405
caagcagaag acggcatacg agatgnncta ccgtctcgtg ggctcggaga tgtgtataag    60
agacag                                                              66

<210> SEQ ID NO 1406
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1406
caagcagaag acggcatacg agatanncta ccgtctcgtg ggctcggaga tgtgtataag    60
agacag                                                              66

<210> SEQ ID NO 1407
<211> LENGTH: 66
<212> TYPE: DNA
<213> ORGANISM: Artificial
<220> FEATURE:
<223> OTHER INFORMATION: synthetic

<400> SEQUENCE: 1407
caagcagaag acggcatacg agatcgacta ccgtctcgtg ggctcggaga tgtgtataag    60
agacag                                                              66

<210> SEQ ID NO 1408
<211> LENGTH: 66
<212> TYPE: DNA
<213> ORGANISM: Artificial
<220> FEATURE:
<223> OTHER INFORMATION: synthetic

<400> SEQUENCE: 1408
caagcagaag acggcatacg agatcaacta ccgtctcgtg ggctcggaga tgtgtataag    60
agacag                                                              66

<210> SEQ ID NO 1409
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1409
caagcagaag acggcatacg agattnnata ccgtctcgtg ggctcggaga tgtgtataag    60
agacag    66

<210> SEQ ID NO 1410
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1410
caagcagaag acggcatacg agatgnnata ccgtctcgtg ggctcggaga tgtgtataag    60
agacag    66

<210> SEQ ID NO 1411
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1411
caagcagaag acggcatacg agatcnnata ccgtctcgtg ggctcggaga tgtgtataag    60
agacag    66

<210> SEQ ID NO 1412
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1412
caagcagaag acggcatacg agatcgntga ccgtctcgtg ggctcggaga tgtgtataag    60
agacag    66

<210> SEQ ID NO 1413
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1413
caagcagaag acggcatacg agatccntga ccgtctcgtg ggctcggaga tgtgtataag    60
agacag    66

<210> SEQ ID NO 1414
<211> LENGTH: 66

```
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1414
caagcagaag acggcatacg agatcantga ccgtctcgtg ggctcggaga tgtgtataag    60
agacag                                                               66

<210> SEQ ID NO 1415
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1415
caagcagaag acggcatacg agattgngga ccgtctcgtg ggctcggaga tgtgtataag    60
agacag                                                               66

<210> SEQ ID NO 1416
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1416
caagcagaag acggcatacg agatggngga ccgtctcgtg ggctcggaga tgtgtataag    60
agacag                                                               66

<210> SEQ ID NO 1417
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1417
caagcagaag acggcatacg agattcngga ccgtctcgtg ggctcggaga tgtgtataag    60
agacag                                                               66

<210> SEQ ID NO 1418
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
```

<223> OTHER INFORMATION: n is a, c, g, or t

<400> SEQUENCE: 1418
caagcagaag acggcatacg agatgcngga ccgtctcgtg ggctcggaga tgtgtataag    60
agacag                                                               66

<210> SEQ ID NO 1419
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1419
caagcagaag acggcatacg agattangga ccgtctcgtg ggctcggaga tgtgtataag    60
agacag                                                               66

<210> SEQ ID NO 1420
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1420
caagcagaag acggcatacg agatgangga ccgtctcgtg ggctcggaga tgtgtataag    60
agacag                                                               66

<210> SEQ ID NO 1421
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1421
caagcagaag acggcatacg agatagncga ccgtctcgtg ggctcggaga tgtgtataag    60
agacag                                                               66

<210> SEQ ID NO 1422
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1422
caagcagaag acggcatacg agatacncga ccgtctcgtg ggctcggaga tgtgtataag    60
agacag                                                               66

<210> SEQ ID NO 1423
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1423
caagcagaag acggcatacg agataancga ccgtctcgtg ggctcggaga tgtgtataag    60
agacag                                                              66

<210> SEQ ID NO 1424
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1424
caagcagaag acggcatacg agattgnaga ccgtctcgtg ggctcggaga tgtgtataag    60
agacag                                                              66

<210> SEQ ID NO 1425
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1425
caagcagaag acggcatacg agatggnaga ccgtctcgtg ggctcggaga tgtgtataag    60
agacag                                                              66

<210> SEQ ID NO 1426
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1426
caagcagaag acggcatacg agattcnaga ccgtctcgtg ggctcggaga tgtgtataag    60
agacag                                                              66

<210> SEQ ID NO 1427
<211> LENGTH: 66
<212> TYPE: DNA
<213> ORGANISM: Artificial
<220> FEATURE:

<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1427
caagcagaag acggcatacg agatgcnaga ccgtctcgtg ggctcggaga tgtgtataag    60
agacag                                                               66

<210> SEQ ID NO 1428
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1428
caagcagaag acggcatacg agattanaga ccgtctcgtg ggctcggaga tgtgtataag    60
agacag                                                               66

<210> SEQ ID NO 1429
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1429
caagcagaag acggcatacg agatganaga ccgtctcgtg ggctcggaga tgtgtataag    60
agacag                                                               66

<210> SEQ ID NO 1430
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1430
caagcagaag acggcatacg agatcgntca ccgtctcgtg ggctcggaga tgtgtataag    60
agacag                                                               66

<210> SEQ ID NO 1431
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1431

-continued caagcagaag acggcatacg agatccntca ccgtctcgtg ggctcggaga tgtgtataag    60
agacag                                                                66

<210> SEQ ID NO 1432
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1432
caagcagaag acggcatacg agatcantca ccgtctcgtg ggctcggaga tgtgtataag    60
agacag                                                                66

<210> SEQ ID NO 1433
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1433
caagcagaag acggcatacg agattgngca ccgtctcgtg ggctcggaga tgtgtataag    60
agacag                                                                66

<210> SEQ ID NO 1434
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1434
caagcagaag acggcatacg agatggngca ccgtctcgtg ggctcggaga tgtgtataag    60
agacag                                                                66

<210> SEQ ID NO 1435
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1435
caagcagaag acggcatacg agattcngca ccgtctcgtg ggctcggaga tgtgtataag    60
agacag                                                                66

<210> SEQ ID NO 1436

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1436
caagcagaag acggcatacg agatgcngca ccgtctcgtg ggctcggaga tgtgtataag    60
agacag                                                              66

<210> SEQ ID NO 1437
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1437
caagcagaag acggcatacg agattangca ccgtctcgtg ggctcggaga tgtgtataag    60
agacag                                                              66

<210> SEQ ID NO 1438
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1438
caagcagaag acggcatacg agatgangca ccgtctcgtg ggctcggaga tgtgtataag    60
agacag                                                              66

<210> SEQ ID NO 1439
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1439
caagcagaag acggcatacg agatagncca ccgtctcgtg ggctcggaga tgtgtataag    60
agacag                                                              66

<210> SEQ ID NO 1440
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
```

<222> LOCATION: (27)..(27)
<223> OTHER INFORMATION: n is a, c, g, or t

<400> SEQUENCE: 1440
caagcagaag acggcatacg agatacncca ccgtctcgtg ggctcggaga tgtgtataag    60
agacag                                                              66

<210> SEQ ID NO 1441
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1441
caagcagaag acggcatacg agataancca ccgtctcgtg ggctcggaga tgtgtataag    60
agacag                                                              66

<210> SEQ ID NO 1442
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1442
caagcagaag acggcatacg agattgnaca ccgtctcgtg ggctcggaga tgtgtataag    60
agacag                                                              66

<210> SEQ ID NO 1443
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1443
caagcagaag acggcatacg agatggnaca ccgtctcgtg ggctcggaga tgtgtataag    60
agacag                                                              66

<210> SEQ ID NO 1444
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1444
caagcagaag acggcatacg agattcnaca ccgtctcgtg ggctcggaga tgtgtataag    60
agacag            66

<210> SEQ ID NO 1445
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1445
caagcagaag acggcatacg agatgcnaca ccgtctcgtg ggctcggaga tgtgtataag     60
agacag            66

<210> SEQ ID NO 1446
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1446
caagcagaag acggcatacg agattanaca ccgtctcgtg ggctcggaga tgtgtataag     60
agacag            66

<210> SEQ ID NO 1447
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1447
caagcagaag acggcatacg agatganaca ccgtctcgtg ggctcggaga tgtgtataag     60
agacag            66

<210> SEQ ID NO 1448
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1448
caagcagaag acggcatacg agattnntna ccgtctcgtg ggctcggaga tgtgtataag     60
agacag            66

-continued

```
<210> SEQ ID NO 1449
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1449
caagcagaag acggcatacg agatgnntna ccgtctcgtg ggctcggaga tgtgtataag    60
agacag                                                              66

<210> SEQ ID NO 1450
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1450
caagcagaag acggcatacg agatanntna ccgtctcgtg ggctcggaga tgtgtataag    60
agacag                                                              66

<210> SEQ ID NO 1451
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1451
caagcagaag acggcatacg agatanngna ccgtctcgtg ggctcggaga tgtgtataag    60
agacag                                                              66

<210> SEQ ID NO 1452
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
```

<223> OTHER INFORMATION: n is a, c, g, or t

<400> SEQUENCE: 1452
caagcagaag acggcatacg agatannana ccgtctcgtg ggctcggaga tgtgtataag    60
agacag                                                              66

<210> SEQ ID NO 1453
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1453
caagcagaag acggcatacg agatcnntaa ccgtctcgtg ggctcggaga tgtgtataag    60
agacag                                                              66

<210> SEQ ID NO 1454
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1454
caagcagaag acggcatacg agatccngaa ccgtctcgtg ggctcggaga tgtgtataag    60
agacag                                                              66

<210> SEQ ID NO 1455
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1455
caagcagaag acggcatacg agattnngaa ccgtctcgtg ggctcggaga tgtgtataag    60
agacag                                                              66

<210> SEQ ID NO 1456
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1456
caagcagaag acggcatacg agatgnngaa ccgtctcgtg ggctcggaga tgtgtataag    60
agacag                                                              66

<210> SEQ ID NO 1457
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1457
caagcagaag acggcatacg agattgncaa ccgtctcgtg ggctcggaga tgtgtataag    60
agacag                                                               66

<210> SEQ ID NO 1458
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1458
caagcagaag acggcatacg agatggncaa ccgtctcgtg ggctcggaga tgtgtataag    60
agacag                                                               66

<210> SEQ ID NO 1459
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1459
caagcagaag acggcatacg agattcncaa ccgtctcgtg ggctcggaga tgtgtataag    60
agacag                                                               66

<210> SEQ ID NO 1460
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1460
caagcagaag acggcatacg agatgcncaa ccgtctcgtg ggctcggaga tgtgtataag    60
agacag                                                               66

<210> SEQ ID NO 1461
<211> LENGTH: 66
<212> TYPE: DNA
<213> ORGANISM: Artificial
<220> FEATURE:

<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1461
caagcagaag acggcatacg agatanncaa ccgtctcgtg ggctcggaga tgtgtataag    60
agacag    66

<210> SEQ ID NO 1462
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1462
caagcagaag acggcatacg agattancaa ccgtctcgtg ggctcggaga tgtgtataag    60
agacag    66

<210> SEQ ID NO 1463
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1463
caagcagaag acggcatacg agatgancaa ccgtctcgtg ggctcggaga tgtgtataag    60
agacag    66

<210> SEQ ID NO 1464
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1464
caagcagaag acggcatacg agatccnaaa ccgtctcgtg ggctcggaga tgtgtataag    60
agacag    66

<210> SEQ ID NO 1465
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1465
caagcagaag acggcatacg agattnnaaa ccgtctcgtg ggctcggaga tgtgtataag  60
agacag  66

<210> SEQ ID NO 1466
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1466
caagcagaag acggcatacg agatgnnaaa ccgtctcgtg ggctcggaga tgtgtataag  60
agacag  66

<210> SEQ ID NO 1467
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(30)
<223> OTHER INFORMATION: n is a, c, g, or t

<400> SEQUENCE: 1467
caagcagaag acggcatacg agatnnnnnn acgtctcgtg ggctcggaga tgtgtataag  60
agacag  66

<210> SEQ ID NO 1468
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(30)
<223> OTHER INFORMATION: n is a, c, g, or t

<400> SEQUENCE: 1468
caagcagaag acggcatacg agatnnnnnn tagtctcgtg ggctcggaga tgtgtataag  60
agacag  66

<210> SEQ ID NO 1469
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(30)
<223> OTHER INFORMATION: n is a, c, g, or t

<400> SEQUENCE: 1469
caagcagaag acggcatacg agatnnnnnn gagtctcgtg ggctcggaga tgtgtataag  60
agacag  66

<210> SEQ ID NO 1470

```
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(29)
<223> OTHER INFORMATION: n is a, c, g, or t

<400> SEQUENCE: 1470
caagcagaag acggcatacg agatnnnnnt cagtctcgtg ggctcggaga tgtgtataag      60
agacag                                                                66

<210> SEQ ID NO 1471
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1471
caagcagaag acggcatacg agatcnnctg cagtctcgtg ggctcggaga tgtgtataag      60
agacag                                                                66

<210> SEQ ID NO 1472
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1472
caagcagaag acggcatacg agatnnntng cagtctcgtg ggctcggaga tgtgtataag      60
agacag                                                                66

<210> SEQ ID NO 1473
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1473
caagcagaag acggcatacg agatnnngng cagtctcgtg ggctcggaga tgtgtataag      60
agacag                                                                66
```

```
<210> SEQ ID NO 1474
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1474
caagcagaag acggcatacg agattnncng cagtctcgtg ggctcggaga tgtgtataag    60
agacag                                                              66

<210> SEQ ID NO 1475
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1475
caagcagaag acggcatacg agatgnncng cagtctcgtg ggctcggaga tgtgtataag    60
agacag                                                              66

<210> SEQ ID NO 1476
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1476
caagcagaag acggcatacg agatanncng cagtctcgtg ggctcggaga tgtgtataag    60
agacag                                                              66

<210> SEQ ID NO 1477
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
```

<223> OTHER INFORMATION: n is a, c, g, or t

<400> SEQUENCE: 1477
caagcagaag acggcatacg agatnnnang cagtctcgtg ggctcggaga tgtgtataag    60
agacag    66

<210> SEQ ID NO 1478
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1478
caagcagaag acggcatacg agatcnncag cagtctcgtg ggctcggaga tgtgtataag    60
agacag    66

<210> SEQ ID NO 1479
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1479
caagcagaag acggcatacg agatcnngtc cagtctcgtg ggctcggaga tgtgtataag    60
agacag    66

<210> SEQ ID NO 1480
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1480
caagcagaag acggcatacg agatcnnctc cagtctcgtg ggctcggaga tgtgtataag    60
agacag    66

<210> SEQ ID NO 1481
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1481
caagcagaag acggcatacg agatcnnatc cagtctcgtg ggctcggaga tgtgtataag    60
agacag    66

<210> SEQ ID NO 1482
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1482
caagcagaag acggcatacg agatcnnggc cagtctcgtg ggctcggaga tgtgtataag      60
agacag                                                                66

<210> SEQ ID NO 1483
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1483
caagcagaag acggcatacg agatcnnagc cagtctcgtg ggctcggaga tgtgtataag      60
agacag                                                                66

<210> SEQ ID NO 1484
<211> LENGTH: 66
<212> TYPE: DNA
<213> ORGANISM: Artificial
<220> FEATURE:
<223> OTHER INFORMATION: synthetic

<400> SEQUENCE: 1484
caagcagaag acggcatacg agatcttgcc cagtctcgtg ggctcggaga tgtgtataag      60
agacag                                                                66

<210> SEQ ID NO 1485
<211> LENGTH: 66
<212> TYPE: DNA
<213> ORGANISM: Artificial
<220> FEATURE:
<223> OTHER INFORMATION: synthetic

<400> SEQUENCE: 1485
caagcagaag acggcatacg agatctcgcc cagtctcgtg ggctcggaga tgtgtataag      60
agacag                                                                66

<210> SEQ ID NO 1486
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1486
caagcagaag acggcatacg agatcgngcc cagtctcgtg ggctcggaga tgtgtataag    60
agacag                                                              66

<210> SEQ ID NO 1487
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1487
caagcagaag acggcatacg agatccngcc cagtctcgtg ggctcggaga tgtgtataag    60
agacag                                                              66

<210> SEQ ID NO 1488
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1488
caagcagaag acggcatacg agatcangcc cagtctcgtg ggctcggaga tgtgtataag    60
agacag                                                              66

<210> SEQ ID NO 1489
<211> LENGTH: 66
<212> TYPE: DNA
<213> ORGANISM: Artificial
<220> FEATURE:
<223> OTHER INFORMATION: synthetic

<400> SEQUENCE: 1489
caagcagaag acggcatacg agatctagcc cagtctcgtg ggctcggaga tgtgtataag    60
agacag                                                              66

<210> SEQ ID NO 1490
<211> LENGTH: 66
<212> TYPE: DNA
<213> ORGANISM: Artificial
<220> FEATURE:
<223> OTHER INFORMATION: synthetic

<400> SEQUENCE: 1490
caagcagaag acggcatacg agatcttacc cagtctcgtg ggctcggaga tgtgtataag    60
agacag                                                              66

<210> SEQ ID NO 1491
<211> LENGTH: 66
<212> TYPE: DNA
<213> ORGANISM: Artificial
<220> FEATURE:
<223> OTHER INFORMATION: synthetic

<400> SEQUENCE: 1491
caagcagaag acggcatacg agatctcacc cagtctcgtg ggctcggaga tgtgtataag    60

```
agacag                                                              66

<210> SEQ ID NO 1492
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1492
caagcagaag acggcatacg agatcgnacc cagtctcgtg ggctcggaga tgtgtataag    60
agacag                                                              66

<210> SEQ ID NO 1493
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1493
caagcagaag acggcatacg agatccnacc cagtctcgtg ggctcggaga tgtgtataag    60
agacag                                                              66

<210> SEQ ID NO 1494
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1494
caagcagaag acggcatacg agatcanacc cagtctcgtg ggctcggaga tgtgtataag    60
agacag                                                              66

<210> SEQ ID NO 1495
<211> LENGTH: 66
<212> TYPE: DNA
<213> ORGANISM: Artificial
<220> FEATURE:
<223> OTHER INFORMATION: synthetic

<400> SEQUENCE: 1495
caagcagaag acggcatacg agatctaacc cagtctcgtg ggctcggaga tgtgtataag    60
agacag                                                              66

<210> SEQ ID NO 1496
<211> LENGTH: 66
<212> TYPE: DNA
<213> ORGANISM: Artificial
<220> FEATURE:
<223> OTHER INFORMATION: synthetic
<220> FEATURE:
```

```
<221> NAME/KEY: misc_feature
<222> LOCATION: (25)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1496
caagcagaag acggcatacg agatnnntnc cagtctcgtg ggctcggaga tgtgtataag    60
agacag                                                               66

<210> SEQ ID NO 1497
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1497
caagcagaag acggcatacg agattnngnc cagtctcgtg ggctcggaga tgtgtataag    60
agacag                                                               66

<210> SEQ ID NO 1498
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1498
caagcagaag acggcatacg agatgnngnc cagtctcgtg ggctcggaga tgtgtataag    60
agacag                                                               66

<210> SEQ ID NO 1499
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1499
caagcagaag acggcatacg agatanngnc cagtctcgtg ggctcggaga tgtgtataag    60
agacag                                                               66
```

<210> SEQ ID NO 1500
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1500
caagcagaag acggcatacg agattnncnc cagtctcgtg ggctcggaga tgtgtataag    60
agacag                                                              66

<210> SEQ ID NO 1501
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1501
caagcagaag acggcatacg agatgnncnc cagtctcgtg ggctcggaga tgtgtataag    60
agacag                                                              66

<210> SEQ ID NO 1502
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1502
caagcagaag acggcatacg agatanncnc cagtctcgtg ggctcggaga tgtgtataag    60
agacag                                                              66

<210> SEQ ID NO 1503
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:

```
<221> NAME/KEY: misc_feature
<222> LOCATION: (29)..(29)
<223> OTHER INFORMATION: n is a, c, g, or t

<400> SEQUENCE: 1503
caagcagaag acggcatacg agattnnanc cagtctcgtg ggctcggaga tgtgtataag    60
agacag                                                               66

<210> SEQ ID NO 1504
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1504
caagcagaag acggcatacg agatgnnanc cagtctcgtg ggctcggaga tgtgtataag    60
agacag                                                               66

<210> SEQ ID NO 1505
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t

<400> SEQUENCE: 1505
caagcagaag acggcatacg agatannanc cagtctcgtg ggctcggaga tgtgtataag    60
agacag                                                               66

<210> SEQ ID NO 1506
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1506
caagcagaag acggcatacg agatcnngac cagtctcgtg ggctcggaga tgtgtataag    60
agacag                                                               66

<210> SEQ ID NO 1507
<211> LENGTH: 66
<212> TYPE: DNA
<213> ORGANISM: Artificial
<220> FEATURE:
<223> OTHER INFORMATION: synthetic
```

<400> SEQUENCE: 1507
caagcagaag acggcatacg agatcttcac cagtctcgtg ggctcggaga tgtgtataag    60
agacag                                                              66

<210> SEQ ID NO 1508
<211> LENGTH: 66
<212> TYPE: DNA
<213> ORGANISM: Artificial
<220> FEATURE:
<223> OTHER INFORMATION: synthetic

<400> SEQUENCE: 1508
caagcagaag acggcatacg agatctccac cagtctcgtg ggctcggaga tgtgtataag    60
agacag                                                              66

<210> SEQ ID NO 1509
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1509
caagcagaag acggcatacg agatcgncac cagtctcgtg ggctcggaga tgtgtataag    60
agacag                                                              66

<210> SEQ ID NO 1510
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1510
caagcagaag acggcatacg agatccncac cagtctcgtg ggctcggaga tgtgtataag    60
agacag                                                              66

<210> SEQ ID NO 1511
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (27)..(27)
<223> OTHER INFORMATION: n is a, c, g, or t

<400> SEQUENCE: 1511
caagcagaag acggcatacg agatcancac cagtctcgtg ggctcggaga tgtgtataag    60
agacag                                                              66

<210> SEQ ID NO 1512
<211> LENGTH: 66
<212> TYPE: DNA

```
<213> ORGANISM: Artificial
<220> FEATURE:
<223> OTHER INFORMATION: synthetic

<400> SEQUENCE: 1512
caagcagaag acggcatacg agatctacac cagtctcgtg ggctcggaga tgtgtataag      60
agacag                                                                66

<210> SEQ ID NO 1513
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t

<400> SEQUENCE: 1513
caagcagaag acggcatacg agatcnnaac cagtctcgtg ggctcggaga tgtgtataag      60
agacag                                                                66

<210> SEQ ID NO 1514
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(29)
<223> OTHER INFORMATION: n is a, c, g, or t

<400> SEQUENCE: 1514
caagcagaag acggcatacg agatnnnnna cagtctcgtg ggctcggaga tgtgtataag      60
agacag                                                                66

<210> SEQ ID NO 1515
<211> LENGTH: 66
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (25)..(30)
<223> OTHER INFORMATION: n is a, c, g, or t

<400> SEQUENCE: 1515
caagcagaag acggcatacg agatnnnnnn aagtctcgtg ggctcggaga tgtgtataag      60
agacag                                                                66

<210> SEQ ID NO 1516
<211> LENGTH: 10
<212> TYPE: DNA
<213> ORGANISM: Artificial
<220> FEATURE:
<223> OTHER INFORMATION: synthetic

<400> SEQUENCE: 1516
gttacacacg                                                            10

<210> SEQ ID NO 1517
<211> LENGTH: 70
```

```
<212> TYPE: DNA
<213> ORGANISM: Artificial
<220> FEATURE:
<223> OTHER INFORMATION: synthetic

<400> SEQUENCE: 1517
aatgatacgg cgaccaccga gatctacacc gcgcagatcg tcggcagcgt cagatgtgta    60
taagagacag                                                            70

<210> SEQ ID NO 1518
<211> LENGTH: 66
<212> TYPE: DNA
<213> ORGANISM: Artificial
<220> FEATURE:
<223> OTHER INFORMATION: synthetic

<400> SEQUENCE: 1518
caagcagaag acggcatacg agattcgtca gagtctcgtg ggctcggaga tgtgtataag    60
agacag                                                                66
```